(12) United States Patent (10) Patent No.: US 7,763,617 B2
Kohno et al. (45) Date of Patent: Jul. 27, 2010

(54) PYRAZOLOPYRIDINE-4-YL PYRIDAZINONE DERIVATIVES AND ADDITION SALTS THEREOF, AND PDE INHIBITORS COMPRISING THE SAME DERIVATIVES OR SALTS AS ACTIVE INGREDIENT

(75) Inventors: Yasushi Kohno, Oyama (JP); David Roger Adams, Edinburgh (GB); Naoki Ando, Oura-gun (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 16 days.

(21) Appl. No.: 11/884,617

(22) PCT Filed: Mar. 6, 2006

(86) PCT No.: PCT/JP2006/304230
§ 371 (c)(1),
(2), (4) Date: Nov. 19, 2007

(87) PCT Pub. No.: WO2006/095666
PCT Pub. Date: Sep. 14, 2006

(65) Prior Publication Data
US 2008/0207902 A1 Aug. 28, 2008

(30) Foreign Application Priority Data
Mar. 7, 2005 (JP) .............................. 2005-061863

(51) Int. Cl.
C07D 401/14 (2006.01)
C07D 403/14 (2006.01)
A61K 31/501 (2006.01)
A61P 11/06 (2006.01)
A61P 33/08 (2006.01)
A61P 29/00 (2006.01)
A61P 25/24 (2006.01)

(52) U.S. Cl. ................................ 514/252.04; 544/238
(58) Field of Classification Search ................ 514/248; 544/235
See application file for complete search history.

(56) References Cited

U.S. PATENT DOCUMENTS 6,265,577 B1 * 7/2001 Kouno et al. ................ 544/239

FOREIGN PATENT DOCUMENTS

JP 10-109988 4/1998
WO 98/14448 4/1998

OTHER PUBLICATIONS

Griesser, Chapter 8, The Importance of Solvates (pp. 211-230), in the text, Polymorphism In the Pharmaceutical Industry, Hilfiker, 2006.*
Wikipedia, Derivative, http://en.wikipedia.org/wiki/Derivative_(chemistry), downloaded Nov. 20, 2008.*
Chapter V, Polymorphism in Pharmaceutical Solids, 1999, pp. 126-127.*
Naldi, et al., Expert Opin. Emerging Drugs (2009) 14(1) 145-163.*
Targan, et al., Inflammatory Bowel Disease: From Bench to Bedside, 2nd Edition, pp. 553-571, 2003.*
Prehn, et al., J. Clin. Immunol., vol. 21, No. 5, 2001, pp. 357-364.*

* cited by examiner

*Primary Examiner*—James O Wilson
*Assistant Examiner*—Cecilia M Jaisle
(74) *Attorney, Agent, or Firm*—Wenderoth, Lind & Ponack, L.L.P.

(57) ABSTRACT

Novel pyrazolopyridine-4-yl pyridazinone derivatives serve as phosphodiesterase inhibitors and are useful compounds for use in pharmaceutical products.

Specifically, the compounds of the present invention are pyrazolopyridine-4-yl pyridazinone derivatives represented by the following general formula (1):

(1)

[Chemical structure of pyrazolopyridine-4-yl pyridazinone with substituents $R_1$, $R_2$, $R_3$, $R_4$, $R_5$, $NR_6$]

(Example: 6-(2-ethyl-7-methoxy-pyrazolo[1,5-a]pyridine-4-yl)-5-methyl-4, 5-dihydro-3(2H)-pyridazinone).

12 Claims, No Drawings

PYRAZOLOPYRIDINE-4-YL PYRIDAZINONE DERIVATIVES AND ADDITION SALTS THEREOF, AND PDE INHIBITORS COMPRISING THE SAME DERIVATIVES OR SALTS AS ACTIVE INGREDIENT

TECHNICAL FIELD

The present invention relates to pyrazolopyridine-4-yl pyridazinone derivatives that serve as effective phosphodiesterase (PDE) inhibitors, as well as to addition salts and hydrates thereof.

BACKGROUND ART

Phosphodiesterases (PDEs) are a class of enzymes that degrade second messengers cyclic AMP (cAMP) and cyclic GMP (cGMP) in the body. To date, eleven families of PDEs (PDE1 to PDE11) have been identified with each family having specificity for cAMP or cGMP or both. The tissue distribution of each PDE family varies from tissue to tissue: It is believed that the cellular reactions in different organs are controlled by different PDE families.

A number of PDE inhibitors have been developed. Examples include PDE3 inhibitors that are intended for the treatment of angina pectoris, heart failure and hypertension and serve as antiplatelet and antiasthmatic agents; PDE4 inhibitors that are intended for the treatment of asthma, chronic obstructive pulmonary disease (COPD), interstitial pneumonia, allergic rhinitis, atopic dermatitis, rheumatoid arthritis, multiple sclerosis, Crohn's disease, inflammatory colitis, Alzheimer's disease, dementia, Parkinson's disease and depression; and PDE5 inhibitors that are already in clinical use as a treatment for erectile dysfunction. A recent study reports that minocycline, a PDE10A modulator, has proven effective in patients with Huntington's disease (Patent Document 1). Also, a patent application describes PDE10 inhibitors as an effective cure for Huntington's disease, Alzheimer's disease, dementia, Parkinson's disease, schizophrenia and other psychiatric disorders (Patent Document 2).

While some pyrazolopyridine pyridazinone derivatives have been described as PDE inhibitors (Patent Documents 3 and 4), no literature exists that describes compounds that have the same characteristic structure as the compounds of the present invention: a pyridazinone ring linked to position 4 of a pyrazolopyridine ring. Certain compounds that have a pyrazolopyridine ring substituted at position 3 with a dihydropyrydazinone group and a pyridazinone group have been reported to serve as adenosine antagonists (Patent Documents 5, 6, 7 and 8). Their structure, however, is apparently different from that of the compounds of the present invention, in which the pyridazinone group is linked to position 4 of pyrazolopyridine ring.

A pyrazolopyridine derivative that acts as a bronchodilator has also been described (Patent Document 9). Nevertheless, none of the above-described compounds share the structural feature of the compounds of the present invention.

Patent Document 1 WO01024781 Pamphlet
Patent Document 2 Japanese Patent Laid-Open Publication No. 2002-363103
Patent Document 3 Domestic re-publication of PCT application No. WO98/14448
Patent Document 4 Japanese Patent Laid-Open Publication No. Hei 10-109988
Patent Document 5 Japanese Patent Laid-Open Publication No. Hei 2-243689
Patent Document 6 Japanese Patent Laid-Open Publication No. Hei 4-253987
Patent Document 7 WO02018382 Pamphlet
Patent Document 8 WO03004494 Pamphlet
Patent Document 9 Japanese Patent Laid-Open Publication No. Hei 8-12673

DISCLOSURE OF THE INVENTION

Problems to be Solved by the Invention

Accordingly, the present invention provides a pyrazolopyridine-4-yl pyridazinone derivative that serves as an effective phosphodiesterase inhibitor with fewer side effects.

Means for Solving the Problem

In an effort to develop effective and safe phosphodiesterase inhibitors, the present inventors have conducted extensive studies and found that novel pyrazolopyridine-4-yl pyridazinone derivatives, a group of compounds structurally different from any of the existing PDE inhibitors, act as potent PDE inhibitors. This finding ultimately led to the present invention.

Specifically, the present invention comprises the following:

1) A pyrazolopyridine-4-yl pyridazinone derivative represented by the following general formula (1):

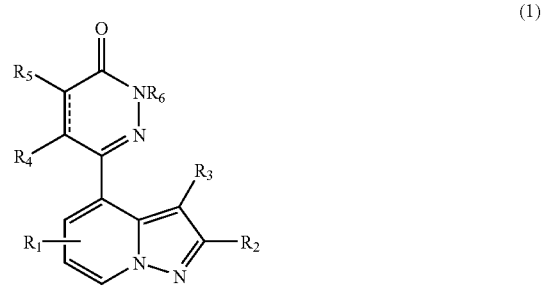

[wherein $R_1$ is a hydrogen atom, a halogen atom, a lower alkyl group having 1 to 4 carbon atoms, a substituted or unsubstituted lower alkoxy group having 1 to 4 carbon atoms, a cyclopropylmethyloxy group, a lower alkylthio group having 1 to 4 carbon atoms, a lower alkylsulfinyl group having 1 to 4 carbon atoms, a lower alkylsulfonyl group having 1 to 4 carbon atoms, a substituted or unsubstituted lower alkylamino group having 1 to 4 carbon atoms, a phenylamino group, an aromatic or saturated heterocyclic ring that may contain 1 or 2 heteroatoms, a lower alkanoyl group having 1 to 4 carbon atoms, an acylamino group having 1 to 4 carbon atoms, a substituted or unsubstituted phenyl group, a carbamoyl group, a cyano group, a lower alkoxycarbonyl group having 1 to 4 carbon atoms, or a carboxyl group;

$R_2$ is a hydrogen atom, a substituted or unsubstituted lower alkyl group having 1 to 4 carbon atoms, a cycloalkyl group having 3 to 8 carbon atoms, a lower alkenyl group having 2 to 4 carbon atoms, a lower alkanoyl group having 1 to 4 carbon atoms, or a lower alkylthio group having 1 to 4 carbon atoms;

$R_3$ is a hydrogen atom, a halogen atom, a carboxyl group, a lower alkoxycarbonyl group having 1 to 4 carbon atoms, or a hydroxyl group;

$R_4$ and $R_5$ are each independently a hydrogen atom or a lower alkyl group having 1 to 4 carbon atoms;

$R_6$ is a hydrogen atom, or $R_7$—(CH$_2$)$_m$— (wherein $R_7$ is a cycloalkyl group having 3 to 8 carbon atoms, a hydroxyl group, or an aromatic or saturated heterocyclic ring that may contain 1 or 2 heteroatoms, and m is an integer of 1 or 2); and -- is a single or double bond], an optical isomer thereof or a pharmaceutically acceptable salt thereof or hydrate thereof.

2) The pyrazolopyridine-4-yl pyridazinone derivative according to 1) above, an optical isomer thereof, or a pharmaceutically acceptable salt thereof or hydrate thereof, wherein the compound represented by the general formula (1) is represented by the following general formula (1a):

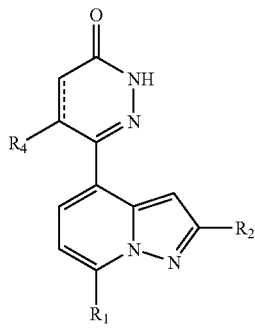

(1a)

[wherein $R_1$, $R_2$, $R_4$ and -- are as defined above].

3) The pyrazolopyridine-4-yl pyridazinone derivative according to 2) above, an optical isomer thereof, or a pharmaceutically acceptable salt thereof or hydrate thereof, wherein in the general formula (1a), $R_1$ is a methoxy group.

4) The pyrazolopyridine-4-yl pyridazinone derivative according to 2) above, an optical isomer thereof, or a pharmaceutically acceptable salt thereof or hydrate thereof, wherein in the general formula (1a), $R_1$ is a methylthio group.

5) The pyrazolopyridine-4-yl pyridazinone derivative according to 2) above, an optical isomer thereof, or a pharmaceutically acceptable salt thereof or hydrate thereof, wherein in the general formula (1a), $R_1$ is a methylamino group.

6) The pyrazolopyridine-4-yl pyridazinone derivative according to 1) above, an optical isomer thereof, or a pharmaceutically acceptable salt thereof or hydrate thereof, wherein the compound of the general formula (1) is
6-(2-ethyl-7-methoxy-pyrazolo[1,5-a]pyridine-4-yl)-5-methyl-4,5-dihydro-3(2H)-pyridazinone,
(+)-6-(2-ethyl-7-methoxy-pyrazolo[1,5-a]pyridine-4-yl)-5-methyl-4,5-dihydro-3(2H)-pyridazinone,
(−)-6-(2-ethyl-7-methoxy-pyrazolo[1,5-a]pyridine-4-yl)-5-methyl-4,5-dihydro-3(2H)-pyridazinone,
6-(2-ethyl-7-methylthio-pyrazolo[1,5-a]pyridine-4-yl)-5-methyl-4,5-dihydro-3(2H)-pyridazinone,
6-(2-ethyl-7-methylamino-pyrazolo[1,5-a]pyridine-4-yl)-5-methyl-4,5-dihydro-3(2H)-pyridazinone,
6-(7-methoxy-2-trifluoromethyl-pyrazolo[1,5-a]pyridine-4-yl)-5-methyl-4,5-dihydro-3(2H)-pyridazinone,
(+)-6-(7-methoxy-2-trifluoromethyl-pyrazolo[1,5-a]pyridine-4-yl)-5-methyl-4,5-dihydro-3(2H)-pyridazinone,
(−)-6-(7-methoxy-2-trifluoromethyl-pyrazolo[1,5-a]pyridine-4-yl)-5-methyl-4,5-dihydro-3(2H)-pyridazinone,
6-(7-methoxy-2-trifluoromethyl-pyrazolo[1,5-a]pyridine-4-yl)-4,5-dihydro-3(2H)-pyridazinone,
6-(7-methoxy-2-trifluoromethyl-pyrazolo[1,5-a]pyridine-4-yl)-5-methyl-3(2H)-pyridazinone, or 6-(7-methoxy-2-trifluoromethyl-pyrazolo[1,5-a]pyridine-4-yl)-3(2H)-pyridazinone.

7) A phosphodiesterase (PDE) inhibitor containing as an active ingredient at least one of pyrazolopyridine-4-yl pyridazinone represented by the following formula:

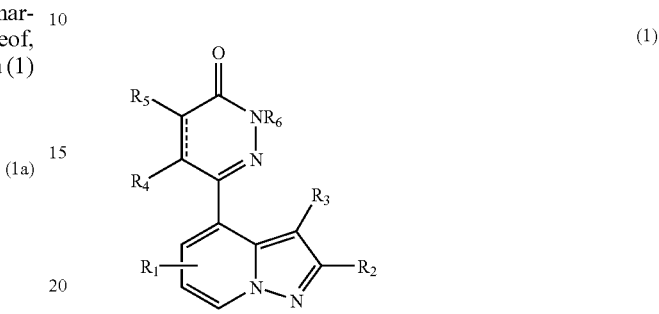

(1)

[wherein $R_1$ is a hydrogen atom, a halogen atom, a lower alkyl group having 1 to 4 carbon atoms, a substituted or unsubstituted lower alkoxy group having 1 to 4 carbon atoms, a cyclopropylmethyloxy group, a lower alkylthio group having 1 to 4 carbon atoms, a lower alkylsulfinyl group having 1 to 4 carbon atoms, a lower alkylsulfonyl group having 1 to 4 carbon atoms, a substituted or unsubstituted lower alkylamino group having 1 to 4 carbon atoms, a phenylamino group, an aromatic or saturated heterocyclic ring that may contain 1 or 2 heteroatoms, a lower alkanoyl group having 1 to 4 carbon atoms, an acylamino group having 1 to 4 carbon atoms, a substituted or unsubstituted phenyl group, a carbamoyl group, a cyano group, a lower alkoxycarbonyl group having 1 to 4 carbon atoms, or a carboxyl group;

$R_2$ is a hydrogen atom, a substituted or unsubstituted lower alkyl group having 1 to 4 carbon atoms, a cycloalkyl group having 3 to 8 carbon atoms, a lower alkenyl group having 2 to 4 carbon atoms, a lower alkanoyl group having 1 to 4 carbon atoms, or a lower alkylthio group having 1 to 4 carbon atoms;

$R_3$ is a hydrogen atom, a halogen atom, a carboxyl group, a lower alkoxycarbonyl group having 1 to 4 carbon atoms, or a hydroxyl group;

$R_4$ and $R_5$ are each independently a hydrogen atom or a lower alkyl group having 1 to 4 carbon atoms;

$R_6$ is a hydrogen atom, or $R_7$—(CH$_2$)$_m$— (wherein $R_7$ is a cycloalkyl group having 3 to 8 carbon atoms, a hydroxyl group, or an aromatic or saturated heterocyclic ring that may contain 1 or 2 heteroatoms, and m is an integer of 1 or 2); and -- is a single or double bond], an optical isomer thereof and a pharmaceutically acceptable salt thereof or hydrate thereof.

8) The PDE inhibitor according to 7) containing as an active ingredient at least one of pyrazolopyridine-4-yl pyridazinone, an optical isomer thereof or a pharmaceutically acceptable salt thereof or hydrate thereof, wherein the compound represented by the general formula (1) is represented by the following general formula (1a):

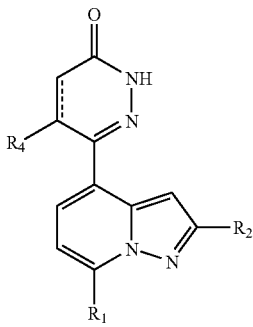

(1a)

[wherein $R_1$, $R_2$, $R_4$ and -- are as defined above].

9) A pharmaceutical composition containing as an active ingredient the pyrazolopyridine-4-yl pyridazinone according to any one of 1) to 6) above, an optical isomer thereof or a pharmaceutically acceptable salt thereof or hydrate thereof.

Effect of the Invention

As described above, the present invention is based on the finding that the novel pyrazolopyridine-4-yl pyridazinone derivatives and their addition salts serve as effective PDE inhibitors. Such PDE inhibitors are useful in the treatment of angina pectoris, heart failure and hypertension, prevent platelet aggregation, and are useful in the treatment and prevention of asthma, chronic obstructive pulmonary disease (COPD), interstitial pneumonia, allergic rhinitis, atopic dermatitis, rheumatoid arthritis, multiple sclerosis, Crohn's disease, inflammatory colitis, psychiatric disorders such as Huntington's disease, Alzheimer's disease, dementia, Parkinson's disease, depression and schizophrenia, and erectile dysfunction.

BEST MODE FOR CARRYING OUT THE INVENTION

The compounds of the general formulas (1) and (1a) are novel compounds.

The compounds represented by the general formula (1) may be provided in the form of pharmaceutically acceptable salts, including acid addition salts, such as hydrochlorides, hydrobromides, acetates, trifluoroacetates, methanesulfonates, citrates and tartrates.

The term "halogen atom" in the general formula (1) refers to a fluorine atom, a chlorine atom, a bromine atom or an iodine atom. The term "lower alkyl group" as in "lower alkyl group having 1 to 4 carbon atoms," "lower alkoxy group having 1 to 4 carbon atoms," "lower alkylthio group having 1 to 4 carbon atoms," "lower alkylsulfinyl group having 1 to 4-carbon atoms," "lower alkylsulfonyl group" and "lower alkylamino group having 1 to 4 carbon atoms" refers to a straight-chained or branched hydrocarbon having 1 to 4 carbon atoms, such as methyl, ethyl, propyl, isopropyl, butyl, isobutyl and t-butyl. The terms "substituted or unsubstituted lower alkoxy group having 1 to 4 carbon atoms," "substituted or unsubstituted lower alkyl group having 1 to 4 carbon atoms" and "substituted or unsubstituted lower alkylamino group having 1 to 4 carbon atoms" refer to a straight-chained or branched carbon backbone with a halogen atom, a hydroxyl group, a lower alkylamino group having 1 to 4 carbon atoms or a lower alkoxy group having 1 to 4 carbon atoms. The term "cycloalkyl group having 3 to 8 carbon atoms" refers to a cyclic hydrocarbon having 3 to 8 carbon atoms, such as cyclopropyl, cyclobutyl, cyclopentyl and cyclohexyl. The term "lower alkenyl group having 2 to 4 carbon atoms" refers to a hydrocarbon having an unsaturated double bond and 2 to 4 carbon atoms, such as vinyl, allyl, 1-propenyl, isopropenyl, 1-butenyl, 2-butenyl, 2-methylallyl and 1-propenyl. The term "lower alkanoyl group having 1 to 4 carbon atoms" refers to a straight-chained or branched lower alkanoyl group having 1 to 4 carbon atoms, such as formyl, acetyl, propionyl, butyryl and isobutyryl. The term "lower acylamino group having 2 to 4 carbon atoms" refers to an amino group acylated with a lower alkanoyl group having 1 to 4 carbon atoms, such as formylamino, acetylamino, propionylamino, butyrylamino and isobutyrylamino. The term "aromatic heterocyclic ring that may contain 1 or 2 heteroatoms" refers to a 5-membered aromatic monocyclic compound, such as pyrrole, furan, thiophene, pyrazole, isoxazole, isothiazole, imidazole, oxazole and thiazole, or a 6-membered aromatic monocyclic compound, such as pyridine, pyridazine, pyrimidine and pyradine. The term "saturated heterocyclic ring that may contain 1 or 2 heteroatoms" refers to a 5- or 6-membered monocyclic compound, such as pyrrolidine, piperidine, piperazine and morpholine. The term "substituted or unsubstituted phenyl group" refers to a phenyl group which optionally have a halogen atom, a lower alkyl group having 1 to 4 carbon atoms, a lower alkoxy group having 1 to 4 carbon atoms or a lower alkylamino group having 1 to 4 carbon atoms on the benzene ring.

Of the compounds represented by the general formula (1), those in which $R_3$ and $R_6$ are each a hydrogen atom and -- is a single bond are represented by the following general formula (1b):

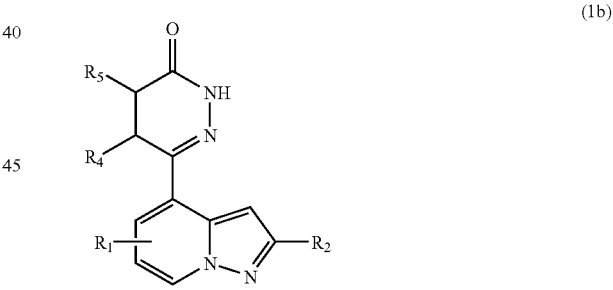

(1b)

[wherein $R_1$, $R_2$, $R_4$ and $R_5$ are as defined above]. According to the present invention, such compounds can be produced by a series of synthetic pathways, as described below.

<Synthetic Pathway A>

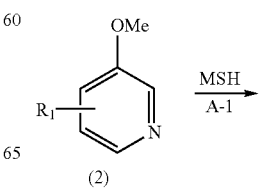

(2)

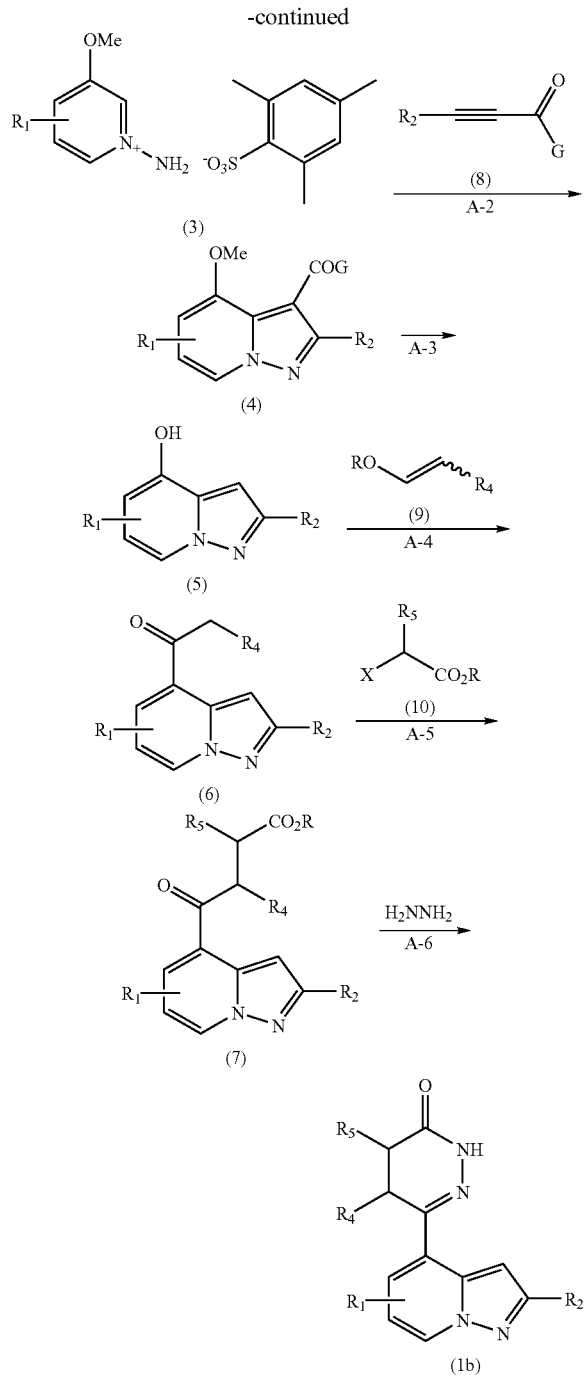

[wherein $R_1$ is as defined above] can be produced by reacting the compound represented by the following general formula (2):

[wherein $R_1$ is as defined above] with O-mesitylenesulfonyl-hydroxylamine (MSH) (Step A-1).

The reaction is preferably carried out by adding a solution of the compound represented by the general formula (2) in methylene chloride to a solution of MSH in methylene chloride at 0° C. to room temperature.

In Synthetic Pathway A, the compound represented by the following general formula (4):

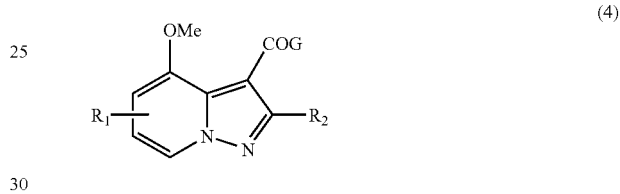

[wherein G is a lower alkoxy group having 1 to 4 carbon atoms, a benzyloxy group or a lower alkyl group having 1 to 4 carbon atoms, and $R_1$ and $R_2$ are as defined above] can be produced by reacting the compound represented by the general formula (3) with the compound represented by the following general formula (8):

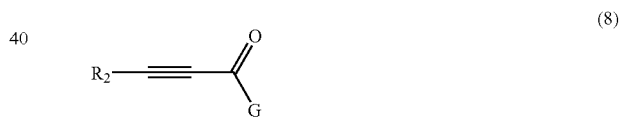

[wherein $R_2$ and G are as defined above] in the presence of a base (Step A-2).

The reaction may be carried out at 0° C., or preferably at room temperature, in a reaction solvent such as methanol, ethanol, 1,4-dioxane, dimethylsulfoxide (DMSO), N,N-dimethylformamide (DMF), tetrahydrofuran (THF), toluene, benzene, cyclohexane, cyclopentane, methylene chloride, chloroform or acetonitrile and in the presence of an inorganic base, such as sodium bicarbonate, sodium carbonate, potassium bicarbonate or potassium carbonate, or an organic base, such as triethylamine.

In Synthetic Pathway A, the compound represented by the following general formula (5):

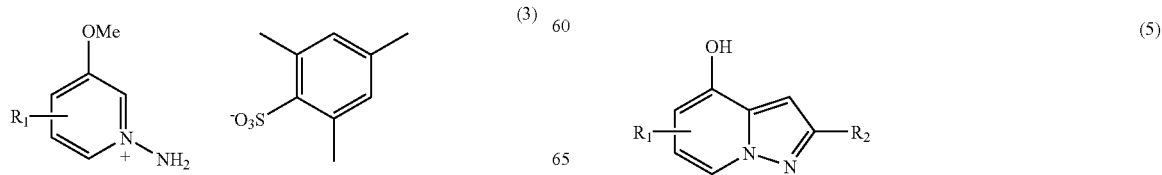

[wherein $R_1$ and $R_2$ are as defined above] can be produced by demethylation, hydrolysis, and decarboxylation or decarbonylation of the compound represented by the general formula (4) (Step A-3).

The reaction is preferably carried out at once by reacting the compound of the general formula (4) with hydrobromic acid or acetic acid containing hydrogen bromide under reflux. Alternatively, the demethylation, hydrolysis and decarboxylation may be individually carried out in the following manner: Using a Lewis acid, such as aluminum chloride, boron trichloride, or preferably, boron tribromide, the compound of the general formula (4) is first demethylated at 0° C. to room temperature in a solvent such as chloroform, or preferably, methylene chloride. Subsequently, using an aqueous potassium hydroxide solution or an aqueous lithium hydroxide solution, the demethylated product is hydrolyzed to a carboxylic acid. This is done at room temperature or at reflux in a solvent such as methanol, ethanol, THF, DMSO, DMF or 1,4-dioxane. The hydrolysate is then decarboxylated. The decarboxylation can be carried out either by heating the product to 140 to 160° C. in an organic solvent such as benzene, chlorobenzene, dichlorobenzene, bromobenzene, toluene or xylene, or by heating the product to 100° C. in ethanol or 1,4-dioxane while adding 2 to 10% aqueous sulfuric acid, or by stirring the product at 100° C. in 50% sulfuric acid. The decarbonylation is preferably carried out under reflux by heating the product in hydrobromic acid, acetic acid containing hydrogen bromide or 50% sulfuric acid.

In Synthetic Pathway A, the compound represented by the following general formula (6):

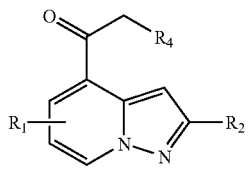

(6)

[wherein $R_1$, $R_2$ and $R_4$ are as defined above] can be produced by adding a trifluoromethanesulfonyl group to the compound represented by the general formula (5) and reacting the resulting product with the compound represented by the following general formula (9):

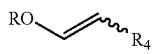

(9)

[wherein R is a lower alkyl group having 1 to 4 carbon atoms or a benzyl group, and $R_4$ is as defined above] in Heck reaction (Step A-4).

The addition of trifluoromethanesulfonyl group is carried out by reacting the compound of the general formula (5) with trifluoromethanesulfonic anhydride in a solvent such as THF, chloroform, or carbon tetrachloride, and preferably, in methylene chloride, in the presence of an organic base such as diisopropylethylamine or triethylamine. Subsequently, the resulting trifluoromethanesulfonate is acid-hydrolyzed in the Heck reaction to obtain the desired product. In the Heck reaction, the trifluoromethanesulfonate is reacted with the compound represented by the general formula (9) in the presence of triethylamine at a room temperature, or preferably at 80° C. The reaction may be carried out in any suitable solvent, typically DMF, and requires palladium acetate and 1,3-bis (dipheylphosphino)propane as catalysts. The resulting product is dissolved in a solvent such as 1,4-dioxane, DMF, or preferably, THF. Diluted hydrochloric acid is then added and the reaction is allowed to proceed further at room temperature.

In Synthetic Pathway A, the compound represented by the following general formula (7):

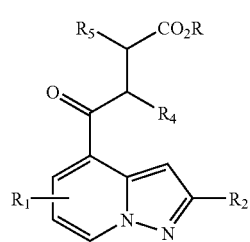

(7)

[wherein $R_1$, $R_2$, $R_4$, $R_5$ and R are as defined above] can be produced by reacting the compound represented by the general formula (6) with the compound represented by the following general formula (10):

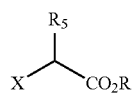

(10)

[wherein X is a halogen atom, and $R_5$ and R are as defined above] in the presence of a base (Step A-5).

The base used in the reaction may be sodium hydride, potassium hydride, sodium alkoxide, potassium alkoxide, lithium diisopropylamide (LDA), lithium-2,2,6,6-tetramethylpiperidide, lithium bistrimethylsilylamide, sodium bistrimethylsilylamide or potassium bistrimethylsilylamide. The reaction is carried out at −78° C. to room temperature in a reaction solvent such as THF, 1,4-dioxane or 1,2-dimethoxyethane.

In Synthetic Pathway A, the compound represented by the general formula (1b) can be produced by reacting the compound represented by the general formula (7) with hydrazine either directly or after hydrolysis (Step A-6).

When hydrolysis is involved, the compound of the general formula (7) is reacted with a base, such as an aqueous solution of sodium hydroxide, potassium hydroxide or lithium hydroxide, in a solvent such as ethanol, methanol, THF or 1,4-dioxane, at 0° C. to room temperature. When R is a t-butyl group, the compound of the general formula (7) is preferably hydrolyzed with trifluoroacetic acid in the absence of solvents or in the presence of methylene chloride as a solvent. The resulting hydrolysate is reacted with hydrazine or hydrazine acetate in a reaction solvent such as benzene, toluene, or acetic acid, and preferably, methanol, at room temperature, or preferably, at reflux. When the compound represented by the general formula (7) is directly reacted with hydrazine, the reaction is carried out either in an alcohol solvent in the presence of a catalytic amount of acetic acid, or in acetic acid as solvent, at room temperature or heated.

<Synthetic Pathway B>

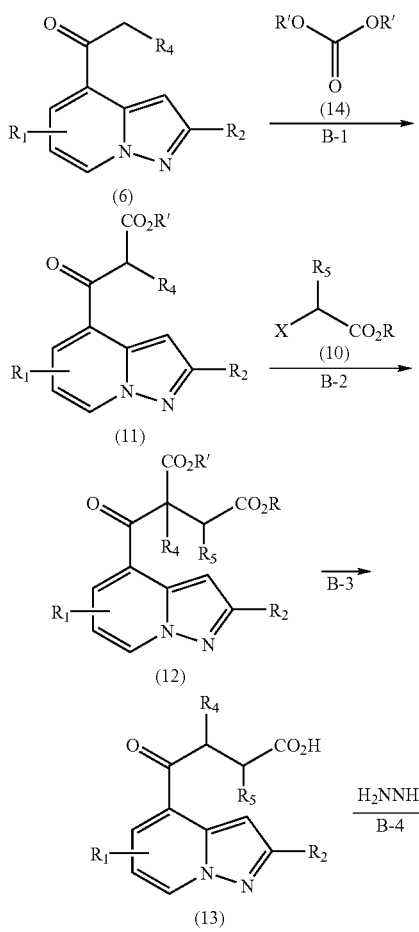

In Synthetic Pathway B, the compound represented by the following general formula (11):

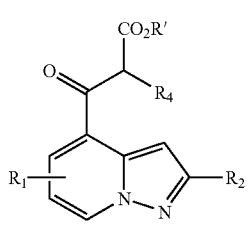

[wherein R' is a lower alkyl group having 1 to 4 carbon atoms, and $R_1$, $R_2$ and $R_4$ are as defined above] can be produced by reacting the compound represented by the general formula (6) with the compound represented by the following general formula (14):

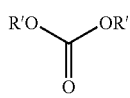

[wherein R' is as defined above] in the presence of a base (Step B-1).

The reaction uses a solvent amount of the compound of the general formula (14) and is preferably carried out under reflux in the presence of an inorganic base such as sodium alkoxide, potassium alkoxide, or potassium hydride, and preferably, sodium hydride.

In Synthetic Pathway B, the compound represented by the following general formula (12):

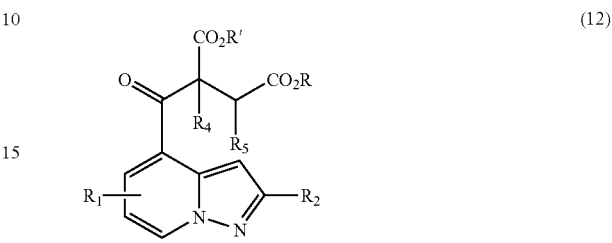

[wherein $R_1$, $R_2$, $R_4$, $R_5$, R and R' areas defined above] can be produced by reacting the compound represented by the general formula (11) with the compound represented by the general formula (10) in the presence of a base (Step B-2).

The base used in the reaction may be sodium hydride, potassium hydride, sodium alkoxide, potassium alkoxide, LDA, lithium-2,2,6,6-tetramethylpiperidide, lithium bistrimethylsilylamide, sodium bistrimethylsilylamide or potassium bistrimethylsilylamide. The reaction is carried out at −78° C. to room temperature in a reaction solvent such as THF, 1,4-dioxane or 1,2-dimethoxyethane.

In Synthetic Pathway B, the compound represented by the following general formula (13):

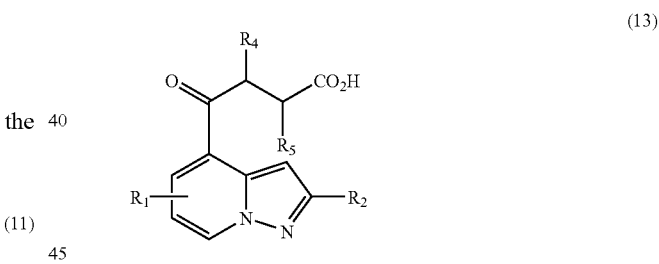

[$R_1$, $R_2$, $R_4$ and $R_5$ are as defined above] can be produced by hydrolysis and decarboxylation of the compound represented by the general formula (12) (Step B-3).

In acidic conditions, the reaction is carried out in hydrochloric acid or hydrobromic acid at 80 to 100° C. In basic conditions, the compound of the general formula (12) is first hydrolyzed with an aqueous sodium hydroxide solution or an aqueous potassium hydroxide solution. This is done at room temperature in an alcohol solvent such as methanol or ethanol or in a reaction solvent such as THF, DMF or DMSO. Subsequently making the reaction mixture acidic can decarboxylate the product.

In Synthetic Pathway B, the compound represented by the general formula (1b) can be produced by reacting the compound represented by the general formula (12) with hydrazine (Step B-4).

The reaction involves hydrazine or hydrazine acetate and is carried out at room temperature, or preferably at reflux, in a reaction solvent such as benzene, toluene, or acetic acid, and preferably, in ethanol.

The compound represented by the general formula (13), an intermediate in the synthesis of the compound (1b) used in Synthetic Pathway B, may also be produced by Synthetic Pathway C, as described below.

<Synthetic Pathway C>

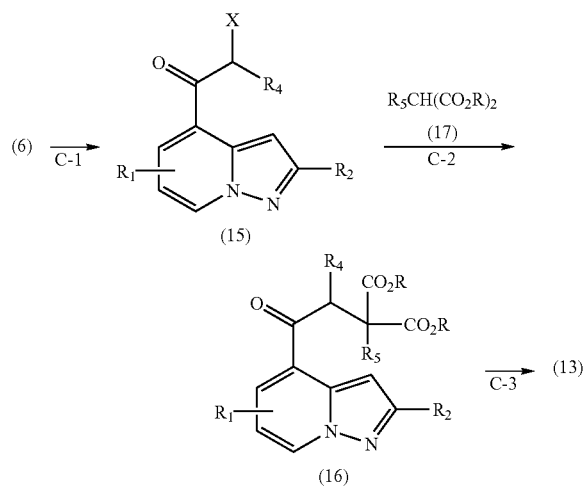

In Synthetic Pathway C, the compound represented by the following general formula (15):

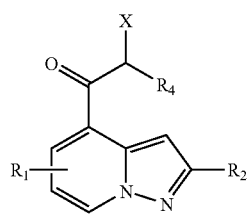

[wherein $R_1$, $R_2$, $R_4$ and X are as defined above] can be produced by halogenating the compound represented by the general formula (6) (Step C-1).

The reaction involves sulfuryl chloride, bromine, iodine, N-chlorosuccinimide (NSC), N-bromosuccinimide (NBS), N-iodosuccinimide (NIS), or preferably, copper (II) chloride, copper (II) bromide or copper (II) iodide, and is preferably carried out under reflux in a solvent such as THF, 1,4-dioxane, methylene chloride, or chloroform, and preferably, in ethyl acetate.

In Synthetic Pathway C, the compound represented by the following general formula (16):

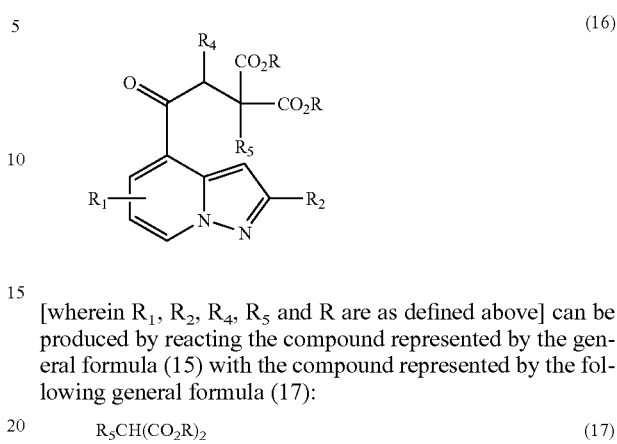

[wherein $R_1$, $R_2$, $R_4$, $R_5$ and R are as defined above] can be produced by reacting the compound represented by the general formula (15) with the compound represented by the following general formula (17):

$$R_5CH(CO_2R)_2 \qquad (17)$$

[wherein $R_5$ and X are as defined above] in the presence of a base (Step C-2).

The base used in the reaction may be an inorganic base, such as sodium alkoxide, potassium alkoxide, LDA, lithium-2,2,6,6-tetramethylpiperidide, lithium bistrimethylsilylamide, sodium bistrimethylsilylamide, potassium bistrimethylsilylamide, or potassium hydride, and preferably, sodium hydride. The reaction is carried out at room temperature to reflux temperature in a reaction solvent such as THF, DMF, 1,4-dioxane or DMSO.

In Synthetic Pathway C, the compound represented by the general formula (13) can be produced by the hydrolysis of the compound represented by the general formula (16) (Step C-3).

The hydrolysis involves an aqueous sodium hydroxide solution or an aqueous potassium hydroxide solution and is carried out at room temperature either in an alcohol solvent such as methanol or ethanol or in a reaction solvent such as THF, DMF or DMSO. Subsequently making the reaction mixture acidic can decarboxylate the product. In case of incomplete decarboxylation, the resulting dicarboxylic acid is dissolved in methanol or ethanol and the solution is refluxed to complete decarboxylation.

The intermediate compound represented by the general formula (6) in Synthetic Pathways A and B may also be produced by Synthetic Pathway D, as described below.

<Synthetic Pathway D>

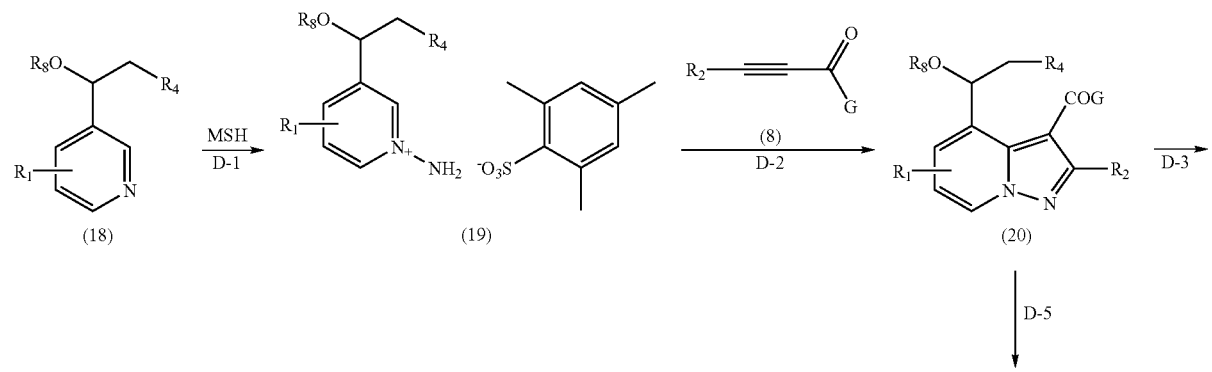

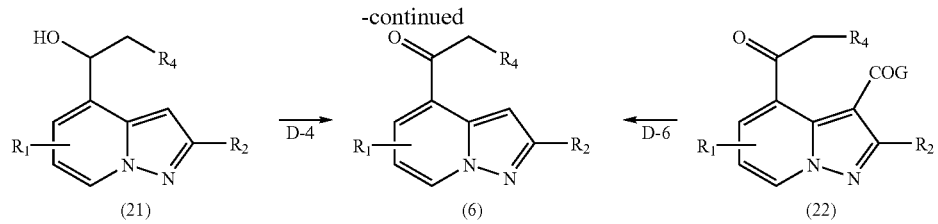

In Synthetic Pathway D, the compound represented by the following general formula (19):

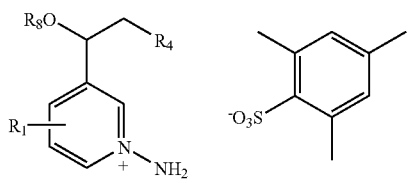

[wherein $R_8$ is a hydrogen atom, a lower alkyl group having 1 to 4 carbon atoms, an acetyl group, a tetrahydropyranyl group, a t-butyldimethylsilyl group, t-butyldiphenylsilyl group or a triisopropylsilyl group, and $R_1$ and $R_4$ are as defined above] can be produced by reacting the compound represented by the following general formula (18):

[wherein $R_1$, $R_4$ and $R_8$ are as defined above] with MSH (Step D-1).

The reaction is preferably carried out by reacting a solution of the compound represented by the general formula (17) in methylene chloride with a solution of MSH in methylene chloride at 0° C. to room temperature.

In Synthetic Pathway D, the compound represented by the following general formula (20):

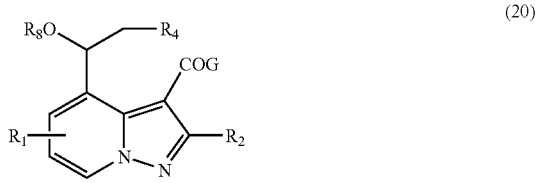

[wherein $R_1$, $R_2$, $R_4$ and $R_8$ and G are as defined above] can be produced by reacting the compound represented by the general formula (19) with the compound represented by the general formula (8) in the presence of a base (Step D-2).

The reaction is carried out at 0° C., or preferably at room temperature, in the presence of an inorganic base, such as sodium bicarbonate, sodium carbonate, potassium bicarbonate or potassium carbonate, or an organic base, such as triethylamine, in a reaction solvent such as methanol, ethanol, 1,4-dioxane, DMSO, DMF, THF, toluene, benzene, cyclohexane, cyclopentane, methylene chloride, chloroform or acetonitrile.

In Synthetic Pathway D, the compound represented by the following general formula (21):

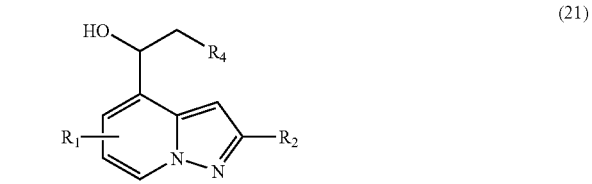

[wherein $R_1$, $R_2$ and $R_4$ are as defined above] can be produced by hydrolysis and subsequent decarboxylation or decarbonylation of the compound represented by the general formula (20) (Step D-3).

When $R_8$ is a lower alkyl group having 1 to 4 carbon atoms or a tetrahydropyranyl group, the compound of the general formula (20) may be reacted with hydrobromic acid or acetic acid containing hydrogen bromide under reflux to effect deprotection, hydrolysis and decarboxylation at once. When $R_8$ is an acetyl group, the compound of the general formula (20) may be first hydrolyzed to a carboxylic acid, prior to decarboxylation, by reacting it with an aqueous solution of potassium hydroxide, lithium hydroxide, or preferably sodium hydroxide, at room temperature to reflux temperature in a solvent such as methanol, ethanol, THF, DMSO, DMF or dioxane. When $R_8$ is a t-butyldimethylsilyl group, a t-butyldiphenylsilyl group or a triisopropylsilyl group, the compound of the general formula (20) may be first reacted with tetrabutylammonium fluoride in THF to eliminate the silyl group. The resulting product is hydrolyzed by the above-described acid or base process prior to decarboxylation. The decarboxylation can be carried out by heating the hydrolysate to 140 to 160° C. in an organic solvent such as benzene, chlorobenzene, dichlorobenzene, bromobenzene, toluene or xylene, by heating the product to 100° C. in ethanol or dioxane while adding 2 to 10% aqueous sulfuric acid, or by stirring the product at 100° C. in 50% sulfuric acid. The decarbonylation is preferably carried out by heating the product under reflux in hydrobromic acid, acetic acid containing hydrogen bromide or 50% sulfuric acid.

In Synthetic Pathway D, the compound represented by the general formula (6) can be produced by oxidizing the compound represented by the general formula (21) (Step D-4).

The reaction can be carried out by any oxidation process commonly used to oxidize alcohols to aldehydes or ketones. For example, the oxidation process may be a DMSO oxidation process that uses a chromium oxide-pyridine complex, such as pyridinium chlorochromate or pyridinium dichromate, a metal oxidizing agent, such as chromium oxide, silver carbonate or manganese dioxide, or a DMSO activating agent, such as oxalyl chloride, trifluoroacetic anhydride, acetic anhydride, DCC or sulfur trioxide/pyridine complexes.

In Synthetic Pathway D, the compound represented by the following general formula (22):

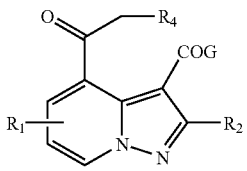

[wherein $R_1$, $R_2$, $R_4$ and G are as defined above] can be produced by deprotection (if necessary) and oxidation of the compound represented by the general formula (20) (Step D-5).

When $R_8$ is a lower alkyl group having 1 to 4 carbon atoms, the compound of the general formula (20) is preferably reacted with boron trichloride or boron tribromide in methylene chloride at 0° C. to room temperature for deprotection. When $R_8$ is a tetrahydropyranyl group, the compound of the general formula (20) is preferably reacted with hydrochloric acid in an alcohol solvent such as methanol or ethanol or in THF at room temperature, though other deprotection processes are also possible. When $R_8$ is an acetyl group, a common deacetylation process can be used: For example, the compound of the general formula (20) may be reacted with a base, such as sodium carbonate, potassium carbonate, sodium hydroxide, potassium hydroxide or lithium hydroxide, in methanol or ethanol at room temperature. When $R_8$ is a silyl protective group, the compound of the general formula (20) may be reacted with tetrabutylammonium fluoride in THF. The oxidation can be carried out by any oxidation process commonly used to oxidize alcohols to aldehydes or ketones. For example, the oxidation process may be a DMSO oxidation process that uses a chromium oxide-pyridine complex, such as pyridinium chlorochromate or pyridinium dichromate, a metal oxidizing agent, such as chromium oxide, silver carbonate or manganese dioxide, or a DMSO activating agent, such as oxalyl chloride, trifluoroacetic anhydride, acetic anhydride, DCC or sulfur trioxide/pyridine complexes.

In Synthetic Pathway D, the compound represented by the general formula (6) can be produced by hydrolysis and subsequent decarboxylation or decarbonylation of the compound represented by the general formula (22) (Step D-6).

The hydrolysis and decarboxylation may be carried out at once by reacting the compound of the general formula (22) with hydrobromic acid or acetic acid containing hydrogen bromide under reflux. Alternatively, the compound of the general formula (22) may be first hydrolyzed to a carboxylic acid, prior to decarboxylation, by reacting it with an aqueous solution of potassium hydroxide, lithium hydroxide, or preferably sodium hydroxide, at room temperature to reflux temperature in a solvent such as methanol, ethanol, THF, DMSO, DMF or dioxane. The decarboxylation can be carried out by heating the hydrolysate to 140 to 160° C. in an organic solvent such as benzene, chlorobenzene, dichlorobenzene, bromobenzene, toluene or xylene, by heating the product to 100° C. in ethanol or dioxane while adding 2 to 10% aqueous sulfuric acid, or by stirring the product at 100° C. in 50% sulfuric acid. The decarbonylation is preferably carried out by heating the product under reflux in hydrobromic acid, acetic acid containing hydrogen bromide or 50% sulfuric acid.

The intermediate compound represented the general formula (6) in Synthetic Pathways A, B and C may also be produced by Synthetic Pathway E, as described below.

<Synthetic Pathway E>

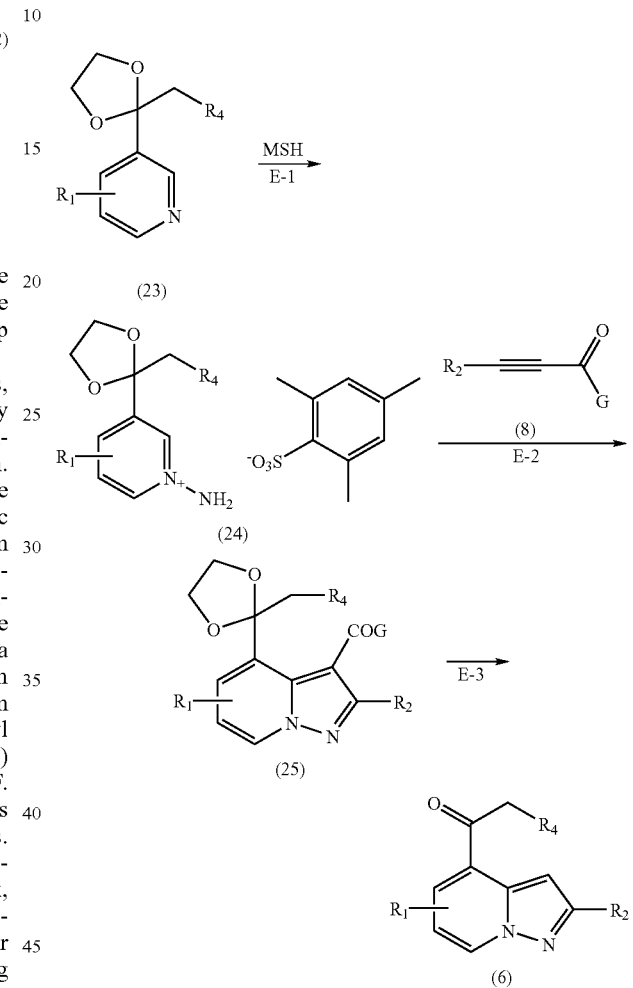

In Synthetic Pathway E, the compound of the following general formula (24):

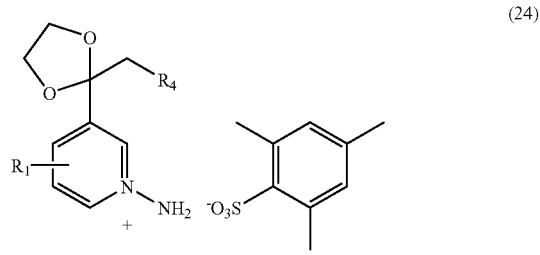

[wherein $R_1$ and $R_4$ are as defined above] can be produced by reacting the compound represented by the following general formula (23):

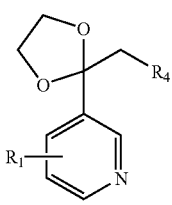

(23)

[wherein $R_1$ and $R_4$ are as defined above] with MSH (Step E-1).

The reaction is preferably carried out by adding a solution of the compound represented by the general formula (23) in methylene chloride to a solution of MSH in methylene chloride at 0° C. to room temperature.

In Synthetic Pathway E, the compound represented by the following general formula (25):

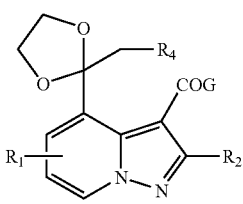

(25)

[wherein $R_1$, $R_2$, $R_4$ and G are as defined above] can be produced by reacting the compound represented by the general formula (24) with the compound represented by the general formula (8) in the presence of a base (Step E-2).

The reaction may be carried out at 0° C., or preferably at room temperature, in a reaction solvent such as methanol, ethanol, 1,4-dioxane, DMSO, DMF, THF, toluene, benzene, cyclohexane, cyclopentane, methylene chloride, chloroform or acetonitrile and in the presence of an inorganic base, such as sodium bicarbonate, sodium carbonate, potassium bicarbonate or potassium carbonate, or an organic base, such as triethylamine.

In Synthetic Pathway E, the compound represented by the general formula (6) can be produced by hydrolysis and subsequent decarboxylation or decarbonylation of the compound represented by the general formula (25) (Step E-3).

The hydrolysis and decarboxylation may be carried out at once by reacting the compound of the general formula (25) with hydrobromic acid or acetic acid containing hydrogen bromide under reflux. Alternatively, the compound of the general formula (25) may be hydrolyzed to a carboxylic acid, prior to decarboxylation, by reacting it with an aqueous solution of potassium hydroxide, lithium hydroxide, or preferably sodium hydroxide, at room temperature to reflux temperature in a solvent such as methanol, ethanol, THF, DMSO, DMF or dioxane. The decarboxylation can be carried out by heating the hydrolysate to 140 to 160° C. in an organic solvent such as benzene, chlorobenzene, dichlorobenzene, bromobenzene, toluene or xylene, by heating the product to 100° C. in ethanol or dioxane while adding 2 to 10% aqueous sulfuric acid, or by stirring the product at 100° C. in 50% sulfuric acid. The decarbonylation is preferably carried out by heating the product under reflux in hydrobromic acid, acetic acid containing hydrogen bromide or 50% sulfuric acid.

The intermediate compound represented by the general formula (21) in Synthetic Pathway D may be produced using as starting materials the two compounds represented by the general formulas (26) and (31), respectively, as shown in Synthetic Pathway F below.

<Synthetic Pathway F>

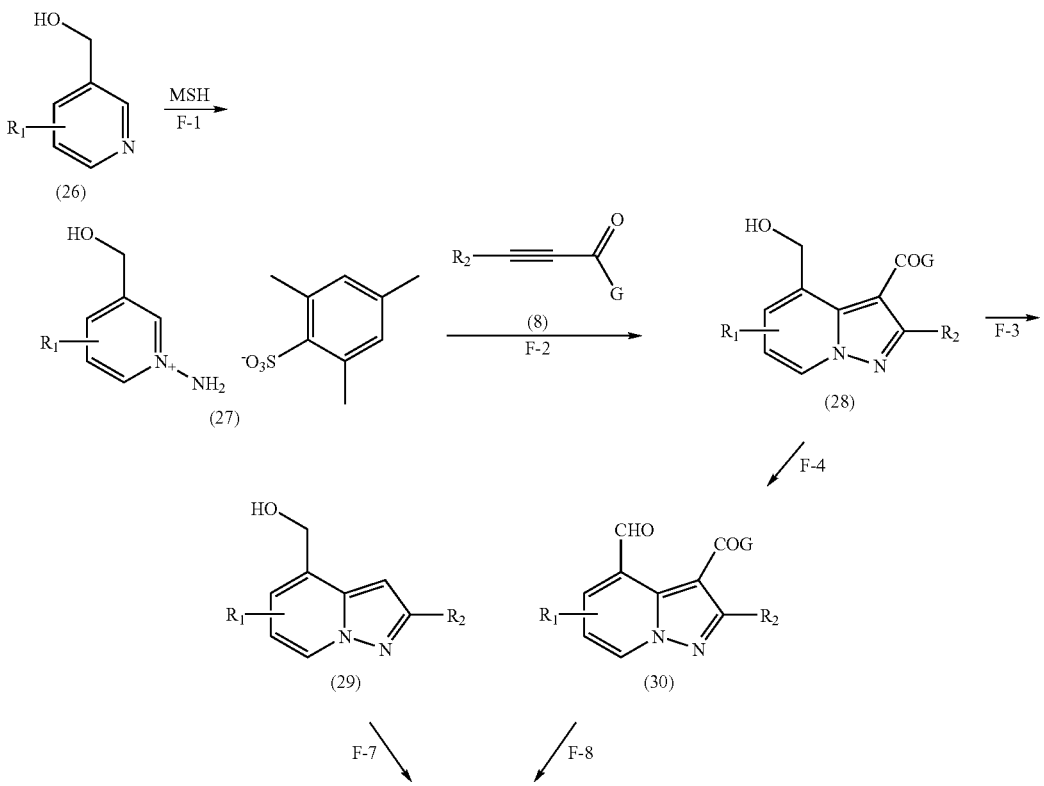

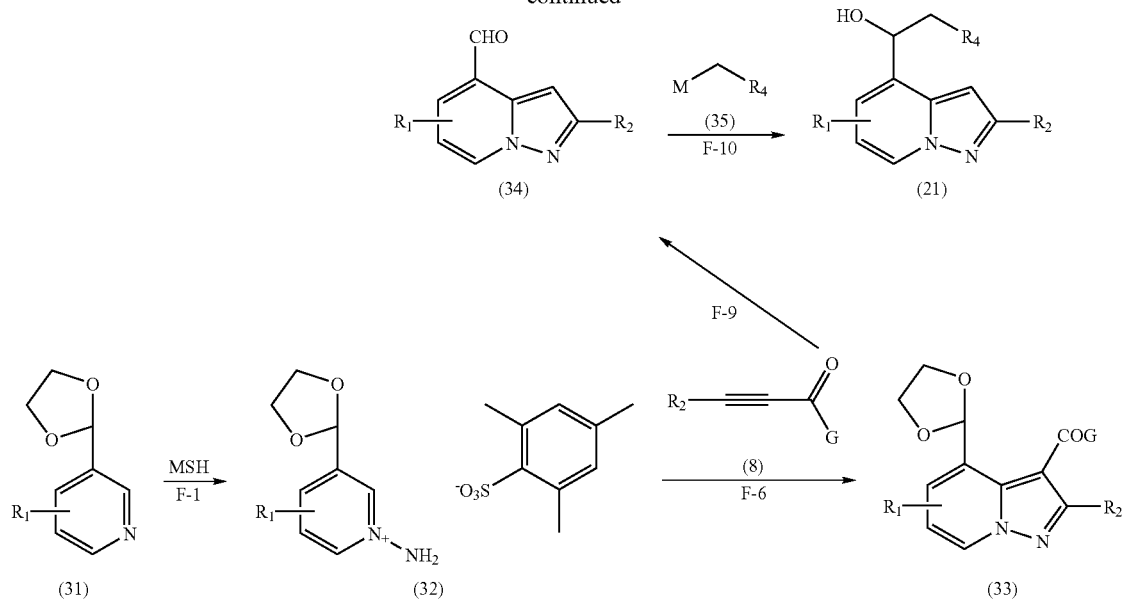

In Synthetic Pathway F, the compound represented by the following general formula (27):

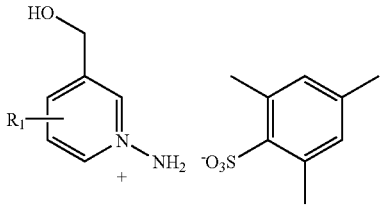

[wherein $R_1$ is as defined above] can be produced by reacting the compound represented by the following general formula (26):

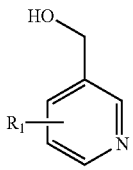

[wherein $R_1$ is as defined above] with MSH (Step F-1).

The reaction is preferably carried out by adding a solution of the compound represented by the general formula (26) in methylene chloride to a solution of MSH in methylene chloride at 0° C. to room temperature.

In Synthetic Pathway F, the compound represented by the following general formula (28):

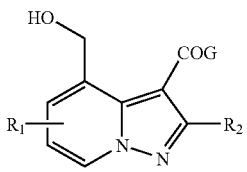

[wherein $R_1$, $R_2$ and G are as defined above] can be produced by reacting the compound of the general formula (27) with the compound represented by the general formula (8) in the presence of a base (Step F-2).

The reaction may be carried out at 0° C., or preferably at room temperature, in a reaction solvent such as methanol, ethanol, 1,4-dioxane, DMSO, DMF, THF, toluene, benzene, cyclohexane, cyclopentane, methylene chloride, chloroform or acetonitrile and in the presence of an inorganic base, such as sodium bicarbonate, sodium carbonate, potassium bicarbonate or potassium carbonate, or an organic base, such as triethylamine.

In Synthetic Pathway F, the compound represented by the following general formula (29):

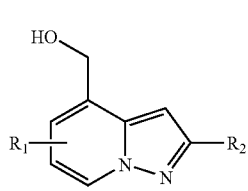

[wherein $R_1$ and $R_2$ are as defined above] can be produced by hydrolysis and subsequent decarboxylation or decarbonylation of the compound represented by the general formula (28) (Step F-3).

The hydrolysis and decarboxylation may be carried out at once by reacting the compound of the general formula (28) with hydrobromic acid or acetic acid containing hydrogen bromide under reflux. Alternatively, the compound of the general formula (28) may be hydrolyzed to a carboxylic acid, prior to decarboxylation, by reacting it with an aqueous solution of potassium hydroxide, lithium hydroxide, or preferably sodium hydroxide, at room temperature to reflux temperature in a solvent such as methanol, ethanol, THF, DMSO, DMF or dioxane. The decarboxylation can be carried out by heating the hydrolysate to 140 to 160° C. in an organic solvent such as benzene, chlorobenzene, dichlorobenzene, bromobenzene, toluene or xylene, by heating the product to 100° C. in ethanol or dioxane while adding 2 to 10% aqueous sulfuric acid, or by stirring the product at 100° C. in 50% sulfuric acid. The decarbonylation is preferably carried out by heating the product under reflux in hydrobromic acid, acetic acid containing hydrogen bromide or 50% sulfuric acid.

In Synthetic Pathway F, the compound represented by the following general formula (30):

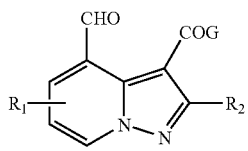

(30)

[wherein $R_1$, $R_2$ and G are as defined above] can be produced by oxidizing the compound represented by the general formula (29) (Step F-4)

The reaction can be carried out by any oxidation process commonly used to oxidize alcohols to aldehydes. For example, the oxidation process may be a DMSO oxidation process that uses a chromium oxide-pyridine complex, such as pyridinium chlorochromate or pyridinium dichromate, a metal oxidizing agent, such as chromium oxide, silver carbonate or manganese dioxide, or a DMSO activating agent, such as oxalyl chloride, trifluoroacetic anhydride, acetic anhydride, DCC or sulfur trioxide/pyridine complexes.

In Synthetic Pathway F, the compound represented by the following general formula (32):

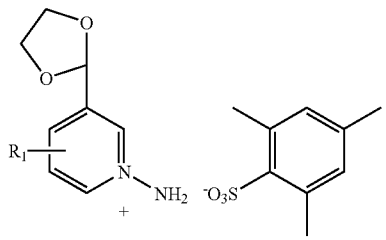

(32)

[wherein $R_1$ is as defined above] can be produced by reacting the compound represented by the following general formula (31):

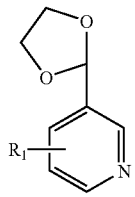

(31)

[wherein $R_1$ is as defined above] with MSH (Step F-5).

The reaction is preferably carried out by reacting a solution of the compound represented by the general formula (31) in methylene chloride with a solution of MSH in methylene chloride at 0° C. to room temperature.

In Synthetic Pathway F, the compound of the following general formula (33):

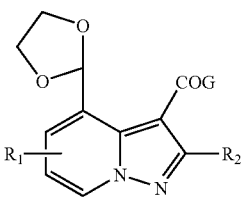

(33)

[wherein $R_1$, $R_2$ and G are as defined above] can be produced by reacting the compound represented by the general formula (32) with the compound represented by the general formula (8) in the presence of a base (Step F-6).

The reaction is carried out at 0° C., or preferably at room temperature, in the presence of an inorganic base, such as sodium bicarbonate, sodium carbonate, potassium bicarbonate or potassium carbonate, or an organic base, such as triethylamine, in a reaction solvent such as methanol, ethanol, 1,4-dioxane, DMSO, DMF, THF, toluene, benzene, cyclohexane, cyclopentane, methylene chloride, chloroform or acetonitrile.

In Synthetic Pathway F, the compound of the following general formula (34):

(34)

[wherein $R_1$ and $R_2$ are as defined above] can be produced from the compound represented by the general formula (29), (30) or (33).

The compound represented by the general formula (29) is oxidized to make the compound represented by the general formula (34) (Step F-7).

The reaction can be carried out by any oxidation process commonly used to oxidize alcohols to aldehydes. For example, the oxidation process may be a DMSO oxidation method that uses a chromium oxide-pyridine complex, such as pyridinium chlorochromate or pyridinium dichromate, a metal oxidizing agent, such as chromium oxide, silver carbonate or manganese dioxide, or a DMSO activating agent, such as oxalyl chloride, trifluoroacetic anhydride, acetic anhydride, DCC or sulfur trioxide/pyridine complexes.

The compound represented by the general formula (30) is first hydrolyzed and subsequently decarboxylated or decarbonylated to make the compound represented by the general formula (34) (Step F-8).

The hydrolysis and decarboxylation may be carried out at once by reacting the compound of the general formula (30) with hydrobromic acid or acetic acid containing hydrogen bromide under reflux. Alternatively, the compound of the general formula (30) may be first hydrolyzed to a carboxylic acid, prior to decarboxylation, by reacting it with an aqueous solution of potassium hydroxide, lithium hydroxide, or preferably sodium hydroxide, at room temperature to reflux temperature in a solvent such as methanol, ethanol, THF, DMSO, DMF or dioxane. The decarboxylation can be carried out by heating the hydrolysate to 140 to 160° C. in an organic solvent such as benzene, chlorobenzene, dichlorobenzene, bromobenzene, toluene or xylene, by heating the product to 100° C. in ethanol or dioxane while adding 2 to 10% aqueous sulfuric acid, or by stirring the product at 100° C. in 50% sulfuric acid. The decarbonylation is preferably carried out by heating the product under reflux in hydrobromic acid, acetic acid containing hydrogen bromide or 50% sulfuric acid.

Similarly, the compound represented by the general formula (33) is first hydrolyzed and subsequently decarboxylated or decarbonylated to make the compound represented by the general formula (34) (Step F-9).

In Synthetic Pathway F, the compound represented by the general formula (21) can be produced by reacting the compound represented by the general formula (34) with the compound represented by the following general formula (35):

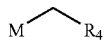
(35)

[wherein M is Li, ClMg, BrMg or IMg, and $R_4$ is as defined above].

The reaction is carried out at −78° C. to room temperature in a reaction solvent such as THF, ether or 1,4-dioxane.

Of the compounds represented by the general formula (6), those in which $R_4$ is a lower alkyl group having 1 to 4 carbon atoms, as shown by the following general formula (6a):

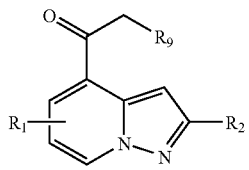
(6a)

[wherein $R_9$ is a lower alkyl group having 1 to 4 carbon atoms and $R_1$ and $R_2$ are as defined above] can be produced by reacting the compound represented by the general formula (6) in which $R_4$ is a hydrogen atom, as shown by the following general formula (6b):

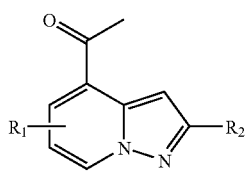
(6b)

[wherein $R_1$ and $R_2$ are as defined above] with the compound represented by the following general formula (36):

X—$R_9$ (36)

[wherein $R_9$ and X are as defined above] in the presence of a base.

The base used in the reaction may be sodium hydride, potassium hydride, sodium alkoxide, potassium alkoxide, LDA, lithium-2,2,6,6-tetramethylpiperidide, lithium bistrimethylsilylamide, sodium bistrimethylsilylamide or potassium bistrimethylsilylamide. The reaction is carried out at −78° C. to room temperature in a reaction solvent such as THF, 1,4-dioxane or 1,2-dimethoxyethane.

Of the compounds represented by the general formula (11) in Synthetic Pathway B, those in which $R_4$ is a lower alkyl group having 1 to 4 carbon atoms, as shown by the following general formula (11a)

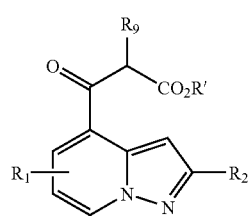
(11a)

[wherein $R_1$, $R_2$, $R_9$ and R' are as defined above] can be produced by reacting the compound represented by the general formula (11) in which $R_4$ is a hydrogen atom, as shown by the following general formula (11b):

(11b)

[wherein $R_1$, $R_2$ and R' are as defined above] with the compound represented by the general formula (36) in the presence of a base.

The base used in the reaction may be sodium hydride, potassium hydride, sodium alkoxide, potassium alkoxide, LDA, lithium-2,2,6,6-tetramethylpiperidide, lithium bistrimethylsilylamide, sodium bistrimethylsilylamide or potassium bistrimethylsilylamide. The reaction is carried out at −78° C. to room temperature in a reaction solvent such as THF, 1,4-dioxane and 1,2-dimethoxyethane.

Of the compounds represented by the general formula (12) in Synthetic Pathway B, those in which $R_4$ is a lower alkyl group having 1 to 4 carbon atoms, as shown by the following general formula (12a)

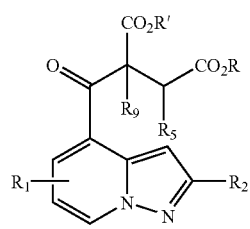
(12a)

[wherein $R_1$, $R_2$, $R_5$, $R_9$, R and R' are as defined above] can be produced by reacting the compound represented by the general formula (12) in which $R_4$ is a hydrogen atom, as shown by the following general formula (12b):

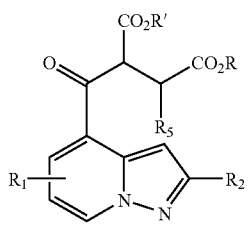

(12b)

[wherein $R_1$, $R_2$, $R_5$, R and R' are as defined above] with the compound represented by the general formula (36) in the presence of a base.

The base used in the reaction may be sodium hydride, potassium hydride, sodium alkoxide, potassium alkoxide, LDA, lithium-2,2,6,6-tetramethylpiperidide, lithium bistrimethylsilylamide, sodium bistrimethylsilylamide or potassium bistrimethylsilylamide. The reaction is carried out at −78° C. to room temperature in a reaction solvent such as THF, 1,4-dioxane and 1,2-dimethoxyethane.

Of the compounds represented by the general formulas (6) and (34), those in which $R_1$ is a halogen atom at position 7 of the pyrazolopyridine ring, as shown by the following general formula (37):

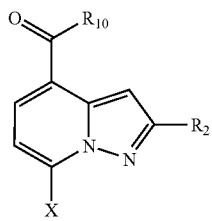

(37)

[wherein $R_{10}$ is a hydrogen atom or a lower alkyl group having 1 to 5 carbon atoms, and $R_2$ and X are as defined above] may also be synthesized by Synthetic Pathway G as shown below.

<Synthetic Pathway G>

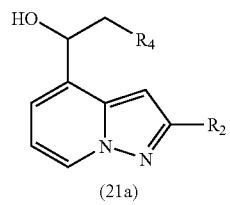

(21a)

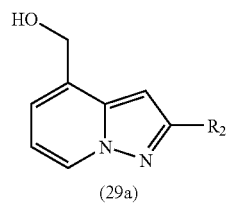

G-1

(29a)

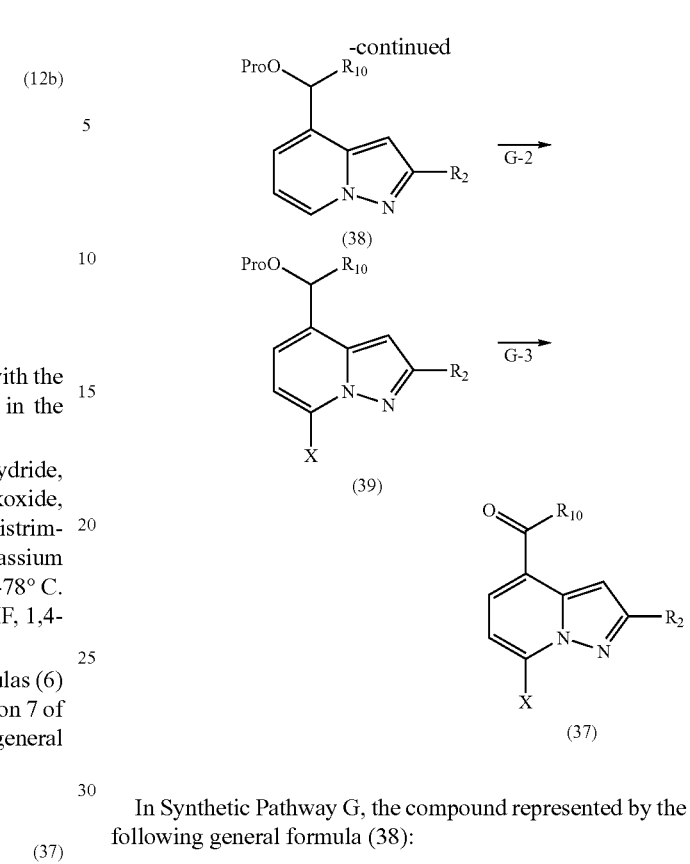

In Synthetic Pathway G, the compound represented by the following general formula (38):

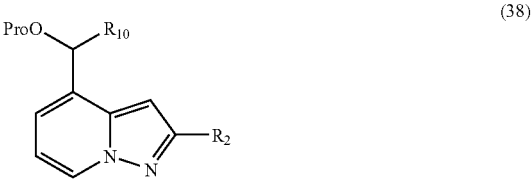

(38)

[wherein Pro is an alcohol protective group, such as methoxymethyl group, t-butyldimethylsilyl group, t-butyldiphenylsilyl group, triisopropylsilyl group, tetrahydropyranyl group or acetyl group, and $R_2$ and $R_{10}$ are as defined above] can be produced by introducing different alcohol protective groups into the compound represented by the general formula (21) in which $R_1$ is a hydrogen atom, as shown by the following general formula (21a):

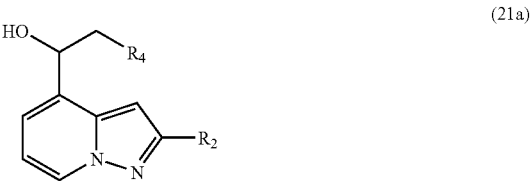

(21a)

[wherein $R_2$ and $R_4$ are as defined above], or into the compound represented by the general formula (29) in which $R_1$ is a hydrogen atom, as shown by the following general formula (29a):

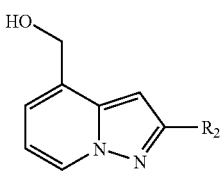

(29a)

[wherein R$_2$ is as defined above] (Step G-1)

Methoxymethyl group can be introduced by reacting the compound of the general formula (21a) or (29a) with methoxymethyl chloride or methoxymethyl bromide in the presence of sodium hydride, triethylamine or ethyldiisopropylamine. The reaction is carried out at 0° C. to room temperature in THF, acetonitrile, or preferably methylene chloride. T-butyldimethylsilyl group, t-butyldiphenylsilyl group and triisopropylsilyl group can be introduced by reacting the compound of the general formula (21a) or (29a) with silyl chloride, silyl bromide and silyl trifluoromethanesulfonate, respectively, in the presence of triethylamine or imidazole. The reaction is carried out at 0° C. to room temperature in a solvent such as THF, DMF, acetonitrile or methylene chloride. Tetrahydropyranyl group can be introduced by reacting the compound of the general formula (21a) or (29a) with dihydropyrane in the presence of p-toluenesulfonic acid or other acid catalysts in methylenechloride. Acetyl group can be introduced by reacting the compound of the general formula (21a) or (29a) with acetylchloride, acetylbromide or acetic anhydride in the presence of an organic base such as triethylamine, ethyldiisopropylamine or pyridine. The reaction is carried out at 0° C. to room temperature either in a solvent such as THF, 1,4-dioxane or methylene chloride, or in pyridine, which serves also as a solvent.

In Synthetic Pathway G, the compound represented by the following general formula (39):

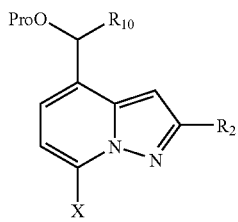

(39)

[wherein R$_2$, R$_{10}$, X and Pro are as defined above] can be produced by halogenation of the compound represented by the general formula (38) (Step G-2).

Specifically, the compound of the general formula (38) is reacted with a base such as butyl lithium, lithium bistrimethylsilylamide or preferably, LDA, in THF at −78° C. to 0° C. and is subsequently reacted with NCS, NBS, NIS, bromine, iodine, 1,2-dibromoethane or 1,2-diiodoethane.

In Synthetic Pathway G, the compound represented by the general formula (37) can be produced by deprotection and oxidation of the compound represented by the general formula (39) (Step G-3).

The methoxymethyl or tetrahydropyranyl protective group can be removed by reacting the compound of the general formula (39) with methanol, ethanol, ethyl acetate or diethyl ether, containing hydrogen chloride, at 0° C. to room temperature. The silyl protective group can be removed by reacting the compound of the general formula (39) with potassium fluoride, cesium fluoride or tetrabutylammonium fluoride in a solvent such as acetonitrile or THF at 0° C. to room temperature. The acetyl group can be removed by reacting the compound of the general formula (39) with an aqueous solution of sodium hydroxide, potassium hydroxide or lithium hydroxide in a solvent such as THF, methanol, ethanol or 1,4-dioxane at 0° C. to room temperature. The oxidation can be carried out by, for example, a DMSO oxidation process that uses a chromium oxide-pyridine complex, such as pyridinium chlorochromate and pyridinium dichromate, a metal oxidizing agent, such as chromium oxide, silver carbonate and manganese dioxide, or a DMSO activating agent, such as oxalyl chloride, trifluoroacetic anhydride, acetic anhydride, DCC and sulfur trioxide/pyridine complexes.

The compound represented by the general formula (37) may also be produced by Synthetic Pathway H as described below.

<Synthetic Pathway H>

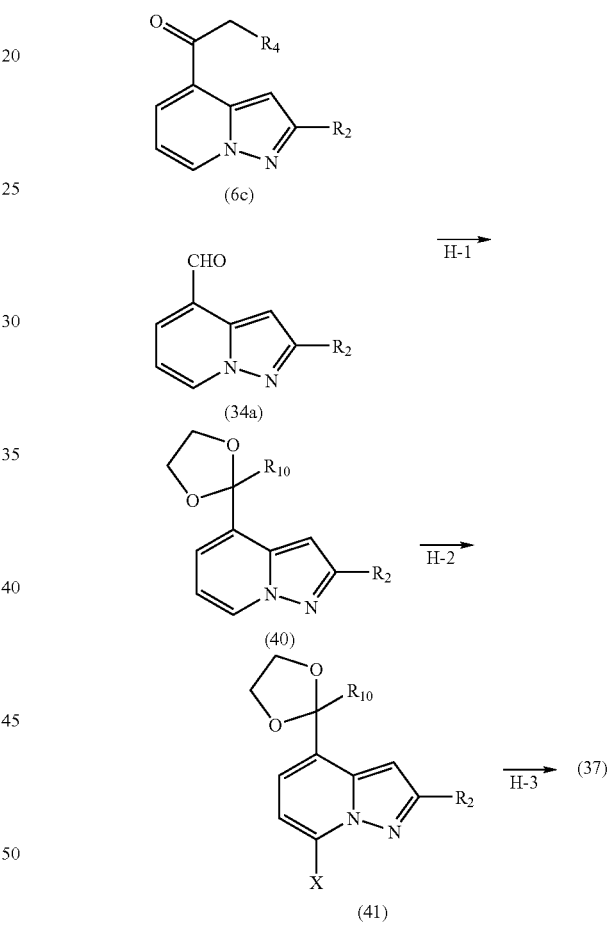

In Synthetic Pathway H, the compound represented by the following general formula (40):

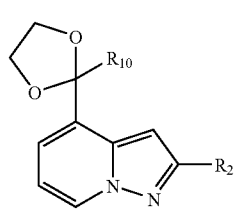

(40)

[wherein $R_2$ and $R_{10}$ are as defined above] can be produced by reacting the compound represented by the general formula (6) in which $R_1$ is a hydrogen atom, as shown by the following general formula (6c):

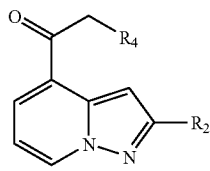

(6c)

[wherein $R_2$ and $R_4$ are as defined above] and the compound represented by the general formula (34) in which $R_1$ is a hydrogen atom, as shown by the following general formula (34a):

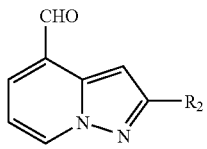

(34a)

[wherein $R_2$ is as defined above] with ethylene glycol (Step H-1)

The reaction uses a catalytic amount of p-toluenesulfonic acid or pyridinium p-toluenesulfonate and is preferably carried out under reflux in benzene, toluene or xylene.

In Synthetic Pathway H, the compound represented by the following general formula (41):

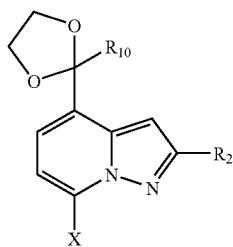

(41)

[wherein $R_2$, $R_{10}$ and X are as defined above] can be produced by halogenation of the compound represented by the general formula (40) (Step H-2).

Specifically, the compound of the general formula (40) is reacted with a base such as butyl lithium, or lithium bistrimethylsilylamide, or preferably, LDA, in THF at −78° C. to 0° C. and is subsequently reacted with NCS, NBS, NIS, bromine, iodine, 1,2-dibromoethane or 1,2-diiodoethane.

In Synthetic Pathway H, the compound represented by the general formula (37) can be produced by deprotection of the compound represented by the general formula (41) (Step H-3).

Specifically, the compound of the general formula (41) is reacted with p-toluenesulfonic acid in acetone at room temperature to reflux temperature or is reacted with methanol, ethanol, ethyl acetate or diethyl ether, containing hydrogen chloride, at 0° C. to room temperature.

Of the compounds represented by the general formulas (6) and (34), shown below by the general formula (42) are those in which $R_1$ is at position 7 of the pyrazolopyridine ring and is a substituted or unsubstituted lower alkoxy group having 1 to 4 carbon atoms, a cyclopropylmethyloxy group, a lower alkylthio group having 1 to 4 carbon atoms, a substituted or unsubstituted lower alkylamino group having 1 to 4 carbon atoms, a phenylamino group, an aromatic or saturated heterocyclic ring that may contain 1 or 2 heteroatoms, a substituted or unsubstituted phenyl group, a lower acylamino group having 1 to 4 carbon atoms or a cyano group:

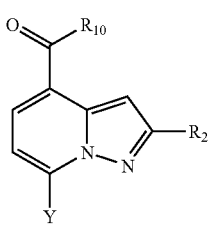

(42)

[where Y is a substituted or unsubstituted lower alkoxy group having 1 to 4 carbon atoms, a cyclopropylmethyloxy group, a lower alkylthio group having 1 to 4 carbon atoms, a substituted or unsubstituted lower alkylamino group having 1 to 4 carbon atoms, a phenylamino group, an aromatic or saturated heterocyclic ring that may contain 1 or 2 heteroatoms, a substituted or unsubstituted phenyl group, a lower acylamino group having 1 to 4 carbon atoms or a cyano group, and $R_2$ and $R_{10}$ are as defined above]. These compounds can be produced by derivatizing the compound represented by the general formula (37) into the corresponding compounds.

The derivatives with Y being a substituted or unsubstituted lower alkoxy group having 1 to 4 carbon atoms, a cyclopropylmethyloxy group or a lower alkylthio group having 1 to 4 carbon atoms can be formed by reacting the compound of the general formula (37) with a corresponding alcohol or thiol in the presence of sodium hydride or potassium hydride as a base. The reaction is preferably carried out at room temperature to 60° C. in a solvent such as THF or DMSO, or preferably, DMF.

The derivatives with Y being a substituted or unsubstituted lower alkylamino group having 1 to 4 carbon atoms, a phenylamino group or an aromatic or saturated heterocyclic ring that may contain 1 or 2 heteroatoms can be formed by reacting the compound of the general formula (37) with a corresponding amine in methanol or THF, or preferably DMF, at 60° C. to 70° C.

The derivatives with Y being a substituted or unsubstituted phenyl group can be formed by reacting the compound of the general formula (37) with a corresponding phenylboric acid derivative in the presence of a palladacycle catalyst, such as tetrakis triphenylphosphine palladium. The reaction involves a base such as sodium carbonate or cesium carbonate and is preferably carried out at 80° C. to reflux temperature in a solvent such as THF, benzene, toluene, xylene or 1,4-dioxane.

The derivatives with Y being a lower acylamino group having 1 to 4 carbon atoms can be formed by reacting the compound of the general formula (37) with a corresponding acylamine in the presence of cesium carbonate. The reaction uses a catalytic amount of dibenzylideneacetate palladium and tributylphosphine and is preferably carried out at 80° C. to 100° C. in 1,4-dioxane.

The derivatives with Y being a cyano group can be preferably formed by reacting the compound of the general formula (37) with sodium cyanide, potassium cyanide or copper cyanide in a solvent such as DMSO, 1,4-dioxane or DMF at 80° C. to 160° C.

Of the compounds represented by the general formula (1), those in which $R_3$ is a halogen atom, $R_6$ is a hydrogen atom and -- is a single bond are shown by the following general formula (1c):

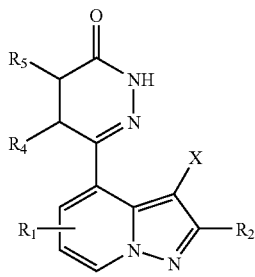
(1c)

[wherein $R_1$, $R_2$, $R_4$, $R_5$ and X are as defined above]. These compounds can be produced by first halogenating the compound represented by the general formula (6) to form a compound represented by the following general formula (6d):

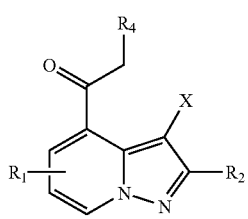
(6d)

[wherein $R_1$, $R_2$, $R_4$ and X are as defined above], and using the resulting compound in Synthetic Pathways A, B or C.

The compound represented by the general formula (6d) can be synthesized by halogenating the compound represented by the general formula (6) with NCS, NBS or NIS in DMF at room temperature. Alternatively, the compound represented by the general formula (6) may be fluorinated with a fluorinating agent such as Selectfluor in acetonitrile at room temperature.

Of the compounds represented by the general formula (1), those in which $R_3$ is a lower alkoxycarbonyl group having 1 to 4 carbon atoms, $R_6$ is a hydrogen atom and -- is a single bond are shown by the following general formula (1d):

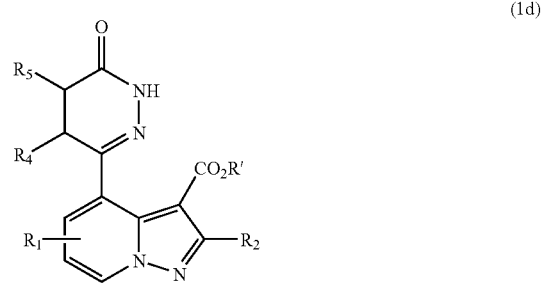
(1d)

[wherein $R_1$, $R_2$, $R_4$, $R_5$ and R' are as defined above]. These compounds can be produced by using in Synthetic Pathway A the compound represented by the general formula (22) (used in Synthetic Pathway D) in which G is a lower alkoxy group having 1 to 4 carbon atoms, as shown by the following general formula (22a):

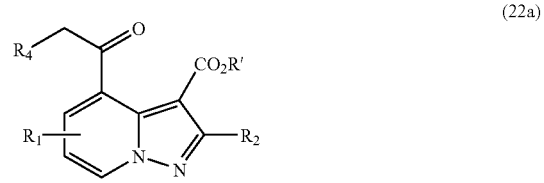
(22a)

[wherein $R_1$, $R_2$, $R_4$ and R' are as defined above]. The compound represented by the general formula (22) is directly used in Synthetic Pathway A without being subjected to hydrolysis or decarboxylation.

Of the compounds represented by the general formula (1), those in which $R_3$ and $R_6$ are each a hydrogen atom and -- is a double bond are shown by the following general formula (1e):

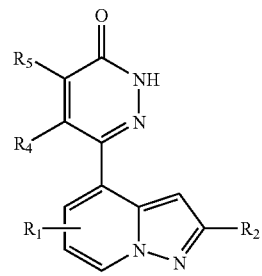
(1e)

[wherein $R_1$, $R_2$, $R_4$ and $R_5$ are as defined above]. These compounds can be produced by Synthetic Pathway J as described below.

<Synthetic Pathway J>

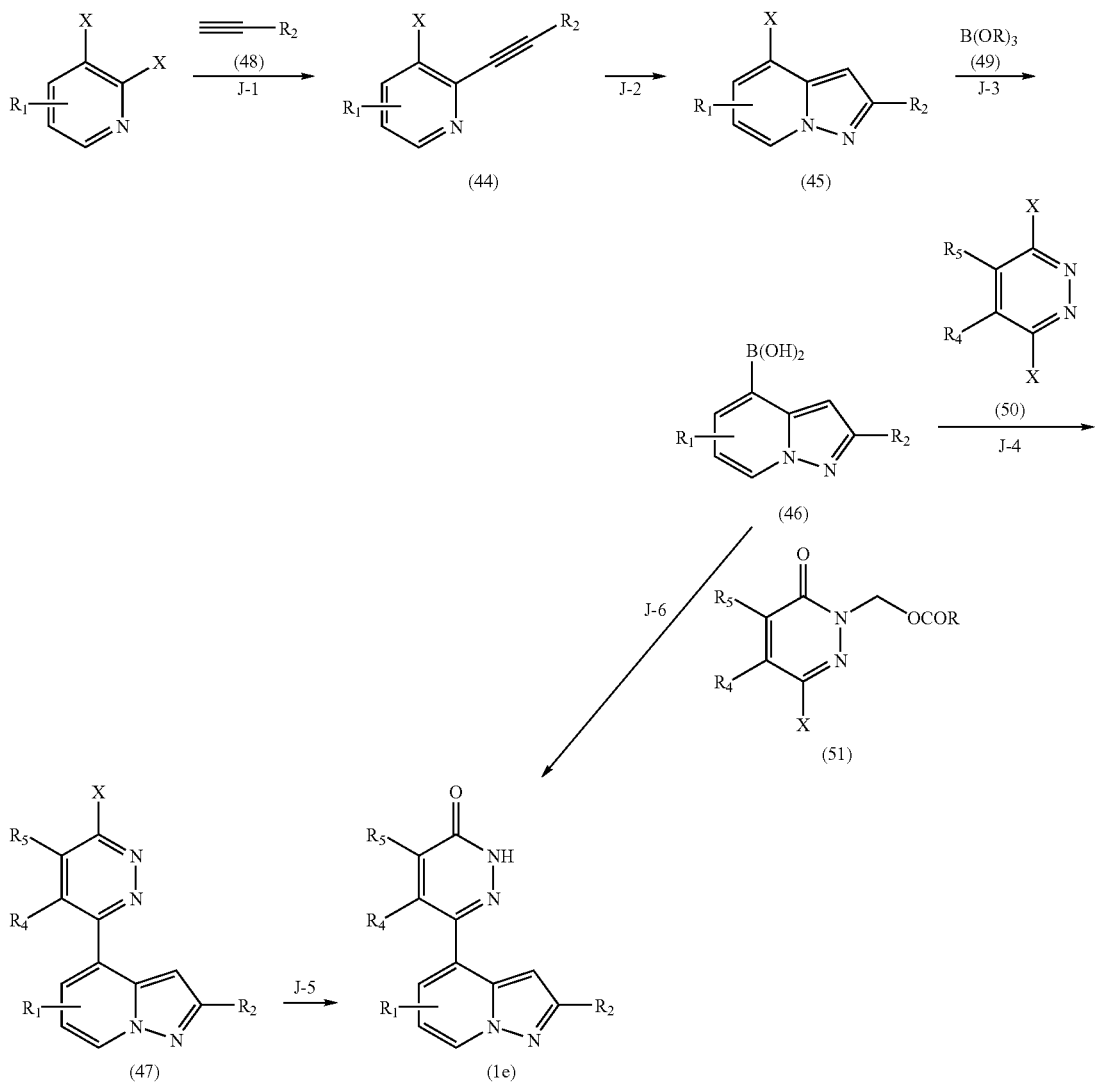

In Synthetic Pathway J, the compound represented by the following general formula (44):

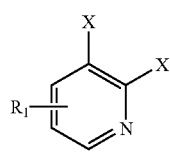

(44)

[wherein $R_1$, $R_2$ and X are as defined above] can be produced by reacting the compound represented by the following general formula (43):

(43)

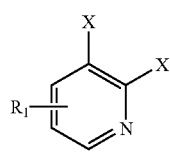

[wherein $R_1$ and X are as defined above] with the compound represented by the following general formula (48):

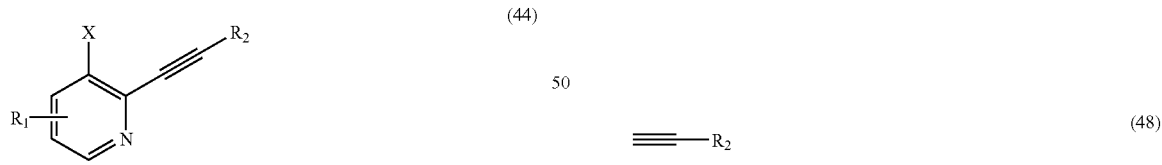

(48)

[wherein $R_2$ is as defined above] in the presence of a palladium catalyst (Step J-1).

The reaction uses an organic base such as triethylamine, diethylamine or dibutylamine and is carried out at room temperature to 80° C. in an organic solvent such as acetonitrile, THF, DMF or benzene in the presence of a palladium catalyst, such as tetrakis triphenylphosphine palladium or bistriphenylphosphine palladium dichloride, and copper bromide or copper iodide (Sonogashira process).

In Synthetic Pathway J, the compound represented by the following general formula (45):

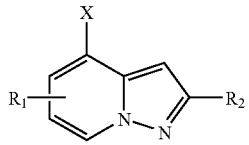
(45)

[wherein $R_1$, $R_2$ and X are as defined above] can be produced by reacting the compound represented by the general formula (44) with MSH (Step J-2).

Specifically, the compound represented by the general formula (44) is dissolved in an organic solvent such as THF, DMF, cyclohexane, benzene, toluene or methylene chloride. This solution is reacted with a solution of MSH in methylene chloride at 0° C. to room temperature. This is followed by addition of an inorganic base, such as sodium carbonate or potassium carbonate, or MSH. Palladium chloride in acetonitrile is then added and the reaction mixture is refluxed to obtain the desired compound.

In Synthetic Pathway J, the compound represented by the following general formula (46):

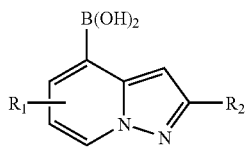
(46)

[wherein $R_1$ and $R_2$ are as defined above] can be produced by adding a metal to the compound represented by the general formula (45) and reacting the resulting product with the compound represented by the following general formula (49):

B(OR)$_3$ (49)

[wherein R is as described above] (Step J-3).

Specifically, the compound represented by the general formula (45) is reacted with LDA, n-butyllithium, s-butyllithium or t-butyllithium in THF at −78° C., or it may be refluxed with magnesium. The resulting product is reacted with the compound represented by the general formula (49) at −78° C. to room temperature.

In Synthetic Pathway J, the compound represented by the general formula (47):

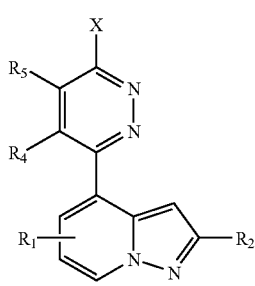
(47)

[wherein $R_1$, $R_2$, $R_4$, $R_5$ and X are as defined above] can be produced by reacting the compound represented by the general formula (46) with the compound represented by the following general formula (50):

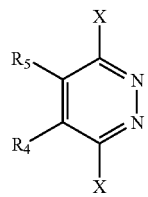
(50)

[wherein $R_4$, $R_5$ and X are as defined above] (Step J-4)

The reaction involves a base such as sodium carbonate or cesium carbonate and is preferably carried out at 80° C. to reflux temperature in a solvent such as THF, benzene, toluene, xylene or 1,4-dioxane in the presence of a palladacycle catalyst, such as tetrakis triphenylphosphine palladium.

In Synthetic Pathway J, the compound represented by the general formula (1e) can be produced by hydrolysis of the compound represented by the general formula (47) (Step J-5).

The reaction is preferably carried out at 80 to 90° C. in acetic acid.

Alternatively, the compound represented by the general formula (1e) may be produced by reacting the compound represented by the general formula (46) with the compound represented by the following general formula (51):

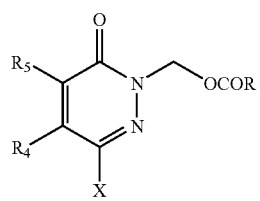
(51)

[wherein $R_4$, $R_5$, R and X are as defined above] in a similar manner to Step J-4 and subsequently hydrolyzing the product (Step J-6).

The reaction is carried out by first reacting the reactants at 80° C. to reflux temperature in a solvent such as THF, benzene, toluene, xylene or 1,4-dioxane in the presence of a palladacycle catalyst, such as tetrakis triphenylphosphine palladium, and a base, such as sodium carbonate or cesium carbonate, followed by addition of aqueous ammonia in a solvent such as methanol, ethanol or THF.

Of the compounds represented by the general formula (1), those in which $R_3$ is a hydrogen atom and -- is a double bond, as shown by the following general formula (1f):

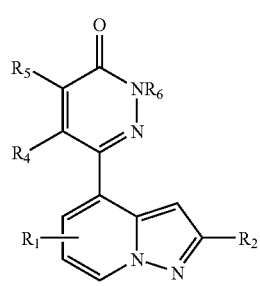
(1f)

[wherein $R_1$, $R_2$, $R_4$, $R_5$ and $R_6$ are as defined above] can be produced by reacting the compound represented by the general formula (46), an intermediate in Synthetic Pathway J, with the compound represented by the following general formula (53):

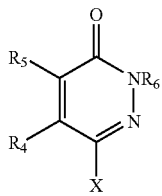

(52)

[wherein $R_4$, $R_5$, $R_6$ and X are as defined above].

The reaction involves a base such as sodium carbonate or cesium carbonate and is preferably carried out at 80° C. to reflux temperature in a solvent such as THF, benzene, toluene, xylene or 1,4-dioxane in the presence of a palladacycle catalyst, such as tetrakis triphenylphosphine palladium.

Of the compounds represented by the general formula (1), those in which $R_3$ is a lower alkoxycarbonyl group having 1 to 4 carbon atoms and -- is a double bond, as shown by the following general formula (1g):

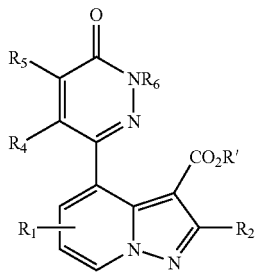

(1g)

[wherein $R_1$, $R_2$, $R_4$, $R_5$, $R_6$ and R' areas defined above] can be produced by Synthetic Pathway K as described below.

<Synthetic Pathway K>

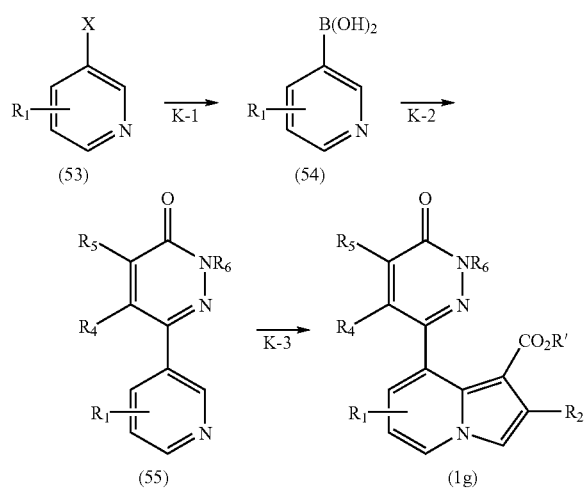

In Synthetic Pathway K, the compound represented by the following general formula (54):

(54)

[wherein $R_1$ is as defined above] can be prepared by adding a metal to the compound represented by the following general formula (53):

(53)

[wherein $R_1$ and X are as defined above] and subsequently reacting the product with the compound represented by the general formula (49) (Step K-1).

Specifically, the compound represented by the general formula (53) is reacted with LDA, n-butyllithium, s-butyllithium or t-butyllithium in THF at −78° C., or it may be refluxed with magnesium. The resulting product is reacted with the compound represented by the general formula (49) at −78° C. to room temperature.

In Synthetic Pathway K, the compound represented by the following general formula (55):

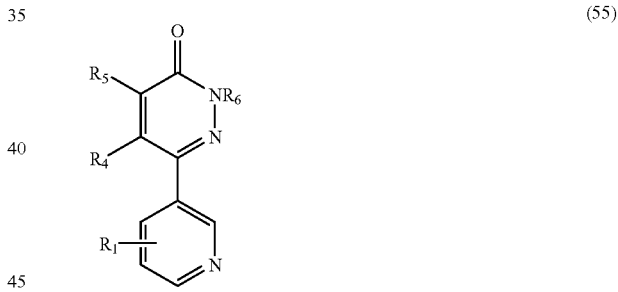

(55)

[wherein $R_1$, $R_4$, $R_5$ and $R_6$ are as defined above] can be produced by reacting the compound represented by the general formula (54) with the compound represented by the general formula (52) (Step K-2).

The reaction involves a base such as sodium carbonate or cesium carbonate and is preferably carried out at 80° C. to reflux temperature in a solvent such as THF, benzene, toluene, xylene or 1,4-dioxane in the presence of a palladacycle catalyst, such as tetrakis triphenylphosphine palladium.

In Synthetic Pathway K, the compound represented by the general formula (1g) can be produced by treating the compound represented by the general formula (55) with MSH and reacting the resulting product with the compound represented by the general formula (8) in which G is a lower alkoxy group having 1 to 4 carbon atoms, as shown by the following general formula (8a):

(8a)

[wherein $R_2$ and R' are as defined above] in the presence of a base (Step K-3). Specifically, the compound represented by the general formula (55) is dissolved in an organic solvent such as THF, DMF, cyclohexane, benzene, toluene or methylene chloride. This solution is reacted with a solution of MSH in methylene chloride at 0° C. to room temperature. Subsequently, the compound of the general formula (8a) is added, along with an inorganic base such as sodium carbonate or potassium carbonate, and the reaction is allowed to proceed at 0° C. to room temperature.

Of the compounds represented by the general formula (1), shown below by the general formula (1h) are compounds in which $R_3$ is a hydrogen atom, a halogen atom or a lower alkoxycarbonyl group having 1 to 4 carbon atoms, $R_6$ is $R_7$—$(CH_2)_m$— (wherein $R_7$ is a cycloalkyl group having 3 to 8 carbon atoms, a hydroxyl group or an aromatic or saturated heterocyclic ring that may contain 1 or 2 heteroatoms, and m is an integer of 1 or 2), and -- is a single bond:

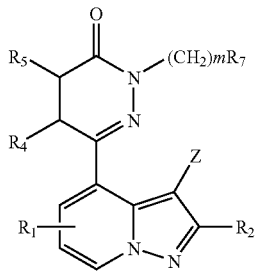

(1h)

[wherein Z is a hydrogen atom, a halogen atom or a lower alkoxycarbonyl group having 1 to 4 carbon atoms, and $R_1$, $R_2$, $R_4$, $R_5$, $R_7$ and m are as defined above]. These compounds can be produced by reacting the compounds represented by the general formulas (1b), (1c) and (1d) with the compound represented by the following general formula (56):

X(CH$_2$)$_m$R$_7$  (56)

[wherein $R_7$, X and m are as defined above] in the presence of a base.

The base used in the reaction may be sodium hydride, potassium hydride, sodium alkoxide or potassium alkoxide. The reaction is carried out at 0 to 60° C. in a reaction solvent such as THF or DMF.

Of the compounds represented by the general formula (1), those in which $R_3$ is a hydrogen atom, a halogen atom or a lower alkoxycarbonyl group having 1 to 4 carbon atoms, and -- is a double bond are shown by the following general formula (1j):

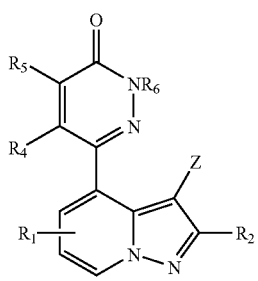

(1j)

[wherein $R_1$, $R_2$, $R_4$, $R_5$, $R_6$ and Z are as defined above]. These compounds can be produced by oxidizing the compounds represented by the general formulas (1b), (1c), (1d) and (1h).

Specifically, the compounds of the general formulas (1b), (1c), (1d) and (1h) may be reacted with bromine in acetic acid at 50 to 60° C., or they may be reacted with copper (II) chloride in acetonitrile at room temperature or under heating. Alternatively, the compounds of the general formulas (1b), (1c), (1d) and (1h) may be reacted with sodium m-nitrobenzenesulfonate in an aqueous sodium hydroxide solution at room temperature to reflux temperature.

Of the compounds represented by the general formula (1), those in which $R_3$ is a hydrogen atom, a halogen atom or a lower alkoxycarbonyl group having 1 to 4 carbon atoms and -- is a single bond are shown by the following general formula (1k):

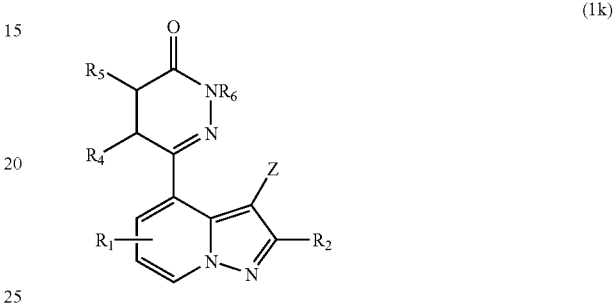

(1k)

[wherein $R_1$, $R_2$, $R_4$, $R_5$, $R_6$ and Z are as defined above]. These compounds can be produced by reduction of the compounds represented by the general formula (1j).

The reaction is preferably carried out in the presence of zinc in acetic acid at 80 to 90° C.

Of the compounds represented by the general formula (1), those in which $R_3$ is a halogen atom, as represented by the following general formula (1m):

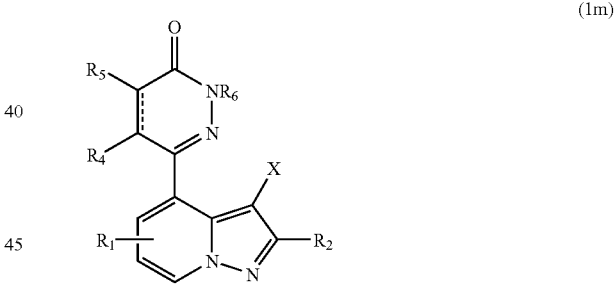

(1m)

[wherein $R_1$, $R_2$, $R_4$, $R_5$, $R_6$ and X are as defined above] may also be produced by halogenation of the compound represented by the general formula (1) in which $R_3$ is a hydrogen atom, as shown by the following general formula (1n):

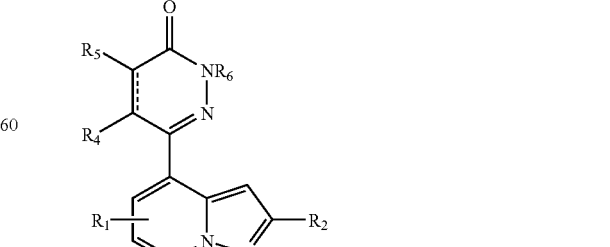

(1n)

[wherein $R_1$, $R_2$, $R_4$, $R_5$ and $R_6$ are as defined above].

Preferably, the compound of the general formula (In) is halogenated with NCS, NBS or NIS in DMF at room temperature. Alternatively, it may be fluorinated with a fluorinating agent such as Selectfluor in acetonitrile at room temperature.

Of the compounds represented by the general formula (1), those in which $R_3$ is a hydroxyl group, as shown by the following general formula (1o):

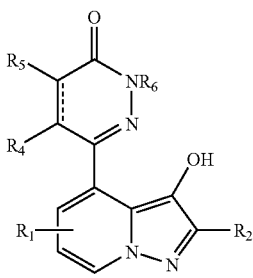

(1o)

[wherein $R_1$, $R_2$, $R_4$, $R_5$ and $R_6$ are as defined above] can be produced by hydroxylation of the compound represented by the general formula (In).

Specifically, the compound of the general formula (In) is reacted with peroxiacetic acid, or preferably m-chloroperoxybenzoic acid, in a solvent such as chloroform or carbon tetrachloride, or preferably in methylene chloride at 0° C. to room temperature.

Of the compounds represented by the general formula (1), those in which $R_3$ is a carboxyl group, as shown by the following general formula (1p):

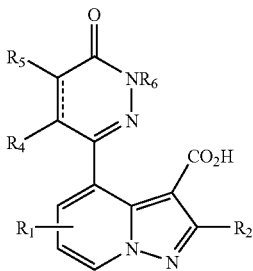

(1p)

[wherein $R_1$, $R_2$, $R_4$, $R_5$ and $R_6$ are as defined above] can be produced by hydrolysis of the compounds represented by the general formulas (1d) and (1g) and the compound represented by the general formula (1h) in which Z is a lower alkyl group having 1 to 4 carbon atoms.

The reaction uses an aqueous solution of sodium hydroxide, potassium hydroxide or lithium hydroxide and is carried out at room temperature to reflux temperature in a solvent such as methanol, ethanol, THF, DMSO, DMF or 1,4-dioxane.

Of the compounds represented by the general formula (1), those in which $R_1$ is a substituted or unsubstituted lower alkoxy group having 1 to 4 carbon atoms at position 7 of the pyrazolopyridine ring are shown by the following general formula (1q):

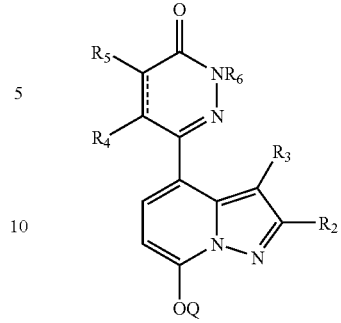

(1q)

[wherein Q is a substituted or unsubstituted lower alkyl group having 1 to 4 carbon atoms, and $R_2$, $R_3$, $R_4$, $R_5$ and $R_6$ are as defined above]. These compounds can be produced by reacting the compound represented by the following general formula (1r):

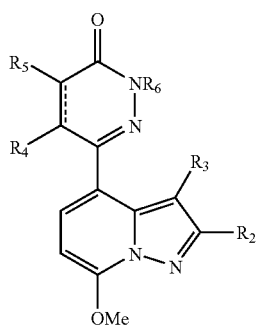

(1r)

[wherein $R_2$, $R_3$, $R_4$, $R_5$ and $R_6$ are as defined above] with the compound represented by the following general formula (57):

HOQ  (57)

[wherein Q is as defined above] in the presence of a base.

The reaction may use a catalytic amount of the compound represented by the general formula (57) or may be carried out at room temperature to 80° C. in the presence of sodium metal, potassium hydride or sodium hydride in THF or DMF.

EXAMPLES

The present invention will now be described in detail with reference to examples, which are not intended to limit the scope of the invention in any way.

Example 1

N-amino-3-chloropyridinium mesitylenesulfonate

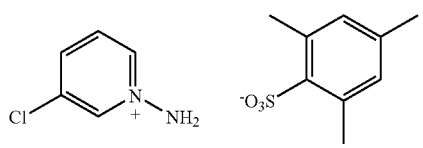

Triethylamine (70 mL) and then mesitylenesulfonyl chloride (100 g) were slowly added to a solution of ethyl N-hydroxyacetimidate (47.2 g) in DMF (200 mL) under stirring at 0° C. The mixture was stirred at the same temperature for 1.5 hours. Subsequently, ice water was added and the mixture was extracted with a mixture of ethyl acetate/hexane (1:1). The extract was washed sequentially with water and saturated brine, dried over anhydrous sodium sulfate, and concentrated to give a colorless solid. The solid product was dissolved in dioxane (100 mL). While the solution was stirred at 0° C., 70% HClO$_4$ (40 mL) was gently added dropwise. The resulting mixture was stirred for 30 min at the same temperature. Subsequently, ice water was added and the resulting crystals were collected by filtration (Caution: The solid will explode if completely dried). The collected product was washed with water and dissolved, while still wet, in approximately 300 mL of methylenechloride. The organic layer was separated and dried over magnesium sulfate. The dried methylene chloride solution was added dropwise to a solution of 3-chloropyridine (43.0 g) in methylene chloride (40 mL) under stirring at 0° C. The resulting mixture was stirred at room temperature for 30 min. Approximately 350 mL of ether was then added and the resulting crystals were collected by filtration. The product was washed with ether and dried to afford the title compound as a colorless powder (69.0 g).

Elemental analysis (%): Calcd. for $C_{14}H_{17}ClN_2O_3S$, C, 51.14; H, 5.21; N, 8.52; Found: C 51.20, H 5.10, H 8.47.

Examples 2 through 15

Using different pyridine derivatives, the reactions were carried out as in Example 1 to afford compounds shown in Table 1 below.

TABLE 1

| Examples | R | R' | R'' | Nature |
|---|---|---|---|---|
| 2 | F | H | H | Colorless powder |
| 3 | F | F | H | Colorless powder |
| 4 | Cl | Cl | H | Colorless powder |
| 5 | MeO | H | H | Colorless oil |
| 6 | MeO | Cl | H | Colorless powder |
| 7 | CH$_2$OH | H | H | Brown oil |
| 8 | CH(OH)Me | H | H | Colorless oil |
| 9 | (1,3-dioxolan-2-yl, 2-Me) | H | H | Colorless oil |
| 10 | H | CH$_2$OH | MeO | Colorless powder |
| 11 | H | CH(OH)Et | MeO | Yellow oil |
| 12 | H | Br | MeO | Colorless powder |
| 13 | CH(OH)Et | H | H | Colorless oil |
| 14 | CH$_2$OTHP | H | H | Colorless powder |
| 15 | H | CH$_2$OTBDMS | MeO | Pale yellow oil |

THP: tetrahydropyran
TBDMS: tBuMe$_2$Si

Example 2

$^1$H-NMR (400 MHz, DMSO-d$_6$) δ 2.17 (3H, s), 2.49 (6H, s), 6.74 (2H, s), 8.05-8.11 (1H, m), 8.28-8.32 (1H, m), 8.68 (1H, t, J=6.4 Hz), 8.71 (2H, br s), 9.06-9.08 (1H, m).

Example 3

$^1$H-NMR (400 MHz, DMSO-d$_6$) δ 2.16 (3H, s), 2.48 (3H, s), 2.49 (6H, s), 6.73 (2H, br s), 8.59-8.65 (1H, m), 8.91 (2H, br s), 9.00-9.01 (2H, m).

Example 4

$^1$H-NMR (400 MHz, DMSO-d$_6$) δ 2.16 (3H, s), 2.48 (3H, s), 2.49 (6H, s), 6.73 (2H, br s), 8.71 (2H, br s), 8.78-8.79 (1H, m), 9.01-9.02 (1H, m)

Example 5

$^1$H-NMR (400 MHz, DMSO-d$_6$) δ 2.17 (3H, s), 2.49 (6H, s), 3.98 (3H, s), 6.74 (2H, s), 8.20-8.21 (1H, m), 8.58 (2H, br s), 8.59-8.60 (1H, m), 8.67-8.68 (1H, m).

Example 6

$^1$H-NMR (400 MHz, DMSO-d$_6$) δ 2.17 (3H, s), 2.49 (6H, s), 3.98 (3H, s), 6.74 (2H, s), 8.19 (1H, s), 8.60 (2H, br s), 8.67 (1H, s).

Example 7

$^1$H-NMR (400 MHz, DMSO-d$_6$) δ 2.33 (3H, s), 2.50 (6H, s), 4.69 (2H, s), 5.86 (1H, br s), 6.74 (2H, s), 7.96 (1H, dd, J=8.0, 6.1 Hz), 8.15 (1H, d, J=8.0 Hz), 8.50 (2H, s), 8.66 (1H, d, J=6.1 Hz), 8.71 (1H, s).

Example 8

$^1$H-NMR (400 MHz, DMSO-d$_6$) δ 1.35 (3H, d, J=6.7 Hz), 2.14 (3H, s), 2.47 (6H, s), 4.84 (1H, q, J=6.7 Hz), 6.72 (2H, s), 7.63 (1H, dd, J=4.9, 7.9 Hz), 8.07-8.09 (1H, m), 8.58 (1H, dd, J=1.5, 4.9 Hz), 8.66 (1H, s).

Example 9

$^1$H-NMR (400 MHz, DMSO-d$_6$) δ 2.14 (3H, s), 2.47 (6H, s), 3.55 (3H, s), 3.72-3.78 (2H, m), 4.01-4.04 (2H, m), 6.72 (2H, s), 7.98 (1H, dd, J=6.7, 7.9 Hz), 8.22 (1H, d, J=7.9 Hz), 8.70-8.72 (1H, m), 8.77 (1H, s).

Example 10

$^1$H-NMR (400 MHz, DMSO-d$_6$) δ 2.15 (3H, s), 2.47 (6H, s), 4.23 (3H, s), 4.56 (2H, s), 6.72 (2H, s), 7.68-7.70 (3H, m), 8.14-8.17 (1H, s), 8.44 (1H, s).

Example 12

$^1$H-NMR (400 MHz, DMSO-d$_6$) δ 2.14 (3H, s), 2.49 (6H, s), 4.26 (3H, s), 6.74 (2H, s), 7.70 (1H, d, J=9.2 Hz), 7.79 (2H, brs), 8.50 (1H, dd, J=9.2, 1.8 Hz), 8.88 (1H, d, J=2.4 Hz).

Example 13

$^1$H-NMR (400 MHz, DMSO-d$_6$) δ 0.81 (3H, t, J=7.3 Hz), 1.54-1.66 (2H, m), 2.11 (3H, s), 2.44 (6H, s), 4.68 (1H, t, J=6.7 Hz), 6.68 (2H, s), 7.89-7.93 (1H, m), 8.14 (1H, d, J=7.9 Hz), 8.41 (2H, brs), 8.58-8.63 (1H, m), 8.68 (1H, s).

Example 14

$^1$H-NMR (400 MHz, DMSO-d$_6$) δ 1.44-1.69 (6H, m), 2.11 (3H, s), 2.44 (6H, s), 3.42-3.47 (1H, m), 3.68-3.73 (1H, m), 4.63 (1H, d, J=14.1 Hz), 4.71 (1H, t, J=3.3 Hz), 4.79 (1H, d, J=14.1 Hz), 7.93 (1H, dd, J=6.5, 7.9 Hz), 8.16 (1H, d, J=7.9 Hz), 8.47 (2H, brs), 8.64 (1H, d, J=6.5 Hz), 8.71 (1H, s).

Example 15

¹H-NMR (400 MHz, DMSO-d₆) δ 0.13 (6H, s), 0.92 (9H, s), 2.18 (3H, s), 2.50 (6H, s), 3.57 (3H, s), 4.25 (2H, d, J=1.2 Hz), 6.76 (2H, s), 7.69-7.73 (2H, m), 8.11-8.16 (1H, m), 8.43-8.48 (1H, m).

Example 16

3-acetyl-2-ethyl-4-methoxy-pyrazolo[1,5-a]pyridine

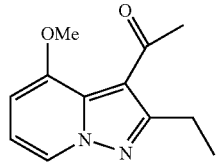

The compound of Example 5 (29.8 g) was dissolved in N,N-dimethylformamide (100 mL). To this solution, 3-hexyne-2-one (10 mL) and potassium carbonate (37.9 g) were added and the mixture was stirred at room temperature for 24 hours. Subsequently, ice water was added and the mixture was extracted with ethyl acetate, washed sequentially with water (×2) and saturated brine, and dried over anhydrous sodium sulfate. The solvent was evaporated and the residue was purified by silica gel column chromatography (hexane:ethyl acetate=10:1 to 5:1) to afford the title compound as a yellow powder (8.02 g).

¹H-NMR (400 MHz, CDCl₃) δ 1.32 (3H, t, J=7.6 Hz), 2.63 (3H, s), 2.98 (2H, q, J=7.6 Hz), 3.97 (3H, s), 6.61 (1H, d, J=7.3 Hz), 6.76 (1H, t, J=7.3 Hz), 8.11 (1H, d, J=7.3 Hz).

Examples 17 to 38

The compounds of Examples 1 through 14 were reacted with different alkyne derivatives to give compounds shown in Table 2.

TABLE 2

| Examples | R | R' | R'' | R2 | R3 | Yields(%) | Nature |
|---|---|---|---|---|---|---|---|
| 17 | F | F | H | Et | $CO_2Et$ | 10 | Colorless powder |
| 18 | H | $CH_2OH$ | OMe | $CH(OEt)_2$ | $CO_2Et$ | 58 | Yellow oil |
| 19 | H | $CH_2OH$ | OMe | $CH_2OMe$ | $CO_2CH_2Ph$ | 20 | Yellow powder |
| 20 | H | $CH_2OH$ | OMe | $CH_2OTHP$ | $CO_2Et$ | 33 | Brown oil |
| 21 | H | CH(OH)Me | H | cycloPr | $CO_2CH_2Ph$ | 30 | Yellow oil |
| 22 | H | CH(OH)Et | H | Pr | $CO_2CH_2Ph$ | 25 | Yellow powder |
| 23 | H | OMe | H | H | $CO_2Et$ | 43 | Yellow oil |
| 24 | H | OMe | H | Me | $CO_2Et$ | 32 | Yellow oil |
| 25 | H | 2-methyl-1,3-dioxolan-2-yl | H | Et | $CO_2Et$ | 12 | Yellow powder |
| 26 | H | 2-methyl-1,3-dioxolan-2-yl | H | $CF_3$ | $CO_2Et$ | 40 | Colorless powder |
| 27 | H | $CH_2OH$ | H | Et | $CO_2Et$ | 23 | Yellow powder |
| 28 | H | $CH_2OH$ | OMe | Et | $CO_2Et$ | 19 | Colorless powder |
| 29 | H | $CH_2OH$ | OMe | $CF_3$ | $CO_2Et$ | 30 | Yellow powder |
| 30 | H | CH(OH)Et | OMe | $CF_3$ | $CO_2Et$ | 42 | Pale yellow powder |
| 31 | H | Br | OMe | $CO_2Me$ | $CO_2Me$ | 15 | Yellow powder |
| 32 | H | $CH_2OH$ | H | $CF_3$ | $CO_2Et$ | 42 | Yellow powder |
| 33 | Cl | OMe | H | Et | $CO_2Et$ | 11 | Pale yellow powder |
| 34 | F | F | H | Et | COEt | 46 | Yellow powder |
| 35 | H | $CH_2OTBDMS$ | OMe | Et | $CO_2Et$ | 31 | Brown oil |
| 38 | H | $CH_2OH$ | OMe | $CH_2OTBDMS$ | $CO_2CH_2Ph$ | 24 | Yellow powder |
| 37 | H | $CH_2OH$ | H | Et | COEt | 29 | Yellow powder |
| 38 | H | OMe | H | Et | $CO_3Et$ | 35 | Yellow powder |

THP: tetrahydropyran
TBDMS: $tBuMe_2Si$

Example 17

LRMS (EI$^+$): 254 [M$^+$]
$^1$H-NMR (CDCl$_3$, 400 MHz) δ 1.34 (3H, t, J=7.6 Hz), 1.40 (3H, t, J=7.0 Hz), 3.10 (2H, q, J=7.6 Hz), 4.37 (2H, q, J=7.0 Hz), 7.00-7.05 (1H, m), 8.27-8.29 (1H, m).

Example 18

LRMS (FAB$^+$): 353 ([M+H]$^+$)
$^1$H-NMR (CDCl$_3$, 400 MHz) δ 1.25 (6H, t, J=7.3 Hz), 1.44 (3H, t, J=7.3 Hz), 3.66-3.74 (4H, m), 4.12 (3H, s), 4.42 (2H, q, J=7.3 Hz), 4.77-4.81 (2H, m), 6.19 (1H, s), 6.22 (1H, d, J=7.3 Hz), 7.31 (1H, d, J=7.3 Hz).

Example 19

$^1$H-NMR (CDCl$_3$, 400 MHz) δ 3.31 (3H, s), 4.15 (3H, s), 4.73-4.86 (5H, m), 5.39 (2H, s), 6.26 (1H, d, J=7.9 Hz), 7.32-7.44 (4H, m), 7.50 (2H, d, J=6.7 Hz).

Example 20

$^1$H-NMR (CDCl$_3$, 400 MHz) δ 1.50-1.70 (2H, m), 1.70-1.90 (2H, m), 3.52-3.61 (2H, m), 3.80-3.88 (2H, m), 4.41 (2H, s), 4.83 (1H, t, J=3.1 Hz).

Example 21

$^1$H-NMR (CDCl$_3$, 400 MHz) δ 0.89-1.06 (4H, m), 1.55 (3H, s), 2.48-2.53 (1H, m), 4.67 (1H, d, J=5.5 Hz), 5.40 (1H, d, J=12.2 Hz), 5.44 (1H, d, J=12.2 Hz), 5.50-5.58 (1H, m), 6.87 (1H, t, J=7.3 Hz), 7.38-7.49 (6H, m), 8.28 (1H, dd, J=1.2, 6.7 Hz).

Example 22

$^1$H-NMR (CDCl$_3$, 400 MHz) δ 0.83 (3H, t, J=7.3 Hz), 0.99 (3H, t, J=7.3 Hz), 1.76-1.82 (4H, m), 2.89-2.91 (2H, m), 4.55-4.57 (1H, m), 5.36 (2H, s), 6.89 (1H, t, J=6.7 Hz), 7.35-7.47 (6H, m), 8.35 (1H, d, J=6.7 Hz).

Example 23

$^1$H-NMR (CDCl$_3$, 400 MHz) δ 1.30 (3H, t, J=7.3 Hz), 3.92 (3H, s), 4.26 (2H, q, J=7.3 Hz), 6.57 (1H, d, J=7.3 Hz), 6.75 (1H, dd, J=7.3, 7.3 Hz), 8.09 (1H, d, J=7.3 Hz).

Example 24

$^1$H-NMR (CDCl$_3$, 400 MHz) δ 1.43 (3H, t, J=7.3 Hz), 2.63 (3H, s), 3.99 (3H, s), 4.39 (2H, q, J=7.3 Hz), 6.62 (1H, d, J=7.3 Hz), 6.78 (1H, dd, J=7.3, 7.3 Hz), 8.09 (1H, d, J=7.3 Hz).

Example 25

$^1$H-NMR (CDCl$_3$, 400 MHz) δ 1.23 (3H, t, J=6.7 Hz), 1.34 (3H, t, J=7.3 Hz), 1.80 (3H, s), 2.77-2.83 (4H, m), 3.61-3.64 (2H, m), 3.96-3.99 (2H, m), 6.73 (1H, t, J=6.7 Hz), 7.31 (1H, d, J=6.7 Hz), 8.33 (1H, d, J=6.7 Hz)

Example 26

$^1$H-NMR (CDCl$_3$, 400 MHz) δ 1.39 (3H, t, J=7.3 Hz), 1.84 (3H, s), 3.60-3.71 (2H, m), 3.97-4.07 (2H, m), 4.40 (2H, q, J=7.3 Hz), 6.98 (1H, t, J=7.3 Hz), 7.52 (1H, dd, J=7.3, 1.2 Hz), 8.44-8.47 (1H, m).

Example 27

LRMS (EI$^+$): 248[M$^+$]
$^1$H-NMR (CDCl$_3$, 400 MHz) δ 1.35 (3H, t, J=7.3 Hz), 1.44 (3H, t, J=7.3 Hz), 3.08 (2H, q, J=7.3 Hz), 4.41 (2H, q, J=7.3 Hz), 4.86 (2H, d, J=7.3 Hz), 5.02 (1H, t, J=7.3 Hz), 6.87 (1H, t, J=6.7 Hz), 7.30 (1H, d, J=6.7 Hz), 8.40 (1H, d, J=6.7 Hz).

Example 28

LRMS (EI$^+$): 278[M$^+$]
$^1$H-NMR (CDCl$_3$, 400 MHz) δ 1.34 (3H, t, J=8.0 Hz), 1.44 (3H, t, J=6.7 Hz), 3.12 (2H, q, J=8.0 Hz), 4.16 (3H, s), 4.41 (2H, q, J=6.7 Hz), 4.81 (2H, d, J=7.3 Hz), 4.94 (1H, d, J=7.3 Hz), 6.22 (1H, d, J=7.3 Hz), 7.30 (1H, d, J=7.3 Hz).

Example 29

$^1$H-NMR (CDCl$_3$, 400 MHz) δ 1.42 (3H, t, J=7.0 Hz), 4.20 (3H, s), 4.43 (2H, q, J=7.0 Hz), 4.62 (1H, t, J=7.6 Hz), 4.83 (2H, d, J=7.6 Hz), 6.36 (1H, d, J=7.6 Hz), 7.44 (1H, d, J=7.6 Hz).

Example 30

$^1$H-NMR (CDCl$_3$, 400 MHz) δ 1.02 (3H, t, J=7.3 Hz), 1.42 (3H, t, J=7.3 Hz), 1.83-1.91 (2H, m), 4.03 (1H, d, J=5.7 Hz), 4.19 (3H, s), 4.38-4.47 (2H, m), 5.17 (1H, q, J=7.3 Hz), 6.39 (1H, d, J=7.9 Hz), 7.58 (1H, d, J=7.9 Hz)

Example 31

$^1$H-NMR (CDCl$_3$, 400 MHz) δ 3.99 (3H, s), 4.00 (3H, s), 4.17 (3H, s), 6.20 (1H, d, J=7.9 Hz), 7.49 (1H, d, J=8.6 Hz).

Example 32

LRMS (EI$^+$): 288[M$^+$]
$^1$H-NMR (400 MHz, CDCl$_3$) δ 1.43 (3H, t, J=7.3 Hz), 4.44 (2H, q, J=7.3 Hz), 4.65 (1H, t, J=7.3 Hz), 4.90 (2H, d, J=7.3 Hz), 7.06 (1H, t, J=7.3 Hz), 7.45 (1H, d, J=7.3 Hz), 8.50 (1H, d, J=7.3 Hz).

Example 33

$^1$H-NMR (CDCl$_3$, 400 MHz) δ 1.32 (3H, t, J=7.3 Hz), 1.40 (3H, t, J=7.3 Hz), 3.01 (2H, q, J=7.3 Hz), 3.96 (3H, s), 4.36 (2H, q, J=7.3 Hz), 6.56 (1H, s), 8.13 (1H, s).

Example 34

$^1$H-NMR (CDCl$_3$, 400 MHz) δ 1.21 (3H, t, J=7.3 Hz), 1.33 (3H, t, J=7.3 Hz), 2.93-2.99 (2H, m), 3.05 (2H, q, J=7.3 Hz), 7.03-7.09 (1H, m), 8.31 (1H, brs).

Example 35

$^1$H-NMR (CDCl$_3$, 400 MHz) δ 0.11 (6H, s), 0.95 (9H, s), 1.33 (3H, t, J=7.3 Hz), 1.41 (3H, t, J=7.3 Hz), 3.09 (2H, q, J=7.3 Hz), 4.14 (3H, s), 4.35 (2H, q, J=7.3 Hz), 5.12 (2H, d, J=1.8 Hz), 6.24 (1H, d, J=7.9 Hz), 7.56 (1H, td, J=1.8, 7.9 Hz).

Example 36

$^1$H-NMR (CDCl$_3$, 400 MHz) δ 0.04 (6H, s), 0.87 (9H, s), 4.14 (3H, s), 4.63 (1H, brs), 4.81 (2H, s), 5.08 (2H, s), 5.38 (2H, s), 6.23 (1H, d, J=7.9 Hz), 7.30-7.42 (4H, m), 7.49 (2H, dd, J=7.9, 1.2 Hz), 8.14 (1H, d, J=2.4 Hz).

Example 37

LRMS (EI+): 232[M+]
1H-NMR (CDCl3, 400 MHz) δ 1.27 (3H, t, J=7.3 Hz), 1.42 (3H, t, J=7.3 Hz), 2.97 (2H, q, J=7.3 Hz), 3.09 (2H, q, J=7.3 Hz), 4.75 (2H, d, J=7.3 Hz), 5.04 (1H, t, J=7.3 Hz), 5.89 (1H, t, J=6.7 Hz), 7.30-7.32 (1H, m), 8.37-8.39 (1H, m).

Example 38

1H-NMR (CDCl3, 400 MHz) δ 1.33 (3H, t, J=7.6 Hz), 1.40 (3H, t, J=7.0 Hz), 3.03 (2H, q, J=7.6 Hz), 3.96 (3H, s), 4.37 (2H, q, J=7.0 Hz), 6.59 (1H, d, J=7.6 Hz), 6.75 (1H, t, J=7.6 Hz), 8.09 (1H, d, J=7.6 Hz).

Example 39

3-ethoxycarbonyl-2-methylthio-4-(tetrahydropyrane-2-yl oxymethyl)-pyrazolo[1,5-a]pyridine

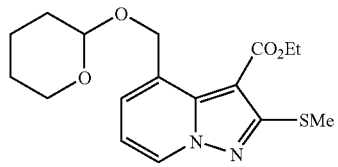

The compound of Example 14 (45.6 g) was dissolved in ethanol (500 mL). To this solution, carbon disulfide (10.3 mL) and dimethylsulfuric acid (16.3 mL) were added. An aqueous solution (100 mL) of potassium hydroxide (14.5 g) was then slowly added dropwise over 1.5 hours. Subsequently, ice water was added and the mixture was extracted with ethyl acetate. The organic layer was washed with saturated brine and dried over sodium sulfate. The solvent was evaporated under reduced pressure and the residue was purified by silica gel column chromatography (hexane:ethyl acetate=1:4) to give a yellow oil (6.78 g). The oily product (8.64 g) was dissolved in chloroform (200 mL). To this solution, bromoethyl acetate (6.66 mL) was added and the resulting mixture was stirred for 6 hours at room temperature. Subsequently, the solvent was evaporated and the residue was washed with diethyl ether to give a yellow oil. The oily product was dissolved in chloroform (290 mL). To the solution, potassium carbonate (20.0 g) was added and the resulting mixture was stirred for 16 hours at room temperature. Subsequently, the mixture was filtered and the solvent was evaporated. Purification of the resulting residue by silica gel column chromatography (hexane:ethyl acetate=8:1) gave an inseparable mixture of the title compound and 3-ethoxycarbonyl-2-methylthio-6-(tetrahydropyrane-2-yl oxymethyl)-pyrazolo[1,5-a]pyridine as a yellow oil (3.71 g, 0.6:1).

Example 40

4-acetyl-3-benzyloxycarbonyl-2-cyclopropyl-pyrazolo[1,5-a]pyridine

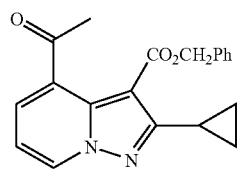

The compound of Example 21 (7.60 g) was dissolved in dichloromethane (100 mL). To this solution, activated manganese dioxide (59.0 g) was added and the mixture was stirred for 30 hours at room temperature. Subsequently, the mixture was filtered through Celite and the solvent was evaporated under reduced pressure. The resulting residue was purified by silica gel column chromatography (hexane:ethyl acetate=8:1 and then 1:1) to give a yellow solid. The obtained solid was dissolved in dichloromethane (90 mL) and activated manganese dioxide (32.0 g) was again added. The resulting mixture was stirred for 24 hours at room temperature. Subsequently, the mixture was filtered through Celite and the solvent was evaporated under reduced pressure to afford the title compound (5.57 g) as a yellow solid.
1H-NMR (CDCl3, 400 MHz) δ 1.02-1.05 (2H, m), 1.07-1.10 (2H, m), 2.42 (3H, s), 2.64-2.70 (1H, m), 5.35 (2H, s), 6.89 (1H, t, J=6.7 Hz), 7.36-7.44 (6H, m), 8.41 (1H, d, J=6.7 Hz).

Example 41

2-ethyl-3-ethoxycarbonyl-6-fluoro-4-methoxypyrazolo[1,5-a]pyridine

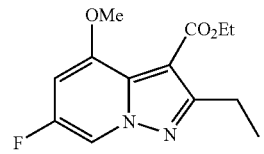

Sodium methoxide (362 mg) was added to a solution of the compound of Example 17 (340 mg) in methanol (15 mL). The mixture was refluxed for 3 hours. Subsequently, additional sodium methoxide (181 mg) was added and the mixture was stirred for 2 hours. After cooling, saturated ammonium chloride was added and the mixture was extracted with ethyl acetate. The organic layer was washed with water and saturated brine and dried over an hydrous sodium sulfate. The solvent was evaporated and the resulting residue was purified by silica gel column chromatography (hexane:ethyl acetate=5:1) to afford the title compound as a colorless powder (302 mg).
1H-NMR (CDCl3, 400 MHz) δ 1.31 (3H, t, J=7.6 Hz), 3.00 (2H, q, J=7.6 Hz), 3.89 (3H, s), 3.98 (3H, s), 6.55 (1H, dd, J=1.8, 10.1 Hz), 8.05 (1H, dd, J=1.8, 3.4 Hz).

Example 42

4-acetyloxymethyl-3-ethoxycarbonyl-2-diethoxymethyl-4-methoxy-pyrazolo[1,5-a]pyridine

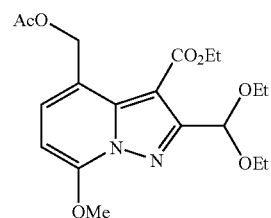

The compound of Example 18 (2.10 g) was dissolved in pyridine (20 mL). To this solution, acetic anhydride (1.12 mL) was added and the mixture was stirred for 6 hours at room temperature. Subsequently, the reaction mixture was diluted with water and extracted with ethyl acetate. The organic layer was washed sequentially with water and saturated brine and dried over anhydrous sodium sulfate. The solvent was evaporated to afford the title compound as a colorless oil (2.01 g).

LRMS (EI$^+$): 394 [M$^+$]

$^1$H-NMR (400 MHz, CDCl$_3$) δ 1.25 (6H, t, J=7.3 Hz), 1.41 (3H, t, J=7.3 Hz), 2.04 (3H, s), 3.67-3.75 (4H, m), 4.13 (3H, s), 4.37 (2H, q, J=7.3 Hz), 5.47 (2H, s), 6.17 (1H, s), 6.19 (1H, d, J=8.0 Hz), 7.35 (1H, d, J=8.0 Hz).

Example 43

4-acetyloxymethyl-3-ethoxycarbonyl-2-formyl-4-methoxy-pyrazolo[1,5-a]pyridine

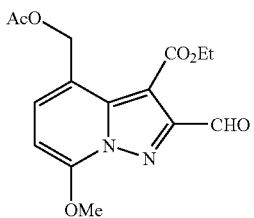

The compound of Example 42 (2.01 g) was dissolved in a mixed solvent of acetone and water (2:1). To this solution, p-toluenesulfonic acid monohydrate (97.3 mg) was added and the mixture was stirred for 2 hours while heated at 70° C. After cooling, the mixture was extracted with ethyl acetate and the organic layer was washed sequentially with water and saturated brine and dried over anhydrous sodium sulfate. The solvent was evaporated and the resulting residue was purified by silica gel column chromatography (hexane:ethyl acetate=1:2) to afford the title compound as a colorless powder (1.47 g).

LRMS (EI$^+$): 320[M$^+$]

$^1$H-NMR (400 MHz, CDCl$_3$): δ 1.43 (3H, t, J=7.3 Hz), 2.05 (3H, s), 4.21 (3H, s), 4.45 (2H, q, J=7.3 Hz), 5.50 (2H, s), 6.36 (1H, d, J=8.0 Hz), 7.46 (1H, d, J=8.0 Hz), 10.49 (1H, s)

Example 44

4-acetyloxymethyl-3-ethoxycarbonyl-2-difluoromethyl-4-methoxy-pyrazolo[1,5-a]pyridine

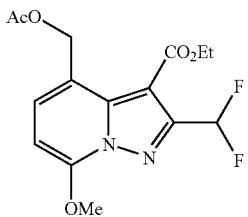

The compound of Example 43 (1.47 g) was dissolved in dichloromethane (23 mL) under a stream of argon. While the solution was chilled in an ice bath, diethylaminosulfur trifluoride (1.52 mL) was added dropwise and the mixture was stirred at room temperature for 1.5 hours. Subsequently, the reaction mixture was quenched by adding a saturated aqueous sodium bicarbonate solution. The mixture was extracted with ethyl acetate and the organic layer was washed sequentially with water and saturated brine and dried over anhydrous sodium sulfate. The solvent was evaporated and the resulting residue was purified by silica gel column chromatography (hexane:ethyl acetate=2:3) to afford the title compound as a colorless powder (1.21 g).

LRMS (EI$^+$): 342 [M$^+$]

$^1$H-NMR (400 MHz, CDCl$_3$) δ 1.42 (3H, t, J=7.3 Hz), 2.06 (3H, s), 4.20 (3H, s), 4.40 (2H, q, J=7.3 Hz), 5.60 (2H, s), 6.35 (1H, d, J=7.9 Hz), 7.26 (1H, t, J=53.8 Hz), 7.49 (1H, d, J=7.9 Hz)

Example 45

2-ethyl-4-hydroxypyrazolo[1,5-a]pyridine

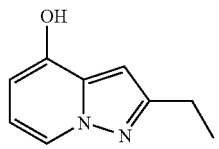

The compound of Example 16 (4.00 g) was dissolved in dichloromethane (50 mL) under a stream of argon. While the solution was chilled in an ice bath, boron tribromide (27.5 mL, 1 mol/L dichloromethane solution) was added and the mixture was stirred for 30 min at the same temperature. Subsequently, ice water was added and the mixture was extracted with ethyl acetate. The organic layer was washed sequentially with water and saturated brine and dried over anhydrous sodium sulfate. The solvent was evaporated and the resulting residue was purified by silica gel column chromatography (hexane:ethyl acetate=10:1 to 5:1) to give a 4-hydroxy form as a yellow powder (1.85 g).

$^1$H-NMR (400 MHz, CDCl$_3$) δ 1.44 (3H, t, J=7.3 Hz), 2.62 (3H, s), 3.08 (2H, q, J=7.3 Hz), 6.81 (1H, dd, J=0.9, 7.6 Hz), 6.90 (1H, dd, J=6.4, 7.6 Hz), 8.00 (1H, dd, J=0.9, 6.4 Hz), 12.98 (1H, s).

The obtained phenol form (1.85 g) was suspended in 50% sulfuric acid (70 mL) and the suspension was stirred at 150° C. for 10 hours. After cooling, the suspension was diluted with water, neutralized with potassium carbonate and extracted with ethyl acetate. The organic layer was washed sequentially with water and saturated brine and dried over an hydrous sodium sulfate. The solvent was evaporated to afford the title compound as a brown powder (1.42 g).

(Process A).

$^1$H-NMR (400 MHz, CDCl$_3$) δ (1.36 (3H, t, J=7.6 Hz), 2.87 (2H, q, J=7.6 Hz), 5.68 (1H, brs), 6.41-6.43 (2H, m), 6.54 (1H, t, J=7.0 Hz), 8.06 (1H, d, J=7.0 Hz).

Example 46

2-ethyl-6-fluoro-4-hydroxypyrazolo[1,5-a]pyridine

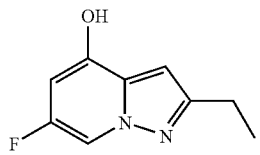

The compound of Example 41 (4.53 g) was dissolved in dichloromethane (50 mL). The solution was kept at 0° C. and boron tribromide (21.6 mL, 1.0 mol/L dichloromethane solution) was added. The resulting mixture was stirred for 1 hour. Subsequently, water was added and the mixture was extracted three times with ethyl acetate. The organic layer was washed with saturated brine and dried over sodium sulfate. The solvent was evaporated under reduced pressure. The resulting solid product (4.29 g) was dissolved in ethanol (40 mL). To this solution, water (40 mL) and potassium hydroxide (4.10 g) were added and the mixture was stirred for 2 hours under reflux. This was followed by addition of water and concentrated hydrochloric acid to make the mixture acidic. The resulting mixture was extracted with three times with ethyl acetate and the organic layer was washed with saturated brine, dried over sodium sulfate and filtered. The solvent was evaporated under reduced pressure. The resulting solid product (3.58 g) was dissolved in ethanol (100 mL). To this solution, concentrated sulfuric acid (2 mL) was added and the mixture was refluxed for 7.5 hours. Subsequently, ethanol was evaporated under reduced pressure and the residue was extracted three times with ethyl acetate. The organic layer was washed with saturated brine and dried over sodium sulfate. The solvent was evaporated under reduced pressure to afford the title compound as a gray powder (2.88 g) (Process B).

$^1$H-NMR (CDCl$_3$, 400 MHz) δ 1.34 (3H, t, J=8.0 Hz), 2.84 (2H, q, J=8.0 Hz), 6.42-6.45 (2H, m), 8.03 (1H, d, J=3.0 Hz).

Example 47

4-hydroxypyrazolo[1,5-a]pyridine

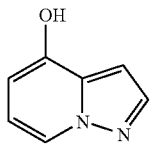

The compound of Example 23 (4.30 g) was dissolved in dichloromethane (50 mL) in an argon atmosphere. While the solution was kept at 0° C., boron tribromide (1.0 mol/L dichloromethane solution, 23.4 mL) was added and the mixture was stirred for 1 hour. Additional boron tribromide (23.4 mL) was then added and the mixture was stirred at room temperature for another 3 hours. Subsequently, water was added and the mixture was extracted with ethyl acetate. The organic layer was washed with saturated brine and dried over sodium sulfate. The solvent was evaporated under reduced pressure to give a yellow powder (4.80 g). To this product, 47% hydrobromic acid (100 mL) was added and the mixture was stirred for 5 hours under reflux. Subsequently, the mixture was made basic by adding sodium hydroxide and then made acidic again by adding hydrochloric acid. The mixture was extracted three times with ethyl acetate and the organic layer was washed with saturated brine and dried over sodium sulfate. Evaporating the solvent under reduced pressure afforded the title compound as a yellow powder (2.10 g) (Process C).

$^1$H-NMR (CDCl$_3$, 400 MHz) δ 5.76 (1H, brs), 6.47 (1H, d, J=7.3 Hz), 6.62-6.65 (2H, m), 7.92 (1H, d, J=2.4 Hz), 8.17 (1H, d, J=6.7 Hz).

Example 48

4-acetyl-2-cyclopropylpyrazolo[1,5-a]pyridine

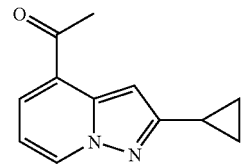

The compound of Example 40 (5.57 g) was dissolved in ethanol (30 mL) and water (30 mL). To this solution, potassium hydroxide (3.70 g) was added and the mixture was stirred for 3.5 hours under reflux. Subsequently, the mixture was neutralized with concentrated hydrochloric acid and extracted three times with ethyl acetate. The organic layer was washed with saturated brine and dried over sodium sulfate. The solvent was evaporated under reduced pressure and the resulting solid product was dissolved in toluene (150 mL). This solution was stirred for 6 hours under reflux. Subsequent removal of the solvent and purification by silica gel column chromatography (hexane:ethyl acetate=4:1 then 1:1) afforded the title compound as a yellow powder (2.64 g) (Process D).

$^1$H-NMR (CDCl$_3$, 400 MHz) δ 0.85-0.89 (2H, m), 0.98-1.03 (2H, m), 2.04-2.11 (1H, m), 2.58 (3H, s), 6.66 (1H, t, J=6.7 Hz), 6.88 (1H, s), 7.68 (1H, d, J=6.7 Hz), 8.44 (1H, d, J=6.7 Hz).

Example 49

2-ethyl-4-methoxy-pyrazolo[1,5-a]pyridine

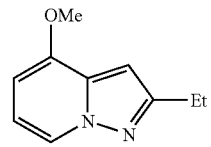

The compound of Example 38 (2.8 g) was dissolved in ethanol (30 mL). To this solution, water (30 mL) and potassium hydroxide (3.35 g) were added and the mixture was stirred for 1.5 hours under reflux. Subsequently, the solvent was partially removed under reduced pressure, followed by addition of a copious amount of water and concentrated hydrochloric acid to make the mixture acidic. The mixture was then extracted three times with ethyl acetate and the organic layer was washed with saturated brine and dried over sodium sulfate. The solvent was evaporated under reduced pressure and the resulting white solid was dissolved in ethanol (75 mL). Concentrated sulfuric acid (1.5 mL) was then added and the mixture was stirred for 4 hours under reflux. Subsequently, the solvent was partially removed under reduced pressure and the residue was extracted three times with ethylacetate. The organic layer was washed with saturated brine and dried over sodium sulfate. Evaporating the solvent under reduced pressure afforded the title compound as a gray oil (2.07 g) (Process E).

$^1$H-NMR (CDCl$_3$, 400 MHz) δ 1.35 (3H, t, J=8.0 Hz), 2.84 (2H, q, J=8.0 Hz), 3.94 (3H, s), 6.32 (1H, d, J=7.3 Hz), 6.42 (1H, s), 6.57 (1H, t, J=7.3 Hz), 8.03 (1H, t, J=7.3 Hz).

Example 50

6-chloro-2-ethyl-4-hydroxy-pyrazolo[1,5-a]pyridine

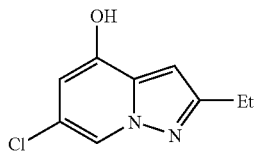

The compound of Example 33 (220 mg) was suspended in 47% hydrobromic acid and the suspension was refluxed for 5 hours. Subsequently, a 20% aqueous potassium hydroxide solution was added to make the mixture basic. The mixture was neutralized by concentrated hydrochloric acid and extracted with ethyl acetate. The organic layer was washed with water and saturated brine and dried over anhydrous sodium sulfate. Subsequent evaporation of the solvent and purification by silica gel column chromatography (hexane: ethyl acetate=4:1) afforded the title compound as a colorless powder (80 mg) (Process F).

$^1$H-NMR (DMSO-$d_6$, 400 MHz) δ 1.24 (3H, t, J=7.6 Hz), 2.71 (2H, q, J=7.6 Hz), 6.40 (1H, d, J=1.5 Hz), 6.48 (1H, s), 8.35 (1H, dd, J=0.9, 1.5 Hz), 10.91 (1H, brs).

Examples 51 through 63

Using the compounds shown in Table 2 and the compounds of Examples 39 and 44, the reactions were carried out as in Examples 45 through 50 to obtain compounds shown in Table 3 below.

Example 51

LRMS (EI$^+$): 228 [M$^+$]
$^1$H-NMR (CDCl$_3$, 400 MHz) δ 1.77 (1H, t, J=5.5 Hz), 4.18 (3H, s), 4.87 (2H, d, J=5.5 Hz), 6.17 (1H, d, J=7.3 Hz), 6.86 (1H, s), 6.94 (1H, t, J=54.4 Hz), 7.22 (1H, d, J=7.3 Hz).

Example 52

$^1$H-NMR (CDCl$_3$, 400 MHz) δ 1.76 (1H, brs), 3.45 (3H, s), 4.14 (3H, s), 4.74 (2H, s), 4.83 (2H, s), 6.05 (1H, d, J=7.9 Hz), 6.64 (1H, s), 7.13 (1H, d, J=6.7 Hz).

Example 53

$^1$H-NMR (CDCl$_3$, 400 MHz) δ 1.28 (3H, t, J=7.3 Hz), 3.03 (2H, q, J=7.3 Hz), 4.27 (3H, s), 6.31 (1H, d, J=7.9 Hz), 7.69 (1H, s), 8.01 (1H, d, J=7.9 Hz).

Example 54

$^1$H-NMR (CDCl$_3$, 400 MHz) δ 0.97 (3H, t, J=7.3 Hz), 1.01 (3H, t, J=7.3 Hz), 1.75-1.90 (4H, m), 2.77-2.81 (2H, m), 4.86 (1H, t, J=6.1 Hz), 6.38 (1H, s), 6.66 (1H, t, J=6.7 Hz), 7.07 (1H, d, J=6.7 Hz), 8.29 (1H, d, J=6.7 Hz).

Example 55

$^1$H-NMR (CDCl$_3$, 400 MHz): δ 2.49 (3H, s), 6.38 (1H, s), 6.42 (1H, d, J=7.3 Hz), 6.54 (1H, dd, J=7.3, 7.3 Hz), 8.05 (1H, d, J=7.3 Hz).

Example 56

$^1$H-NMR (CDCl$_3$, 400 MHz) δ 2.70 (3H, s), 7.04 (1H, t, J=6.7 Hz), 7.62 (1H, s), 7.92 (1H, d, J=7.9 Hz), 8.67 (1H, d, J=6.7 Hz).

TABLE 3

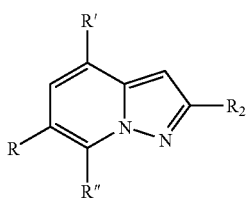

| Examples | R | R' | R" | R2 | Yields(%) | Method | Nature |
|---|---|---|---|---|---|---|---|
| 51 | H | CH$_2$OH | OMe | CHF$_2$ | 77 | D | Brown powder |
| 52 | H | CH$_2$OH | OMe | CH$_2$OMe | 61 | D | Colorless powder |
| 53 | H | CH$_2$OH | OMe | CH$_2$OTHP | 54 | D | Pale brown oil |
| 54 | H | CH(OH)Et | H | Pr | 39 | D | Yellow oil |
| 55 | H | OH | H | Me | 96 | C | Brown powder |
| 56 | H | Ac | H | CF$_3$ | 83 | F | Colorless powder |
| 57 | H | CH$_2$OH | H | Et | 79 | D | Brown powder |
| 58 | H | CH$_2$OH | OMe | Et | 61 | D | Brown powder |
| 59 | H | CH$_2$OH | OMe | CF$_3$ | 73 | D | Colorless powder |
| 60 | H | CH(OH)Et | OMe | CF$_3$ | 44 | D | Brown oil |
| 61 | H | Br | OMe | CO$_2$Et | 91 | E | Colorless powder |
| 62 | Cl | OH | H | Et | 100 | A, B | Colorless powder |
| 63 | H | CH$_2$OTHP | H | SMe | 21 | D | Yellow oil |

THP: tetrahydropyran

Example 57

LRMS (EI+) 176[M+]
¹H-NMR (CDCl₃, 400 MHz) δ 1.37 (3H, t, J=7.3 Hz), 2.87 (2H, q, J=7.3 Hz), 4.86 (2H, brs), 6.38 (1H, s), 6.68 (1H, t, J=7.3 Hz), 7.09-7.10 (1H, m), 8.33 (1H, d, J=7.3 Hz).

Example 58

LRMS (EI+): 206 [M+]
¹H-NMR (CDCl₃, 400 MHz) δ 1.36 (3H, t, J=8.0 Hz), 1.65 (1H, brs), 2.92 (2H, q, J=8.0 Hz), 4.13 (3H, s), 4.81 (2H, s), 5.99 (1H, d, J=7.3 Hz), 6.43 (1H, s), 7.08 (1H, d, J=7.3 Hz).

Example 59

¹H-NMR (CDCl₃, 400 MHz) δ 1.56 (1H, br s), 4.18 (3H, s), 4.87 (2H, d, J=0.9 Hz), 6.22 (1H, d, J=7.6 Hz), 6.92 (1H, s), 7.24-7.27 (1H, m).

Example 60

¹H-NMR (CDCl₃, 400 MHz) δ0.96 (3H, t, J=7.3 Hz), 1.88-1.96 (2H, m), 1.98 (1H, br s), 4.17 (3H, s), 4.87 (1H, t, J=5.8 Hz), 6.23 (1H, d, J=7.6 Hz), 6.93 (1H, s), 7.25 (1H, d, J=7.6 Hz).

Example 61

¹H-NMR (CDCl₃, 400 MHz) δ 1.44 (3H, t, J=7.3 Hz), 4.15 (3H, s), 4.48 (2H, q, J=7.3 Hz), 6.12 (1H, d, J=7.9 Hz), 7.20 (1H, s), 7.37 (1H, d, J=7.9 Hz).

Example 62

Identical Compound to Example 50

¹H-NMR (CDCl₃, 400 MHz) δ 1.34 (3H, t, J=7.6 Hz), 2.84 (2H, q, J=7.6 Hz), 6.12 (1H, br s), 6.43 (1H, s), 6.46 (1H, d, J=1.5 Hz), 8.10-8.11 (1H, m).

Example 63

¹H-NMR (CDCl₃, 400 MHz) δ 1.57-1.86 (6H, m), 2.61 (3H, s), 3.55-3.60 (1H, m), 3.89-3.92 (1H, m), 4.64 (1H, d, J=12.8 Hz), 4.72-4.74 (1H, m), 4.90 (1H, d, J=12.8 Hz), 6.65 (1H, s), 6.66 (1H, t, J=7.3 Hz), 7.11 (1H, d, J=7.3 Hz), 8.30 (1H, d, J=7.3 Hz).

Example 64

2-trifluoromethyl-4-hydroxymethyl-pyrazolo[1,5-a]pyridine

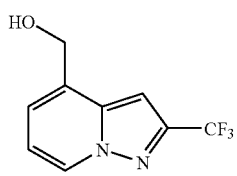

A solution of the compound of Example 32 (10.0 g) in 40% aqueous sulfuric acid (300 mL) was stirred at 100° C. for 2.5 hours. After cooling, the reaction mixture was poured into ice water, neutralized with potassium carbonate and made acidic by the addition of concentrated hydrochloric acid. The mixture was then extracted three times with ethyl acetate. The organic layer was washed sequentially with water and saturated brine and dried over anhydrous sodium sulfate. Evaporation of the solvent and purification of the residue by silica gel column chromatography (hexane:ethyl acetate=4:1) afforded the title compound as a brown powder (5.17 g, crude). This product was used in the subsequent process without further purification.

Example 65

3-chloro-2-ethyl-4-methoxy-pyrazolo[1,5-a]pyridine

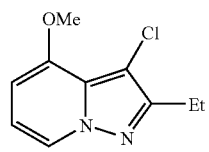

The compound of Example 49 (2.07 g) was dissolved in DMF (60 mL). To this solution, NCS (1.88 g) was added and the mixture was stirred at room temperature for 5.5 hours. Subsequently, water was added and the mixture was extracted three times with ethyl acetate. The organic layer was washed with saturated brine and dried over sodium sulfate. Evaporation of the solvent under reduced pressure and purification by silica gel column chromatography (hexane:ethyl acetate=3:1) afforded the title compound as a gray powder (2.28 g).

¹H-NMR (CDCl₃, 400 MHz) δ 1.33 (3H, t, J=8.0 Hz), 2.82 (2H, q, J=8.0 Hz), 3.94 (3H, s), 6.33 (1H, d, J=8.0 Hz), 6.56 (1H, t, J=7.8 Hz), 7.95 (1H, d, J=7.3 Hz).

Example 66

3-chloro-2-ethyl-4-hydroxy-pyrazolo[1,5-a]pyridine

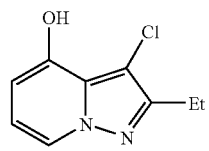

The compound of Example 65 (3.07 g) was dissolved in dichloromethane (40 mL) in an argon atmosphere. While this solution was kept at 0° C., borane tribromide (17.6 mL, 1.0 mol/mL dichloromethane solution) was added and the mixture was stirred for 26 hours at 0° C. to reflux temperature. Subsequently, the reaction was terminated by adding water and the mixture was extracted three times with ethylacetate. The organic layer was washed with saturated brine and dried over sodium sulfate. The solvent was evaporated under reduced pressure to afford the title compound as a yellow powder (2.91 g).

¹H-NMR (CDCl₃, 400 MHz) δ 1.34 (3H, t, J=8.0 Hz), 2.82 (2H, q, J=8.0 Hz), 6.32 (1H, brs), 6.50 (1H, d, J=6.7 Hz), 6.59 (1H, dd, J=6.7, 6.7 Hz), 7.98 (1H, d, J=6.7 Hz).

Example 67

2-ethyl-6-fluoro-4-trifluoromethanesulfonyloxy-pyrazolo[1,5-a]pyridine

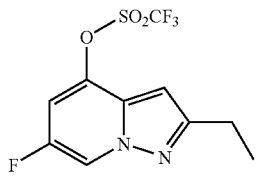

The compound of Example 46 (2.88 g) was dissolved in dichloromethane (100 mL). To this solution, triethylamine (4.51 mL) was added, followed by addition of anhydrous trifluoromethanesulfonic acid (2.97 mL) at 0° C. The mixture was stirred at room temperature for 1 hour. Subsequently, the reaction was terminated by adding water and the mixture was extracted three times with ethylacetate. The organic layer was washed with saturated brine and dried over sodium sulfate. Evaporation of the solvent under reduced pressure and purification by silica gel column chromatography (hexane:ethyl acetate=20:1) afforded the title compound as a yellow oil (4.25).

$^1$H-NMR (CDCl$_3$, 400 MHz) δ 1.36 (3H, t, J=8.0 Hz), 2.87 (2H, q, J=8.0 Hz), 6.51 (1H, s), 7.10 (1H, dd, J=1.8, 8.6 Hz), 8.39-8.40 (1H, m).

Examples 68 through 72

Using the compounds of Examples 45, 47, 50 (62), 55 and 66, the reactions were carried out as in Example 67 to obtain compounds shown in Table 4 below.

TABLE 4

| Examples | R1 | R2 | R3 | Nature |
|---|---|---|---|---|
| 68 | H | Et | Cl | Yellow oil |
| 69 | H | H | H | Yellow oil |
| 70 | H | Me | H | Brown oil |
| 71 | H | Et | H | Yellow oil |
| 72 | Cl | Et | H | Yellow powder |

Example 68

$^1$H-NMR (CDCl$_3$, 400 MHz) δ 1.36 (3H, t, J=7.3 Hz), 2.87 (2H, q, J=7.3 Hz), 6.69 (1H, t, J=8.0 Hz), 7.10 (1H, d, J=8.0 Hz), 8.33 (1H, d, J=6.7 Hz).

Example 69

$^1$H-NMR (CDCl$_3$, 400 MHz) δ 6.70 (1H, d, J=2.1 Hz), 6.79 (1H, dd, J=7.3, 7.3 Hz), 7.13 (1H, d, J=7.3 Hz), 8.03 (1H, d, J=2.1H), 8.50 (1H, d, J=7.3 Hz).

Example 70

$^1$H-NMR (CDCl$_3$, 400 MHz) δ 2.51 (3H, s), 6.47 (1H, s), 6.67 (1H, dd, J=7.3, 7.3 Hz), 7.06 (1H, d, J=7.3 Hz), 8.37 (1H, d, J=7.3 Hz).

Example 71

$^1$H-NMR (400 MHz, CDCl$_3$) δ 1.37 (3H, t, J=7.6 Hz), 2.89 (2H, q, J=7.6 Hz), 6.49 (1H, s), 6.68 (1H, dd, J=7.0, 7.6 Hz), 7.07 (1H, d, J=7.6 Hz), 8.39 (1H, d, J=7.0 Hz).

Example 72

$^1$H-NMR (400 MHz, CDCl$_3$) δ 1.36 (3H, t, J=7.6 Hz), 2.87 (2H, q, J=7.6 Hz), 6.51 (1H, s), 7.10 (1H, d, J=1.5 Hz), 8.43-8.44 (1H, m).

Example 73

2-ethyl-6-fluoro-4-propionyl-pyrazolo[1,5-a]pyridine

Palladium acetate (101.8 mg) was dissolved in DMF (25 mL) in an argon atmosphere. To this solution, 1,3-bis(diphenylphosphino)propane (373.9 mg) was added and the mixture was stirred at room temperature for 15 min. Subsequently, the compound of Example 67 (4.25 g) in DMF (65 mL), ethyl-1-propenyl ether (15.0 mL) and triethylamine (3.8 mL) were added and the mixture was stirred at 80° C. for 20 hours. The reaction was terminated by adding water and the mixture was extracted three times with ethyl acetate. The organic layer was washed with saturated brine and dried over sodium sulfate, followed by evaporation of the solvent under reduced pressure. THF (50 mL) and 3 mol/L hydrochloric acid (50 mL) were added and the mixture was stirred at room temperature for 16 hours. Subsequently, the mixture was extracted three times with ethyl acetate. The organic layer was washed with saturated brine and dried over sodium sulfate. Evaporation of the solvent under reduced pressure and purification by silica gel column chromatography (hexane:ethyl acetate=6:1) afforded the title compound as a yellow powder (670 mg).

$^1$H-NMR (CDCl$_3$, 400 MHz) δ 1.29 (3H, t, J=7.0 Hz), 1.38 (3H, t, J=7.6 Hz), 2.89 (2H, q, J=7.6 Hz), 3.06 (2H, q, J=7.3 Hz), 7.13 (4H, s), 7.71 (1H, dd, J=2.1, 7.8 Hz), 8.53 (1H, t, J=2.4 Hz).

Examples 74 through 79

Using the compounds shown in Table 4, the reactions were carried out as in Example 73 to obtain compounds shown in Table 5 below. Vinyl butyl ether was used for the compounds with R being methyl.

TABLE 5

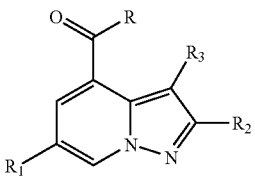

| Examples | R1 | R2 | R3 | R | Nature |
|---|---|---|---|---|---|
| 74 | H | Et | Cl | Me | Yellow powder |
| 75 | H | H | H | Me | Yellow powder |
| 76 | H | Me | H | Me | Yellow powder |
| 77 | H | Et | H | Me | Yellow powder |
| 78 | Cl | Et | H | Me | Yellow powder |
| 79 | Cl | Et | H | Et | Yellow powder |

Example 74

$^1$H-NMR (CDCl$_3$, 400 MHz) δ 1.35 (3H, t, J=7.3 Hz), 2.87 (2H, q, J=7.3 Hz), 6.73 (1H, dd, J=6.1, 6.1 Hz), 7.37 (1H, d, J=6.1 Hz), 8.42 (1H, d, J=6.1 Hz)

Example 75

$^1$H-NMR (CDCl$_3$, 400 MHz) δ 2.64 (3H, s), 6.85 (1H, t, J=7.3 Hz), 7.32 (1H, d, J=7.3 Hz), 7.82 (1H, d, J=6.1 Hz), 8.10 (1H, d, J=1.8 Hz), 8.66 (1H, J=6.7 Hz).

Example 76

$^1$H-NMR (CDCl$_3$, 400 MHz) δ 2.53 (3H, s), 2.67 (3H, s), 6.75 (1H, dd, J=7.3, 7.3 Hz), 7.09 (1H, s), 7.77 (1H, d, J=7.3 Hz), 8.54 (1H, d, J=7.3 Hz).

Example 77

$^1$H-NMR (400 MHz, CDCl$_3$) δ 1.38 (3H, t, J=7.6 Hz), 2.67 (3H, s), 2.90 (2H, q, J=7.6 Hz), 6.75 (1H, t, J=7.0 Hz), 7.78 (1H, dd, J=0.9, 7.0 Hz), 8.55 (1H, td, J=0.9, 7.0 Hz).

Example 78

$^1$H-NMR (400 MHz, CDCl$_3$) δ 1.36 (3H, t, J=7.6 Hz), 2.67 (3H, s), 2.88 (2H, q, J=7.6 Hz), 7.11 (1H, s), 7.71 (1H, d, J=1.8 Hz), 8.58-8.59 (1H, m).

Example 79

$^1$H-NMR (400 MHz, CDCl$_3$) δ 1.27 (3H, t, J=7.3 Hz), 1.36 (3H, t, J=7.6 Hz), 2.88 (2H, q, J=7.6 Hz), 3.04 (2H, q, J=7.3 Hz), 7.12 (1H, s), 7.72 (1H, d, J=1.8 Hz), 8.58 (1H, d, J=1.8 Hz).

Example 80

3,6-dichloro-2-ethyl-4-propionyl-pyrazolo[1,5-a]pyridine

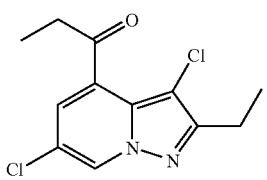

Using the compound of Example 79, the reaction was carried out as in Example 65 to obtain the title compound as a yellow powder.

$^1$H-NMR (400 MHz, CDCl$_3$) δ 1.27 (3H, t, J=7.3 Hz), 1.33 (3H, t, J=7.6 Hz), 2.84 (2H, q, J=7.6 Hz), 2.97 (2H, q, J=7.3 Hz), 7.18 (1H, d, J=1.8 Hz), 8.44 (1H, d, J=1.8 Hz).

Example 81

2-ethyl-4-propionyl-pyrazolo[1,5-a]pyridine

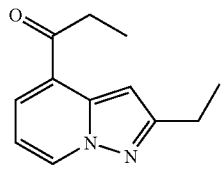

The compound of Example 77 (3.08 g) was dissolved in THF (160 mL) in an argon atmosphere. While this solution was kept at −78° C., 1.00 mol/L lithium bistrimethylsilylamide/THF solution (18.0 mL) was added dropwise. The resulting mixture was stirred for 3.5 hours as it was allowed to gradually warm to −30° C. Subsequently, methyl iodide (1.10 mL) was added dropwise at −78° C. and the mixture was stirred for another 6 hours as it was allowed to gradually warm to room temperature. A saturated aqueous solution of ammonium chloride was then added and the mixture was extracted with ethyl acetate. The organic layer was washed sequentially with water and saturated brine and dried over anhydrous sodium sulfate. Evaporation of the solvent and subsequent purification by silica gel column chromatography (hexane: ethyl acetate=3:1) afforded the title compound as a yellow powder (1.37 g).

LRMS (EI$^+$) 202 [M$^+$]

$^1$H-NMR (400 MHz, CDCl$_3$) δ 1.27 (3H, t, J=7.3 Hz), 1.38 (3H, t, J=7.3 Hz), 2.90 (2H, q, J=7.3 Hz), 3.05 (2H, q, J=7.3 Hz), 6.75 (1H, t, J=7.3 Hz), 7.13 (1H, s), 7.80 (1H, dd, J=1.2, 7.3 Hz), 8.55 (1H, dd, J=1.2, 7.3 Hz).

Example 82

4-propionyl-2-propyl-pyrazolo[1,5-a]pyridine

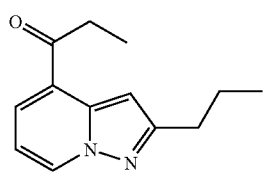

The compound of Example 54 (3.17 g) containing inseparable isomers was dissolved in toluene (72.5 mL). To this solution, activated manganese dioxide (6.31 g) was added and the mixture was stirred for 7 hours under reflux. Subsequently, additional activated manganese dioxide (6.31 g) was added and the mixture was stirred for another 6 hours under reflux. The insoluble material was removed by filtration and the filtrate was evaporated. The residue was purified by silica gel column chromatography (hexane:ethyl acetate=4:1). The resulting yellow oil was again oxidized and purified to afford the title compound as a yellow powder (850 mg).

¹H-NMR (CDCl₃, 400 MHz) δ 1.01 (3H, t, J=7.3 Hz), 1.27 (3H, t, J=7.3 Hz), 1.76-1.84 (2H, m), 2.84 (2H, t, J=7.3 Hz), 3.05 (2H, q, J=7.3 Hz), 6.74 (1H, t, J=6.7 Hz), 7.12 (1H, s), 7.79 (1H, d, J=6.7 Hz), 8.54 (1H, d, J=6.7 Hz).

Example 83

3-chloro-2-ethyl-4-(2-methyl-[1,3]dioxolane-2-yl)-pyrazolo[1,5-a]pyridine

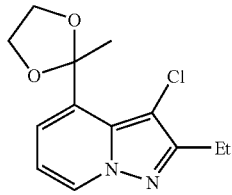

The compound of Example 74 (2.60 g) was dissolved in benzene (100 mL). To this solution, ethylene glycol (5 mL) and p-toluenesulfonic acid monohydrate (130 mg) were added and the mixture was stirred for 5.5 hours under reflux (Dean-Stark apparatus). The reaction was terminated by adding a saturated aqueous sodium bicarbonate solution and the mixture was extracted three times with ethyl acetate. The organic layer was washed with saturated brine and dried over sodium sulfate. Evaporation of the solvent under reduced pressure and purification by silica gel column chromatography (hexane:ethyl acetate=4:1) afforded the title compound as a colorless oil (3.07 g).

¹H-NMR (CDCl₃, 400 MHz) δ 1.36 (3H, t, J=7.3 Hz), 2.87 (2H, q, J=7.3 Hz), 3.79-3.82 (2H, m), 4.08-4.13 (2H, m), 6.65 (1H, dd, J=6.4, 6.4 Hz), 7.34 (1H, dd, J=1.2, 6.4 Hz), 8.29 (1H, dd, J=1.2, 6.4 Hz).

Examples 84 through 90

Using the compounds of Examples 48, 56, 75, 76, 77, 81 and 82, the reactions were carried out as in Example 83 to obtain compounds shown in Table 6 below.

TABLE 6

| Examples | R2 | R | Nature |
|---|---|---|---|
| 84 | H | Me | Yellow oil |
| 85 | Me | Me | Yellow powder |
| 86 | Et | Me | Pale yellow oil |
| 87 | Pr | Et | Colorless powder |
| 88 | cPr | Me | Colorless powder |
| 89 | CF₃ | Me | Colorless powder |
| 90 | Et | Et | Yellow oil |

Example 84

¹H-NMR (CDCl₃, 400 MHz) δ 1.77 (3H, s), 3.79-3.85 (2H, m), 4.05-4.13 (2H, m), 6.73 (1H, dd, J=7.3, 7.3 Hz), 6.78 (1H, d, J=2.4 Hz), 7.22 (1H, d, J=7.3 Hz), 7.95 (1H, d, J=2.4 Hz), 8.42 (1H, d, J=7.3 Hz).

Example 85

¹H-NMR (CDCl₃, 400 MHz) δ 1.76 (3H, s), 2.49 (3H, s), 3.79-3.82 (2H, m), 4.07-4.10 (2H, m), 6.53 (1H, s), 6.63 (1H, dd, J=7.3, 7.3 Hz), 7.17 (1H, d, J=7.3 Hz), 8.30 (1H, d, J=7.3 Hz).

Example 86

¹H-NMR (400 MHz, CDCl₃) δ 1.38 (3H, t, J=7.6 Hz), 1.77 (3H, s), 2.87 (2H, q, J=7.6 Hz), 3.79-3.83 (2H, m), 4.07-4.10 (2H, m), 6.56 (1H, s), 6.65 (1H, t, J=6.7 Hz), 7.18 (1H, d, J=6.7 Hz), 8.35 (1H, d, J=6.7 Hz).

Example 87

¹H-NMR (CDCl₃, 400 MHz) δ 0.89 (3H, t, J=7.3 Hz), 1.02 (3H, t, J=7.3 Hz), 1.77-1.83 (2H, m), 2.06 (2H, q, J=7.3 Hz), 2.80 (2H, t, J=7.3 Hz), 3.82-3.84 (2H, m), 4.04-4.08 (2H, m), 6.53 (1H, s), 6.64 (1H, t, J=6.7 Hz), 7.14 (1H, d, J=6.7 Hz), 8.32 (1H, d, J=6.7 Hz).

Example 88

¹H-NMR (CDCl₃, 400 MHz) δ 0.90-0.92 (2H, m), 0.92-1.04 (2H, m), 2.07-2.12 (1H, m), 3.78-3.84 (2H, m), 4.03-4.09 (2H, m), 6.41 (1H, s), 6.61 (1H, t, J=7.3 Hz), 7.15 (1H, d, J=7.3 Hz).

Example 89

¹H-NMR (CDCl₃, 400 MHz) δ 1.76 (3H, s), 3.75-3.86 (2H, m), 4.06-4.16 (2H, m), 6.90 (1H, t, J=6.7 Hz), 7.08 (1H, s), 7.35 (1H, dd, J=6.7, 1.2 Hz), 8.44 (1H, d, J=6.7 Hz).

Example 90

LRMS (EI⁺) 246 [M⁺]
¹H-NMR (CDCl₃, 400 MHz) δ 0.89 (3H, t, J=7.3 Hz), 1.37 (3H, t, J=7.3 Hz), 2.07 (2H, q, J=7.3 Hz), 2.86 (2H, q, J=7.3 Hz), 3.80-3.84 (2H, m), 4.05-4.08 (2H, m), 6.54 (1H, s), 6.64 (1H, t, J=7.3 Hz), 7.13-7.15 (1H, m), 8.32 (1H, d, J=7.3 Hz).

Example 91

4-t-butyldimethylsilyloxymethyl-2-trifluoromethyl-pyrazolo[1,5-a]pyridine

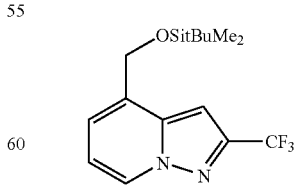

The compound of Example 64 (5.17 g, crude product) was dissolved in DMF (100 mL). To this solution, imidazole (4.89 g) and t-butyldimethylsilyl chloride (4.33 g) were added and the mixture was stirred at room temperature for 1.5 hours. Subsequently, water was added and the mixture was extracted with ethyl acetate. The organic layer was washed sequentially with water and saturated brine and dried over anhydrous sodium sulfate. Evaporation of the solvent and subsequent purification by silica gel column chromatography (hexane: ethyl acetate=9:1) afforded the title compound as a yellow oil (3.42 g).

LRMS (EI$^+$): 330 [M$^+$]

$^1$H-NMR (400 MHz, CDCl$_3$): δ 0.14 (6H, s), 0.96 (9H, s), 4.90 (2H, s), 6.78 (1H, s), 6.93 (1H, t, J=7.3 Hz), 7.28 (1H, m), 8.41 (1H, d, J=7.3 Hz).

Example 92

4-t-butyldimethylsilyloxymethyl-2-trifluoromethyl-7-iodo-pyrazolo[1,5-a]pyridine

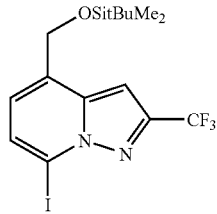

The compound of Example 94 (3.42 g) was dissolved in tetrahydrofuran (30.0 mL) in an argon atmosphere. While the solution was kept at −78° C., 1.59 mol/L n-butyl lithium/n-hexane solution (8.50 mL) was added dropwise and the mixture was stirred for 1 hour. With the mixture kept at −78° C., a solution of 1,2-diiodoethane (3.52 g) in tetrahydrofuran (30.0 mL) was added and the mixture was stirred for 2 hours. Subsequently, a saturated aqueous sodium bicarbonate solution was added and the mixture was extracted with ethyl acetate. The organic layer was washed sequentially with water and saturated brine and dried over anhydrous sodium sulfate. Evaporation of the solvent and subsequent purification by silica gel column chromatography (hexane:ethyl acetate=19:1) afforded the title compound as a pale yellow powder (4.57 g).

LRMS (EI$^+$): 456 [M$^+$]

$^1$H-NMR (400 MHz, CDCl$_3$): δ 0.14 (6H, s), 0.96 (9H, s), 4.89 (2H, s), 7.01 (1H, s), 7.04 (1H, d, J=7.3 Hz), 7.49 (1H, d, J=7.3 Hz).

Examples 93 through 100

Using the compounds shown in Table 6 and the compound of Example 83, the reactions were carried out as in Example 92 to obtain compounds shown in Table 7 below.

TABLE 7

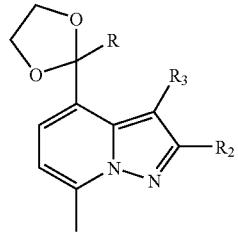

| Examples | R2 | R3 | R | Nature |
|---|---|---|---|---|
| 93 | Et | Cl | Me | Reddish powder |
| 94 | H | H | Me | Brown powder |

TABLE 7-continued

| Examples | R2 | R3 | R | Nature |
|---|---|---|---|---|
| 95 | Me | H | Me | Yellow oil |
| 96 | Et | H | Me | Reddish oil |
| 97 | Pr | H | Et | Brown powder |
| 98 | cPr | H | Me | Yellow powder |
| 99 | CF$_3$ | H | Me | Pale brown powder |
| 100 | Et | H | Et | Brown oil |

Example 93

$^1$H-NMR (CDCl$_3$, 400 MHz) δ 1.37 (3H, t, J=7.3 Hz), 1.89 (3H, s), 2.92 (2H, q, J=7.3 Hz), 3.77-3.83 (2H, m), 4.08-4.13 (2H, m), 7.09 (1H, d, J=7.3 Hz), 7.24 (1H, d, J=7.3 Hz).

Example 94

$^1$H-NMR (CDCl$_3$, 400 MHz) δ 1.77 (3H, s), 3.75-3.81 (2H, m), 4.08-4.11 (2H, m), 6.99 (1H, d, J=7.3 Hz), 7.04 (1H, d, J=2.1 Hz), 7.32 (1H, d, J=7.3 Hz), 8.06 (1H, d, J=2.1 Hz).

Example 95

$^1$H-NMR (CDCl$_3$, 400 MHz) δ 1.75 (3H, s), 2.55 (3H, s), 3.77-3.80 (2H, m), 4.03-4.10 (2H, m), 6.80 (1H, s), 6.92 (1H, d, J=7.3 Hz), 7.21 (1H, d, J=7.3 Hz).

Example 96

$^1$H-NMR (400 MHz, CDCl$_3$) δ 1.38 (3H, t, J=7.6 Hz), 1.76 (3H, s), 2.93 (2H, q, J=7.6 Hz), 3.77-3.81 (2H, m), 4.06-4.13 (2H, m), 6.83 (1H, s), 6.92 (1H, d, J=7.3 Hz), 7.21 (1H, d, J=7.3 Hz).

Example 97

$^1$H-NMR (CDCl$_3$, 400 MHz) δ 0.89 (3H, t, J=7.3 Hz), 1.04 (3H, t, J=7.3 Hz), 1.78-1.84 (2H, m), 2.04 (2H, q, J=7.3 Hz), 2.85 (2H, t, J=7.3 Hz), 3.78-3.82 (2H, m), 4.04-4.07 (2H, m), 6.80 (1H, s), 6.88 (1H, d, J=7.3 Hz), 7.21 (1H, d, J=7.3 Hz).

Example 98

$^1$H-NMR (CDCl$_3$, 400 MHz): δ 0.89-0.93 (2H, m), 1.04-1.09 (2H, m), 1.73 (3H, s), 2.19-2.23 (1H, m), 3.76-3.79 (2H, m), 4.05-4.09 (2H, m), 6.60 (1H, S), 6.90 (1H, d, J=7.3 Hz), 7.19 (1H, d, J=7.3 Hz).

Example 99

$^1$H-NMR (CDCl$_3$, 400 MHz) δ 1.75 (3H, s), 3.74-3.84 (2H, m), 4.06-4.16 (2H, m), 7.09 (1H, d, J=7.3 Hz), 7.33 (1H, s), 7.47 (1H, d, J=7.3 Hz).

Example 100

LRMS (EI⁺) 372 [M⁺]

¹H-NMR (CDCl₃, 400 MHz) δ 0.89 (3H, t, J=7.3 Hz), 1.37 (3H, t, J=7.3 Hz), 2.06 (2H, q, J=7.3 Hz), 2.92 (2H, q, J=7.3 Hz), 3.79-3.82 (2H, m), 4.04-4.08 (2H, m), 6.81 (1H, s), 6.89 (1H, d, J=7.3 Hz), 7.22 (1H, d, J=7.3 Hz).

Example 101

7-iodo-2-methylthio-4-(tetrahydropyrane-2-yl oxymethyl)-pyrazolo[1,5-a]pyridine

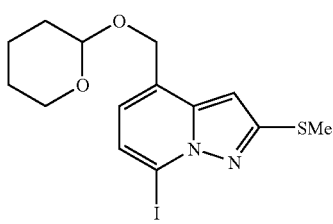

Using the compound of Example 63 containing in separable isomers, the reaction was carried out as in Example 92 to afford the title compound as a brown oil.

¹H-NMR (400 MHz, CDCl₃): δ 1.55-1.87 (6H, m), 2.65 (3H, s), 3.53-3.57 (1H, m), 3.87-3.92 (1H, m), 4.63 (1H, d, J=7.9 Hz), 4.71 (1H, t, J=6.7 Hz), 4.88 (1H, d, J=7.9 Hz), 6.68 (1H, s), 6.87 (1H, d, J=7.3 Hz), 7.21 (1H, d, J=7.3 Hz).

Example 102

2-ethyl-4-(2-ethyl-[1,3]dioxolane-2-yl)-7-methoxycarbonyl-pyrazolo[1,5-a]pyridine

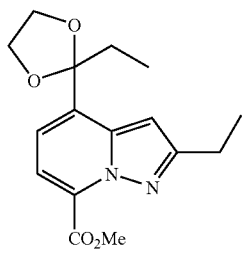

The compound of Example 90 (1.50 g) was dissolved in THF (60.0 mL) in an argon atmosphere. While this solution was kept at −78° C., 1.59 mol/L n-butyl lithium/n-hexane solution (4.40 mL) was added dropwise and the mixture was stirred for 0.5 hours. Subsequently, carbon dioxide was blown into the reaction mixture at −78° C. for 0.5 hours and the mixture was stirred at room temperature for 2 hours. Water was then added and the reaction mixture was extracted twice with chloroform. The organic layer was washed with saturated brine and dried over anhydrous sodium sulfate. Evaporation of the solvent gave a 7-carboxylated form as a yellow solid (1.75 g, crude). The crude carboxylated product (1.75 g, crude) was dissolved in DMF (30.0 mL). To this solution, potassium carbonate (1.25 g) and methyl iodide (0.45 mL) were added and the mixture was stirred for 13 hours at room temperature. Subsequently, water was added and the mixture was extracted with ethyl acetate. The organic layer was washed sequentially with water and saturated brine and dried over anhydrous sodium sulfate. Evaporation of the solvent and purification of the residue by silica gel column chromatography (hexane:ethyl acetate=4:1) afforded the title compound as a yellow oil (1.04 g).

LRMS (EI⁺): 304 [M⁺]

¹H-NMR (400 MHz, CDCl₃): δ 0.89 (3H, t, J=7.3 Hz), 1.38 (3H, t, J=7.3 Hz), 2.06 (2H, q, J=7.3 Hz), 2.95 (2H, q, J=7.3 Hz), 3.79-3.82 (2H, m), 4.03 (3H, s), 4.06-4.09 (2H, m), 6.72 (1H, s), 7.17 (1H, d, J=7.3 Hz), 7.35 (1H, d, J=7.3 Hz).

Example 103

4-acetyl-3-chloro-2-ethyl-7-iodo-pyrazolo[1,5-a]pyridine

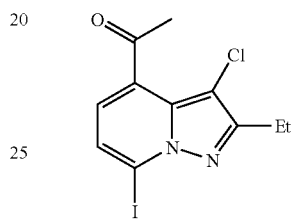

The compound of Example 93 (3.48 g) was dissolved in acetone (40 mL) and water (20 mL). To this solution, p-toluenesulfonic acid monohydrate (169 mg) was added and the mixture was stirred at 50° C. to 70° C. for 25 hours. Subsequently, the reaction was terminated by adding a saturated sodium bicarbonate solution. The mixture was extracted three times with ethyl acetate. The organic layer was washed with saturated brine and dried over sodium sulfate. Evaporation of the solvent under reduced pressure afforded the title compound as a yellow powder (3.48 g).

¹H-NMR (CDCl₃, 400 MHz): δ 1.37 (3H, t, J=7.3 Hz), 2.65 (3H, s), 2.92 (2H, q, J=7.3 Hz), 7.05 (1H, d, J=7.3 Hz), 7.32 (1H, d, J=7.3 Hz).

Examples 104 through 111

Using the compounds of Examples 94 through 100 and Example 102, the reactions were carried out as in Example 103 to obtain compounds shown in Table 8 below.

TABLE 8

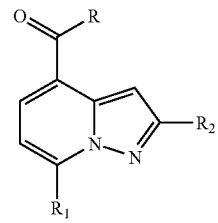

| Examples | R1 | R2 | R | Nature |
|---|---|---|---|---|
| 104 | I | H | Me | Yellow powder |
| 105 | I | Me | Me | Yellow powder |
| 106 | I | Et | Me | Yellow powder |
| 107 | I | Pr | Et | Yellow powder |
| 108 | I | cPr | Me | Yellow powder |

TABLE 8-continued

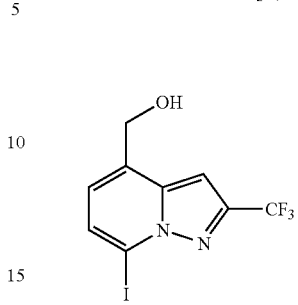

| Examples | R1 | R2 | R | Nature |
|---|---|---|---|---|
| 109 | I | CF₃ | Me | Pale yellow powder |
| 110 | I | Et | Et | Yellow powder |
| 111 | CO₂Me | Et | Et | Yellow powder |

Example 104

¹H-NMR (CDCl₃, 400 MHz) δ 2.70 (3H, s), 7.47 (1H, d, J=7.3 Hz), 7.54 (1H, d, J=7.3 Hz), 7.61 (1H, d, J=2.1 Hz), 8.20 (1H, d, J=2.1 Hz).

Example 105

¹H-NMR (CDCl₃, 400 MHz) δ 2.58 (3H, s), 2.65 (3H, s), 7.34 (1H, d, J=7.3 Hz), 7.36 (1H, s), 7.46 (1H, d, J=7.3 Hz).

Example 106

¹H-NMR (400 MHz, CDCl₃) δ 1.39 (3H, t, J=7.6 Hz), 2.66 (3H, s), 2.95 (2H, q, J=7.6 Hz), 7.35 (1H, d, J=7.3 Hz), 7.40 (1H, s), 7.46 (1H, d, J=7.6 Hz).

Example 107

¹H-NMR (CDCl₃, 400 MHz) δ 1.03 (3H, t, J=7.3 Hz), 1.26 (3H, t, J=7.3 Hz), 1.79-1.85 (2H, m), 2.89 (2H, t, J=7.3 Hz), 3.03 (2H, q, J=7.3 Hz), 7.33 (1H, d, J=7.9 Hz), 7.40 (1H, s), 7.48 (1H, d, J=7.9 Hz).

Example 108

¹H-NMR (CDCl₃, 400 MHz) δ 0.96-0.98 (2H, m), 1.10-1.14 (2H, m), 2.23-2.29 (1H, m), 2.67 (3H, s), 7.19 (1H, s), 7.34 (1H, d, J=7.3 Hz), 7.47 (1H, d, J=7.3 Hz).

Example 109

¹H-NMR (CDCl₃, 400 MHz) δ 2.69 (3H, s), 7.59 (2H, d, J=7.3 Hz), 7.62 (2H, d, J=7.9 Hz), 7.87 (1H, s).

Example 110

LRMS (EI⁺) 328 [M⁺]
¹H-NMR (CDCl₃, 400 MHz) δ 1.26 (3H, t, J=7.3 Hz), 1.38 (3H, t, J=7.3 Hz), 2.95 (2H, q, J=7.3 Hz), 3.04 (2H, q, J=7.3 Hz), 7.34 (1H, d, J=7.3 Hz), 7.41 (1H, s), 7.49 (1H, d, J=7.3 Hz).

Example 111

LRMS (EI⁺) 260 [M⁺]
¹H-NMR (CDCl₃, 400 MHz) δ 1.28 (3H, t, J=7.3 Hz), 1.38 (3H, t, J=7.3 Hz), 2.97 (2H, q, J=7.3 Hz), 3.07 (2H, q, J=7.3 Hz), 4.07 (3H, s), 7.26 (1H, s), 7.34 (1H, d, J=7.3 Hz), 7.76 (1H, d, J=7.3 Hz).

Example 112

2-trifluoromethyl-4-hydroxymethyl-7-iodo-pyrazolo[1,5-a]pyridine

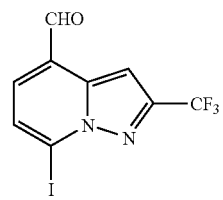

The compound of Example 92 (4.57 g) was dissolved in tetrahydrofuran (50.0 mL). While this solution was chilled in an ice bath, 1.0 mol/L tetran-butyl ammonium fluoride/tetrahydrofuran solution (12.0 mL) was added and the mixture was stirred at room temperature for 1 hour. Subsequently, water was added and the reaction mixture was extracted with ethylacetate. The organic layer was washed sequentially with water and saturated brine and dried over anhydrous sodium sulfate. Evaporation of the solvent and subsequent purification of the residue by silica gel column chromatography (hexane:ethyl acetate=2:1) afforded the title compound as a pale yellow powder (3.26 g).

LRMS (EI⁺): 342 [M⁺].
¹H-NMR (400 MHz, CDCl₃) δ 1.88 (1H, t, J=5.5 Hz), 4.93 (2H, d, J=5.5 Hz), 7.04 (1H, d, J=7.3 Hz), 7.11 (1H, s), 7.50 (1H, d, J=7.3 Hz).

Example 113

2-trifluoromethyl-4-formyl-7-iodo-pyrazolo[1,5-a]pyridine

The compound of Example 112 (3.26 g) was dissolved in dichloromethane (50.0 mL). To this solution, activated manganese dioxide (8.29 g) was added and the mixture was stirred at room temperature for 14 hours. Subsequently, the reaction mixture was filtered through Celite and the filtrate was evaporated. Purification of the resulting residue by silica gel column chromatography (hexane:ethyl acetate=4:1) afforded the title compound as a yellow powder (2.97 g).

LRMS (EI⁺): 340 [M⁺]
¹H-NMR (400 MHz, CDCl₃) δ 7.52 (1H, d, J=7.3 Hz), 7.74 (1H, d, J=7.3 Hz), 7.86 (1H, s), 10.1 (1H, s).

Example 114

4-formyl-7-iodo-2-methylthio-pyrazolo[1,5-a]pyridine

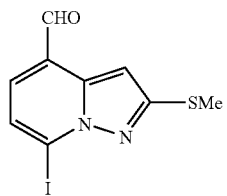

The compound of Example 101 (665 mg, 1.64 mmol) containing inseparable isomers was dissolved in methanol (15 mL). To this solution, p-toluenesulfonic acid (31.2 mg) was added and the mixture was stirred at room temperature for 2 hours. Subsequently, a saturated aqueous sodium bicarbonate solution was added and the mixture was extracted three times with ethyl acetate. The organic layer was washed with saturated brine and dried over sodium sulfate. The solvent was evaporated under reduced pressure and the resulting solid product was dissolved in dichloromethane (20 mL). To this solution, activated manganese dioxide (1.37 g) was added and the mixture was sonicated at room temperature for 3 hours. Subsequently, the mixture was filtered through Celite and the filtrate was evaporated. Purification of the resulting residue by silica gel column chromatography (hexane:ethyl acetate=20:1) afforded the title compound as a yellow powder (333 mg).

$^1$H-NMR (CDCl$_3$, 400 MHz) δ 2.69 (3H, s), 7.36 (3H, d, J=7.3 Hz), 7.43 (1H, d, J=7.3 Hz), 7.44 (1H, s), 10.0 (1H, s).

Example 115

2-trifluoromethyl-4-formyl-7-methoxy-pyrazolo[1,5-a]pyridine

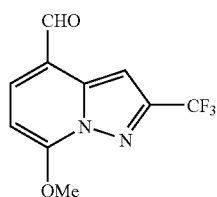

The compound of Example 113 (2.97 g) was dissolved in methanol (50.0 mL). To this solution, sodium methoxide (1.42 g) was added and the mixture was stirred for 2 hours under reflux. After cooling, the solvent was evaporated. Water was added to the resulting residue and the mixture was extracted with ethyl acetate. The organic layer was washed sequentially with water and saturated brine and dried over anhydrous sodium sulfate. The solvent was evaporated and the residue was suspended in diisopropyl ether. The solid product was collected by filtration to afford the title compound as a yellowish green powder (1.93 g).

LRMS (EI$^+$): 244 [M$^+$]

$^1$H-NMR (400 MHz, CDCl$_3$) δ 4.41 (3H, s), 6.43 (1H, d, J=7.3 Hz), 7.65 (1H, s), 7.87 (1H, d, J=7.3 Hz), 9.98 (1H, s)

Examples 116 through 123

Using the compounds of Examples 103 through 109 and Example 114, the reactions were carried out as in Example 115 to obtain compounds shown in Table 9 below.

TABLE 9

| Examples | R2 | R3 | R | Nature |
|---|---|---|---|---|
| 116 | Et | Cl | Me | Yellow powder |
| 117 | H | H | Me | Yellow powder |
| 118 | Me | H | Me | Yellow powder |
| 119 | Et | H | Me | Pale yellow powder |
| 120 | Pr | H | Et | Yellow powder |
| 121 | cPr | H | Me | Yellow powder |
| 122 | CF$_3$ | H | Me | Colorless powder |
| 123 | SMe | H | H | Yellow powder |

Example 116

$^1$H-NMR (CDCl$_3$, 400 MHz) δ 1.36 (3H, t, J=7.3 Hz), 2.64 (3H, s), 2.92 (2H, q, J=7.3 Hz), 4.21 (3H, s), 6.07 (1H, d, J=8.0 Hz), 7.56 (1H, d, J=8.0 Hz).

Example 117

$^1$H-NMR (CDCl$_3$, 400 MHz) δ 2.64 (3H, s), 4.25 (3H, s), 6.16 (1H, d, J=8.0 Hz), 7.37 (1H, d, J=2.4 Hz), 7.90 (1H, d, J=8.0 Hz), 8.12 (1H, d, J=2.4 Hz).

Example 118

$^1$H-NMR (CDCl$_3$, 400 MHz) δ 2.55 (3H, s), 2.62 (3H, s), 4.23 (3H, s), 6.08 (1H, d, J=7.9 Hz), 7.14 (1H, s), 7.85 (1H, d, J=7.9 Hz).

Example 119

$^1$H-NMR (400 MHz, CDCl$_3$) δ 1.38 (3H, t, J=7.6 Hz), 2.62 (3H, s), 2.93 (2H, q, J=7.6 Hz), 4.23 (3H, s), 6.09 (1H, d, J=7.9 Hz), 7.19 (1H, s), 7.86 (1H, d, J=7.9 Hz).

Example 120

$^1$H-NMR (CDCl$_3$, 400 MHz) δ 1.00 (3H, t, J=7.3 Hz), 1.26 (3H, t, J=7.3 Hz), 1.78-1.84 (2H, m), 2.87 (2H, t, J=7.3 Hz), 3.00 (2H, q, J=7.3 Hz), 4.22 (3H, s), 6.07 (1H, d, J=7.9 Hz), 7.19 (1H, s), 7.88 (1H, d, J=7.9 Hz).

Example 121

$^1$H-NMR (CDCl$_3$, 400 MHz) δ 0.90-0.94 (2H, m), 1.04-1.08 (2H, m), 2.20-2.26 (1H, m), 2.60 (3H, s), 4.22 (3H, s), 6.06 (1H, d, J=8.2 Hz), 6.94 (1H, s), 7.83 (1H, d, J=8.2 Hz).

Example 122

2.65 (3H, s), 4.28 (3H, s), 6.31 (1H, d, J=7.9 Hz), 7.67 (1H, s), 7.98 (1H, d, J=7.9 Hz).

Example 123

$^1$H-NMR (CDCl$_3$, 400 MHz) δ 2.66 (3H, s), 4.25 (3H, s), 6.20 (1H, d, J=7.9 Hz), 7.22 (1H, s), 7.72 (1H, s), 7.72 (1H, d, J=7.9 Hz), 9.91 (1H, s).

Example 124

2-ethyl-7-methylthio-4-propionyl-pyrazolo[1,5-a]pyridine

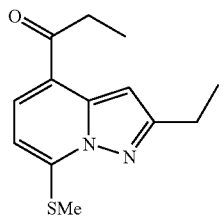

The compound of Example 110 (400 mg) was dissolved in DME (10.0 mL). To this solution, sodium thiomethoxide (128 mg) was added and the mixture was stirred at 60° C. for 1.5 hours. Subsequently, water was added and the reaction mixture was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=4:1) afforded the title compound as a yellow powder (253 mg).

LRMS (EI$^+$): 248 [M$^+$]
$^1$H-NMR (400 MHz, CDCl$_3$) δ 1.27 (3H, t, J=7.3 Hz), 1.38 (3H, t, J=7.3 Hz), 2.66 (3H, s), 2.94 (2H, q, J=7.3 Hz), 3.04 (2H, q, J=7.3 Hz), 6.52 (1H, d, J=8.0 Hz), 7.20 (1H, s), 7.82 (1H, d, J=8.0 Hz).

Example 125

7-dimethylamino-2-ethyl-4-propionyl-pyrazolo[1,5-a]pyridine

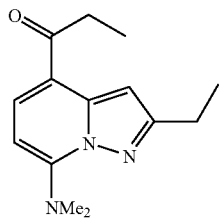

The compound of Example 110 (400 mg) was dissolved in 2.00 mol/L dimethylamine/methanol solution (6.10 mL) and the mixture was stirred at 60° C. for 7 hours. Evaporation of the solvent and purification of the residue by silica gel column chromatography (hexane:ethyl acetate=5:1) afforded the title compound as a yellow oil (289 mg).

LRMS (EI$^+$): 245 [M$^+$]
$^1$H-NMR (400 MHz, CDCl$_3$) δ 1.25 (3H, t, J=7.3 Hz), 1.38 (3H, t, J=7.3 Hz), 2.91 (2H, q, J=7.3 Hz), 2.98 (2H, q, J=7.3 Hz), 3.25 (6H, s), 6.04 (1H, d, J=8.0 Hz), 7.21 (1H, s), 7.82 (1H, d, J=8.0 Hz).

Example 126

2-ethyl-7-methylamino-4-propionyl-pyrazolo[1,5-a]pyridine

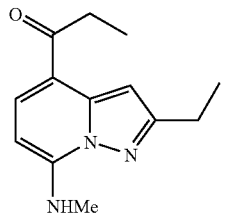

The compound of Example 110 (400 mg) was dissolved in 2.00 mol/L methylamine/THF solution (6.10 mL) and the mixture was stirred at 60° C. for 10 hours. Subsequently, the solvent was evaporated and the resulting residue was again dissolved in 2.00 mol/L methylamine/THF solution (6.10 mL) and the mixture was stirred at 60° C. for another 4 hours. Evaporation of the solvent and subsequent purification of the residue by silica gel column chromatography (hexane:ethyl acetate=4:1) afforded the title compound as a yellow powder (209 mg).

LRMS (EI$^+$): 231 [M$^+$]
$^1$H-NMR (400 MHz, CDCl$_3$) δ 1.25 (3H, t, J=7.3 Hz), 1.37 (3H, t, J=7.3 Hz), 2.86 (2H, q, J=7.3 Hz), 2.96 (2H, q, J=7.3 Hz), 3.15 (3H, d, J=5.5 Hz), 5.82 (1H, d, J=8.0 Hz), 6.54 (1H, brs), 7.14 (1H, s), 7.89 (1H, d, J=8.0 Hz).

Example 127

N-t-butoxycarbonyl-2-ethyl-7-methylamino-4-propionyl-pyrazolo[1,5-a]pyridine

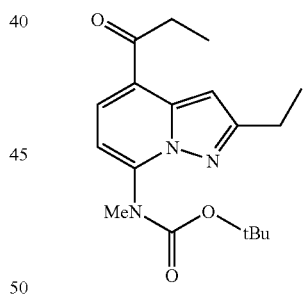

The compound of Example 126 (208 mg) was dissolved in acetonitrile (10.0 mL). To this solution, di-tert-butyl-di-carbonate (236 mg) and a catalytic amount of 4-dimethylaminopyridine were added and the mixture was stirred for 6 hours under reflux. Subsequently, water was added and the mixture was extracted with ethyl acetate. The organic layer was washed with saturated brine and dried over anhydrous sodium sulfate. Evaporation of the solvent and subsequent purification of the residue by silica gel column chromatography (hexane:ethyl acetate=5:1) afforded the title compound as a yellow powder (298 mg).

LRMS (EI$^+$): 331 [M$^+$]
$^1$H-NMR (400 MHz, CDCl$_3$) δ 1.27 (3H, t, J=7.3 Hz), 1.31 (9H, s), 1.36 (3H, t, J=7.3 Hz), 2.90 (2H, q, J=7.3 Hz), 3.05 (2H, q, J=7.3 Hz), 3.35 (3H, s), 6.66 (1H, d, J=8.0 Hz), 7.20 (1H, s), 7.80 (1H, d, J=8.0 Hz).

Example 128

2-ethyl-7-(morpholine-4-yl)-4-propionyl-pyrazolo[1,5-a]pyridine

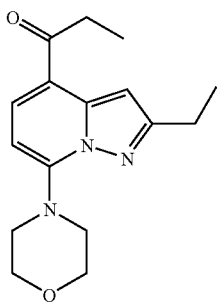

The compound of Example 110 (210 mg) was dissolved in DMF (10.0 mL). To this solution, morpholine (0.56 mL) was added and the mixture was stirred at 60° C. for 3 hours. Subsequently, water was added and the mixture was extracted with ethyl acetate. The organic layer was washed sequentially with water and saturated brine and dried over sodium sulfate. Evaporation of the solvent and subsequent purification of the residue by silica gel column chromatography (hexane:ethyl acetate=4:1) afforded the title compound as a pale yellow powder (176 mg).

LRMS (EI$^+$): 287 [M$^+$]

$^1$H-NMR (400 MHz, CDCl$_3$) δ 1.25 (3H, t, J=6.7 Hz), 1.37 (3H, t, J=6.7 Hz), 2.90 (2H, q, J=6.7 Hz), 3.00 (2H, q, J=6.7 Hz), 3.64 (2H, t, J=4.9 Hz), 4.00 (2H, t, J=4.9 Hz), 6.10 (1H, d, J=8.0 Hz), 7.22 (1H, s), 7.82 (1H, d, J=8.0 Hz)

Example 129

2-ethyl-7-(piperidine-1-yl)-4-propionyl-pyrazolo[1,5-a]pyridine

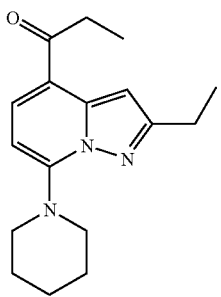

The compound of Example 110 (218 mg) was dissolved in DMF (10.0 mL). To this solution, piperidine (0.66 mL) was added and the mixture was stirred at 60° C. for 5 hours. Subsequently, water was added and the mixture was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=5:1) afforded the title compound as a pale yellow powder (190 mg).

LRMS (EI$^+$): 285 [M$^+$]

$^1$H-NMR (400 MHz, CDCl$_3$) δ 1.25 (3H, t, J=7.3 Hz), 1.38 (3H, t, J=7.3 Hz), 1.71-1.87 (6H, m), 2.90 (2H, q, J=7.3 Hz), 2.98 (2H, q, J=7.3 Hz), 3.57-3.59 (4H, m), 6.10 (1H, d, J=8.0 Hz), 7.20 (1H, s), 7.80 (1H, d, J=8.0 Hz).

Example 130

2-ethyl-4-formyl-7-iodo-pyrazolo[1,5-a]pyridine

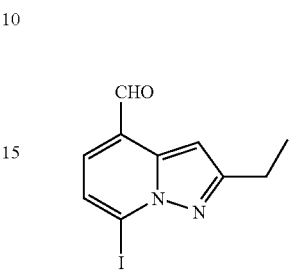

Using the compound of Example 57, the reaction was carried out sequentially following the procedures of Examples 91, 92, 112 and 113 to afford the title compound as a yellow powder.

$^1$H-NMR (400 MHz, CDCl$_3$) δ 1.40 (3H, t, J=7.3 Hz), 2.97 (2H, q, J=7.3 Hz), 7.36 (1H, d, J=7.3 Hz), 7.40 (1H, s), 7.46 (1H, d, J=7.3 Hz), 10.1 (1H, s)

Example 131

7-acetylamino-2-ethyl-4-formyl-pyrazolo[1,5-a]pyridine

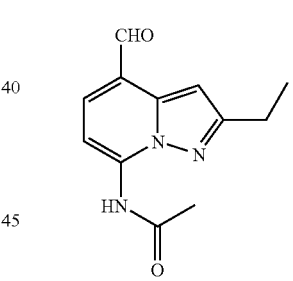

The compound of Example 130 (100 mg), acetamide (23.6 mg), tris(dibenzylideneacetone)dipalladium (15.3 mg), Xantphos (28.9 mg) and cesium carbonate (152 mg) were suspended in dioxane (3.00 mL) in an argon atmosphere. The suspension was stirred at 100° C. for 5 hours. Subsequently, the mixture was diluted with methylene chloride and filtered through Celite. The filtrate was evaporated and the resulting residue was purified by silica gel column chromatography (hexane:ethyl acetate=5:1) to afford the title compound as a yellow powder (62.5 mg).

LRMS (EI$^+$): 231 [M$^+$]

$^1$H-NMR (400 MHz, CDCl$_3$) δ 1.39 (3H, t, J=7.3 Hz), 2.42 (3H, s), 2.90 (2H, q, J=7.3 Hz), 7.16 (1H, s), 7.74 (1H, d, J=8.0 Hz), 7.82 (1H, d, J=8.0 Hz), 9.56 (1H, brs), 9.95 (1H, brs).

Example 132

2-ethyl-4-formyl-7-phenyl-pyrazolo[1,5-a]pyridine

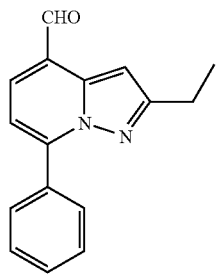

The compound of Example 130 (50.0 mg), phenylboric acid (22.4 mg), tris(dibenzylideneacetone)dipalladium (3.1 mg), tri-n-butylphosphine (17.0 µL) and cesium carbonate (65.3 mg) were suspended in dioxane in an argon atmosphere. The suspension was stirred at 80° C. for 6.5 hours. Subsequently, the reaction mixture was diluted with methylene chloride and filtered through Celite. The filtrate was evaporated and the resulting residue was purified by silica gel column chromatography (hexane:ethyl acetate=9:1) to afford the title compound as a yellow oil (38.7 mg).

LRMS (EI$^+$): 250 [M$^+$]

$^1$H-NMR (400 MHz, CDCl$_3$) δ 1.37 (3H, t, J=7.3 Hz), 2.91 (2H, q, J=7.3 Hz), 6.93 (1H, d, J=7.3 Hz), 7.26 (1H, s), 7.54-7.55 (3H, m), 7.73 (1H, d, J=7.3 Hz), 7.99-8.01 (2H, m), 10.1 (1H, s).

Example 133

7-cyano-2-ethyl-4-propionyl-pyrazolo[1,5-a]pyridine

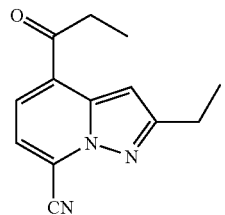

The compound of Example 110 (300 mg) was dissolved in DMF (10.0 mL). To this solution, copper cyanide (147 mg) was added and the mixture was stirred at 100° C. for 3 hours. Subsequently, additional copper cyanide (16.4 mg) was added and the mixture was stirred at 100° C. for 1 hour. The reaction mixture was diluted with water and filtered through Celite. The filtrate was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=4:1) afforded the title compound as a yellow powder (175 mg).

LRMS (EI$^+$): 227 [M$^+$]

$^1$H-NMR (400 MHz, CDCl$_3$) δ 1.28 (3H, t, J=7.3 Hz), 1.39 (3H, t, J=7.3 Hz), 2.96 (2H, q, J=7.3 Hz), 3.07 (2H, q, J=7.3 Hz), 7.25 (1H, s), 7.30 (1H, d, J=7.3 Hz), 7.74 (1H, d, J=7.3 Hz).

Example 134

2-trifluoromethyl-4-(1-hydroxyethyl)-7-methoxy-pyrazolo[1,5-a]pyridine

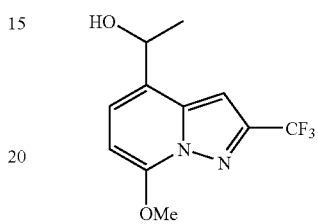

The compound of Example 115 (1.63 g) was dissolved in THF (70.0 mL) in an argon atmosphere. While the solution was kept at −78° C., 0.90 mol/L methyl magnesium bromide/THF solution (8.90 mL) was added dropwise and the mixture was stirred for 1.5 hours as it was allowed to gradually warm to −40° C. Subsequently, a saturated aqueous solution of ammonium chloride was added and the mixture was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=1:1) afforded the title compound as a white powder (1.64 g).

LRMS (EI$^+$): 260 [M$^+$]

$^1$H-NMR (400 MHz, CDCl$_3$) δ 1.62 (3H, d, J=6.1 Hz), 1.92 (1H, d, J=3.7 Hz), 4.17 (3H, s), 5.15-5.17 (1H, m), 6.22 (1H, d, J=8.0 Hz), 6.93 (1H, s), 7.28 (1H, d, J=8.0 Hz).

Example 135

4-(1-hydroxypropyl)-7-methoxy-2-trifluoromethyl-pyrazolo[1,5-a]pyridine

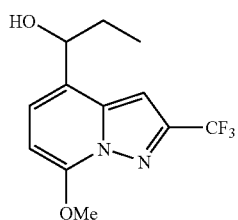

The compound of Example 115 was reacted with ethyl magnesium bromide as in Example 134 to afford the title compound as a pale yellow oil.

$^1$H-NMR (400 MHz, CDCl$_3$) δ 0.96 (3H, t, J=7.6 Hz), 1.88-1.96 (3H, m), 4.17 (3H, s), 4.87 (1H, t, J=6.4 Hz), 6.23 (1H, d, J=7.6 Hz), 6.93 (1H, s), 7.25 (1H, d, J=7.6 Hz).

Example 136

4-(1-hydroxybutyl)-7-methoxy-2-trifluoromethyl-pyrazolo[1,5-a]pyridine

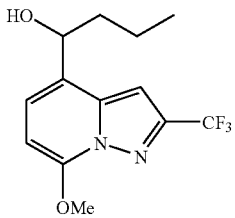

The compound of Example 115 (300 mg) was dissolved in tetrahydrofuran (12.0 mL) in an argon atmosphere. While this solution was kept at −78° C., 1.04 mol/L n-propyl magnesium bromide/tetrahydrofuran solution (1.40 mL) was added dropwise and the mixture was stirred for 3 hours as it was allowed to gradually warm to −40° C. Subsequently, a saturated aqueous solution of ammonium chloride was added and the mixture was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=1:1) afforded the title compound as a yellow oil (265 mg).

LRMS (EI$^+$): 288 [M$^+$]

$^1$H-NMR (400 MHz, CDCl$_3$) δ 0.96 (3H, t, J=7.3 Hz), 1.35-1.49 (2H, m), 1.84-1.87 (2H, m), 1.95 (1H, d, J=3.1 Hz), 4.17 (3H, s), 4.93-4.97 (1H, m), 6.22 (1H, d, J=7.3 Hz), 6.92 (1H, s), 7.25 (1H, d, J=7.3 Hz).

Example 137

4-acetyl-2-trifluoromethyl-7-methoxy-pyrazolo[1,5-a]pyridine

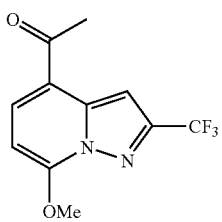

The compound of Example 134 (1.64 g) was dissolved in dichloromethane (30.0 mL). To this solution, activated manganese dioxide (5.48 g) was added and the mixture was stirred at room temperature for 16 hours. Subsequently, a second portion of activated manganese dioxide (5.48 g) was added and the mixture was stirred at room temperature for 10 hours. A third portion of activated manganese dioxide (5.48 g) was then added and the mixture was stirred at room temperature for 10.5 hours. Finally, a fourth portion of activated manganese dioxide (2.74 g) was added and the mixture was stirred for 13.5 hours. Subsequently, the reaction mixture was filtered through Celite and the filtrate was evaporated to afford the title compound as a pale yellow powder (1.08 g).

LRMS (EI$^+$): 258[M$^+$]

$^1$H-NMR (400 MHz, CDCl$_3$) δ 2.65 (3H, s), 4.28 (3H, s), 6.32 (1H, d, J=8.0 Hz), 7.68 (1H, s), 7.99 (1H, d, J=8.0 Hz).

Example 138

4-butyryl-7-methoxy-2-trifluoromethyl-pyrazolo[1,5-a]pyridine

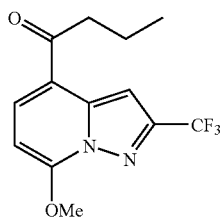

The compound of Example 136 (265 mg) was dissolved in dichloromethane (5.00 mL). To this solution, activated manganese dioxide (801 mg) was added and the mixture was stirred at room temperature for 16 hours. Subsequently, a second portion of activated manganese dioxide (801 mg) was added and the mixture was stirred at room temperature for 10 hours. A third portion of activated manganese dioxide (801 mg) was then added and the mixture was stirred at room temperature for 10.5 hours. Finally, a fourth portion of activated manganese dioxide (400 mg) was added and the mixture was stirred for 13.5 hours. Subsequently, the reaction mixture was filtered through Celite and the filtrate was evaporated to afford the title compound as a pale yellow powder (174 mg).

LRMS (EI$^+$): 286[M$^+$]

$^1$H-NMR (400 MHz, CDCl$_3$) δ 1.04 (3H, t, J=7.3 Hz), 1.82 (2H, q, J=7.3 Hz), 2.97 (2H, t, J=7.3 Hz), 4.27 (3H, s), 6.31 (1H, d, J=8.0 Hz), 7.70 (1H, s), 8.00 (1H, d, J=8.0 Hz).

Example 139

7-methoxy-4-propionyl-2-trifluoromethyl-pyrazolo[1,5-a]pyridine

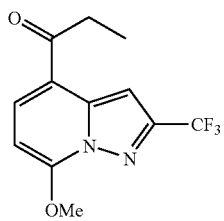

Using the compound of Example 135, the reaction was carried out as in Example 138 to afford the title compound as a colorless powder.

The compound of Example 135 (32.1 g) was dissolved in DMSO (780 mL) in an argon atmosphere. To this solution, triethylamine (163 mL) and sulfur trioxide-pyridine complex (93.1 g) were sequentially added and the mixture was stirred at room temperature for 1 hour. The reaction mixture was then poured into ice water and the resulting solid product was collected by filtration. The product was washed with water and dissolved in ethyl acetate. The solution was dried over anhydrous sodium sulfate. Evaporation of the solvent afforded the title compound as a colorless powder (24.0 g).

$^1$H-NMR (400 MHz, CDCl$_3$) δ 1.28 (3H, t, J=7.3 Hz), 3.03 (2H, q, J=7.3 Hz), 4.27 (3H, s), 6.31 (1H, d, J=8.0 Hz), 7.70 (1H, s), 8.01 (1H, d, J=8.0 Hz).

Example 140

7-methoxy-2-methoxymethyl-4-propionyl-pyrazolo[1,5-a]pyridine

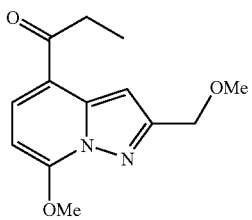

The compound of Example 52 was oxidized as in Example 137 and the resulting product was alkylated as in Example 135. Oxidizing the alkylated product as in Example 137 afforded the title compound as a colorless powder.

$^1$H-NMR (400 MHz, CDCl$_3$) δ 1.26 (3H, t, J=7.3 Hz), 3.02 (2H, q, J=7.3 Hz), 3.45 (3H, s), 4.23 (3H, s), 4.75 (2H, s), 6.14 (1H, d, J=7.9 Hz), 7.39 (1H, s), 7.92 (1H, d, J=7.9 Hz).

Example 141

2-difluoromethyl-7-methoxy-4-propionyl-pyrazolo[1,5-a]pyridine

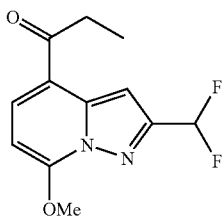

The compound of Example 51 was oxidized as in Example 137 and the resulting product was alkylated as in Example 135. Oxidizing the alkylated product as in Example 137 afforded the title compound as a colorless powder.

LRMS (EI$^+$): 254 [M$^+$]

$^1$H-NMR (400 MHz, CDCl$_3$) δ 1.27 (3H, t, J=7.3 Hz), 3.03 (2H, q, J=7.3 Hz), 4.27 (3H, s), 6.26 (1H, d, J=8.0 Hz), 6.94 (1H, t, J=55.0 Hz), 7.62 (1H, s), 7.98 (1H, d, J=8.0 Hz).

Example 142

7-methoxy-4-propionyl-2-(tetrahydropyranyl-2-yl oxymethyl)-pyrazolo[1,5-a]pyridine

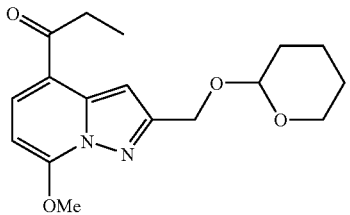

The compound of Example 53 was oxidized as in Example 137 and the resulting product was alkylated as in Example 135. Oxidizing the alkylated product as in Example 137 afforded the title compound as a pale yellow powder.

$^1$H-NMR (400 MHz, CDCl$_3$,) δ 1.26 (3H, t, J=7.3 Hz), 1.48-1.80 (5H, m), 1.81-1.95 (1H, m), 3.02 (2H, q, J=7.3 Hz), 3.53-3.61 (1H, m), 3.91-4.00 (1H, m), 4.23 (3H, s), 4.80 (1H, d, J=12.8 Hz), 4.81-4.84 (1H, m), 5.03 (1H, d, J=12.8 Hz), 6.13 (1H, d, J=7.9 Hz), 7.42 (1H, s), 7.91 (1H, d, J=7.9 Hz).

Example 143

7-acetylamino-2-ethyl-4-propionyl-pyrazolo[1,5-a]pyridine

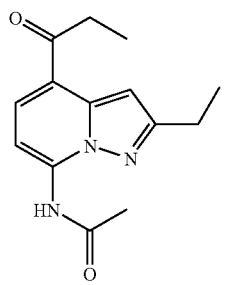

The compound of Example 131 was alkylated as in Example 135. Oxidizing the alkylated product as in Example 137 afforded the title compound as a yellow powder.

LRMS (EI$^+$): 259[M$^+$]

$^1$H-NMR (400 MHz, CDCl$_3$) δ 1.26 (3H, t, J=7.3 Hz), 1.38 (3H, t, J=7.3 Hz), 2.40 (3H, s), 2.89 (2H, q, J=7.3 Hz), 3.03 (2H, q, J=7.3 Hz), 7.20 (1H, s), 7.71 (1H, d, J=8.0 Hz), 7.90 (1H, d, J=8.0 Hz), 9.55 (1H, brs).

Example 144

2-ethyl-7-phenyl-4-propionyl-pyrazolo[1,5-a]pyridine

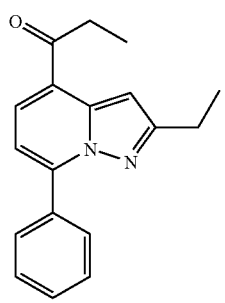

Using the compound of Example 145, the reaction was carried out as in Example 143 to afford the title compound as a yellow powder.

LRMS (EI$^+$): 278 [M$^+$]

$^1$H-NMR (400 MHz, CDCl$_3$) δ 1.29 (3H, t, J=7.3 Hz), 1.36 (3H, t, J=7.3 Hz), 2.89 (2H, q, J=7.3 Hz), 3.08 (2H, q, J=7.3

Hz), 6.82 (1H, d, J=7.3 Hz), 7.28 (1H, s), 7.52-7.53 (3H, m), 7.87 (1H, d, J=7.3 Hz), 7.96-7.99 (2H, m).

Example 145

3-chloro-2-ethyl-7-methoxy-4-propionyl-pyrazolo[1,5-a]pyridine

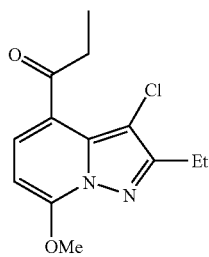

The compound of Example 116 (1.96 g) was dissolved in tetrahydrofuran (80 mL). While this solution was kept at −78° C., 1 mol/L lithium bis(trimethylsilyl)amide/tetrahydrofuran solution (9.11 mL) was added and the mixture was stirred at −78° C. to room temperature for 30 min. Iodomethane (567 μL) was added at −78° C. and the mixture was stirred at −78° C. to room temperature for 5 hours. Subsequently, the reaction was terminated by adding a saturated aqueous solution of ammonium chloride and the mixture was extracted three times with ethyl acetate. The organic layer was washed with saturated brine and dried over sodium sulfate. Evaporation of the solvent under reduced pressure and purification by silica gel column chromatography (hexane:ethyl acetate=1:4) afforded the title compound as a yellow powder (495.6 mg).

$^1$H-NMR (CDCl$_3$, 400 MHz) δ 1.24 (6H, d, J=6.7 Hz), 1.36 (3H, t, J=7.3 Hz), 2.92 (2H, q, J=7.3 Hz), 3.39 (1H, m), 4.20 (3H, s), 6.07 (1H, d, J=7.9 Hz), 7.38 (1H, d, J=7.9 Hz).

Examples 146 through 149

Using the compounds of Examples 117, 118, 121 and 122, the reactions were carried out as in Example 143 to obtain compounds shown in Table 10 below.

TABLE 10

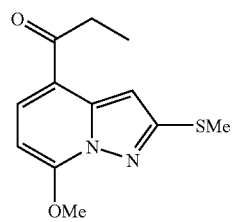

| Examples | R2 | Nature |
|---|---|---|
| 146 | H | Yellow powder |
| 147 | Me | Yellow powder |
| 148 | cPr | Yellow powder |
| 149 | CF$_3$ | Colorless powder |

Example 146

$^1$H-NMR (CDCl$_3$, 400 MHz) δ 1.27 (3H, t, J=7.3 Hz), 3.03 (2H, q, J=7.3 Hz), 4.25 (3H, s), 6.15 (1H, d, J=7.9 Hz), 7.38 (1H, d, J=1.8 Hz), 7.93 (1H, d, J=7.9 Hz), 8.12 (1H, d, J=1.8 Hz).

Example 147

$^1$H-NMR (CDCl$_3$, 400 MHz) δ 1.25 (1H, t, J=7.3 Hz), 2.55 (3H, s), 3.00 (2H, q, J=7.3 Hz), 4.22 (3H, s), 6.08 (1H, d, J=7.9 Hz), 7.15 (1H, s), 7.88 (1H, d, J=7.9 Hz).

Example 148

$^1$H-NMR (CDCl$_3$, 400 MHz) δ 0.91-0.93 (2H, m), 1.05-1.08 (2H, m), 1.25 (3H, t, J=7.3 Hz), 2.21-2.26 (1H, m), 2.99 (2H, q, J=7.3 Hz), 4.22 (3H, s), 6.05 (1H, d, J=7.9 Hz), 6.96 (1H, s), 7.86 (1H, d, J=7.9 Hz).

Example 149

Same as in Example 139

Example 150

4-propionyl-7-methoxy-3-methylthio-pyrazolo[1,5-a]pyridine

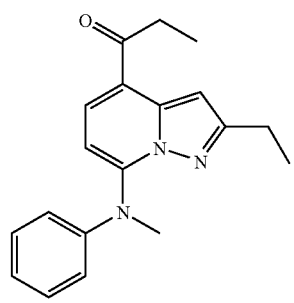

The compound of Example 123 was alkylated as in Example 135. Oxidizing the alkylated product as in Example 137 afforded the title compound as a yellow powder.

$^1$H-NMR (400 MHz, CDCl$_3$) δ 1.27 (3H, t, J=7.3 Hz), 2.66 (3H, s), 3.01 (2H, q, J=7.3 Hz), 4.23 (3H, s), 6.10 (1H, d, J=7.9 Hz), 7.30 (1H, s), 7.90 (1H, d, J=7.9 Hz).

Example 151

N-methyl-2-ethyl-7-phenylamino-4-propionyl-pyrazolo[1,5-a]pyridine

The following compounds were suspended in toluene in an argon atmosphere (6.00 mL): the compound of Example 110 (200 mg), N-methylaniline (80.0 μL), tris(dibenzylideneacetone)dipalladium (27.9 mg), 1,3-diphenylphosphino propane (25.2 mg) and sodium t-butoxide (82.1 mg). The suspension was stirred at 80° C. for 16 hours. Subsequently, the reaction mixture was diluted with ethyl acetate and filtered through Celite. The filtrate was washed sequentially with water, diluted hydrochloric acid and saturated brine and dried over anhydrous sodium sulfate. Evaporation of the solvent and subsequent purification of the residue by silica gel column chromatography (hexane:ethyl acetate=9:1) afforded the title compound as a yellow oil (54.5 mg).

LRMS (EI$^+$): 307[M$^+$]

$^1$H-NMR (400 MHz, CDCl$_3$) δ 1.26 (3H, t, J=7.3 Hz), 1.30 (3H, t, J=7.3 Hz), 2.85 (2H, q, J=7.3 Hz), 3.01 (2H, q, J=7.3 Hz), 3.62 (3H, s), 6.32 (1H, d, J=8.0 Hz), 7.05-7.09 (3H, m), 7.23 (1H, s), 7.27-7.31 (2H, m), 7.77 (1H, d, J=8.0 Hz).

Example 152

2-ethyl-4-(2-ethyl-[1,3]dioxolane-2-yl)-7-formyl-pyrazolo[1,5-a]pyridine

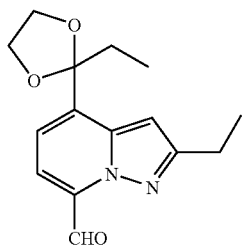

The compound of Example 90 (415 mg) was dissolved in THF (10.0 mL) in a stream of argon gas. While the solution was kept at −78° C., 1.54 mol/L n-butyl lithium/hexane solution (1.40 mL) was added dropwise. The resulting mixture was stirred at the same temperature for 30 min. Subsequently, ethyl formate (164 μL) in THF (10.0 mL) was added dropwise at −78° C. and the mixture was stirred for 3 hours as it was allowed to gradually warm to room temperature. This was followed by addition of a saturated aqueous solution of ammonium chloride. The mixture was then extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=9:1) afforded the title compound as a yellow solid (322 mg).

LRMS (EI$^+$): 274 [M$^+$]

$^1$H-NMR (400 MHz, CDCl$_3$) δ 0.91 (3H, t, J=7.3 Hz), 1.40 (3H, t, J=7.3 Hz), 2.07 (2H, q, J=7.3 Hz), 2.92 (2H, q, J=7.3 Hz), 3.08-3.84 (2H, m), 4.07-4.10 (2H, m), 6.74 (1H, s), 7.25 (1H, d, J=7.3 Hz), 7.38 (1H, d, J=7.3 Hz), 10.9 (1H, s)

Example 153

2-ethyl-4-(2-ethyl-[1,3]dioxolane-2-yl)-7-(1-hydroxyethyl)-pyrazolo[1,5-a]pyridine

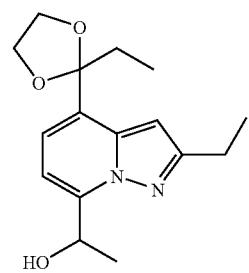

The compound of Example 152 (321 mg) was dissolved in THF (12.0 mL) in an argon atmosphere. While the solution was kept at −78° C., 0.90 mol/L methyl magnesium bromide/THF solution (1.70 mL) was added dropwise and the mixture was stirred for 3.5 hours as it was allowed to gradually warm to room temperature. Subsequently, a saturated aqueous solution of ammonium chloride was added and the mixture was extracted with ethyl acetate. The organic layer was washed sequentially with water and saturated brine and dried over anhydrous sodium sulfate. Evaporation of the solvent afforded the title compound as a yellow oil (340 mg).

LRMS (EI$^+$): 290[M$^+$]

$^1$H-NMR (400 MHz, CDCl$_3$) δ 0.89 (3H, t, J=7.3 Hz), 1.37 (3H, t, J=7.3 Hz), 1.73 (3H, d, J=6.1 Hz), 2.06 (2H, q, J=7.3 Hz), 2.87 (2H, q, J=7.3 Hz), 3.78-3.82 (2H, m), 4.04-4.08 (2H, m), 5.28 (1H, q, J=6.1 Hz), 5.73 (1H, brs), 6.58 (1H, s), 6.61 (1H, d, J=8.0 Hz), 7.17 (1H, d, J=8.0 Hz).

Example 154

2-ethyl-7-(1-hydroxyethyl)-4-propionyl-pyrazolo[1,5-a]pyridine

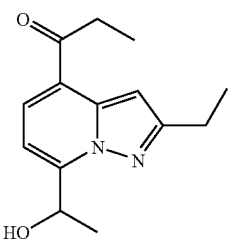

Using the compound of Example 153, the reaction was carried out as in Example 103 to afford the title compound as a yellow oil.

LRMS (EI$^+$): 246[M$^+$]

$^1$H-NMR (400 MHz, CDCl$_3$) δ 1.27 (3H, t, J=7.3 Hz), 1.38 (3H, t, J=7.3 Hz), 1.75 (3H, d, J=6.1 Hz), 2.91 (2H, q, J=7.3 Hz), 3.05 (2H, q, J=7.3 Hz), 5.34 (1H, q, J=6.1 Hz), 5.46 (1H, brs), 6.73 (1H, d, J=8.0 Hz), 7.18 (1H, s), 7.82 (1H, d, J=8.0 Hz).

Example 155

7-(1-t-butyldimethylsiloxyethyl)-2-ethyl-4-propionyl-pyrazolo[1,5-a]pyridine

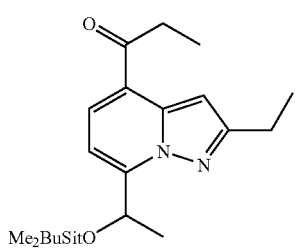

Using the compound of Example 154, the reaction was carried out as in Example 91 to afford the title compound as a yellow oil.

LRMS (EI+): 360[M+]

$^1$H-NMR (400 MHz, CDCl$_3$) δ 0.05 (3H, s), 0.14 (3H, s), 0.96 (9H, s), 1.27 (3H, t, J=7.3 Hz), 1.37 (3H, t, J=7.3 Hz), 1.60 (3H, d, J=6.1 Hz), 2.90 (2H, q, J=7.3 Hz), 3.05 (2H, q, J=7.3 Hz), 5.65 (1H, q, J=6.1 Hz), 7.00 (1H, d, J=7.3 Hz), 7.19 (1H, s), 7.86 (1H, d, J=7.3 Hz).

Example 156 t-butyl 4-(3-chloro-2-ethyl-7-methoxy-pyrazolo[1,5-a]pyridine-4-yl)-3-methyl-4-oxobutyrate

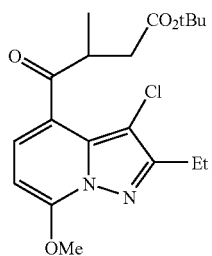

The compound of Example 145 (280 mg) was dissolved in tetrahydrofuran (12 mL) in an argon atmosphere. While the solution was kept at −78° C., 1 mol/L lithium bis(trimethylsilyl)amide/tetrahydrofuran solution (1.23 mL) was added and the mixture was stirred at −78° C. to room temperature for 30 min. t-butyl bromoacetate (181.6 μL) was then added at −78° C. and the mixture was stirred at room temperature for 7 hours. Subsequently, the reaction was terminated by adding a saturated aqueous solution of ammonium chloride and the mixture was extracted three times with ethyl acetate. The organic layer was washed with saturated brine and dried over sodium sulfate. Evaporation of the solvent under reduced pressure and purification by silica gel column chromatography (hexane:ethyl acetate=1:1) afforded the title compound as a green powder (237.1 mg).

$^1$H-NMR (CDCl$_3$, 400 MHz) δ 1.22 (3H, d, J=7.3 Hz), 1.36 (3H, t, J=7.3 Hz), 1.43 (9H, s), 2.39 (1H, dd, J=5.5, 17.1 Hz), 2.92 (1H, dd, J=7.3, 17.1 Hz), 2.93 (2H, q, J=7.3 Hz), 3.73-3.78 (1H, m), 4.22 (3H, s), 6.11 (1H, d, J=8.0 Hz), 7.70 (1H, d, J=8.0 Hz).

Examples 157 through 179

Using the compounds of Examples 119, 120, 124, 125, 127 through 129, 133, 137 (122), 138, 140 through 144, 146 through 148, 149 (139), 150, 151, 155 and 185, the reactions were carried out as in Example 156 to obtain compounds shown in Table 11 below.

TABLE 11

| Examples | R1 | R2 | R4 | Nature |
|---|---|---|---|---|
| 157 | MeO | H | Me | Yellow oil |
| 158 | MeO | Me | Me | Yellow oil |
| 159 | MeO | Et | Me | Yellow oil |
| 160 | MeO | Pr | Me | Yellow oil |
| 161 | MeO | cPr | Me | Yellow oil |
| 162 | MeO | CF$_3$ | Me | Yellow oil |
| 163 | MeO | CF$_3$ | H | Yellow oil |
| 164 | MeO | SMe | Me | Yellow powder |
| 165 | MeO | Et | H | Yellow oil |
| 166 | MeO | CF$_3$ | Et | Yellow oil |
| 167 | MeS | Et | Me | Yellow oil |
| 168 | NMe$_2$ | Et | Me | Yellow oil |
| 169 | NMeBoc | Et | Me | Yellow oil |
| 170 | morpholino | Et | Me | Yellow oil |
| 171 | piperidino | Et | Me | Yellow oil |
| 172 | NHAc | Et | Me | Brown oil |
| 173 | Ph | Et | Me | Yellow oil |
| 174 | MeO | CH$_2$OMe | Me | Yellow oil |
| 175 | MeO | CHF$_2$ | Me | Yellow powder |
| 176 | MeO | CH$_2$OTHP | Me | Yellow powder |
| 177 | CN | Et | Me | Brown oil |
| 178 | NMePh | Et | Me | Yellow oil |
| 179 | CH(OSitBuMe2)Me | Et | Me | Yellow powder |

Example 157

$^1$H-NMR (CDCl$_3$, 400 MHz) δ 1.24 (3H, d, J=7.3 Hz), 1.37 (9H, s), 2.40 (1H, dd, J=5.8, 16.5 Hz), 2.90 (1H, dd, J=8.5, 16.5 Hz), 3.90-3.95 (1H, m), 4.25 (3H, s), 6.18 (1H, d, J=7.9 Hz), 7.36 (1H, d, J=1.8 Hz), 8.01 (1H, d, J=7.9 Hz), 8.11 (1H, d, J=1.8 Hz).

Example 158

$^1$H-NMR (CDCl$_3$, 400 MHz) δ 1.23 (3H, d, J=6.7 Hz), 2.39 (1H, dd, J=5.5, 16.5 Hz), 2.54 (3H, s), 2.89 (1H, dd, J=8.5, 16.5 Hz), 3.88-3.93 (1H, m), 4.23 (3H, s), 6.10 (1H, d, J=7.9 Hz), 7.14 (1H, s), 7.96 (1H, d, J=7.9 Hz).

Example 159

$^1$H-NMR (400 MHz, CDCl$_3$) δ 1.23 (3H, d, J=7.0 Hz), 1.37 (3H, t, J=7.6 Hz), 1.38 (9H, s), 2.39 (1H, dd, J=5.8, 16.5 Hz), 2.87-2.95 (3H, m), 3.89-3.94 (1H, m), 4.23 (3H, s), 6.11 (1H, d, J=7.9 Hz), 7.20 (1H, s), 7.97 (1H, d, J=7.9 Hz).

Example 160

$^1$H-NMR (CDCl$_3$, 400 MHz) δ 1.00 (3H, t, J=7.3 Hz), 1.23 (3H, d, J=6.7 Hz), 1.76-1.85 (2H, m), 2.38 (1H, dd, J=5.5, 16.5 Hz), 2.85-2.93 (3H, m), 3.89-3.94 (1H, m), 4.23 (3H, s), 6.10 (1H, d, J=7.9 Hz), 7.18 (1H, s), 7.97 (1H, d, J=7.9 Hz).

Example 161

$^1$H-NMR (CDCl$_3$, 400 MHz) δ 0.91-0.92 (2H, m), 1.04-1.07 (2H, m), 1.22 (3H, d, J=6.5 Hz), 1.37 (9H, s), 2.21-2.25 (1H, m), 2.37 (1H, dd, J=6.1, 16.5 Hz), 2.88 (1H, 1dd, J=8.6, 16.5 Hz), 3.87-3.92 (1H, m), 4.22 (3H, s), 6.08 (1H, d, J=7.9 Hz), 6.96 (1H, s), 7.95 (1H, d, J=7.9 Hz).

Example 162

$^1$H-NMR (CDCl$_3$, 400 MHz) δ 1.24 (3H, d, J=7.3 Hz), 1.39 (9H, s), 2.42 (1H, dd, J=17.1, 5.5 Hz), 2.93 (1H, dd, J=17.1, 9.2 Hz), 3.86-3.97 (1H, m), 4.28 (3H, s), 6.34 (1H, d, J=7.9 Hz), 7.67 (1H, s), 8.10 (1H, d, J=7.9 Hz).

Example 163

The product was used in the subsequent reaction without further purification.

Example 164

$^1$H-NMR (CDCl$_3$, 400 MHz) δ 1.22 (3H, d, J=7.3 Hz), 1.38 (9H, s), 2.38 (1H, dd, J=5.5, 16.5 Hz), 2.64 (3H, s), 2.89 (1H, dd, J=8.6, 16.5 Hz), 3.87-3.94 (1H, m), 4.22 (3H, s), 6.11 (1H, d, J=7.9 Hz), 7.27 (1H, s), 7.98 (1H, d, J=7.9 Hz).

Example 165

The product was used in the subsequent reaction without further purification.

Example 166

The product was used in the subsequent reaction without further purification.

Example 167

The product was used in the subsequent reaction without further purification.

Example 168

The product was used in the subsequent reaction without further purification.

Example 169

The product was used in the subsequent reaction without further purification.

Example 170

The product was used in the subsequent reaction without further purification.

Example 171

The product was used in the subsequent reaction without further purification.

Example 172

The product was used in the subsequent reaction without further purification.

Example 173

The product was used in the subsequent reaction without further purification.

Example 174

$^1$H-NMR (CDCl$_3$, 400 MHz) δ 1.23 (3H, d, J=6.7 Hz), 1.38 (9H, s), 2.39 (1H, dd, J=16.5, 5.5 Hz), 2.91 (1H, dd, J=16.5, 8.6 Hz), 3.44 (3H, s), 3.84-3.98 (1H, m), 4.24 (3H, s), 4.74 (2H, s), 6.17 (1H, d, J=8.6 Hz), 7.39 (1H, s), 8.00 (1H, d, J=7.9 Hz).

Example 175

$^1$H-NMR (CDCl$_3$, 400 MHz) δ 1.24 (3H, d, J=7.3 Hz), 1.39 (9H, s), 2.41 (1H, dd, J=5.5, 16.5 Hz), 2.93 (1H, dd, J=8.6, 16.5 Hz), 3.87-3.96 (1H, m), 4.27 (3H, s), 6.28 (1H d, J=8.0 Hz), 6.94 (1H, t, J=55.0 Hz), 7.61 (1H, s), 8.07 (1H, d, J=8.0 Hz).

Example 176

$^1$H-NMR (CDCl$_3$, 400 MHz) δ 1.23 (3H, d, J=6.7 Hz), 1.38 (9H, s), 1.50-1.80 (5H, m), 1.81-1.93 (1H, m), 2.39 (1H, dd, J=16.5, 6.1 Hz), 2.90 (1H, dd, J=16.5, 8.6 Hz), 3.52-3.61 (1H, m), 3.86-4.00 (2H, m), 4.24 (3H, s), 4.79 (1H, d, J=12.2 Hz), 4.82 (1H, t, J=3.7 Hz), 5.02 (1H, d, J=12.8 Hz), 6.16 (1H, d, J=7.9 Hz), 7.42 (1H, s), 8.00 (1H, d, J=7.9 Hz).

Example 177

The product was used in the subsequent reaction without further purification.

Example 178

The product was used in the subsequent reaction without further purification.

Example 179

The product was used in the subsequent reaction without further purification.

Example 180

Methyl 3-(2-ethyl-pyrazolo[1,5-a]pyridine-4-yl)-3-oxo-propionate

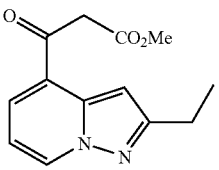

The compound of Example 77 (1.38 g) was dissolved in dimethyl carbonate (20 mL) in an argon atmosphere. To this solution, 60% sodium hydride (520 mg) was added and the mixture was refluxed for 30 min. After cooling, saturated aqueous ammonium chloride was added and the mixture was extracted with ethyl acetate. The organic layer was washed sequentially with water and saturated brine and dried over anhydrous sodium sulfate. Evaporation of the solvent and subsequent purification by silica gel column chromatography (hexane:ethyl acetate=1:1) afforded the title compound as a yellow powder (1.66 g).

$^{1}$H-NMR (400 MHz, CDCl$_3$) δ 1.37 (3H, t, J=7.6 Hz), 2.90 (2H, q, J=7.6 Hz), 3.77 (3H, s), 4.06 (2H, s), 6.77 (1H, t, J=7.0 Hz), 7.16 (1H, s), 7.77 (1H, dd, J=0.9, 7.0 Hz), 8.58 (1H, td, J=0.9, 7.0 Hz).

Example 181

Methyl 3-(2-ethyl-7-methoxy-pyrazolo[1,5-a]pyridine-4-yl)-3-oxopropionate

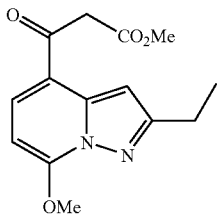

Using the compound of Example 119, the reaction was carried out as in Example 180 to afford the title compound as a yellow powder.

$^{1}$H-NMR (400 MHz, CDCl$_3$) δ 1.37 (3H, t, J=7.6 Hz), 2.93 (2H, q, J=7.6 Hz), 3.76 (3H, s), 4.01 (2H, s), 4.24 (3H, s), 6.11 (1H, d, J=7.9 Hz), 7.22 (1H, s), 7.86 (1H, d, J=7.9 Hz).

Example 182

Ethyl 4-(2-ethyl-pyrazolo[1,5-a]pyridine-4-yl)-3-methoxycarbonyl-4-oxo-butyrate

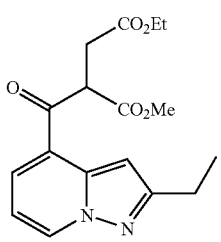

60% sodium hydride (135 mg) was added to a solution of the compound of Example 180 (830 mg) in N,N-dimethylformamide (40 mL) in a stream of argon gas while the solution was stirred in an ice bath. The mixture was then stirred at room temperature for 15 min. Subsequently, bromoethyl acetate (374 µL) was added to the mixture under stirring in an ice bath. The mixture was further stirred at room temperature for 3 hours. Subsequently, a saturated aqueous solution of ammonium chloride was added and the mixture was extracted with ethyl acetate. The organic layer was washed sequentially with water (×2) and saturated brine and dried over anhydrous sodium sulfate. Evaporation of the solvent and subsequent purification by silica gel column chromatography (hexane:ethyl acetate=2:1) afforded the title compound as a mixture with o-alkylated form. This product was used in the subsequent reaction without further purification.

Example 183

Methyl 3-(2-ethyl-pyrazolo[1,5-a]pyridine-4-yl)-2-methyl-3-oxopropionate

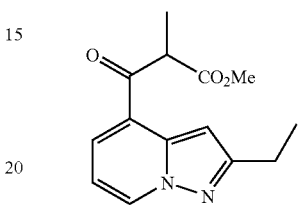

The compound of Example 180 (830 mg) was dissolved in N,N-dimethylformamide (50 mL) in a stream of argon gas and 60% sodium hydride (135 mg) was added while the solution was stirred in an ice bath. The resulting mixture was stirred at room temperature for 15 min, followed by chilling in an ice bath and addition of methyl iodide (210 µL). The mixture was then stirred at room temperature for 3 hours. Subsequently, a saturated aqueous solution of ammonium chloride was added and the mixture was extracted with ethyl acetate. The organic layer was washed sequentially with water (×2) and saturated brine and dried over anhydrous sodium sulfate. Evaporation of the solvent and subsequent purification of the residue by silica gel column chromatography (hexane:ethyl acetate=3:1) afforded the title compound as a pale yellow oil (700 mg).

$^{1}$H-NMR (400 MHz, CDCl$_3$) δ 1.38 (3H, t, J=7.6 Hz), 1.54 (3H, d, J=7.0 Hz), 2.91 (2H, q, J=7.6 Hz), 3.70 (3H, s), 4.46 (1H, q, J=7.0 Hz), 6.77 (1H, t, J=7.0 Hz), 7.17 (1H, s), 7.84 (1H, dd, J=1.8, 7.0 Hz), 8.56-8.59 (1H, m).

Example 184

Methyl 3-(2-ethyl-7-methoxy-pyrazolo[1,5-a]pyridine-4-yl)-2-methyl-3-oxopropionate

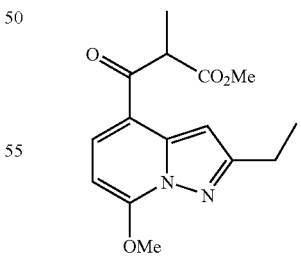

Using the compound of Example 181, the reaction was carried out as in Example 183 to afford the title compound as a yellow powder.

$^{1}$H-NMR (400 MHz, CDCl$_3$) δ 1.37 (3H, t, J=7.6 Hz), 1.53 (3H, d, J=7.0 Hz), 2.93 (2H, q, J=7.6 Hz), 3.70 (3H, s), 4.24 (3H, s), 4.43 (1H, q, J=7.0 Hz), 6.12 (1H, d, J=7.9 Hz), 7.24 (1H, s), 7.95 (1H, d, J=7.9 Hz).

Example 185

2-ethyl-7-methoxy-4-propionyl-pyrazolo[1,5-a]pyridine

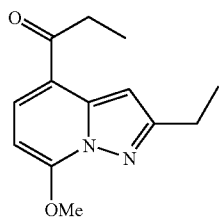

A 1 mol/L aqueous sodium hydroxide solution (12 mL) was added to a solution of the compound of Example 184 (460 mg) in methanol (30 mL). The mixture was stirred at room temperature for 2 days. Subsequently, diluted hydrochloric acid was added to make the mixture acidic. Methanol was evaporated and the residue was extracted with ethyl acetate (×2). The organic layer was washed with saturated brine and dried over anhydrous sodium sulfate. Evaporation of the solvent and subsequent purification of the residue by silica gel column chromatography (hexane:ethyl acetate=2:3) afforded the title compound as a pale green powder (295 mg).

$^1$H-NMR (400 MHz, CDCl$_3$) δ 1.26 (3H, t, J=7.3 Hz), 1.37 (3H, t, J=7.6 Hz), 2.93 (2H, q, J=7.6 Hz), 3.01 (2H, q, J=7.3 Hz), 4.23 (3H, s), 6.08 (1H, d, J=8.2 Hz), 7.20 (1H, s), 7.88 (1H, d, J=8.2 Hz).

Example 186

4-(2-ethyl-pyrazolo[1,5-a]pyridine-4-yl)-4-oxo-butyric acid

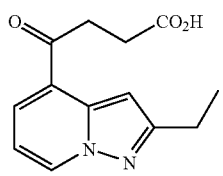

The compound of Example 182 (as a mixture) was dissolved in 47% hydrobromic acid (20 mL) and the mixture was stirred at 130° C. for 1 hour. After cooling, a 20% aqueous potassium hydroxide solution was added to make the mixture basic. The mixture was then washed with diethyl ether and diluted hydrochloric acid was added to make the aqueous layer acidic. The mixture was extracted with ethyl acetate and the organic layer was washed with water and saturated brine and dried over anhydrous sodium sulfate. Evaporation of the solvent afforded a pale yellow powder. The crude product was used in the subsequent reaction without further purification.

Example 187

4-(2-ethyl-pyrazolo[1,5-a]pyridine-4-yl)-3-methyl-4-oxo-butyric acid

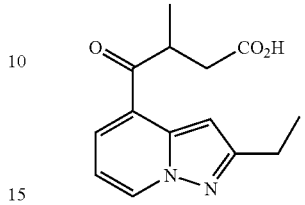

60% sodium hydride (162 mg) was added to a solution of the compound of Example 183 (700 mg) in N,N-dimethylformamide (40 mL) in a stream of argon gas while the solution was stirred in an ice bath. The mixture was then stirred at room temperature for 15 min. Subsequently, bromoethyl acetate (597 µL) was added to the mixture under stirring in an ice bath. The mixture was further stirred at room temperature for 3 hours. Subsequently, a saturated aqueous solution of ammonium chloride was added and the mixture was extracted with ethyl acetate. The organic layer was washed sequentially with water (×2) and saturated brine and dried over anhydrous sodium sulfate. Evaporation of the solvent and subsequent purification by silica gel column chromatography (hexane: ethyl acetate=2:1) gave the title compound as a mixture with o-alkylated form. This mixture was dissolved in 47% hydrobromic acid (20 mL) and the solution was stirred at 130° C. for 1 hour. After cooling, a 20% aqueous potassium hydroxide solution was added to make the mixture basic. The resulting crystals were separated by filtration and diluted hydrochloric acid was added to the filtrate to make it acidic. The filtrate was then extracted with ethyl acetate. The organic layer was washed sequentially with water and saturated brine and dried over anhydrous sodium sulfate. Evaporation of the solvent afforded the title compound as a yellow amorphous material (490 mg).

$^1$H-NMR (400 MHz, CDCl$_3$) δ 1.28 (3H, d, J=7.3 Hz), 1.36 (3H, t, J=7.6 Hz), 2.54 (1H, dd, J=5.2, 17.1 Hz), 2.88 (2H, q, J=7.8 Hz), 3.06 (1H, dd, J=8.9, 17.1 Hz), 3.93-3.99 (1H, m), 6.76 (1H, t, J=7.0 Hz), 7.11 (1H, s), 7.85 (1H, d, J=7.0 Hz), 8.60 (1H, d, J=7.0 Hz).

Example 188

2-ethyl-6-fluoro-4-(2-bromopropionyl)-pyrazolo[1,5-a]pyridine

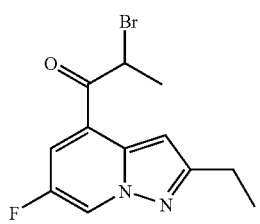

The compound of Example 73 (460 mg) was dissolved in ethyl acetate (46 mL) in an argon atmosphere. To this solution, copper (II) bromide (1.03 g) was added and the mixture was stirred for 5 hours under reflux. Subsequently, the reaction was terminated by adding water at 0° C. and the mixture was filtered through Celite. The filtrate was extracted three times with ethyl acetate. The organic layer was washed with saturated brine and dried over sodium sulfate. Evaporation of the solvent under reduced pressure and purification by silica gel column chromatography (hexane:ethyl acetate=10:1) afforded the title compound as a yellow powder (540 mg).

$^1$H-NMR (CDCl$_3$, 400 MHz) δ 1.37 (3H, t, J=7.3 Hz), 1.95 (3H, d, J=6.9 Hz), 2.89 (2H, q, J=7.3 Hz), 5.27 (1H, q, J=6.9 Hz), 7.15 (1H, s), 7.80 (1H, dd, J=1.8, 8.6 Hz), 8.5,7 (1H, m).

Examples 189 through 178

Using the compounds of Examples 78, 80, 111 and 139, the reactions were carried out as in Example 188 to obtain compounds shown in Table 12 below.

TABLE 12

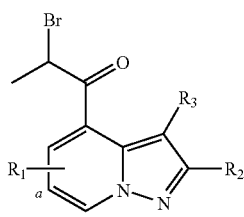

| Examples | R1 | R2 | R3 | Nature |
|---|---|---|---|---|
| 189 | a-Cl | Et | Cl | Yellow powder |
| 190 | a-Cl | Et | H | Yellow powder |
| 191 | b-CO$_2$Me | Et | H | Yellow powder |
| 192 | b-MeO | CF$_3$ | H | Pale yellow powder |

Example 189

$^1$H-NMR (CDCl$_3$, 400 MHz) δ 1.33 (3H, t, J=7.3 Hz), 1.96 (3H, d, J=6.7 Hz), 2.85 (2H, q, J=7.3 Hz), 5.12 (1H, q, J=6.7 Hz), 7.31 (1H, d, J=1.2 Hz), 8.47 (1H, d, J=1.2 Hz).

Example 191

LRMS (EI$^+$): 338[M$^+$]

$^1$H-NMR (400 MHz, CDCl$_3$) δ 1.39 (3H, t, J=7.3 Hz), 1.95 (3H, d, J=6.7 Hz), 2.98 (2H, q, J=7.3 Hz), 4.08 (3H, s), 5.33 (1H, q, J=6.7 Hz), 6.31 (1H, d, J=8.0 Hz), 7.70 (1H, s), 8.00 (1H, d, J=8.0 Hz).

Example 192

LRMS (EI$^+$): 350[M$^+$]

$^1$H-NMR (400 MHz, CDCl$_3$) δ 1.95 (3H, t, J=6.7 Hz), 4.30 (3H, s), 5.31 (1H, q, J=6.7 Hz), 6.35 (1H, d, J=8.0 Hz), 7.70 (1H, s), 8.13 (1H, d, J=8.0 Hz)

Example 193

Dimethyl 2-[2-(2-ethyl-6-fluoro-pyrazolo[1,5-a]pyridine-4-yl)-1-methyl-2-oxoethyl]-malonate

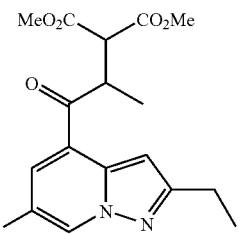

Dimethyl malonate (327 μL) was added to DMF (4.6 mL) in an argon atmosphere. While the solution was kept at 0° C., 60% sodium hydride (105 mg) was added and the mixture was stirred at room temperature for 30 min. Subsequently, the compound of Example 188 (655 mg) in DMF (10 mL) was added at 0° C. and the mixture was stirred at room temperature for 4 hours. The reaction was terminated by adding a saturated aqueous solution of ammonium chloride and the mixture was extracted three times with ethyl acetate. The organic layer was washed with saturated brine and dried over sodium sulfate. Evaporation of the solvent under reduced pressure and purification by silica gel column chromatography (hexane:ethyl acetate=6:1) afforded the title compound as a yellow oil (680 mg).

$^1$H-NMR (CDCl$_3$, 400 MHz) δ 1.23 (3H, d, J=7.3 Hz), 1.35 (3H, t, J=7.5 Hz), 2.87 (2H, q, J=7.5 Hz), 3.68 (3H, s), 3.83 (3H, s), 4.06 (1H, d, J=10.4 Hz), 4.16 (1H, dq, J=7.3, 10.4 Hz), 7.06 (1H, s), 7.81 (1H, dd, J=1.8, 8.6 Hz), 8.53-8.55 (1H, m).

Examples 194 through 198

The compounds shown in Table 12 were reacted with diethyl malonate or di-t-butyl malonate to obtain compounds shown in Table 13 below.

TABLE 13

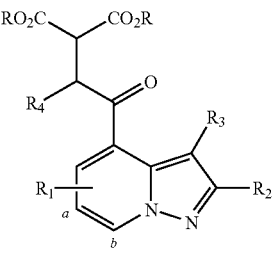

| Examples | R1 | R2 | R3 | R4 | R | Nature |
|---|---|---|---|---|---|---|
| 194 | a-Cl | Et | Cl | Me | Me | Yellow oil |
| 195 | a-Cl | Et | H | H | Me | Yellow amorphous |
| 196 | b-CO$_2$Me | Et | H | Me | tBu | Yellow oil |
| 197 | b-MeO | CF$_3$ | H | Me | Me | Yellow powder |
| 198 | b-MeO | CF$_3$ | H | Me | tBu | Pale Yellow powder |

Example 194

$^1$H-NMR (CDCl$_3$, 400 MHz) δ 1.23 (3H, d, J=7.3 Hz), 1.34 (3H, t, J=7.8 Hz), 2.85 (2H, q, J=7.8 Hz), 3.74 (3H, s), 3.82

(3H, s), 3.95-3.99 (1H, m), 4.05 (1H, d, J=10.4 Hz), 7.68 (1H, d, J=1.2 Hz), 8.48 (1H, d, J=1.2 Hz).

Example 195

$^1$H-NMR (400 MHz, CDCl$_3$) δ 1.35 (3H, t, J=7.6 Hz), 2.87 (2H, q, J=7.6 Hz), 3.67 (2H, d, J=7.0 Hz), 3.81 (6H, s), 4.12 (1H, t, J=7.0 Hz), 7.09 (1H, s), 7.81 (1H, d, J=1.8 Hz), 8.60-8.61 (1H, m).

Example 196

LRMS (EI$^+$): 474[M$^+$]
$^1$H-NMR (CDCl$_3$, 400 MHz) δ 1.20 (3H, d, J=7.3 Hz), 1.21 (3H, d, J=7.8 Hz), 1.36 (9H, s), 1.52 (9H, s), 2.96 (2H, q, J=7.3 Hz), 3.84 (1H, d, J=11.0 Hz), 4.06-4.11 (1H, m), 4.08 (3H, s), 7.18 (1H, s), 7.36 (1H, d, J=7.3 Hz), 7.88 (1H, d, J=7.3 Hz).

Example 197

LRMS (EI$^+$): 402[M$^+$]
$^1$H-NMR (CDCl$_3$, 400 MHz) δ 1.24 (3H, d, J=6.7 Hz), 3.67 (3H, s), 3.83 (3H, s), 4.17-4.25 (1H, m), 4.29 (3H, s), 6.36 (1H, d, J=8.0 Hz), 7.64 (1H, s), 8.15 (1H, d, J=8.0 Hz)

Example 198

LRMS (FAB$^+$): 487[M+H]$^+$
$^1$H-NMR (CDCl$_3$, 400 MHz) δ 1.21 (3H, d, J=6.7 Hz), 1.36 (9H, s), 1.53 (9H, s), 3.85 (2H, q, J=6.7 Hz), 4.05-4.10 (1H, m), 4.28 (3H, s), 6.35 (1H, d, J=8.0 Hz), 7.64 (1H, s), 8.15 (1H, d, J=8.0 Hz).

Example 199

6-(2-ethyl-6-fluoro-pyrazolo[1,5-a]pyridine-4-yl)-4,5-dihydro-5-methyl-3-(2H)-pyridazinone

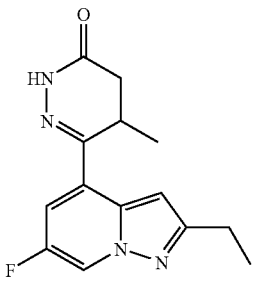

The compound of Example 193 (680 mg) was dissolved in ethanol (10 ml) and water (10 mL). To this solution, potassium hydroxide (326 mg) was added and the mixture was stirred for 2 hours under reflux. Subsequently, water and several droplets of concentrated hydrochloric acid were added and the mixture was extracted three times with ethylacetate. The organic layer was washed with saturated brine and dried over sodium sulfate. The solvent was evaporated under reduced pressure. The resulting solid product (579 mg) was dissolved in ethanol (18 mL) and the solution was stirred for 17 hours under reflux. This was followed by addition of hydrazine monohydrate (262 μL) and stirring for 1.5 hours under reflux. Evaporation of the solvent under reduced pressure and purification by silica gel column chromatography (hexane:ethyl acetate=4:1 then 1:1) afforded the title compound as a yellow powder (359 mg).

$^1$H-NMR (400 MHz, CDCl$_3$) δ 1.31 (3H, d, J=7.3 Hz), 1.36 (3H, t, J=7.3 Hz), 2.55 (1H, d, J=15.9 Hz), 2.78 (1H, dd, J=6.7, 17.0 Hz), 2.87 (2H, q, J=7.3 Hz), 3.35-3.42 (1H, m), 7.03 (1H, s), 7.27 (1H, dd, J=2.4, 9.2 Hz), 8.40 (1H, dd, J=2.4, 2.4 Hz), 8.79 (1H, s).

LRMS (EI$^+$): 274 [M$^+$]

HRMS (EI$^+$): 274.1215 (−1.5 mmu) [M$^+$]

Examples 200 through 205

Using the compounds of Examples 186, 187, and 194 through 197, the reactions were carried out as in Example 199 to obtain compounds shown in Table 14 below.

TABLE 14

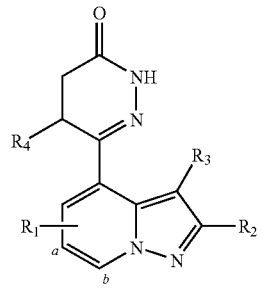

| Examples | R1 | R2 | R3 | R4 | Nature |
|---|---|---|---|---|---|
| 200 | H | Et | H | H | Orange powder |
| 201 | H | Et | H | Me | Orange powder |
| 202 | a-Cl | Et | H | H | Pale brown amorphous |
| 203 | a-Cl | Et | Cl | Me | Yellow powder |
| 204 | b-CO$_2$Et | Et | H | Me | Yellow powder |
| 205 | b-MeO | CF$_3$ | H | Me | Pale yellow powder |

Example 200 mp: 201-203° C.

Elemental analysis (%): Calcd. for C13H14N4O: C, 64.45; H, 5.82; N, 23.12;

Found: C, 64.33; H, 5.80; N, 22.98.

HRMS (EI$^+$): 242.1181 (+1.4 mmu) [M$^+$]

$^1$H-NMR (400 MHz, CDCl$_3$) δ 1.38(3H, t, J=7.6 Hz), 2.66 (1H, d, J=9.2 Hz), 2.68 (1H, d, J=8.6 Hz), 2.89 (2H, q, J=7.6 Hz), 3.07 (1H, d, J=8.6 Hz), 3.08 (1H, d, J=9.2 Hz), 6.73 (1H, t, J=7.0 Hz), 6.97 (1H, s), 7.30 (1H, dd, J=0.9, 7.0 Hz), 8.43 (1H, td, J=0.9, 7.0 Hz).

Example 201 mp: 231-233° C.

HRMS (EI$^+$): 256.1304 (−2.0 mmu) [M$^+$]

$^1$H-NMR (400 MHz, CDCl$_3$) δ 1.30 (3H, d, J=7.3 Hz), 1.38 (3H, t, J=7.6 Hz), 2.53 (1H, dd, J=0.9, 16.8 Hz), 2.77 (1H, dd, J=6.7, 16.8 Hz), 2.89 (2H, q, J=7.6 Hz), 3.40-3.47 (1H, m), 6.74 (1H, t, J=7.0 Hz), 7.02 (1H, s), 7.34 (1H, d, J=7.0 Hz), 8.44 (1H, d, J=7.0 Hz), 8.66 (1H, br s).

Example 202

HRMS (EI⁺): 276.0745 (−3.3 mmu) [M⁺]

¹H-NMR (400 MHz, CDCl₃) δ 1.36 (3H, t, J=7.6 Hz), 2.66-2.70 (2H, m), 2.87 (2H, q, J=7.6 Hz), 3.04-3.08 (2H, m), 6.97 (1H, s), 7.27 (1H, d, J=1.8 Hz), 8.46-8.47 (1H, m), 8.68 (1H, br s).

Example 203

¹H-NMR (CDCl₃, 400 MHz) δ 1.16 (3H, d, J=7.3 Hz), 1.34 (3H, t, J=7.3 Hz), 2.51 (1H, dd, J=17.1, 4.3 Hz), 2.84 (2H, q, J=7.3 Hz), 3.00 (1H, dd, J=17.1, 7.3 Hz), 3.18 (1H, m), 7.05 (1H, d, J=1.8 Hz), 8.43 (1H, d, J=1.8 Hz), 8.66 (1H, s).

LRMS (EI⁺): 324[M⁺]

HRMS (EI⁺): 324.0511 (−3.4 mmu) [M⁺]

Example 204

HRMS (EI⁺): 328.1565 (+3.0 mmu) [M⁺]

¹H-NMR (400 MHz, CDCl₃) δ 1.30 (3H, d, J=7.3 Hz), 1.38 (3H, t, J=7.3 Hz), 1.46 (3H, t, J=7.3 Hz), 2.53-2.57 (1H, m), 2.80 (1H, dd, J=6.7, 17.1 Hz), 2.97 (2H, q, J=7.3 Hz), 3.40-3.48 (1H, m), 4.53 (2H, q, J=7.3 Hz), 7.16 (1H, s), 7.33 (1H, d, J=8.0 Hz), 7.38 (1H, d, J=8.0 Hz), 8.74 (1H, brs).

Example 205

¹H-NMR (CDCl₃, 400 MHz) δ 1.30 (3H, d, J=7.3 Hz), 2.54 (1H, d, J=16.5 Hz), 2.78 (1H, dd, J=17.1, 6.7 Hz), 3.36-3.46 (1H, m), 4.24 (3H, s), 6.30 (1H, d, J=7.9 Hz), 7.51 (1H, d, J=7.9 Hz), 7.60 (1H, s), 8.65 (1H, br s).

Example 206

6-(7-carboxy-2-ethyl-pyrazolo[1,5-a]pyridine-4-yl)-4,5-dihydro-5-methyl-3-(2H)-pyridazinone

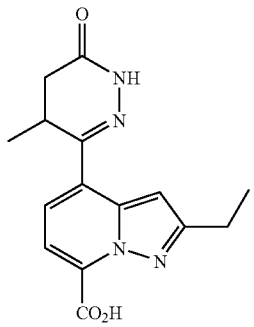

The compound of Example 204 (19.7 mg) was dissolved in ethanol (1.00 mL). To this solution, 1.00 mol/L aqueous sodium hydroxide solution (0.20 mL) was added and the mixture was stirred at room temperature for 2 hours. Subsequently, the solvent was evaporated and the residue was diluted with water. The mixture was then extracted with diethyl ether and diluted hydrochloric acid was added to the aqueous layer to make it acidic. The aqueous layer was extracted twice with ethyl acetate. The ethyl acetate layer was then washed with saturated brine and dried over anhydrous sodium sulfate. Evaporation of the solvent afforded the title compound as a yellow powder (13.5 mg).

HRMS (EI⁺): 300.1193 (−2.9 mmu) [M⁺]

¹H-NMR (400 MHz, CDCl₃) δ 1.32 (3H, d, J=7.3 Hz), 1.42 (3H, t, J=7.3 Hz), 2.59 (1H, d, J=17.1 Hz), 2.81 (1H, dd, J=6.7, 17.1 Hz), 2.95 (2H, q, J=7.3 Hz), 3.43-3.50 (1H, m), 7.23 (1H, s), 7.52 (1H, d, J=8.0 Hz), 7.91 (1H, d, J=8.0 Hz), 8.82 (1H, brs), 15.7 (1H, brs).

Example 207

4-(7-methoxy-2-trifluoromethyl-pyrazolo[1,5-a]pyridine-4-yl)oxobutyric acid

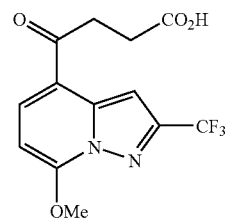

The compound of Example 163 (636 mg, crude product) was dissolved in dichloromethane (10.0 mL). To this solution, trifluoroacetic acid (5.00 mL) was added and the mixture was stirred at room temperature for 7 hours. Subsequently, the solvent was evaporated and the residue was diluted with water. A 10% aqueous sodium hydroxide solution was added to the mixture to make it basic and the mixture was extracted with diethyl ether. The resulting aqueous layer was made acidic by adding concentrated hydrochloric acid and the layer was extracted twice with ethyl acetate. The ethyl acetate layer was washed with saturated brine and dried over anhydrous sodium sulfate. Evaporation of the solvent afforded the title compound as a brown oil (616 mg, crude). This product was used in the subsequent reaction without further purification.

Example 208

4-(2-ethyl-7-methoxy-pyrazolo[1,5-a]pyridine-4-yl)oxobutyric acid

Using the compound of Example 165, the reaction was carried out as in Example 207 to afford the title compound as a pale yellow powder.

¹H-NMR (400 MHz, CDCl₃) δ 1.37 (3H, t, J=7.6 Hz), 2.85 (2H, t, J=6.4 Hz), 2.93 (2H, q, J=7.6 Hz), 3.34 (2H, t, J=6.4 Hz), 4.24 (3H, s), 6.11 (1H, d, J=7.9 Hz), 7.19 (1H, s), 7.94 (1H, d, J=7.9 Hz).

Example 209

6-(7-methoxy-2-trifluoromethyl-pyrazolo[1,5-a]pyridine-4-yl)-4,5-dihydro-3-(2H)-pyridazinone

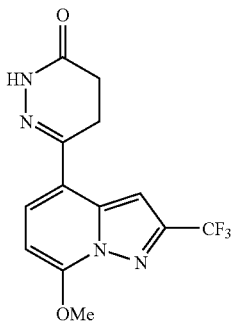

The compound of Example 207 (616 mg, crude) was dissolved in ethanol (15.0 mL). To this solution, hydrazine monoacetate (428 mg) was added and the mixture was stirred for 8 hours under reflux. Subsequently, the solvent was evaporated and the residue was purified by amino-silica gel column chromatography (ethyl acetate) to afford the title compound as a yellow powder (123 mg).

Elemental analysis (%): Calcd. for C13H11F3N4O2.1/5H2O: C, 49.44; H, 3.64; N, 17.94; Found: C, 49.52; H, 3.63; N, 17.82.

HRMS (EI$^+$): 312.0817 (−1.7 mmu) [M$^+$]

$^1$H-NMR (400 MHz, CDCl$_3$) δ 2.68 (2H, t, J=8.0 Hz), 3.06 (2H, t, J=8.0 Hz), 4.23 (3H, s), 6.30 (1H, d, J=8.0 Hz), 7.47 (1H, d, J=8.0 Hz), 7.56 (1H, s), 8.63 (1H, brs).

Example 210

6-(2-ethyl-7-methoxy-pyrazolo[1,5-a]pyridine-4-yl)-4,5-dihydro-3-(2H)-pyridazinone

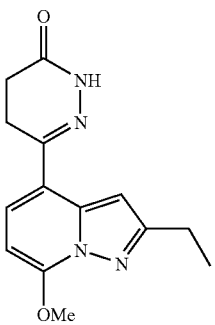

Using the compound of Example 208, the reaction was carried out as in Example 209 to afford the title compound as an orange powder.

Elemental analysis (%) Calcd. for C14H16N4O2.1/5H2O: C, 60.95; H 5.99; N, 20.31; Found: C, 60.80; H, 5.86; N, 20.08.

HRMS (EI$^+$): 272.1242 (−3.1 mmu) [M$^+$]

$^1$H-NMR (400 MHz, CDCl$_3$) δ 1.38 (3H, t, J=7.6 Hz), 2.63-2.67 (2H, m), 2.93 (2H, q, J=7.6 Hz), 3.03-3.07 (2H, m), 4.19 (3H, s), 6.08 (1H, d, J=7.9 Hz), 7.04 (1H, s), 7.35 (1H, d, J=7.9 Hz), 8.56 (1H, br s).

Example 211

6-(7-methoxy-2-trifluoromethyl-pyrazolo[1,5-a]pyridine-4-yl)-4,5-dihydro-5-methyl-3-(2H)-pyridazinone

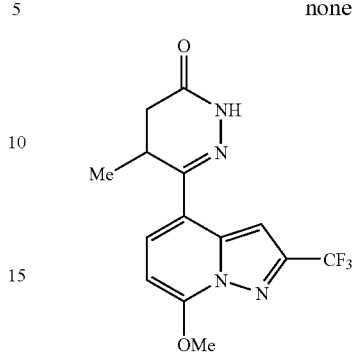

Trifluoroacetic acid (2.47 g) was added to a solution of the compound of Example 162 (836 mg) in dichloromethane (1.0 mL). This mixture was stirred at room temperature for 5 hours. Subsequently, the mixture was concentrated and was azeotropically distilled twice with toluene. The residue was dissolved in ethanol (10 mL). To this solution, acetic acid (781 mg) and hydrazine monohydrate (324 mg) were added and the mixture was refluxed for 36 hours. The reaction mixture was filtered and the filtrate was concentrated. The concentrate was recrystallized from ethanol and the resultant crystals were recrystallized from ethyl acetate-hexane for further purification. This afforded the title compound as a pale yellow powder (488 mg). The product was identical to the compound of Example 205.

$^1$H-NMR (400 MHz, CDCl$_3$,) δ 1.30 (3H, d, J=7.3 Hz), 2.54 (1H, d, J=16.5 Hz), 2.78 (1H, dd, J=17.1, 6.7 Hz), 3.36-3.46 (1H, m), 4.24 (3H, s), 6.30 (1H, d, J=7.9 Hz), 7.51 (1H, d, J=7.9 Hz), 7.60 (1H, s), 8.65 (1H, br s).

LRMS (EI$^+$): 326[M$^+$]

HRMS (EI$^+$): 326.0991 (+3.5 mmu) [M$^+$]

Elemental analysis (%): Calcd. for C14H13F3N4O2.3/8H2O: C, 50.49; H, 4.16; N, 16.82; Found: C, 50.33; H, 3.98; N, 17.05.

Examples 212 through 232

Using the compounds of Examples 156 through 161 and 164 through 179, the reactions were carried out as in Example 211 to obtain compounds shown in Table 15 below.

TABLE 15

| Examples | R1 | R2 | R3 | R4 | Nature |
|---|---|---|---|---|---|
| 212 | b-MeO | CF$_3$ | H | Et | Pale yellow powder |
| 213 | b-MeO | Et | Cl | Me | Yellow powder |
| 214 | b-MeO | H | H | Me | Yellow powder |
| 215 | b-MeO | Me | H | Me | Yellow powder |

TABLE 15-continued

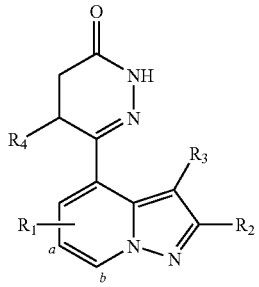

| Examples | R1 | R2 | R3 | R4 | Nature |
|---|---|---|---|---|---|
| 216 | b-MeO | Et | H | Me | Brown powder |
| 217 | b-MeO | Pr | H | Me | Yellow powder |
| 218 | b-MeO | c-Pr | H | Me | Yellow powder |
| 219 | b-MeO | MeS | H | Me | Yellow powder |
| 220 | b-MeO | CH$_2$OMe | H | Me | Pale yellow powder |
| 221 | b-MeO | CH$_2$OH | H | Me | Colorless powder |
| 222 | b-MeO | CHF$_2$ | H | Me | Colorless powder |
| 223 | b-MeS | Et | H | Me | Yellow powder |
| 224 | b-Me$_2$N | Et | H | Me | Yellow powder |
| 225 | b-MeHN | Et | H | Me | Yellow powder |
| 226 | b—N(morpholino) | Et | H | Me | Pale yellow powder |
| 227 | b—N(piperidino) | Et | H | Me | Yellow powder |
| 228 | b-AcNH | Et | H | Me | Pale yellow powder |
| 229 | b-Ph | Et | H | Me | Yellow powder |
| 230 | b-CN | Et | H | Me | Orange powder |
| 231 | b-NMePh | Et | H | Me | Yellow powder |
| 232 | b-CH(OH)Me | Et | H | Me | Yellow oil |

Example 212

HRMS (EI$^+$): 340.1171 (+2.4 mmu) [M$^+$]

$^1$H-NMR (400 MHz, CDCl$_3$) δ 1.01 (3H, t, J=7.3 Hz), 1.64-1.73 (2H, m), 2.71 (2H, d, J=4.3 Hz), 3.18-3.23 (1H, m), 4.23 (3H, s), 6.30 (1H, d, J=8.0 Hz), 7.48 (1H, d, J=8.0 Hz), 7.60 (1H, s), 8.60 (1H, brs).

Example 213

Elemental analysis (%): Calcd. for C15H17ClN4O2: C, 56.17; H, 5.34; N, 17.47; Found: C, 55.95; H, 5.37; N, 17.18.

HRMS (EI$^+$): 320.1002 (−3.8 mmu) [M$^+$]

$^1$H-NMR (CDCl$_3$, 400 MHz) δ 1.12 (3H, d, J=7.3 Hz), 1.35 (3H, t, J=7.3 Hz), 2.49 (1H, dd, J=3.9, 16.8 Hz), 2.90 (2H, q, J=7.3 Hz), 3.01 (1H, dd, J=7.0, 16.8 Hz), 4.18 (3H, s), 6.09 (1H, d, J=7.9 Hz), 7.10 (1H, d, J=7.9 Hz), 8.49 (1H, brs).

Example 214

Elemental analysis (%): Calcd. for C15H17ClN4O2.1/3H2O: C, 56.08; H, 5.59; N, 21.20; Found: C, 56.17; H, 5.30; N, 20.91.

HRMS (EI$^+$): 258.1155 (+3.8 mmu) [M$^+$]

$^1$H-NMR (CDCl$_3$, 400 MHz) δ 1.30 (3H, d, J=7.3 Hz), 2.52 (1H, d, J=17.0 Hz), 2.77 (1H, dd, J=6.7, 17.0 Hz), 3.40-3.44 (1H, m), 4.20 (3H, s), 6.16 (1H, d, J=7.9 Hz), 7.27 (1H, d, J=1.8 Hz), 7.42 (1H, d, J=7.9 Hz), 8.08 (1H, d, J=1.8 Hz), 8.59 (1H, brs).

Example 215

HRMS (EI$^+$): 272.1311 (+3.7 mmu) [M$^+$]

$^1$H-NMR (CDCl$_3$, 400 MHz) δ 1.28 (3H, d, J=7.3 Hz), 2.51 (1H, d, J=17.1 Hz), 2.55 (3H, s), 2.76 (1H, dd, J=6.7, 17.1 Hz), 4.21 (3H, s), 6.08 (1H, d, J=7.9 Hz), 7.06 (1H, s), 7.37 (1H, d, J=7.9 Hz), 8.69 (1H, brs).

Example 216

Elemental analysis (%): Calcd. for C15H18N4O2, 1/10H2O: C, 62.53; H, 6.37; N, 19.44; Found: C, 62.24; H, 6.27; N, 19.43.

HRMS (EI$^+$): 286.1414 (−1.6 mmu) [M$^+$]

$^1$H-NMR (CDCl$_3$, 400 MHz) δ 1.29 (3H, d, J=7.3 Hz), 1.38 (3H, t, J=7.6 Hz), 2.51 (1H, d, J=16.8 Hz), 2.76 (1H, dd, J=6.4, 16.8 Hz), 2.93 (1H, q, J=7.6 Hz), 3.38-3.44 (1H, m), 4.19 (3H, s), 6.09 (1H, d, J=7.9 Hz), 7.09 (1H, s), 7.38 (1H, d, J=7.9 Hz), 8.62 (1H, br s).

Example 217

Elemental analysis (%): Calcd. for C16H20N4O2: C, 63.98; H, 6.71; N, 18.65; Found: C, 63.93; H, 6.69; N, 18.60.

HRMS (EI$^+$): 300.1605 (+1.8 mmu) [M$^+$]

$^1$H-NMR (CDCl$_3$, 400 MHz) δ 1.02 (3H, t, J=7.3 Hz), 1.29 (3H, d, J=6.7 Hz), 1.78-1.84 (2H, m), 2.50 (1H, d, J=17.1 Hz), 2.76 (1H, dd, J=6.7, 17.1 Hz), 2.87 (2H, t, J=7.3 Hz), 3.39-3.43 (1H, m), 4.20 (3H, s), 6.08 (1H, d, J=7.9 Hz), 7.08 (1H, s), 7.38 (1H, d, J=7.9 Hz).

Example 218

HRMS (EI$^+$): 298.1421 (−0.9 mmu) [M$^+$]

$^1$H-NMR (CDCl$_3$, 400 MHz) δ 0.90-0.92 (2H, m), 1.04-1.06 (2H, m), 1.27 (3H, d, J=7.3 Hz), 2.21-2.25 (1H, m), 2.50 (1H, d, J=15.9 Hz), 2.74 (1H, dd, J=6.5, 17.1 Hz), 4.18 (3H, s), 6.06 (1H, d, J=7.9 Hz), 6.85 (1H, s), 7.36 (1H, d, J=7.9 Hz), 8.57 (1H, brs).

Example 219

HRMS (EI$^+$): 304.1024 (+3.0 mmu) [M$^+$]

$^1$H-NMR (CDCl$_3$, 400 MHz): δ 1.30 (3H, d, J=7.3 Hz), 2.52 (1H, d, J=17.7 Hz), 2.66 (3H, s), 2.76 (1H, dd, J=6.7, 17.7 Hz), 3.37-3.42 (1H, m), 4.19 (3H, s), 6.10 (1H, d, J=7.9 Hz), 7.18 (1H, s), 7.40 (1H, d, J=7.9 Hz), 8.63 (1H, brs).

Example 220

$^1$H-NMR (CDCl$_3$, 400 MHz) δ 1.29 (3H, d, J=7.3 Hz), 2.51 (1H, d, J=17.1 Hz), 2.76 (1H, dd, J=17.1, 6.7 Hz), 3.36-3.45 (1H, m), 3.46 (3H, s), 4.21 (3H, s), 4.75 (2H, s), 6.14 (1H, d, J=7.9 Hz), 7.31 (1H, s), 7.41 (1H, d, J=7.9 Hz), 8.59 (1H, br s).

Example 221

$^1$H-NMR (CDCl$_3$, 400 MHz) δ 1.29 (3H, d, J=7.3 Hz), 2.00-2.11 (1H, m), 2.52 (1H, d, J=17.1 Hz), 2.77 (1H, dd,

J=16.5, 6.7 Hz), 3.35-3.46 (1H, m), 4.21 (3H, s), 4.96 (2H, d, J=3.7 Hz), 6.16 (1H, d, J=7.9 Hz), 7.30 (1H, s), 7.42 (1H, d, J=7.9 Hz), 8.62 (1H, s).

Example 222

$^1$H-NMR (CDCl$_3$, 400 MHz) δ 1.30 (3H, d, J=7.3 Hz), 2.53 (1H, d, J=17.1 Hz), 2.78 (1H, dd, J=6.7, 17.1 Hz), 3.37-3.45 (1H, m), 4.23 (3H, s), 6.25 (1H, d, J=8.0 Hz), 6.95 (1H, t, J=55.0 Hz), 7.48 (1H, d, J=8.0 Hz), 7.54 (1H, s), 8.63 (1H, brs).

Elemental analysis (%): Calcd. for C12H12N4O: C, 54.54; H, 4.58; N, 18.17; Found: C, 54.23; H, 4.54; N, 18.44.

Example 223

Elemental analysis (%): Calcd. for C15H18N4OS, 1/5H$_2$O: C, 58.88; H, 6.06; N, 18.31; Found: C, 58.52; H, 5.92; N, 18.02.

HRMS (EI$^+$): 302.1169 (−3.3 mmu) [M$^+$]

$^1$H-NMR (400 MHz, CDCl$_3$) δ 1.30 (3H, d, J=8.0 Hz), 1.39 (3H, t, J=7.3 Hz), 2.53 (1H, d, J=17.1 Hz), 2.64 (3H, s), 2.77 (1H, dd, J=6.7, 17.1 Hz), 2.94 (1H, q, J=7.3 Hz), 3.39-3.47 (1H, m), 6.52 (1H, d, J=8.0 Hz), 7.10 (1H, s), 7.36 (1H, d, J=8.0 Hz), 8.61 (1H, brs).

Example 224

Elemental analysis (%) Calcd. for C16H21N5O: C, 64.19; H, 7.07; N, 23.39; Found: C, 64.41; H, 7.06; N, 23.41.

HRMS (EI$^+$): 299.1755 (+0.9 mmu) [M$^+$]

$^1$H-NMR (400 MHz, CDCl$_3$) δ 1.29 (3H, d, J=7.3 Hz), 1.39 (3H, t, J=7.3 Hz), 2.50 (1H, d, J=17.1 Hz), 2.74 (1H, dd, J=6.7, 17.1 Hz), 2.91 (1H, q, J=7.3 Hz), 2.95 (6H, s), 3.38-3.45 (1H, m), 6.11 (1H, d, J=8.0 Hz), 7.09 (1H, s), 7.35 (1H, d, J=8.0 Hz), 8.56 (1H, brs).

Example 225

Elemental analysis (%): Calcd. for C15H19N5O: C, 63.14; H, 6.71; N, 24.54; Found: C, 62.94; H, 6.70; N, 24.32.

HRMS (EI$^+$): 285.1558 (−3.2 mmu) [M$^+$]

$^1$H-NMR (400 MHz, CDCl$_3$) δ 1.28 (3H, d, J=7.3 Hz), 1.37 (3H, t, J=7.3 Hz), 2.48 (1H, d, J=16.5 Hz), 2.74 (1H, dd, J=6.7, 16.5 Hz), 2.87 (1H, q, J=7.3 Hz), 3.12 (3H, d, J=5.5 Hz), 3.37-3.46 (1H, m), 5.83 (1H, d, J=7.9 Hz), 6.30 (1H, brs), 7.02 (1H, s), 7.41 (1H, d, J=7.9 Hz), 8.50 (1H, brs).

Example 226

Elemental analysis (%): Calcd. for C18H23N5O2,1/5H2O: C, 62.66; H, 6.84; N, 20.30; Found: C, 62.83; H, 6.74; N, 20.19.

HRMS (EI$^+$): 341.1855 (+0.4 mmu)[M$^+$]

$^1$H-NMR (400 MHz, CDCl$_3$) δ 1.29 (3H, d, J=7.3 Hz), 1.38 (3H, t, J=7.3 Hz), 2.50 (1H, d, J=15.9 Hz), 2.75 (1H, dd, J=6.7, 15.9 Hz), 2.90 (1H, q, J=7.3 Hz), 3.38-3.46 (1H, m), 3.51-3.58 (4H, m), 4.01 (4H, t, J=4.9 Hz), 6.15 (1H, d, J=7.9 Hz), 7.09 (1H, s), 7.35 (1H, d, J=7.9 Hz), 8.56 (1H, brs).

Example 227

Elemental analysis (%): Calcd. for C19H25N5O: C, 67.23; H, 7.42; N, 20.63; Found: C, 67.03; H, 7.39; N, 20.47.

HRMS (EI$^+$): 339.2041 (−1.8 mmu) [M$^+$]

$^1$H-NMR (400 MHz, CDCl$_3$) δ 1.28 (3H, d, J=8.0 Hz), 1.39 (3H, t, J=7.3 Hz), 1.66-1.88 (6H, m), 2.49 (1H, d, J=16.5 Hz), 2.74 (1H, dd, J=6.7, 16.5 Hz), 3.38-3.47 (5H, m), 6.14 (1H, d, J=8.0 Hz), 7.07 (1H, s), 7.34 (1H, d, J=8.0 Hz), 8.55 (1H, brs).

Example 228

HRMS (EI$^+$): 313.1552 (+1.3 mmu) [M$^+$]

$^1$H-NMR (400 MHz, CDCl$_3$) δ 1.29 (3H, d, J=7.3 Hz), 1.39 (3H, t, J=7.3 Hz), 2.39 (3H, s), 2.52 (1H, d, J=16.5 Hz), 2.76 (1H, dd, J=6.7, 16.5 Hz), 2.89 (1H, q, J=7.3 Hz), 3.40-3.48 (1H, m), 7.08 (1H, s), 7.42 (1H, d, J=8.6 Hz), 7.71 (1H, d, J=8.6 Hz), 8.62 (1H, brs), 9.49 (1H, brs).

Example 229

Elemental analysis (%): Calcd. for C20H20N4O,1/5H2O: C, 71.49; H, 6.12; N, 16.68; Found: C, 71.50; H, 6.10; N, 16.39.

HRMS (EI$^+$): 332.1672 (+3.5 mmu) [M$^+$]

$^1$H-NMR (400 MHz, CDCl$_3$) δ 1.33 (3H, d, J=7.3 Hz), 1.37 (3H, t, J=7.3 Hz), 2.55 (1H, d, J=17.1 Hz), 2.79 (1H, dd, J=6.7, 17.1 Hz), 2.88 (1H, q, J=7.3 Hz), 3.44-3.52 (1H, m), 6.81 (1H, d, J=7.3 Hz), 7.16 (1H, s), 7.42 (1H, d, J=7.3 Hz), 7.49-7.53 (3H, m), 7.95-7.98 (2H, m), 8.66 (1H, brs).

Example 230

HRMS (EI$^+$): 281.1259 (−1.7 mmu) [M$^+$]

$^1$H-NMR (400 MHz, CDCl$_3$) δ 1.31 (3H, d, J=7.3 Hz), 1.39 (3H, t, J=7.3 Hz), 2.57 (1H, d, J=17.1 Hz), 2.79 (1H, dd, J=6.7, 17.1 Hz), 2.95 (2H, q, J=7.3 Hz), 3.38-3.46 (1H, m), 7.18 (1H, s), 7.28 (1H, d, J=8.0 Hz), 8.77 (1H, brs).

Example 231

HRMS (EI$^+$): 361.1932 (+2.9 mmu) [M$^+$]

$^1$H-NMR (400 MHz, CDCl$_3$) δ 1.31 (3H, d, J=6.7 Hz), 1.32 (3H, t, J=7.3 Hz), 2.52 (1H, d, J=17.1 Hz), 2.76 (1H, dd, J=6.7, 17.1 Hz), 2.86 (2H, q, J=6.7 Hz), 3.40-3.44 (1H, m), 3.53 (3H, s), 6.44 (1H, d, J=7.3 Hz), 6.99-7.01 (3H, m), 7.12 (1H, s), 7.24-7.28 (2H, m), 7.33 (1H, d, J=7.3 Hz), 8.60 (1H, brs).

Example 232

HRMS (EI$^+$): 300.1575 (−1.2 mmu) [M$^+$]

$^1$H-NMR (400 MHz, CDCl$_3$) δ 1.30 (3H, d, J=7.3 Hz), 1.38 (3H, t, J=7.3 Hz), 1.75 (3H, d, J=6.7 Hz), 2.53 (1H, d, J=17.1 Hz), 2.77 (1H, dd, J=6.7, 17.1 Hz), 2.90 (2H, q, J=7.3 Hz), 3.39-3.47 (1H, m), 5.34 (1H, q, J=6.7 Hz), 5.51 (1H, brs), 6.71 (1H, d, J=7.3 Hz), 7.07 (1H, s), 7.36 (1H, d, J=7.3 Hz), 8.73 (1H, brs).

Examples 233 and 234

6-(7-carbamoyl-2-ethyl-pyrazolo[1,5-a]pyridine-4-yl)-4,5-dihydro-5-methyl-3-(2H)-pyridazinone and 6-(2-ethyl-7-methoxycarboimidoyl-pyrazolo[1,5-a]pyridine-4-yl)-4,5-dihydro-5-methyl-3-(2H)-pyridazinone

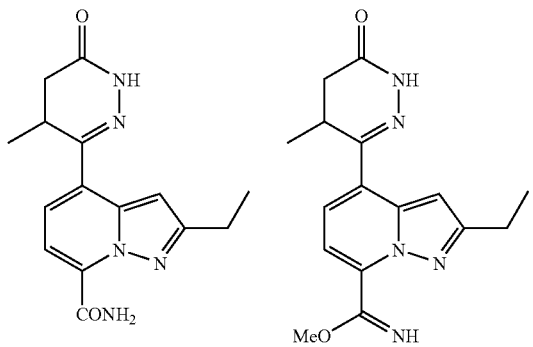

The compound of Example 230 (22.1 mg) was dissolved in methanol (2.00 μL). To this solution, 30% aqueous hydrogen peroxide (36.0 mL) and 25% aqueous potassium hydroxide solution (27.0 μL) were added and the mixture was stirred at room temperature for 3.5 hours. Subsequently, the reaction mixture was diluted with water and extracted with ethyl acetate. The organic layer was washed sequentially with water and saturated brine and dried over anhydrous sodium sulfate. Evaporation of the solvent and subsequent purification of the residue by amino-silica gel column chromatography (hexane:ethyl acetate=1:2) afforded a $CONH_2$-form (9.5 mg) as a yellow solid powder and a C(=NH)OMe-form as an orange solid powder.

$CONH_2$-form
HRMS (EI$^+$): 299.1364 (−1.8 mmu) [M$^+$]
$^1$H-NMR (400 MHz, CDCl$_3$) δ 1.33 (3H, d, J=7.3 Hz), 1.40 (3H, t, J=8.0 Hz), 2.58 (1H, dd, J=1.2, 17.1 Hz), 2.80 (1H, dd, J=6.7, 17.1 Hz), 2.92 (2H, q, J=8.0 Hz), 3.43-3.52 (1H, m), 6.19 (1H, brs), 7.21 (1H, s), 7.47 (1H, d, J=8.0 Hz), 7.94 (1H, d, J=8.0 Hz), 8.74 (1H, brs), 10.7 (1H, brs).

C(=NH)OMe-form
HRMS (EI$^+$): 313.1546 (+0.7 mmu)[M$^+$]
$^1$H-NMR (400 MHz, CDCl$_3$) δ 1.31 (3H, d, J=7.3 Hz), 1.41 (3H, t, J=8.0 Hz), 2.55 (1H, d, J=17.1 Hz), 2.80 (1H, dd, J=6.7, 17.1 Hz), 2.95 (2H, q, J=8.0 Hz), 3.43-3.49 (1H, m), 4.01 (3H, s), 7.08 (1H, s), 7.40 (1H, d, J=8.0 Hz), 7.53 (1H, d, J=8.0 Hz), 8.71 (1H, brs), 11.4 (1H, brs).

Example 235

6-(7-acetyl-2-ethyl-pyrazolo[1,5-a]pyridine-4-yl)-4,5-dihydro-5-methyl-3-(2H)-pyridazinone

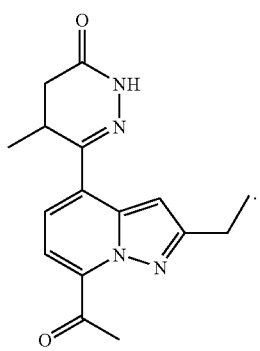

The compound of Example 232 (30.0 mg) was dissolved in DMSO (1.00 mL) in an argon atmosphere. To this solution, triethylamine (140 μL) and sulfur trioxide-pyridine complex (79.5 mg) were sequentially added and the mixture was stirred at room temperature for 2 hours. Subsequently, water was added and the mixture was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=1:1) afforded the title compound as a yellow amorphous material (28.9 mg).

HRMS (EI$^+$): 298.1409 (−2.1 mmu) [M$^+$]
$^1$H-NMR (400 MHz, CDCl$_3$) δ 1.30 (3H, d, J=7.3 Hz), 1.39 (3H, t, J=7.3 Hz), 2.55 (1H, dd, J=1.2, 17.1 Hz), 2.79 (1H, dd, J 6.7, 17.1 Hz), 2.92 (2H, q, J=7.3 Hz), 2.98 (3H, s), 3.42-3.48 (1H, m), 7.15 (1H, s), 7.25 (1H, d, J=7.3 Hz), 7.37 (1H, d, J=7.3 Hz), 8.73 (1H, brs).

Example 236

6-(2-fluoromethyl-7-methoxy-pyrazolo[1,5-a]pyridine-4-yl)-4,5-dihydro-5-methyl-3-(2H)-pyridazinone

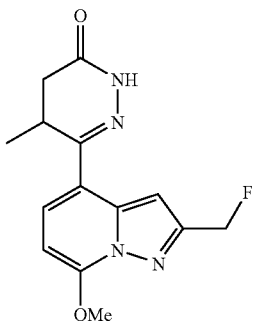

Diethylaminosulfur trifluoride (DAST) (55.9 mg) was added dropwise to a solution of the compound of Example 221 (100 mg) in chloroform (10 mL) at 0° C. The mixture was stirred at 0° C. for 30 min. Subsequently, the reaction was quenched by adding a saturated aqueous sodium bicarbonate solution. The mixture was extracted with ethyl acetate (50 mL) and the extract was washed with water and saturated brine and dried over anhydrous sodium sulfate. The dried extract was concentrated and purified by amino-silica gel column chromatography (hexane:ethyl acetate=1:3) to afford the title compound as a colorless powder (34.2 mg).

$^1$H-NMR (400 MHz, CDCl$_3$) δ 1.30 (3H, d, J=7.3 Hz), 2.53 (1H, d, J=17.7 Hz), 2.77 (1H, dd, J=17.1, 6.7 Hz), 3.35-3.47 (1H, m), 4.22 (3H, s), 5.65 (2H, d, J=47.7 Hz), 6.19 (1H, d, J=7.9 Hz), 7.41 (1H, s), 7.44 (1H, d, J=7.9 Hz), 8.59 (1H, s).
LRMS (EI$^+$): 290[M$^+$]
HRMS (EI$^+$): 290.1170(−0.9 mmu) [M$^+$]

Example 237

6-(2-formyl-7-methoxy-pyrazolo[1,5-a]pyridine-4-yl)-4,5-dihydro-5-methyl-3-(2H)-pyridazinone

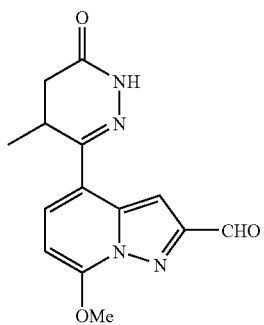

Activated manganese dioxide (226 mg) was added to a solution of the compound of Example 221 (150 mg) in chloroform (10 mL) and the mixture was stirred at 60° C. for 6 hours. Subsequently, the reaction mixture was filtered through Celite and the filtrate was concentrated to afford the title compound as a yellow powder (90.6 mg).

$^1$H-NMR (400 MHz, CDCl$_3$) δ 1.30 (3H, d, J=7.3 Hz), 2.54 (1H, d, J=17.1 Hz), 2.78 (1H, dd, J=16.5, 6.7 Hz), 3.35-3.46 (1H, m), 4.27 (3H, s), 6.32 (1H, d, J=7.9 Hz), 7.48 (1H, d, J=7.9 Hz), 7.82 (1H, s), 8.63 (1H, s), 10.32 (1H, s).

Example 238

6-[2-(1-hydroxyethyl)-7-methoxy-pyrazolo[1,5-a]pyridine-4-yl]-4,5-dihydro-5-methyl-3-(2H)-pyridazinone

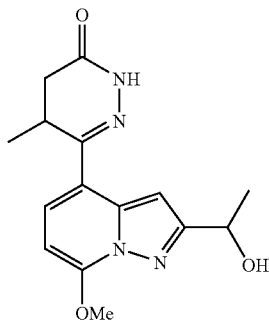

A 0.90 mol/L methyl magnesium bromide-tetrahydrofuran solution (0.878 mL) was added dropwise to a solution of the compound of Example 237 (90.6 mg) in THF (15 mL) at −78° C. in an argon atmosphere. The mixture was allowed to gradually warm to room temperature. The reaction was quenched by adding a saturated aqueous solution of ammonium chloride and the mixture was extracted with THF (100 mL). The extract was washed with water and saturated brine and dried over anhydrous sodium sulfate. The dried extract was concentrated and purified by recrystallization (methanol-ethyl acetate-hexane) to afford the title compound as a pale yellow powder (38.0 mg).

$^1$H-NMR (400 MHz, CDCl$_3$) δ 1.29 (3H, dd, J=7.3, 1.8 Hz), 1.67 (3H, d, J=6.7 Hz), 2.35 (1H, br s), 2.52 (1H, d, J=16.5 Hz), 2.76 (1H, dd, J=17.1, 6.7 Hz), 3.34-3.47 (1H, m), 4.21 (3H, s), 5.24 (1H, q, J=6.7 Hz), 6.15 (1H, d, J=8.6 Hz), 7.27 (1H, s), 7.42 (1H, d, J=8.6 Hz), 8.62 (1H, s)

LRMS (EI$^+$): 302 [M$^+$]
HRMS (EI$^+$): 302.1362(−1.7 mmu) [M$^+$]

Example 239

6-(7-methoxy-2-vinyl-pyrazolo[1,5-a]pyridine-4-yl)-4,5-dihydro-5-methyl-3-(2H)-pyridazinone

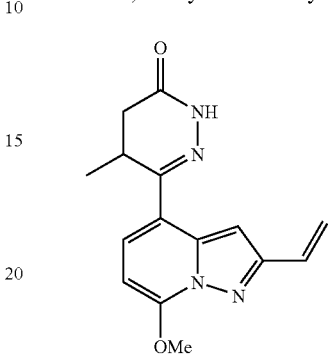

A 2.71 mol/L n-butyl lithium-hexane solution (0.52 mL) was added dropwise to a solution of methyltriphenylphosphonium bromide (499 mg) in THF (5 mL) at 0° C. The mixture was stirred at room temperature for 30 min. The compound of Example 237 (80.0 mg) in THF (5 mL) was then added dropwise at 0° C. and the mixture was further stirred at room temperature for 2 hours. Subsequently, the reaction was quenched by adding a saturated aqueous solution of ammonium chloride and the reaction mixture was extracted with ethyl acetate (50 mL). The extract was washed with water and saturated brine and dried over anhydrous sodium sulfate. The dried extract was concentrated and purification by silica gel column chromatography (hexane:ethyl acetate=1:2) and recrystallization (ethyl acetate-hexane) afforded the title compound as a pale yellow powder (7.1 mg).

$^1$H-NMR (400 MHz, CDCl$_3$) δ 1.30 (3H, d, J=7.9 Hz), 2.52 (1H, d, J=17.7 Hz), 2.77 (1H, dd, J=17.1, 6.7 Hz), 3.35-3.47 (1H, m), 4.21 (3H, s), 5.52 (1H, dd, J=11.0, 1.2 Hz), 6.06 (1H, dd, J=17.7, 1.2 Hz), 6.12 (1H, d, J=7.9 Hz), 6.97 (1H, dd, J=17.7, 11.0 Hz), 7.39 (1H, d, J=7.9 Hz), 7.40 (1H, s), 8.59 (1H, s).

LRMS (EI$^+$): 284 [M$^+$]
HRMS (EI$^+$): 284.1245(−2.9 mmu) [M$^+$]

Example 240

6-[2-(1-fluoroethyl)-7-methoxy-pyrazolo[1,5-a]pyridine-4-yl]-4,5-dihydro-5-methyl-3-(2H)-pyridazinone

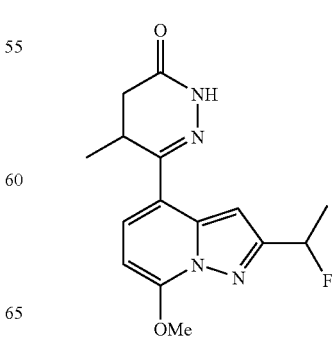

DAST (51.2 mg) was added dropwise to a solution of the compound of Example 238 (80.0 mg) in chloroform (10 mL) at 0° C. and the mixture was stirred at 0° C. for 30 min. The reaction was quenched by adding a saturated aqueous sodium bicarbonate solution and the reaction mixture was extracted with chloroform (30 mL). The extract was washed with water and saturated brine and dried over anhydrous sodium sulfate. The dried extract was concentrated and purified by silica gel column chromatography (hexane:ethyl acetate=1:4) to afford the title compound as a pale yellow powder (30.6 mg).

$^1$H-NMR (400 MHz, CDCl$_3$) δ 1.28 (1.5H, d, J=3.7 Hz), 1.30 (1.5H, d, J=3.7 Hz), 1.78 (1.5H, d, J=6.7 Hz), 1.84 (1.5H, d, J=6.1 Hz), 2.52 (1H, d, J=17.1 Hz), 2.77 (1H, dd, J=17.1, 6.7 Hz), 3.35-3.47 (1H, m), 4.21 (3H, s), 5.90 (0.5H, q, J=6.7 Hz), 6.02 (0.5H, q, J=6.7 Hz), 6.17 (1H, d, J=7.9 Hz), 7.36 (1H, s), 7.43 (1H, d, J=7.9 Hz), 8.61 (1H, s).

LRMS (EI$^+$): 304 [M$^+$]

HRMS (EI$^+$): 304.1329(−0.7 mmu)[M$^+$]

Example 241

6-(2-acetyl-7-methoxy-pyrazolo[1,5-a]pyridine-4-yl)-4,5-dihydro-5-methyl-3-(2H)-pyridazinone

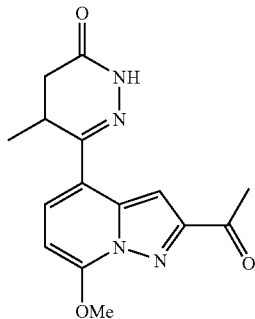

Triethylamine (1.46 mL) was added to a solution of the compound of Example 238 (315 mg) in DMSO (10 mL). While the mixture was stirred at room temperature, sulfur trioxide-pyridine complex (829 mg) was added at once and the mixture was further stirred at room temperature for 1 hour. Subsequently, the reaction was quenched by adding water (100 mL). Filtration of the resulting crystals afforded the title compound as a colorless powder (187 mg).

$^1$H-NMR (400 MHz, CDCl$_3$) δ 1.29 (3H, d, J=7.3 Hz), 2.53 (1H, d, J=17.1 Hz), 2.77 (1H, dd, J=17.1, 6.7 Hz), 2.79 (3H, s), 3.33-3.45 (1H, m), 4.24 (3H, s), 6.27 (1H, d, J=7.9 Hz), 7.44 (1H, d, J=8.6 Hz), 7.79 (1H, s), 8.60 (1H, s).

LRMS (EI$^+$): 300[M$^+$]

HRMS (EI$^+$): 300.1193(−2.9 mmu) [M$^+$]

Example 242

6-[2-(1-hydroxy-1-methylethyl)-7-methoxy-pyrazolo[1,5-a]pyridine-4-yl]-4,5-dihydro-5-methyl-3-(2H)-pyridazinone

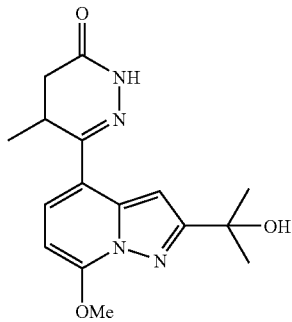

A 0.90 mol/L methyl magnesium bromide-tetrahydrofuran solution (0.614 mL) was added dropwise to a solution of the compound of Example 241 (55.4 mg) in THF (5 mL) at −78° C. in an argon atmosphere. The mixture was allowed to gradually warm to room temperature and was stirred for 3 hours. Subsequently, a second portion of 0.90 mol/L methyl magnesium bromide-tetrahydrofuran solution (0.614 mL) was added dropwise at −78° C. and the mixture was stirred at room temperature for another 3 hours. The reaction was then quenched by adding a saturated aqueous solution of ammonium chloride and the mixture was extracted with ethyl acetate (100 mL). The extract was washed with water and saturated brine and dried over anhydrous sodium sulfate. The dried extract was concentrated and purified by silica gel column chromatography (ethyl acetate) to afford the title compound as a pale yellow powder (14.0 mg).

$^1$H-NMR (400 MHz, CDCl$_3$) δ 1.29 (3H, d, J=7.3 Hz), 1.72 (6H, s), 2.52 (1H, dd, J=17.1, 1.2 Hz), 2.76 (1H, dd, J=17.1, 6.7 Hz), 2.77 (1H, br s), 3.35-3.47 (1H, m), 4.20 (3H, s), 6.14 (1H, d, J=7.9 Hz), 7.23 (1H, s), 7.41 (1H, d, J=7.9 Hz), 8.63 (1H, s).

HRMS (EI$^+$): 316.1544(+0.8 mmu) [M$^+$]

Example 243

6-[2-(1-fluoro-1-methylethyl)-7-methoxy-pyrazolo[1,5-a]pyridine-4-yl]-4,5-dihydro-5-methyl-3-(2H)-pyridazinone

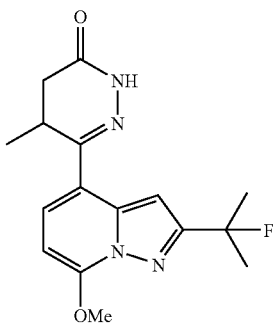

DAST (27.9 mg) was added dropwise to a solution of the compound of Example 242 (21.9 mg) in chloroform (5.0 mL) and the mixture was stirred at 0° C. for 30 min. Subsequently, the reaction was quenched by adding a saturated aqueous sodium bicarbonate solution and the mixture was extracted with chloroform (30 mL). The extract was washed with water and saturated brine and dried over anhydrous sodium sulfate. The dried extract was concentrated and purified by silica gel column chromatography (hexane:ethyl acetate=1:3→:4) to afford the title compound as a colorless powder (16.0 mg).

$^1$H-NMR (400 MHz, CDCl$_3$) δ 1.29 (3H, d, J=7.3 Hz), 1.87 (6H, d, J=22.0 Hz), 2.52 (1H, d, J=17.1 Hz), 2.76 (1H, dd, J=17.1, 6.7 Hz), 3.35-3.46 (1H, m), 4.20 (3H, s), 6.15 (1H, d, J=7.9 Hz), 7.32 (1H, s), 7.42 (1H, d, J=7.9 Hz), 8.59 (1H, s).

LRMS (EI$^+$): 318 [M$^+$]

HRMS (EI$^+$): 318.1474(−1.8 mmu)[M$^+$]

Example 244

6-(7-ethoxy-2-ethyl-pyrazolo[1,5-a]pyridine-4-yl)-4,5-dihydro-5-methyl-3-(2H)-pyridazinone

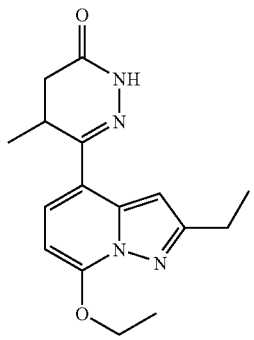

60% sodium hydride (35 mg) was added to ethanol (1.8 mL) at 0° C. in an argon atmosphere and the mixture was stirred at room temperature for 30 min. The compound of Example 216 (50 mg) was then added and the mixture was further stirred for 2 hours under reflux. Subsequently, the reaction was quenched by adding water and the mixture was extracted with ethyl acetate. The organic layer was washed with saturated brine, and dried over magnesium sulfate and filtered. The solvent was evaporated under reduced pressure and the residue was purified by amino-silica gel column chromatography (hexane:ethyl acetate=1:1). Washing the purified product with diisopropyl ether afforded the title compound as a colorless powder (26.9 mg).

HRMS (EI$^+$): 300.1561 (−2.6 mmu) [M$^+$]

$^1$H-NMR (CDCl$_3$, 400 MHz) δ 1.29 (3H, d, J=7.3 Hz), 1.38 (3H, t, J=7.3 Hz), 1.65 (3H, t, J=7.3 Hz), 2.50 (1H, d, J=16.2 Hz), 2.75 (1H, dd, J=6.7, 16.2 Hz), 2.94 (2H, q, J=7.3 Hz), 3.39-3.42 (1H, m), 4.46 (2H, q, J=7.3 Hz), 6.07 (1H, d, J=7.9 Hz), 7.09 (1H, s), 7.36 (1H, d, J=7.9 Hz), 8.56 (1H, brs).

Example 245

6-(7-isopropoxy-2-ethyl-pyrazolo[1,5-a]pyridine-4-yl)-4,5-dihydro-5-methyl-3-(2H)-pyridazinone

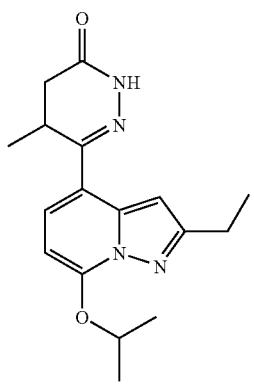

Using isopropanol, the reaction was carried out as in Example 244 to afford the title compound as a colorless powder.

HRMS (EI$^+$): 314.1719 (−2.3 mmu) [M$^+$]

$^1$H-NMR (CDCl$_3$, 400 MHz) δ 1.29 (3H, d, J=7.3 Hz), 1.37 (3H, t, J=7.3 Hz), 1.59 (6H, dd, J=1.8, 6.2 Hz), 2.50 (1H, d, J=16.2 Hz), 2.75 (1H, dd, J=6.7, 16.2 Hz), 2.94 (2H, q, J=7.3 Hz), 3.39-3.42 (1H, m), 4.90-4.96 (1H, m), 6.07 (1H, d, J=7.9 Hz), 7.09 (1H, s), 7.36 (1H, d, J=7.9 Hz), 8.56 (1H, brs).

Example 246

6-(7-cyclopropylmethyloxy-2-ethyl-pyrazolo[1,5-a]pyridine-4-yl-4,5-dihydro-5-methyl-3-(2H)-pyridazinone

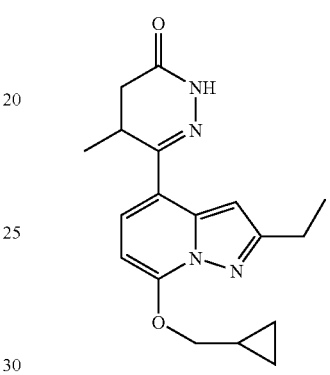

Using cyclopropylmethanol, the reaction was carried out as in Example 244 to afford the title compound as a colorless powder.

HRMS (EI$^+$): 326.1747 (+0.4 mmu) [M$^+$]

$^1$H-NMR (CDCl$_3$, 400 MHz) δ 0.47-0.50 (2H, m), 0.74-0.76 (2H, m), 1.48-1.51 (1H, m), 1.28 (3H, d, J=7.3 Hz), 1.38 (3H, t, J=7.3 Hz), 2.50 (1H, d, J=16.5 Hz), 2.75 (1H, dd, J=6.5, 16.5 Hz), 2.94 (2H, q, J=7.3 Hz), 3.37-3.46 (1H, m), 4.21 (2H, d, J=6.7 Hz), 6.07 (1H, d, J=7.9 Hz), 7.09 (1H, s), 7.35 (1H, d, J=7.9 Hz), 8.57 (1H, brs).

Example 247

6-[2-ethyl-7-(2-hydroxyethylamino)-pyrazolo[1,5-a]pyridine-4-yl]-4,5-dihydro-5-methyl-3-(2H)-pyridazinone

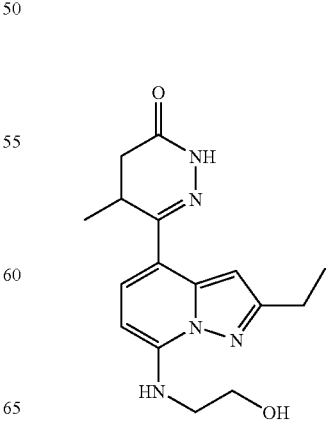

The compound of Example 216 (30.0 mg) was dissolved in ethanolamine (2.00 mL) and the solution was stirred first at 60° C. for 4 hours and then at 100° C. for 2 hours. Subsequently, the reaction mixture was diluted with ethyl acetate, washed sequentially with water and saturated brine and dried over anhydrous sodium sulfate. Evaporation of the solvent and subsequent purification of the residue by amino-silica gel column chromatography (ethyl acetate) afforded the title compound as a pale yellow powder (11.9 mg).

HRMS (EI$^+$): 315.1692 (−0.3 mmu) [M$^+$]

$^1$H-NMR (400 MHz, CDCl$_3$) δ 1.28 (3H.3 Hz, d, J=7.3 Hz), 1.38 (3H, t, J=7.3 Hz), 1.80 (1H, brs), 2.48 (1H, d, J=16.5 Hz), 2.73 (1H, dd, J=6.7, 16.5 Hz), 2.88 (2H, q, J=7), 3.38-3.44 (1H, m), 3.60 (2H, q, J=7.3 Hz), 3.97-3.99 (2H, m), 5.91 (1H, d, J=8.0 Hz), 6.59 (1H, brs), 7.38 (1H, d, J=8.0 Hz), 8.51 (1H, brs).

Example 248

6-[2-ethyl-7-(2-dimethylaminoethyloxy)-pyrazolo[1,5-a]pyridine-4-yl]-4,5-dihydro-5-methyl-3-(2H)-pyridazinone

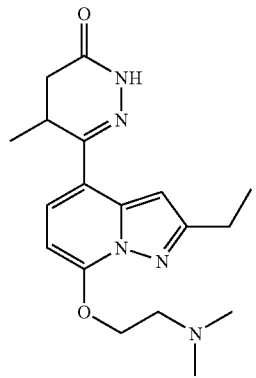

The compound of Example 216 (50.0 mg) was dissolved in 2-dimethylaminoethanol (2.00 mL) in an argon atmosphere. While the solution was kept at 0° C., 60% sodium hydride (21.0 mg) was added and the mixture was stirred at 60° C. for 4 hours. Subsequently, a saturated aqueous solution of ammonium chloride was added and the mixture was extracted with ethyl acetate. The organic layer was washed sequentially with water and saturated brine and dried over an hydrous sodium sulfate. Evaporation of the solvent and subsequent purification of the residue by silica gel column chromatography (NH, ethyl acetate) afforded the title compound as a yellow powder (22.5 mg).

HRMS (EI$^+$): 343.2011 (+0.3 mmu) [M$^+$]

$^1$H-NMR (400 MHz, CDCl$_3$) δ 1.29 (3H, d, J=7.3 Hz), 1.37 (3H, t, J=7.3 Hz), 2.39 (3H, s), 2.51 (1H, d, J=17.1 Hz), 2.76 (1H, dd, J=6.7, 17.1 Hz), 2.92 (2H, q, J=7.3 Hz), 2.96 (2H, t, J=6.1 Hz), 3.36-3.43 (1H, m), 4.44 (2H, t, J=6.1 Hz), 6.10 (1H, d, J=8.0 Hz), 7.08 (1H, s), 7.36 (1H, d, J=8.0 Hz), 8.60 (1H, brs).

Examples 249 through 252

6-(2-ethyl-7-methylsulfinyl-pyrazolo[1,5-a]pyridine-4-yl)-4,5-dihydro-5-methyl-3-(2H)-pyridazinone

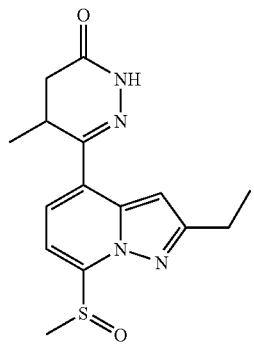

6-(2-ethyl-4-hydroxy-7-methylsulfinyl-pyrazolo[1,5-a]pyridine-4-yl)-4,5-dihydro-5-methyl-3-(2H)-pyridazinone

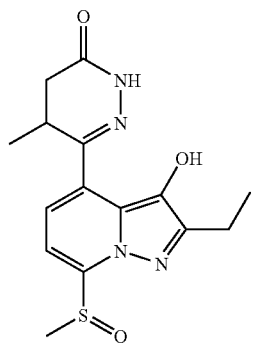

6-(2-ethyl-7-methylsulfonyl-pyrazolo[1,5-a]pyridine-4-yl)-4,5-dihydro-5-methyl-3-(2H)-pyridazinone

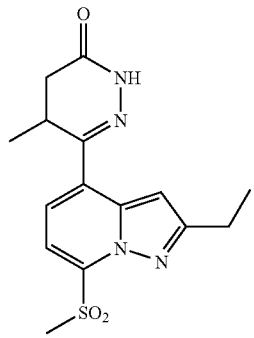

6-(2-ethyl-4-hydroxy-7-methylsulfonyl-pyrazolo[1,5-a]pyridine-4-yl)-4,5-dihydro-5-methyl-3-(2H)-pyridazinone

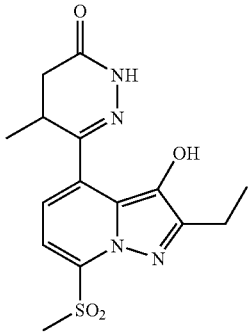

The compound of Example 219 (100 mg) was dissolved in methylene chloride (5.00 mL). While this solution was kept at 0° C., 65% m-chloroperbenzoic acid (mCPBA) (132 mg) was added and the solution was stirred for 1 hour. Subsequently, a saturated aqueous sodium bicarbonate solution was added and the mixture was extracted with ethyl acetate. The organic layer was washed sequentially with a saturated aqueous sodium bicarbonate solution and saturated brine and was dried over anhydrous sodium sulfate. The solvent was evaporated and the residue was purified by silica gel column chromatography (hexane:ethyl acetate=1:2→ethyl acetate). The product was further purified by amino-silica gel column chromatography (methylene chloride) to afford 7-sulfoxide form, 3-hydroxy-7-sulfoxide form, 7-sulfone form and 3-hydroxy-7-sulfone form as a yellow powder (79.1 mg), reddish orange powder (26.5 mg), yellow oil (13.0 mg) and reddish orange powder (3.00 mg), respectively.

Example 249

7-sulfoxide Form

HRMS (EI$^+$): 318.1165 (+1.5 mmu) [M$^+$]
$^1$H-NMR (400 MHz, CDCl$_3$) δ 1.32 (3H, d, J=7.9 Hz), 1.36 (3H, t, J=7.9 Hz), 2.57 (1H, d, J=17.1 Hz), 2.75-2.83 (1H, m), 2.88 (2H, q, J=7.9 Hz), 3.15 (3H, s), 3.46-3.50 (1H, m), 7.13 (1H, s), 7.38 (1H, d, J=7.3 Hz), 7.54 (1H, d, J=7.3 Hz), 8.72 (1H, brs).

Example 250

3-hydroxy-7-sulfoxide form

HRMS (EI$^+$): 334.1089 (−1.0 mmu) [M$^+$]
$^1$H-NMR (400 MHz, CDCl$_3$) δ 1.32 (3H, d, J=7.3 Hz), 1.36 (3H, t, J=7.3 Hz), 2.59 (1H, d, J=17.1 Hz), 2.74-2.85 (3H, m), 3.12 (3H, s), 3.51-3.55 (1H, m), 7.08 (1H, d, J=7.3 Hz), 7.29 (1H, d, J=7.3 Hz), 8.75 (1H, brs), 9.85 (1H, s).

Example 251

7-sulfone form

HRMS (EI$^+$): 334.1137 (+3.7 mmu) [M$^+$]
$^1$H-NMR (400 MHz, CDCl$_3$) δ 1.31 (3H, d, J=7.9 Hz), 1.39 (3H, t, J=7.3 Hz), 2.58 (1H, dd, J=1.2, 17.1 Hz), 2.80 (1H, dd, J=6.7, 17.1 Hz), 2.96 (2H, q, J=7.3 Hz), 3.43-3.47 (1H, m), 3.62 (3H, s), 7.21 (1H, s), 7.43 (1H, d, J=7.3 Hz), 7.62 (1H, d, J=7.3 Hz), 8.75 (1H, brs).

Example 252

3-hydroxy-7-sulfone form

HRMS (EI$^+$): 350.1026 (−2.3 mmu) [M$^+$]
$^1$H-NMR (400 MHz, CDCl$_3$) δ 1.34-1.37 (6H, m), 2.60 (1H, d, J=17.1 Hz), 2.80 (1H, dd, J=7.3, 17.1 Hz), 2.88 (2H, q, J=7.3 Hz), 3.49-3.53 (1H, m), 3.57 (3H, s), 7.16 (1H, d, J=8.0 Hz), 7.31 (1H, d, J=8.0 Hz), 8.76 (1H, brs), 9.82 (1H, s).

Example 253

6-chloro-5-methyl-2H-pyradazine-3-one

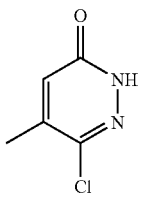

3,6-dichloro-4-methylpyridazine (30.6 g) was dissolved in glacial acetic acid (800 mL) and the solution was stirred at 110 to 115° C. for 4 hours. Subsequently, acetic acid was concentrated under reduced pressure. A saturated aqueous sodium bicarbonate solution (approx. 200 mL) was added to the residue to adjust the pH to 6 and the mixture was vigorously stirred at room temperature. The reaction mixture was then extracted with methylene chloride, washed with saturated brine and dried over magnesium sulfate. Evaporation of the solvent and subsequent purification of the residue by silica gel column chromatography (1% MeOH/CH$_2$Cl$_2$, followed by 5% MeOH/CH$_2$Cl$_2$) afforded the title compound as a colorless powder (5.00 g).
$^1$H NMR (200 MHz, CDCl$_3$-CD$_3$OD) δ 6.82 (1H, s), 2.90 (1H, brs), 2.20 (3H, s).
$^{13}$C NMR (50 MHz, CDCl$_3$) δ 161.9, 144.8, 141.2, 129.6, 19.8

Example 254

3-chloro-4-methyl-6-oxo-6H-pyridazine-1-yl-methyl 2,2-dimethylpropionate

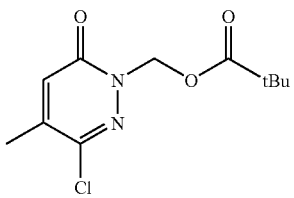

The compound of Example 253 (2.15 g) was dissolved in DMF (70 mL) in an argon atmosphere. To this solution, potassium carbonate (4.11 g) was added and the mixture was stirred at 40° C. to 50° C. for 20 min. The mixture was then allowed to warm to room temperature. Chloromethyl pivalate (2.60 mL) was added and the mixture was stirred at room temperature for 18 hours. Subsequently, the solvent was evaporated and the residue was dissolved in ethyl acetate. The solution was washed with saturated brine and dried over magnesium sulfate. The solvent was concentrated and the residue was purified by silica gel column chromatography (ethyl acetate:petroleum ether=3:7) to afford the title compound as a colorless powder (3.22 g).

$^1$H NMR (200 MHz, CDCl$_3$) δ 6.82 (1H, s), 6.07 (2H, s), 2.40 (3H, s), 1.35 (9H, s).

$^{13}$C NMR (50 MHz, CDCl$_3$) δ 177.2, 159.2, 144.2, 140.3, 129.8, 72.6, 38.8, 26.9, 19.6

Example 255

2-benzyl-6-chloro-2H-pyridazine-3-one

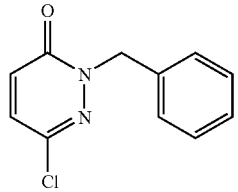

6-chloro-2H-pyridazine-3-one (3.50 g) was dissolved in DME (130 mL). To this solution, cesium carbonate (17.5 g) was added and the mixture was stirred at room temperature for 15 min in an argon atmosphere. Subsequently, benzyl bromide (4.00 mL) was added and the mixture was stirred at room temperature for 3.5 hours. The insoluble inorganic residue was removed by filtration and the filtrate was concentrated. Water was then added to the residue and the mixture was extracted with ethyl acetate, washed with saturated brine and dried over magnesium sulfate. The solvent was evaporated and the resulting crystals were recrystallized from ethyl acetate/petroleum ether to afford the title compound as a pale yellow powder (4.94 g).

$^1$H NMR (200 MHz, CDCl$_3$) δ 7.28-7.47 (5H, m), 7.15 (1H, d, J=9.6 Hz), 6.90 (1H, d, J=9.6 Hz), 5.25 (2H, s).

$^{13}$C NMR (50 MHz, CDCl$_3$) δ 158.77, 137.43, 135.48, 133.66, 132.20, 128.86, 128.67, 128.20, 55.43

Example 256

6-chloro-2-(pyridine-3-ylmethyl)-2H-pyridazine-3-one

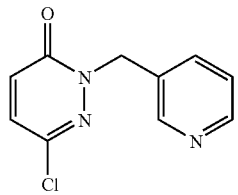

6-chloro-2H-pyridazine-3-one (1.00 g) was dissolved in DMF (76 mL). To this solution, 60% sodium hydride (370 mg) was added at room temperature in an argon atmosphere and the mixture was vigorously stirred at 50° C. Meanwhile, 60% sodium hydride (370 mg) was added to a solution of 3-(chloromethyl)pyridine hydrochloride (1.51 g) in DMF at −40° C. in an argon atmosphere and the solution was allowed to warm to room temperature. Using a cannula, this solution was poured into the pyridazinone solution and the mixture was stirred first at 50° C. for 90 min and then at room temperature for 18 hours. Subsequently, a saturated ammonium chloride solution was added and the solvent was concentrated. Water was then added to the residue and the mixture was extracted with ethyl acetate. The organic layer was washed with saturated brine and dried over anhydrous sodium sulfate. Evaporation of the solvent and subsequent purification by silica gel column chromatography (ethyl acetate: petroleum ether=7:3, followed by methanol:ethyl acetate=5: 95) afforded the title compound as a colorless powder (1.30 g).

$^1$H NMR (200 MHz, CDCl$_3$) δ 8.70 (1H, d, J=1.5 Hz), 8.55 (1H, dd, J=4.8, 1.5 Hz), 7.78 (1H, dt, J=7.9, 1.5 Hz), 7.26 (1H, dd, J=7.9, 4.9 Hz), 7.16 (1H, d, J=9.6 Hz), 6.90 (1H, d, J=9.6 Hz), 5.24 (2H, s).

$^{13}$C NMR (50 MHz, CDCl$_3$) δ 158.63, 150.17, 149.62, 137.82, 136.64, 133.91, 132.17, 131.07, 123.54, 52.95

Example 257

6-chloro-2-(pyridine-2-ylmethyl)-2H-pyridazine-3-one

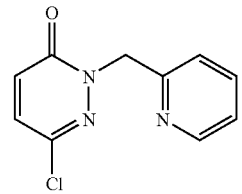

Using 2-(bromomethyl)pyridine hydrobromide, the reaction was carried out as in Example 256 to afford the title compound as a colorless powder.

$^1$H NMR (200 MHz, CDCl$_3$) δ 8.55 (1H, ddd, J=5.0, 1.7, 0.8 Hz), 7.65 (1H, td, J=7.7, 1.7 Hz), 7.21 (1H, d, J=9.6 Hz), 7.15-7.26 (2H, m), 6.95 (1H, d, J=9.6 Hz), 5.40 (2H, s).

$^{13}$C NMR (50 MHz, CDCl$_3$) δ 158.98, 154.90, 149.66, 137.73, 136.74, 133.98, 132.16, 122.73, 122.24, 57.10

Example 258

6-chloro-2-(pyridine-3-ylmethyl)-2H-pyridazine-3-one

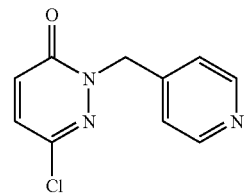

Using 4-(bromomethyl)pyridine hydrobromide, the reaction was carried out as in Example 256 to afford the title compound as a colorless powder.

¹H NMR (200 MHz, CDCl₃) δ 8.58 (2H, br m), 7.27 (2H, br d, J=5.7 Hz), 7.21 (1H, d, J=9.6 Hz), 6.95 (1H, d, J=9.6 Hz), 5.24 (2H, s).

¹³C NMR (50 MHz, CDCl₃) δ 158.62, 150.13, 143.90, 137.97, 134.03, 132.15, 123.03, 54.17

Example 259

2-bromo-6-methoxypyridine

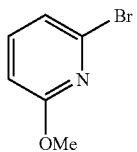

In a nitrogen atmosphere, sodium methoxide (36.6 g) was added to 2,6-dibromopyridine (93.0 g) in methanol (200 mL) in an ice bath. The mixture was refluxed for 5 hours and was allowed to cool. The resulting crystals were collected by filtration and the filtrate was concentrated. Water was then added to the residue and the mixture was extracted with methylene chloride. The organic layer was dried over anhydrous sodium sulfate. Evaporation of the solvent gave the title compound as a yellow oil (69.5 g, substantially pure product).

¹H NMR (200 MHz, CDCl₃) δ 7.37 (1H, t, J=7.8 Hz), 7.00 (1H, d, J=7.5 Hz), 6.64 (1H, d, J=8.3 Hz), 3.89 (3H, s).

¹³C NMR (50 MHz, CDCl₃) δ 163.59, 140.22, 138.48, 120.04, 109.29, 53.91

Example 260

2,3-dibromo-6-methoxypyridine

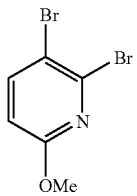

NBS (302 g) was added to the compound of Example 259 (295 g) in acetonitrile (575 mL) and the mixture was stirred at 80 to 90° C. for 1 day in a nitrogen atmosphere. After cooling, the crystallized imide was removed by filtration and the filtrate was concentrated. Purification of the resulting residue by silica gel column chromatography (ether:petroleum ether=1:1) gave a 6:1 mixture of the title compound and 2,5-dibromo form. This product was crystallized from cold petroleum ether to afford the title compound as a colorless powder (223 g).

¹H NMR (200 MHz, CDCl₃) δ 6.68 (1H, d, J=8.7 Hz), 6.60 (1H, d, J=8.7 Hz), 3.91 (3H, s).

¹³C NMR (50 MHz, CDCl₃) δ 162.01, 143.29, 139.68, 113.69, 111.10, 54.40

LRMS (EI⁺): 264[M⁺]

Example 261

3-bromo-6-methoxy-2-(3-methyl-1-butynyl)pyridine

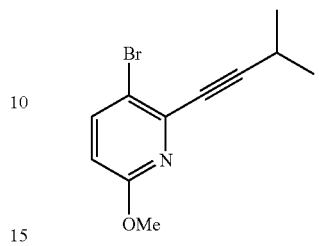

In a nitrogen atmosphere, tetrakis-triphenylphosphine palladium (5.15 g), copper iodide (5.95 g), diisopropylamine (15 mL) and 3-methyl-2-butyne (38.1 g) were added to the compound of Example 260 (131 g) in THF (150 mL). The mixture was placed in a sealed vessel and stirred at 70° C. for 21 hours. The resulting salt was removed by filtration and the filtrate was mixed with silica gel for condensation. The silica gel was directly eluted (ether:petroleumether=5:95) and the collected eluate was distilled (93° C., 0.1 mmHg) to afford the title compound as a pale yellow oil (121 g).

¹H NMR (200 MHz, CDCl₃) δ 7.63 (1H, d, J=8.7 Hz), 6.51 (1H, d, J=8.7 Hz), 3.88 (3H, s), 2.83 (1H, septet, J=6.9 Hz), 1.28 (6H, d, J=6.9 Hz).

¹³C NMR (50 MHz, CDCl₃) δ 162.37, 141.72, 140.23, 115.06, 111.73, 100.84, 78.60, 53.73, 22.42, 21.29

Example 262

4-bromo-2-isopropyl-7-methoxypyrazolo[1,5-a]pyridine

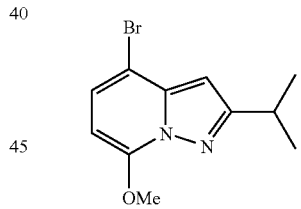

The compound of Example 261 (28.9 g) was added to a solution of MSH (26.1 g) in methylene chloride (250 mL) and the mixture was stirred for 4 hours, followed by concentration of the solvent and sequential addition of DMF (250 mL) and potassium carbonate (65.1 g). The resulting mixture was vigorously stirred at room temperature for 2 hours. Subsequently, saturated brine was added and the mixture was extracted with ether. The organic layer was dried over magnesium sulfate. The solvent was evaporated and the residue was purified by silica gel column chromatography (10 to 30% methylene chloride/petroleum ether). The purified product was solidified in petroleum ether to afford the title compound as a colorless powder (5.14 g).

¹H NMR (200 MHz, CDCl₃) δ 7.23 (1H, d, J=7.9 Hz), 6.43 (1H, s), 5.90 (1H, d, J=7.9 Hz), 4.11 (3H, s), 3.26 (1H, septet, J=7.1 Hz), 1.37 (6H, d, J=7.1 Hz).

¹³C NMR (50 MHz, CDCl₃) δ 163.15, 150.61, 142.20, 126.55, 100.99, 95.20, 87.87, 56.81, 28.36, 23.09

Example 263

2-isopropyl-7-methoxypyrazolo[1,5-a]pyridine-4-boric acid

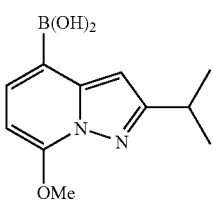

The compound of Example 262 (1.60 g) was dissolved in THF (60 mL) in an argon atmosphere. While this solution was stirred at −78° C., butyl lithium (2.5 mol/L hexane solution, 2.62 mL) was added. After 15 min, trimethylborate (1.7 mL) was added and the mixture was stirred at the same temperature for 1 hour and then at room temperature for 15 min. Subsequently, ethanol (5 mL) was added. The solvent was concentrated and the residue was purified by silica gel column chromatography (ethyl acetate:methanol=10:0.3) to afford the title compound as a colorless powder (899 mg).

$^1$H NMR (200 MHz, CDCl$_3$) δ 7.99 (1H, d, J=7.5 Hz), 7.03 (1H, s), 6.05 (1H, d, J=7.5 Hz), 4.20 (3H, s), 3.34 (1H, septet, J=7.1 Hz), 1.46 (6H, d, J=7.1 Hz), 1.15-1.65 (2H, br).

Example 264

2-methoxypyridine-5-boric acid

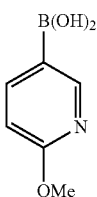

In an argon atmosphere, butyl lithium (2.5 mol/L hexane solution, 26 mL) was added to a solution of 5-bromo-2-methoxypyridine (11.3 g) in THF (120 mL) under stirring at −78° C. After 15 min, trimethylborate (20 mL) was added and the mixture was stirred for 1 hour as it was allowed to gradually warm to room temperature. Subsequently, the solvent was concentrated and water was added to the residue. Concentrated hydrochloric acid was then added to adjust the pH to 6 and the resulting crystals were collected by filtration. This product was washed with petroleum ether and dried to afford the title compound as a white powder (8.23 g).

$^1$H NMR (200 MHz, DMSO-d$_6$) δ 8.52 (1H, br d, J=2.1 Hz), 8.15 (2H, br s), 8.00 (1H, dd, J=8.7, 2.1 Hz), 6.76 (1H, d, J=8.3 Hz), 3.85 (3H, s).

Example 265

2-benzyl-6-(6-methoxypyridine-3-yl)-2H-pyridazine-3-one

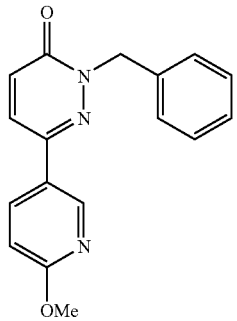

2-benzyl-6-chloro-2H-pyridazine-3-one (4.00 g), tetrakis(triphenylphosphine)palladium (1.05 g) and 2 mol/L aqueous sodium carbonate solution (27 mL) were added to a solution of the compound of Example 264 (3.33 g) in THF (90 mL) in an argon atmosphere. The mixture was refluxed for 18 hours. Subsequently, water was added and the mixture was extracted with ethyl acetate. The organic layer was washed with saturated brine and dried over magnesium sulfate. The solvent was concentrated and the residue was purified by silica gel column chromatography (ethyl acetate:petroleum ether=6:4). The product was recrystallized (ethyl acetate/petroleum ether) to afford the title compound as a colorless powder (3.94 g).

$^1$H NMR (200 MHz, CDCl$_3$) δ 8.52 (1H, d, J=2.5 Hz), 8.00 (1H, dd, J=8.7, 2.5 Hz), 7.57 (1H, d, J=10.0 Hz), 7.49 (2H, dd, J=7.9, 1.7 Hz), 7.26-7.37 (3H, m), 7.00 (1H, d, J=10.0 Hz), 6.81 (1H, d, J=8.7 Hz), 5.37 (2H, s), 3.96 (3H, s)

$^{13}$C NMR (50 MHz, CDCl$_3$) δ 164.70, 159.34, 144.49, 142.07, 136.07, 130.57, 129.28, 128.81, 128.53, 127.90, 124.03, 111.24, 55.35, 53.68

Example 266

2-benzyl-6-(7-methoxy-3-methoxycarbonyl-2-isopropyl-pyrazolo[1,5-a]pyridine-4-yl)-3-(2H)-pyridazinone

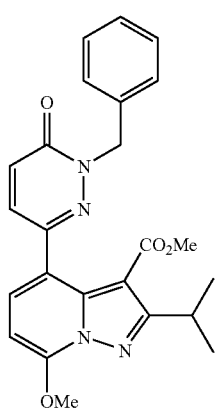

A solution of Example 265 (2.50 g) in methylene chloride (10 mL) was added to a solution of MSH (1.93 g) in methylene chloride (10 mL) at −15° C. in an argon atmosphere. The mixture was stirred for 1 hour as it was slowly warmed to room temperature. This was followed by evaporation of the solvent and addition of DMF (42 mL), methyl 4-methyl-2-pentynoate (1.07 g) and potassium carbonate (2.35 g) at 0° C. The resulting mixture was stirred at room temperature for 18 hours. Subsequently, the inorganic residue was removed by filtration and the filtrate was concentrated. A 2 mol/L sodium hydroxide solution was added and the mixture was extracted with ethyl acetate. The organic layer was washed with saturated brine and dried over magnesium sulfate. The solvent was concentrated and the residue was purified by silica gel column chromatography (ethyl acetate:petroleum ether=8:2) to afford the title compound as a brown oil (0.23 g).

$^1$H NMR (200 MHz, CDCl$_3$) δ 7.21-7.71 (7H, m), 6.92 (1H, d, J=9.6 Hz), 6.30 (1H, d, J=7.9 Hz), 5.36 (2H, s), 4.19 (3H, s), 3.71 (1H, septet, J=7.1 Hz), 1.41 (6H, d, J=7.1 Hz).

$^{13}$C NMR (50 MHz, CDCl$_3$) δ 164.97, 163.75, 159.45, 151.68, 145.12, 140.32, 136.16, 132.80, 130.59, 128.77, 128.53, 127.89, 118.66, 101.46, 90.10, 57.28, 55.41, 50.78, 27.35, 21.92

Example 267

2-benzyl-6-(3-carboxy-7-methoxy-2-isopropyl-pyrazolo[1,5-a]pyridine-4-yl)-3-(2H)-pyridazinone

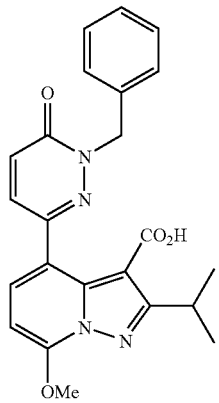

A solution of the compound of Example 266 (250 mg) and lithium hydroxide (140 mg) in a mixture of THF, water and methanol (6 mL, THF:water:methanol=3:2:1) was refluxed for 18 hours. Subsequently, water was added, followed by addition of 2 mol/L hydrochloric acid to adjust the pH to 4. The mixture was extracted with ethyl acetate and the organic layer was washed with saturated brine and dried over magnesium sulfate. The solvent was concentrated and the residue was purified by silica gel column chromatography (ethyl acetate:methanol=98:2) to afford the title compound as a colorless powder (120 mg).

$^1$H NMR (200 MHz, CDCl$_3$) δ 10.00 (1H, br s), 7.15-7.70 (7H, m), 6.97 (1H, d, J=9.6 Hz), 6.25 (1H, d, J=7.9 Hz), 5.25 (2H, s), 4.19 (3H, s), 3.79 (1H, septet, J=7.1 Hz), 1.45 (6H, d, J=7.1 Hz).

$^{13}$C NMR (50 MHz, CDCl$_3$) δ 166.46, 164.95, 160.37, 151.72, 145.96, 140.61, 135.98, 133.72, 130.38, 128.53, 128.42, 128.15, 127.71, 118.58, 102.21, 90.03, 57.31, 55.54, 27.34, 22.11

Example 268

4-(6-chloropyridazine-3-yl)-7-methoxy-2-isopropyl-pyrazolo[1,5-a]pyridine

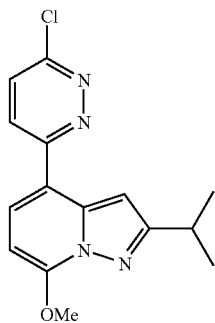

Using the compound of Example 263 and 3,6-dichloropyridazine, the reaction was carried out as in Example 265 to afford the title compound as a pale yellow powder.

$^1$H NMR (200 MHz, CDCl$_3$) δ 7.87 (1H, d, J=9.1 Hz), 7.64 (1H, d, J=7.9 Hz), 7.56 (1H, d, J=9.1 Hz), 7.04 (1H, s), 6.17 (1H, d, J=7.9 Hz), 4.20 (3H, s), 3.30 (1H, septet, J=7.1 Hz), 1.38 (6H, d, J=7.1 Hz).

$^{13}$C NMR (50 MHz, CDCl$_3$) δ 164.41, 157.33, 154.85, 152.28, 140.40, 128.16, 126.56, 126.07, 117.16, 95.58, 87.78, 56.96, 28.49, 23.14

Examples 269 and 270

4-(6-chloro-5-methylpyridazine-3-yl)-7-methoxy-2-isopropyl-pyrazolo[1,5-a]pyridine and -(6-chloro-4-methylpyridazine-3-yl)-7-methoxy-2-isopropyl-pyrazolo[1,5-a]pyridine

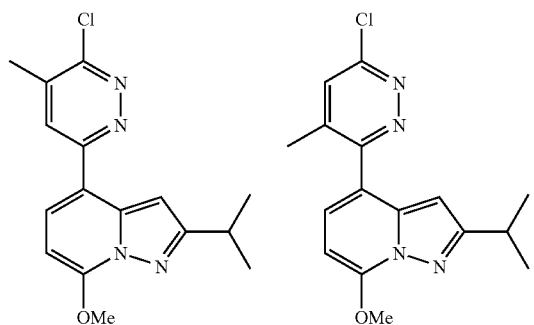

Using the compound of Example 263 and 3,6-dichloro-4-methylpyridazine, the reaction was carried out as in Example 265 to afford the title compound as a pale yellow powder.

Example 269

5-methyl-form $^1$H NMR (400 MHz, DMSO-d$_6$) δ 8.23 (1H, q, J=1.2 Hz), 7.88 (1H, d, J=7.9 Hz), 7.07 (1H, s), 6.48 (1H, d, J=7.9 Hz), 4.18 (3H, s), 3.17 (1H, septet, J=6.9 Hz), 2.47 (3H, d, J=1.2 Hz), 1.34 (6H, d, J=6.9 Hz).

$^{13}$C NMR (100 MHz, DMSO-d$_6$ 60° C.) δ 162.09, 157.00, 155.36, 151.75, 139.60, 137.79, 127.24, 126.20, 116.16, 95.52, 88.37, 56.81, 27.52, 22.38, 18.23
LRMS (EI$^+$): 316 [M$^+$]
HRMS (EI$^+$): 316.1091 (0.0 mmu) [M$^+$]

Example 270

4-methyl form $^1$H NMR (200 MHz, CDCl$_3$) δ 7.48 (1H, q, J=1.2 Hz), 7.20 (1H, d, J=7.9 Hz), 6.16 (1H, d, J=7.9 Hz), 6.14 (1H, s), 4.20 (3H, s), 3.25 (1H, septet, J=7.1 Hz), 2.29 (3H, d, J=1.2 Hz), 1.32 (6H, d, J=7.1 Hz).
$^{13}$C NMR (50 MHz, CDCl$_3$) δ 163.71, 159.06, 155.42, 151.46, 141.31, 139.88, 129.13, 126.27, 117.48, 93.6, 87.32, 56.81, 28.27, 23.03, 19.09
LRMS (EI$^+$): 316 [M$^+$]
HRMS (EI$^+$): 316.1067 (−2.4 mmu) [M$^+$]

Examples 271 through 275

Using the compound of Example 263, the compounds of Examples 254 through 258 were reacted as in Example 265 to afford compounds shown in Table 16 below.

TABLE 16

| Examples | R4 | R6 | Nature |
|---|---|---|---|
| 271 | Me | CH$_2$OCOtBu | Pale green yellow powder |
| 272 | H | CH$_2$Ph | Colorless powder |
| 273 | H | H$_2$C-(3-pyridyl) | Pale Yellow powder |
| 274 | H | H$_2$C-(2-pyridyl) | Yellow powder |
| 275 | H | H$_2$C-(4-pyridyl) | Yellow powder |

Example 271

$^1$H NMR (200 MHz, CDCl$_3$) δ 7.07 (1H, d, J=7.9 Hz), 6.85 (1H, q, J=1.2 Hz), 6.18 (1H, s), 6.09 (1H, d, J=7.9 Hz), 6.05 (2H, s), 4.16 (3H, s), 3.24 (1H, septet, J=7.1 Hz), 2.09 (3H, d, J=1.2 Hz), 1.32 (6H, d, J=7.1 Hz), 1.19 (9H, s).
$^{13}$C NMR (50 MHz, CDCl$_3$) δ 177.36, 163.63, 159.69, 151.39, 145.72, 144.34, 141.50, 129.09, 125.70, 116.55, 93.43, 87.14, 73.04, 56.80, 38.80, 28.29, 26.96, 23.02, 19.42

Example 272

$^1$H NMR (200 MHz, CDCl$_3$) δ 7.67 (1H, d, J=10.0 Hz), 7.54 (2H, br dd, J=7.5, 1.9 Hz), 7.36 (1H, d, J=7.9 Hz), 7.30-7.43 (3H, br m), 7.05 (1H, d, J=10.0 Hz), 6.72 (1H, s), 6.09 (1H, d, J=7.9 Hz), 5.46 (2H, s), 4.17 (3H, s), 3.27 (1H, septet, J=7.19 Hz), 1.36 (6H, d, J=7.1 Hz).
$^{13}$C NMR (50 MHz, CDCl$_3$) δ 163.90, 159.35, 151.50, 142.93, 139.73, 136.45, 132.07, 130.23, 128.88, 128.65, 127.98, 124.06, 116.70, 95.98, 87.25, 56.82, 54.88, 28.33, 23.08

Example 273

$^1$H NMR (200 MHz, CDCl$_3$) δ 8.81 (1H, d, J=1.7 Hz), 8.58 (1H, dd, J=4.6, 1.7 Hz), 7.87 (1H, dt, J=7.9, 1.9 Hz), 7.71 (1H, d, J=10.0 Hz), 7.38 (1H, d, J=7.9 Hz), 7.29 (1H, dd, J=7.9, 4.6 Hz), 7.05 (1H, d, J=10.0 Hz), 6.71 (1H, s), 6.11 (1H, d, J=7.9 Hz), 5.46 (2H, s), 4.18 (3H, s), 3.28 (1H, septet, J=6.9 Hz), 1.38 (6H, d, J=6.9 Hz).
$^{13}$C NMR (50 MHz, CDCl$_3$) δ 164.06, 159.31, 151.73, 150.26, 149.53, 143.37, 139.78, 136.65, 132.03, 130.61, 130.23, 124.36, 123.59, 116.53, 95.69, 87.37, 56.91, 52.72, 28.40, 23.13

Example 274

$^1$H NMR (200 MHz, CDCl$_3$) δ 8.62 (1H, ddd, J=5.0, 1.7, 0.8 Hz), 7.72 (1H, d, J=10.0 Hz), 7.67 (1H, td, J=7.7, 1.7 Hz), 7.38 (1H, d, J=7.9 Hz), 7.33 (1H, dt, J=7.8, 0.8 Hz), 7.22 (1H, ddd, J=7.6, 5.0, 0.8 Hz), 7.08 (1H, d, J=10.0 Hz), 6.74 (1H, s), 6.09 (1H, d, J=7.9 Hz), 5.62 (2H, s), 4.17 (3H, s), 3.24 (1H, septet, J=7.1 Hz), 1.33 (6H, d, J=7.1 Hz).
$^{13}$C NMR (50 MHz, CDCl$_3$) δ 164.00, 159.54, 156.06, 151.64, 149.68, 143.13, 139.87, 136.74, 130.54, 130.18, 124.09, 122.65, 122.46, 116.78, 96.08, 87.25, 56.85, 56.71, 28.38, 23.09

Example 275

$^1$H NMR (200 MHz, CDCl$_3$) δ 8.59-8.62 (2H, m), 7.74 (1H, d, J=10.0 Hz), 7.39 (1H, d, J=7.9 Hz), 7.35-7.38 (2H, m), 7.08 (1H, d, J=10.0 Hz), 6.66 (1H, s), 6.11 (1H, d, J=7.9 Hz), 5.45 (2H, s), 4.18 (3H, s), 3.26 (1H, septet, J=7.1 Hz), 1.34 (6H, d, J=7.1 Hz).
$^{13}$C NMR (50 MHz, CDCl$_3$) δ 164.06, 159.34, 151.79, 150.25, 145.01, 143.49, 139.75, 130.76, 130.26, 124.42, 123.26, 116.43, 95.72, 87.37, 56.91, 53.96, 28.36, 23.09

Example 276

6-(7-methoxy-2-isopropyl-pyrazolo[1,5-a]pyridine-4-yl)-3-(2H)pyridazinone

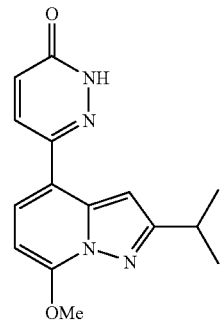

The compound of Example 268 (50 mg) was dissolved in acetic acid (2 mL) and the solution was stirred at 90° C. for 3 hours. Subsequently, the solvent was concentrated and the residue was purified by silica gel column chromatography (methanol:ethyl acetate 1:9) to afford the title compound as a pale yellow powder (26 mg).

$^1$H NMR (200 MHz, CDCl$_3$-CD$_3$OD) δ 7.76 (1H, d, J=9.6 Hz), 7.38 (1H, d, J=7.9 Hz), 7.00 (1H, d, J=9.6 Hz), 6.85 (1H, s), 6.09 (1H, d, J=7.9 Hz), 4.13 (3H, s), 3.21 (1H, septet, J=7.1 Hz), 1.31 (6H, d, J=7.1 Hz).

$^{13}$C NMR (50 MHz, CDCl$_3$-CD$_3$OD) 163.89, 161.19, 151.54, 144.10, 139.72, 131.97, 129.79, 124.53, 116.34, 95.70, 87.45, 56.75, 28.24, 22.90

Example 277

6-(7-methoxy-2-isopropyl-pyrazolo[1,5-a]pyridine-4-yl)-5-methyl-3-(2H)-pyridazinone

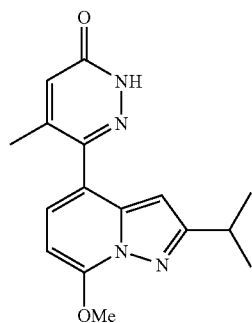

Using the compound of Example 270, the reaction was carried out as in Example 276 to afford the title compound, or the title compound was produced by the following alternative process: The compound of Example 271 (3.55 g) was dissolved in methanol (70 mL)

To this solution, concentrated aqueous ammonia (20 mL) was added and the mixture was stirred at room temperature for 18 hours. Subsequently, additional concentrated aqueous ammonia (20 mL) was added and the mixture was stirred for another 18 hours. The solvent was concentrated and the residue was recrystallized (chloroform:petroleum ether) to afford the title compound as a yellow brown powder (1.80 g).

$^1$H NMR (200 MHz, CDCl$_3$) δ 11.80 (1H, br s), 7.08 (1H, d, J=7.9 Hz), 6.89 (1H, q, J=1.2 Hz), 6.16 (1H, s), 6.10 (1H, d, J=7.9 Hz), 4.18 (3H, s), 3.26 (1H, septet, J=7.1 Hz), 2.11 (3H, d, J=1.2 Hz), 1.34 (6H, d, J=7.1 Hz).

$^{13}$C NMR (50 MHz, CDCl$_3$) δ 163.68, 161.58, 151.39, 146.07, 144.87, 141.59, 128.83, 125.69, 117.00, 93.41, 87.22, 56.81, 28.33, 23.08, 19.67

LRMS (EI$^+$): 298 [M$^+$]
HRMS (EI$^+$): 298.1433 (+0.3 mmu) [M$^+$]

Example 278

6-(7-methoxy-2-isopropyl-pyrazolo[1,5-a]pyridine-4-yl)-4-methyl-3-(2H)-pyridazinone

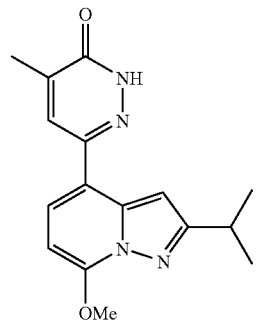

Using the compound of Example 269, the reaction was carried out as in Example 276 to afford the title compound as a colorless powder.

$^1$H NMR (200 MHz, CDCl$_3$) δ 11.92 (1H, br s), 7.62 (1H, q, J=1.2 Hz), 7.39 (1H, d, J=7.9 Hz), 6.89 (1H, s), 6.10 (1H, d, J=7.9 Hz), 4.18 (3H, s), 3.30 (1H, septet, J=7.1 Hz), 2.33 (3H, d, J=1.2 Hz), 1.39 (6H, d, J=7.1 Hz).

$^{13}$C NMR (50 MHz, CDCl$_3$) δ 163.92, 162.28, 151.52, 144.20, 140.59, 140.01, 129.09, 124.22, 117.03, 95.60, 87.28, 56.81, 28.44, 23.14, 16.66

LRMS (EI$^+$): 298 [M$^+$]
HRMS (EI$^+$): 298.1398 (−3.2 mmu) [M$^+$]

Examples 279 and 280

6-(3-fluoro-7-methoxy-2-isopropyl-pyrazolo[1,5-a]pyridine-4-yl)-5-methyl-3-(2H)-pyridazinone and
6-(3-fluoro-7-methoxy-2-isopropyl-pyrazolo[1,5-a]pyridine-4-yl)-4-methyl-3-(2H)-pyridazinone

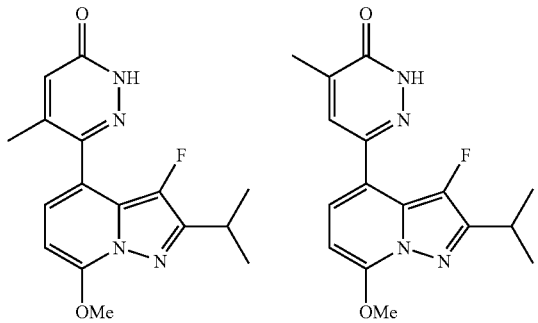

1-fluoro-4-hydroxy-1,4-diazoniabicyclo[2.2.2]octane bis(tetrafluoroborate) (990 mg) was added to a solution of a 5:2 mixture (458 mg) of the compounds of Examples 277 and 278 in methylene chloride (20 mL) and acetonitrile (20 mL). The mixture was stirred at room temperature for 16 hours. Subsequently, aqueous sodium bicarbonate solution and water was added and the mixture was extracted with methylenechloride. The organic layer was washed with saturated brine and dried over anhydrous sodium sulfate. Evaporation of the solvent and subsequent purification of the residue by silica gel column chromatography (ethyl acetate:methylene chloride=1:1, followed by methanol:methylene chloride: ethyl acetate=3:48.5:48.5) afforded the 5-methyl form as a colorless powder (87 mg) and the 4-methyl form as a pale yellow powder (17 mg).

Example 279

$^1$H NMR (200 MHz, CDCl$_3$) δ 11.68 (1H, br s), 7.03 (1H, d, J=7.9 Hz), 6.85 (1H, q, J=1.2 Hz), 6.05 (1H, d, J=7.9 Hz), 4.18 (3H, s), 3.29 (1H, septet, J=7.1 Hz), 2.03 (3H, d, J=1.2 Hz), 1.39 (6H, d, J=7.1 Hz).

Example 280

$^1$H NMR (400 MHz, CDCl$_3$) δ 12.04 (1H, br s), 7.45 (1H, dq, 3.8, J=1.2 Hz), 7.26 (1H, d, J=7.6 Hz), 6.05 (1H, d, J=7.9 Hz), 4.17 (3H, s), 3.33 (1H, septet, J=7.1 Hz), 2.30 (3H, d, J=1.2 Hz), 1.42 (6H, d, J=7.1 Hz).
$^{13}$C NMR (101 MHz, CDCl$_3$) δ 162.43, 151.03, 148.15, 143.43, 140.03, 137.96, 131.20, 126.81, 125.18, 117.04, 87.22, 57.03, 26.78, 21.51, 16.43

Example 281

6-(7-methoxy-2-isopropyl-pyrazolo[1,5-a]pyridine-4-yl)-4,5-dihydro-3-(2H)-pyridazinone

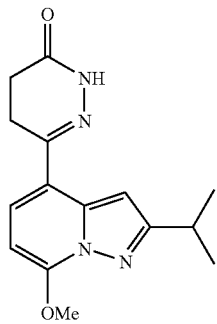

A mixture of the compound of Example 276 (45 mg), zinc (52 mg) and acetic acid (1.6 mL) was stirred at 100° C. for 30 min. The insoluble material was removed by filtration and the filtrate was concentrated. A saturated sodium bicarbonate solution was added to the residue and the mixture was extracted with ethyl acetate. The organic layer was washed sequentially with 0.1 mol/L EDTA disodium solution and saturated brine and dried over magnesium sulfate. The solvent was concentrated and the resulting residue was purified by silica gel column chromatography (methanol:ethyl acetate=1:9) to afford the title compound as a pale yellow oil (16 mg).
$^1$H NMR (200 MHz, CDCl$_3$) δ 8.79 (1H, br s), 7.33 (1H, d, J=7.9 Hz), 7.04 (1H, s), 6.06 (1H, d, J=7.9 Hz), 4.17 (3H, s), 3.28 (1H, septet, J=7.1 Hz), 2.99-3.08 (2H, m), 2.59-2.68 (2H, m), 1.38 (6H, d, J=7.1 Hz).
$^{13}$C NMR (50 MHz, CDCl$_3$) δ 167.17, 164.19, 151.79, 149.03, 139.47, 125.24, 117.47, 97.40, 86.93, 56.88, 28.46, 26.51, 23.14, 22.45

Examples 282 through 286

Using the compounds of Examples 272, 273 and 277 through 279, the reactions were carried out as in Example 281 to obtain compounds shown in Table 17 below.

TABLE 17

| Examples | R3 | R4 | R5 | R6 | Nature |
|---|---|---|---|---|---|
| 282 | H | Me | H | H | Pale yellow powder |
| 283 | H | H | Me | H | Pale yellow powder |
| 284 | H | H | H | CH$_2$Ph | Pale green yellow powder |
| 285 | H | H | H | H$_2$C-(3-pyridyl) | Colorless oil |
| 286 | F | Me | H | H | Colorless powder |

Example 282

$^1$H NMR (200 MHz, CDCl$_3$) δ 9.30 (1H, s), 7.32 (1H, d, J=8.3 Hz), 7.06 (1H, s), 6.03 (1H, d, J=8.3 Hz), 4.12 (3H, s), 3.22-3.42 (1H, m), 3.23 (1H, septet, J=7.1 Hz), 2.71 (1H, dd, J=6.6, 17.0 Hz), 2.45 (1H, dd, J=1.3, 17.0 Hz), 1.33 (6H, d, J=7.1 Hz), 1.23 (3H, d, J=7.5 Hz).
$^{13}$C NMR (50 MHz, CDCl$_3$) δ 166.53, 163.98, 152.44, 151.60, 139.48, 124.83, 116.25, 97.67, 86.84, 56.71, 33.79, 28.31, 27.77, 23.00, 16.45

Example 283

$^1$H NMR (400 MHz, CDCl$_3$) δ 8.69 (1H, s), 7.33 (1H, d, J=7.9,Hz), 7.03 (1H, s), 6.06 (1H, d, J=7.9 Hz), 4.17 (3H, s), 3.28 (1H, septet, J=7.1 Hz), 3.05-3.19 (1H, m), 2.59-2.73 (2H, m), 1.38 (6H, d, J=7.1 Hz), 1.33 (3H, d, J=7.5 Hz).
$^{13}$C NMR (50 MHz, CDCl$_3$) δ 170.60, 164.01, 151.64, 149.12, 139.37, 125.10, 117.65, 97.33, 86.86, 56.78, 30.91, 30.09, 28.38, 23.06, 14.97
HRMS (EI$^+$): 300.1609 (+2.3 mmu) [M$^+$]

Example 284

$^1$H NMR (200 MHz, CDCl$_3$) δ 7.24-7.50 (6H, m), 6.81 (1H, s), 6.03 (1H, d, J=7.9 Hz), 5.10 (2H, s), 4.15 (3H, s), 3.23 (1H, septet, J=7.1 Hz), 2.96-3.04 (2H, m), 2.64-2.72 (2H, m), 1.33 (6H, d, J=7.1 Hz).

Example 285

$^1$H NMR (200 MHz, CDCl$_3$) δ 8.40-8.90 (2H, br m), 7.75 (1H, br d, J=7.5 Hz), 7.30 (1H, d, J=7.9 Hz), 7.20-7.33 (1H, br m), 6.77 (1H, s), 6.02 (1H, d, J=7.9 Hz), 5.08 (2H, s), 4.13 (3H, s), 3.22 (1H, septet, J=7.1 Hz), 2.94-3.03 (2H, m), 2.60-2.68 (2H, m), 1.32 (3H, d, J=7.1 Hz).
$^{13}$C NMR (50 MHz, CDCl$_3$) δ 165.27, 164.03, 151.70, 149.86, 149.55, 148.89, 139.25, 136.08, 133.13, 125.38, 123.40, 117.08, 97.46, 86.87, 56.77, 49.44, 28.27, 27.06, 23.00, 22.67

Example 286

¹H NMR (400 MHz, CDCl₃) δ 8.91 (1H, br s), 7.11 (1H, d, J=7.7 Hz), 5.99 (1H, d, J=7.8 Hz), 4.15 (3H, s), 3.30 (1H, septet, J=7.1 Hz), 3.19-3.28 (1H, m), 2.84 (1H, dd, J 16.9, 6.8 Hz), 2.49 (1H, dd, J=16.9, 3.2 Hz), 1.39-1.41 (6H, m), 1.14 (3H, d, J=7.3 Hz).

¹³C NMR (101 MHz, CDCl₃) δ 166.96, 153.61, 151.10, 148.13, 138.08, 127.13, 124.73, 117.25, 86.84, 56.98, 33.91, 30.81, 26.75, 21.46, 15.71

Example 287

6-(2-ethyl-6-fluoro-pyrazolo[1,5-a]pyridine-4-yl)-4,5-dihydro-5-methyl-2-(pyridine-3-ylmethyl)-3-(2H)-pyridazinone

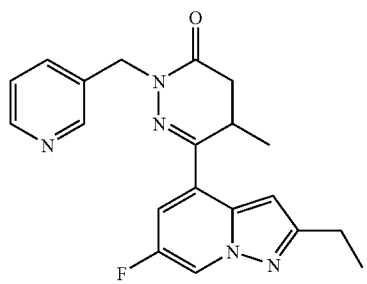

The compound of Example 199 (100 mg) was dissolved in DMF (3.6 mL) and 60% sodium hydride (32 mg) was added at 0° C. The mixture was stirred at room temperature for 30 min. Subsequently, 3-(chloromethyl)pyridine-hydrochloride (65.8 mg) was added and the mixture was stirred at 60° C. for 6 hours. The reaction was terminated by adding a saturated aqueous ammonium chloride solution and the mixture was extracted three times with ethyl acetate. The organic layer was washed with saturated brine and dried over sodium sulfate. Evaporation of the solvent under reduced pressure and purification by silica gel column chromatography (hexane:ethyl acetate=1:4) afforded the title compound as a yellow powder (98.5 mg).

Elemental analysis (%): Calcd. for C20H20FN5O: C, 65.74; H, 5.52; N, 19.17; Found: C, 65.42; H, 5.55; N, 18.86.

HRMS (EI⁺): 365.1627 (−2.5 mmu) [M⁺]

¹H-NMR (CDCl₃, 400 MHz) δ 1.22 (3H, d, J=7.3 Hz), 1.33 (3H, t, J=7.3 Hz), 2.61 (1H, dd, J=1.5, 16.5 Hz), 2.79 (1H, dd, J=6.7, 16.5 Hz), 2.82 (2H, q, J=7.3 Hz), 3.32-3.39 (1H, m), 5.15 (2H, d, J=2.4 Hz), 6.75 (1H, s), 7.24 (1H, dd, J=2.4, 9.8 Hz), 7.28 (1H, dd, J=4.9, 8.0 Hz), 7.75 (1H, dd, J=1.8, 8.0 Hz), 8.37 (1H, t, J=2.4 Hz), 8.56 (1H, dd, J=1.2, 4.9 Hz), 8.72 (1H, d, J=1.8 Hz).

Examples 288 through 301

Using different halogen derivatives and the compounds of Examples 200, 201, 205, 216, 278, 282, 304 and 305, the reactions were carried out as in Example 287 to obtain compounds shown in Table 18 below.

TABLE 18

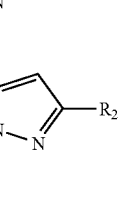

| Examples | R1 | R2 | R4 | R5 | R6 | Nature |
|---|---|---|---|---|---|---|
| 288 | H | Et | H | H | H₂C—(3-pyridyl) | Pale yellow powder |
| 289 | H | Et | Me | H | H₂C—(3-pyridyl) | Yellow oil |
| 290 | MeO | Et | Me | H | H₂C—(3-pyridyl) | Yellow amorphous |

TABLE 18-continued

| Examples | R1 | R2 | R4 | R5 | ┊ | R6 | Nature |
|---|---|---|---|---|---|---|---|
| 291 | EtO | CF₃ | Me | H | 1 | H₂C-(3-pyridyl) | Pale yellow powder |
| 292 | MeO | Et | Me | H | 1 | CH₂Ph | Colorless powder |
| 293 | MeO | Et | Me | H | 1 | H₂C-(3-NO₂-phenyl) | Yellow powder |
| 294 | MeO | Et | Me | H | 1 | CH₂CH₂Ph | Pale yellow oil |
| 295 | MeO | CF₃ | Me | H | 1 | H₂C-(3-pyridyl) | Pale yellow powder |
| 296 | MeO | CF₃ | Me | H | 1 | CH₂CH₂OH | Pale brown powder |
| 297 | MeO | iPr | Me | H | 1 | Me | Colorless powder |
| 298 | MeO | iPr | Me | H | 1 | H₂C-(3-pyridyl) | Colorless powder |
| 299 | MeO | iPr | H | Me | 2 | H₂C-(3-pyridyl) | Colorless powder |
| 300 | H | Et | H | H | 2 | H₂C-(3-pyridyl) | Pale yellow powder |
| 301 | H | Et | Me | H | 2 | H₂C-(3-pyridyl) | Yellow amorphous |

Example 288 mp: 171-173° C.

Elemental analysis (%):Calcd. for C19H19N5O: C, 68.45; H, 5.74; N, 21.01; Found: C, 68.17; H, 5.81; N, 20.86.

HRMS (EI⁺): 333.1607 (+1.7 mmu) [M⁺]

¹H-NMR (400 MHz, CDCl₃) δ 1.35 (3H, t, J=7.6 Hz), 2.69 (1H, d, J=9.2 Hz), 2.71 (1H, d, J=8.6 Hz), 2.85 (2H, q, J=7.6 Hz), 3.04 (1H, d, J=8.6 Hz), 3.06 (1H, d, J=9.2 Hz), 5.13 (2H, s), 6.69-6.73 (2H, m), 7.26-7.30 (2H, m), 7.76-7.79 (1H, m), 8.40 (1H, d, J=6.7 Hz), 8.56 (1H, dd, J=1.8, 4.9 Hz), 8.73 (1H, d, J=1.8 Hz).

Example 289

HRMS (EI⁺): 347.1737(−0.9 mmu) [M⁺]

¹H-NMR (400 MHz, CDCl₃) δ 1.21 (3H, d, J=7.3 Hz), 1.34 (3H, t, J=7.6 Hz), 2.59 (1H, dd, J=1.8, 16.8 Hz), 2.78 (1H, dd, J=6.7, 16.8 Hz), 2.85 (2H, q, J=7.8 Hz), 3.38-3.44 (1H, m), 5.13 (1H, d, J=14.7 Hz), 5.18 (1H, d, J=14.7 Hz), 6.71 (1H, t,

J=7.0 Hz), 6.75 (1H, s), 7.26-7.29 (1H, m), 7.32 ((1H, d, J=7.0 Hz), 7.75-7.79 (1H, m), 8.41 (1H, d, J=7.0 Hz), 8.56 (1H, d, J=4.3 Hz), 8.73 (1H, brs).

Example 290

HRMS (EI$^+$): 377.1824 (−2.8 mmu) [M$^+$]
$^1$H-NMR (400 MHz, CDCl$_3$) δ 1.20 (3H, d, J=7.3 Hz), 1.34 (3H, t, J=7.3 Hz), 2.57 (1H, dd, J=1.2, 16.5 Hz), 2.77 (1H, dd, J=6.7, 16.5 Hz), 2.89 (2H, q, J=7.3 Hz), 3.35-3.42 (1H, m), 4.17 (3H, s), 5.14 (2H, s), 6.06 (1H, d, J=8.5 Hz), 6.83 (1H, s), 7.28 (1H, dd, J=4.9, 7.9 Hz), 7.36 (1H, d, J=8.5 Hz), 7.78 (1H, td, J=1.8, 7.9 Hz), 8.55 (1H, dd, J=1.8, 4.9 Hz), 8.73 (1H, d, J=1.8 Hz).

Example 291

Ethanol was used as a reaction solvent. HRMS (EI$^+$): 431.1550 (−1.9 mmu) [M$^+$]
$^1$H-NMR (400 MHz, CDCl$_3$) δ 1.21 (3H, d, J=7.3 Hz), 1.65 (3H, t, J=7.3 Hz), 2.59 (1H, dd, J=16.5, 1.2 Hz), 2.78 (1H, dd, J=16.5, 6.7 Hz), 3.32-3.43 (1H, m), 4.49 (2H, q, J=7.3 Hz), 5.08-5.20 (2H, m), 6.26 (1H, d, J=7.9 Hz), 7.26-7.32 (1H, m), 7.46 (1H, d, J=7.9 Hz), 7.77 (1H, dt, J=7.9, 1.8 Hz), 8.55 (1H, dd, J=4.9, 1.8 Hz), 8.70 (1H, d, J=1.8 Hz).

Example 292

Elemental analysis (%):Calcd. for C22H24N4O2: C70.19, H 6.43, N 14.88; Found: C, 69.94; H, 6.46; N, 14.76.
HRMS (EI$^+$): 376.1890 (−0.9 mmu) [M$^+$]
$^1$H-NMR (400 MHz, CDCl$_3$) δ 1.21 (3H, d, J=7.3 Hz), 1.32 (3H, t, J=7.3 Hz), 2.56 (1H, d, J=16.5 Hz), 2.77 (1H, dd, J=6.1, 16.5 Hz), 2.86 (2H, q, J=7.3 Hz), 3.32-3.40 (1H, m), 4.16 (3H, s), 5.11 (1H, d, J=14.7 Hz), 5.15 (1H, d, J=14.7 Hz), 6.05 (1H, d, J=7.9 Hz), 6.79 (1H, s), 7.29-7.46 (6H, m).

Example 293

HRMS (EI$^+$): 421.1781 (+3.1 mmu) [M$^+$]
$^1$H-NMR (400 MHz, CDCl$_3$) δ 1.24 (3H, d, J=7.3 Hz), 1.30 (3H, t, J=7.6 Hz), 2.60 (1H, dd, J=1.5, 16.5 Hz), 2.80 (1H, dd, J=6.4, 16.5 Hz), 2.87 (1H, q, J=7.6 Hz), 3.38-3.45 (1H, m), 4.18 (3H, s), 5.22 (2H, s), 6.07 (1H, d, J=8.3 Hz), 6.80 (1H, s), 7.38 (1H, d, J=8.3 Hz), 7.54 (1H, t, J=7.9 Hz), 7.79 (1H, d, J=7.9 Hz), 8.17 (1H, d, J=7.9 Hz), 8.31 (1H, s).

Example 294

HRMS (EI$^+$): 390.2097 (+4.2 mmu) [M$^+$]
$^1$H-NMR (400 MHz, CDCl$_3$) δ 1.10 (3H, d, J=7.3 Hz), 1.41 (3H, t, J=7.6 Hz), 2.46 (1H, dd, J=1.5, 16.5 Hz), 2.68 (1H, dd, J=6.4, 16.5 Hz), 2.96 (1H, q, J=7.6 Hz), 3.06-3.19 (2H, m), 3.29-3.36 (1H, m), 4.10-4.18 (1H, m), 4.19 (3H, s), 4.24-4.35 (1H, m), 6.09 (1H, d, J=7.9 Hz), 7.12 (1H, s), 7.17-7.29 (5H, m), 7.36 (1H, d, J=7.9 Hz).

Example 295

HRMS (EI$^+$): 471.1440 (+2.8 mmu) [M$^+$]
$^1$H-NMR (400 MHz, CDCl$_3$) δ 1.21 (3H, d, J=7.3 Hz), 2.61 (1H, dd, J=1.2, 16.5 Hz), 2.79 (1H, dd, J=6.7, 16.5 Hz), 3.36-3.40 (1H, m), 4.22 (3H, s), 5.13 (1H, d, J=22.6 Hz), 5.17 (1H, d, J=22.6 Hz), 6.28 (1H, d, J=8.0 Hz), 7.29 (1H, s), 7.49 (1H, d, J=8.6 Hz), 7.78 (1H, d, J=8.0 Hz), 8.56 (1H, brs), 8.70 (1H, brs).

Example 296

HRMS (FAB$^+$): 371.1364 (+3.3 mmu) [M+H]$^+$
$^1$H-NMR (400 MHz, CDCl$_3$) δ 1.29 (3H, d, J=7.3 Hz), 2.33 (1H, brs), 2.58 (1H, dd, J=1.8, 17.1 Hz), 2.80 (1H, dd, J=6.7, 17.1 Hz), 3.96-4.14 (4H, m), 4.24 (3H, s), 4.24-4.29 (1H, m), 6.32 (1H, d, J=8.0 Hz), 7.53 (1H, d, J=8.0 Hz), 7.57 (1H, brs)

Example 297

$^1$H NMR (200 MHz, CDCl$_3$) δ 7.37 (1H, d, J=8.3 Hz), 7.12 (1H, s), 6.07 (1H, d, J=8.3 Hz), 4.17 (3H, s), 3.55 (3H, s), 3.29 (1H, septet, J=7.1 Hz), 3.18-3.43 (1H, m), 2.71 (1H, dd, J=16.6, 6.4 Hz), 2.45 (1H, dd, J=16.6, 1.6 Hz), 1.39 (6H, d, J=7.1 Hz), 1.22 (3H, d, J=7.5 Hz).
$^{13}$C NMR (50 MHz, CDCl$_3$) δ 164.63, 164.13, 152.34, 151.71, 139.59, 124.91, 116.22, 97.77, 86.99, 56.85, 36.76, 34.39, 28.42, 28.24, 23.09, 16.69

Example 298

$^1$H NMR (200 MHz, CDCl$_3$) δ 8.40-8.90 (2H, br m), 7.76 (1H, br d, J=7.9 Hz), 7.34 (1H, d, J=8.3 Hz), 7.21-7.35 (1H, br m), 6.83 (1H, s), 6.04 (1H, d, J=8.3 Hz), 5.18 (1H, d, J=14.5 Hz), 5.08 (1H, d, J=14.5 Hz), 4.15 (3H, s), 3.55 (3H, s), 3.28-3.44 (1H, m), 3.23 (1H, septet, J=7.1 Hz), 2.76 (1H, dd, J=16.6, 6.2 Hz), 2.55 (1H, dd, J=16.6, 1.7 Hz), 1.34 (3H, d, J=7.1 Hz), 1.33 (3H, d, J=7.1 Hz), 1.18 (3H, d, J=7.5 Hz).
$^{13}$C NMR (50 MHz, CDCl$_3$) δ 164.60, 164.16, 153.24, 151.81, 149.83, 148.97, 139.46, 135.97, 125.15, 123.00, 116.03, 97.84, 86.93, 56.85, 49.43, 34.44, 28.35, 28.21, 23.07, 16.61

Example 299

$^1$H NMR (200 MHz, CDCl$_3$) δ 8.40-9.00 (2H, br m), 7.86 (1H, br d, J=7.9 Hz), 7.55 (1H, q, J=1.2 Hz), 7.37 (1H, d, J=7.9 Hz), 7.23-7.38 (1H, br m), 6.70 (1H, s), 6.09 (1H, d, J=7.9 Hz), 5.45 (2H, s), 4.17 (3H, s), 3.27 (1H, septet, J=7.1 Hz), 2.30 (3H, d, J=1.2 Hz), 1.37 (6H, d, J=7.1 Hz).
$^{13}$C NMR (50 MHz, CDCl$_3$) δ 163.89, 162.46, 151.54, 150.22, 149.36, 143.08, 144.20, 140.01, 136.65, 127.89, 124.19, 123.00, 116.92, 95.60, 87.29, 56.83, 52.95, 28.37, 23.11, 17.22

Example 300 mp: 182-184° C.
Elemental analysis (%): Calcd. for C19H19N5O: C 68.45, H 5.74, N 21.01; Found: C, 68.17; H, 5.81; N, 20.86
HRMS (EI$^+$): 333.1607 (+1.7 mmu) [M$^+$]
$^1$H-NMR (400 MHz, CDCl$_3$) δ 1.37(3H, t, J=7.6 Hz), 2.88 (2H, q, J=7.6 Hz), 5.48 (2H, s), 6.63 (1H, s), 6.77 (1H, t, J=7.0 Hz), 7.08 (1H, d, J=9.5 Hz), 7.30 (1H, dd, J=4.9, 7.0 Hz), 7.35 (1H, dd, J=0.9, 7.0 Hz), 7.74 (1H, d, J=9.5 Hz), 7.85-7.88 (1H, m), 8.45 (1H, d, J=7.0 Hz), 8.59 (1H, dd, J=1.8, 4.9 Hz), 8.81 (1H, d, J=1.8 Hz).

Example 301

HRMS (EI$^+$): 345.1605 (+1.6 mmu) [M$^+$]
$^1$H-NMR (400 MHz, CDCl$_3$) δ 1.33 (3H, t, J=7.6 Hz), 2.09 (3H, d, J=1.2 Hz), 2.84 (2H, q, J=7.6 Hz), 5.38 (2H, s), 6.03 (1H, s), 6.77 (1H, t, J=7.0 Hz), 6.88 (1H, d, J=1.2 Hz), 7.02 (1H, dd, J=0.9, 7.0 Hz), 7.26-7.29 (1H, m), 7.83 (1H, td, J=1.8, 7.9 Hz), 8.45 (1H, td, J=0.9, 7.0 Hz), 8.57 (1H, dd, J=1.5, 4.9 Hz), 8.73 (1H, d, J=1.8 Hz).

Example 302

6-(2-trifluoromethyl-7-methoxy-pyrazolo[1,5-a]pyridine-4-yl)-3-(2H)-pyridazinone

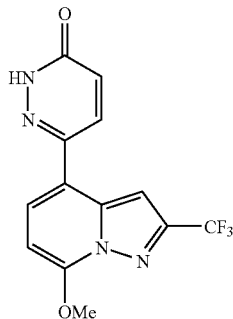

The compound of Example 209 (79.8 mg) and sodium m-nitrosulfonate (57.6 mg) were suspended in a 0.5 mol/L aqueous sodium hydroxide solution (5.00 mL). The suspension was refluxed for 8 hours. Subsequently, diluted hydrochloric acid was added to make the mixture acidic and the mixture was extracted twice with ethyl acetate. The organic layer was washed with saturated brine and dried over anhydrous sodium sulfate. Evaporation of the solvent and subsequent purification of the residue by amino-silica gel column chromatography (ethyl acetate) afforded the title compound as a yellow powder (23.1 mg).

HRMS (EI$^+$): 310.0681 (+0.3 mmu) [M$^+$]

$^1$H-NMR (400 MHz, CDCl$_3$) δ 4.25 (3H, s), 6.36 (1H, d, J=8.0 Hz), 7.12 (1H, d, J=9.8 Hz), 7.46 (1H, s), 7.58 (1H, d, J=8.0 Hz), 7.79 (1H, d, J=9.8 Hz), 10.8 (1H, brs).

Examples 303 through 306

Using the compounds of Examples 200, 201, 215 and 210, the reactions were carried out as in Example 302 to obtain compounds shown in Table 19 below.

TABLE 19

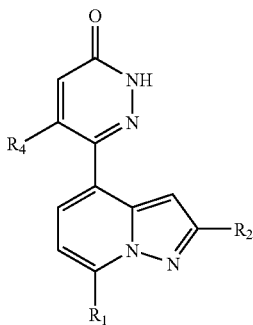

| Examples | R1 | R2 | R4 | Nature |
|---|---|---|---|---|
| 303 | MeO | CF$_3$ | Me | Colorless powder |
| 304 | H | Et | H | Pale yellow powder |
| 305 | H | Et | Me | Colorless powder |
| 306 | MeO | Et | H | Pale brown powder |

Example 303

Elemental analysis (%): Calcd. for C14H11F3N4O2: C, 51.86; H, 3.42; N, 17.28; Found: C, 51.53; H, 3.31; N, 17.18.

HRMS (EI$^+$): 324.0846 (+1.2 mmu) [M$^+$]

$^1$H-NMR (400 MHz, CDCl$_3$) δ 2.14 (2H, d, J=1.2 Hz), 4.25 (3H, s), 6.36 (1H, d, J=7.9 Hz), 6.70 (1H, s), 6.92 (1H, d, J=1.2 Hz), 7.28 (1H, d, J=7.9 Hz), 11.2 (1H, brs).

Example 304 mp: 207-209° C.

Elemental analysis (%): Calcd. for C13H12N4O: C 64.99, H 5.03, N 23.32; Found: C, 64.63; H, 5.03; N, 23.15.

LRMS (EI$^+$): 240 [M$^+$]

$^1$H-NMR (400 MHz, CDCl$_3$) δ 1.39 (3H, t, J=7.6 Hz), 2.90 (2H, q, J=7.6 Hz), 6.79 (1H, t, J=7.0 Hz), 6.85 (1H, s), 7.11 (1H, d, J=10.1 Hz), 7.38 (1H, dd, J=0.9, 7.0 Hz), 7.82 (1H, d, J=10.1 Hz), 8.47-8.49 (1H, m), 11.10 (1H, br).

Example 305 mp: 229-231° C.

HRMS (EI$^+$): 254.1152 (−1.6 mmu) [M$^+$]

$^1$H-NMR (400 MHz, CDCl$_3$) δ 1.34 (3H, t, J=7.6 Hz), 2.13 (3H, d, J=1.2 Hz), 2.86 (2H, q, J=7.6 Hz), 6.16 (1H, s), 6.78 (1H, t, J=7.0 Hz), 6.90 (1H, d, J=1.2 Hz), 7.06 (1H, dd, J=0.9, 7.0 Hz), 8.45-8.48 (1H, m), 10.55 (1H, br s).

Example 306

HRMS (EI$^+$): 270.1109 (−0.7 mmu) [M$^+$]

$^1$H-NMR (400 MHz, CDCl$_3$) δ 1.38 (3H, t, J=7.6 Hz), 2.94 (2H, q, J=7.6 Hz), 4.20 (3H, s), 6.14 (1H, d, J=7.9 Hz), 6.91 (1H, s), 7.08 (1H, d, J=9.8 Hz), 7.42 (1H, d, J=7.9 Hz), 7.79 (1H, d, J=9.8 Hz), 10.69 (1H, br s).

Example 307

N-amino-5-propionyl-2-methylpyridinium mesitylene sulfonium

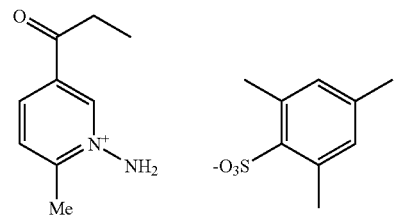

Using 5-propionyl-2-methylpyridinium, the reaction was carried out as in Example 1 to afford the title compound as a yellow amorphous solid.

$^1$H-NMR (400 MHz, DMSO-d$_6$) δ 1.11 (3H, t, J=7.3 Hz), 2.17 (3H, s), 2.50 (6H, s), 2.77 (3H, s), 3.12 (2H, q, J=7.3 Hz), 6.74 (1H, s), 8.10 (1H, d, J=8.0 Hz), 8.23 (2H, brs), 8.64 (1H, d, J=8.0 Hz), 9.32 (1H, s)

Example 308

3-ethoxycarbonyl-2-ethyl-7-methyl-4-propionyl-pyrazolo[1,5-a]pyridine

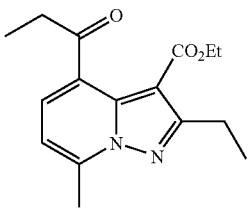

The compound of Example 307 was reacted with 2-buthyne acid ethyl ester as in Example 16 to afford the title compound as a yellow amorphous solid.

LRMS (EI+): 288 [M+]

$^1$H-NMR (400 MHz, CDCl$_3$) δ 1.22 (3H, t, J=7.3 Hz), 1.35 (3H, t, J=7.3 Hz), 1.36 (3H, t, J=7.3 Hz), 2.79 (3H, s), 2.84 (2H, q, J=7.3 Hz), 3.10 (2H, q, J=7.3 Hz), 4.33 (2H, q, J=7.3 Hz), 6.76 (1H, d, J=7.3 Hz), 7.29 (1H, d, J=7.3 Hz).

Example 309

2-ethyl-7-methyl-4-propionyl-pyrazolo[1,5-a]pyridine

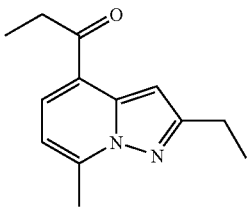

Using the compound of Example 308, the reaction was carried out as in Example 50 to afford the title compound as an orange powder.

LRMS (EI+): 216 [M+]

$^1$H-NMR (400 MHz, CDCl$_3$) δ 1.27 (3H, t, J=7.3 Hz), 1.39 (3H, t, J=7.3 Hz), 2.81 (3H, s), 2.93 (2H, q, J=7.3 Hz), 3.04 (2H, q, J=7.3 Hz), 6.62 (1H, d, J=7.3 Hz), 7.21 (1H, s), 7.76 (1H, d, J=7.3 Hz).

Example 310

6-(2-ethyl-7-methyl-pyrazolo[1,5-a]pyridine-4-yl)-4,5-dihydro-5-methyl-2-(pyridine-3-ylmethyl)-3-(2H)-pyridazinone

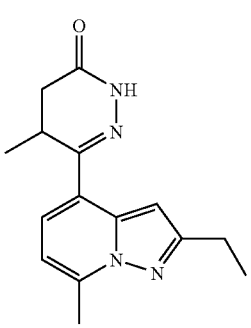

The compound of Example 309 was reacted as in Example 156 and the product was reacted as in Example 211 to afford the title compound as a pale yellow powder.

Elemental analysis (%): Calcd. for C15H18N4O: C, 66.64; H, 6.71; N, 20.73; Found: C, 66.59; H, 6.68; N, 20.64.

HRMS (EI+): 270.1492 (+1.2 mmu) [M+]

$^1$H-NMR (400 MHz, CDCl$_3$) δ 1.29 (3H, d, J=7.3 Hz), 1.39 (3H, t, J=7.3 Hz), 2.50-2.54 (1H, m), 2.77 (1H, dd, J=6.7, 16.5 Hz), 2.79 (3H, s), 2.93 (2H, q, J=7.3 Hz), 3.40-3.47 (1H, m), 6.62 (1H, d, J=7.3 Hz), 7.09 (1H, s), 7.30 (1H, d, J=7.3 Hz), 8.63 (1H, brs).

Example 311

6-(6-chloro-2-ethyl-pyrazolo[1,5-a]pyridine-4-yl)-5-methyl-4,5-dihydro-3-(2H)-pyridazinone

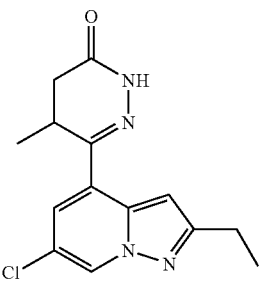

The compound of Example 190 was reacted as in Example 193 and the product was reacted as in Example 199 to afford the title compound as a pale yellow powder.

HRMS (EI+): 290.0967 (+3.3 mmu) [M+]

$^1$H-NMR (400 MHz, CDCl$_3$) δ 1.31 (3H, d, J=7.3 Hz), 1.36 (3H, t, J=7.3 Hz), 2.55 (1H, dd, J=16.5, 1.8 Hz), 2.77 (1H, dd, J=6.7, 16.5 Hz), 2.87 (2H, q, J=7.3 Hz), 3.36-3.43 (1H, m), 7.02 (1H, s), 7.29 (1H, d, J=1.8 Hz), 8.47 (1H, d, J=1.8 Hz), 8.69 (1H, brs).

mp: 172-174° C.

Example 312

6-(6-chloro-2-ethyl-pyrazolo[1,5-a]pyridine-4-yl)-4,5-dihydro-5-methyl-2-(pyridine-3-ylmethyl)-3-(2H)-pyridazinone

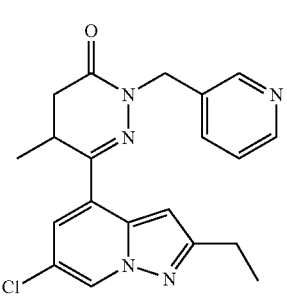

Using the compound of Example 311, the reaction was carried out as in Example 287 to afford the title compound as a yellow amorphous solid.
HRMS (EI$^+$): 381.1325 (−3.1 mmu) [M$^+$]
$^1$H-NMR (400 MHz, CDCl$_3$) δ 1.22 (3H, d, J=7.3 Hz), 1.33 (3H, t, J=7.6 Hz), 2.60 (1H, dd, J=16.8, 1.5 Hz), 2.78 (1H, dd, J=6.4, 16.8 Hz), 2.83 (2H, q, J=7.6 Hz), 3.33-3.41 (1H, m), 5.13 (1H, d, J=14.7 Hz), 5.17 (1H, d, J=14.7 Hz), 6.74 (1H, s), 7.26-7.30 (2H, m), 7.76 (1H, dt, J=7.9, 1.8 Hz), 8.44 (1H, d, J=0.6 Hz), 8.56 (1H, dd, J=4.9, 1.5 Hz), 8.72 (1H, d, J=1.8 Hz).

Examples 313 and 314

(+)-6-(6-chloro-2-ethyl-pyrazolo[1,5-a]pyridine-4-yl)-5-methyl-4,5-dihydro-3-(2H)-pyridazinone and (−)-6-(6-chloro-2-ethyl-pyrazolo[1,5-a]pyridine-4-yl)-5-methyl-4,5-dihydro-3-(2H)-pyridazinone The product of Example 311 was optically resolved by high performance liquid chromatography (Daicel Chiralpak AS-H column, eluent: n-hexane/EtOH=25/75, flow rate: 3.00 ml/min, detection: 293 nm). The first fraction gave the (+)-form (Example 313) and the second fraction gave the (−)-form (Example 314), each being as a pale yellow powder.

Example 313

[α]$_D$+4280 (c=0.59, CHCl$_3$)
HRMS (EI$^+$): 290.0926 (−0.8 mmu) [M$^+$]

Example 314

[α]$_D$−4880 (c=0.54, CHCl$_3$)
HRMS (EI$^+$): 290.0923 (−1.2 mmu) [M$^+$]

Examples 315 and 316

(+)-6-(2-ethyl-7-methoxy-pyrazolo[1,5-a]pyridine-4-yl)-5-methyl-4,5-dihydro-3-(2H)-pyridazinone and (−)-6-(2-ethyl-7-methoxy-pyrazolo[1,5-a]pyridine-4-yl)-5-methyl-4,5-dihydro-3-(2H)-pyridazinone The product of Example 216 was optically resolved by high performance liquid chromatography (Daicel Chiralpak AS-H column, eluent: n-hexane/EtOH=60/40, flow rate: 3.00 ml/min, detection: 293 nm). The first fraction gave the (+)-form (Example 315) and the second fraction gave the (−)-form (Example 316), each as a pale yellow amorphous material.

Example 315

[α]$_D$+4170 (c=0.56, CHCl$_3$)

Example 316

[α]$_D$−437° (c=0.58, CHCl$_3$)

Examples 317 and 318

(+)-6-(7-methoxy-2-trifluoromethyl-pyrazolo[1,5-a]pyridine-4-yl)-5-methyl-4,5-dihydro-3-(2H)-pyridazinone and (−)-6-(7-methoxy-2-trifluoromethyl-pyrazolo[1,5-a]pyridine-4-yl)-5-methyl-4,5-dihydro-3-(2H)-pyridazinone The product of Example 205 (211) was optically resolved by high performance liquid chromatography (Daicel Chiralpak IA column, eluent: n-hexane/AcOEt=40/60, flow rate: 3.00 ml/min, detection: 293 nm). The first fraction gave the (+)-form (Example 317) and the second fraction gave the (−)-form (Example 318), each as a colorless powder.

Example 317

[α]$_D$+414° (c=0.454, CHCl$_3$)
Elemental analysis (%): Calcd. for C14H13F3N4O2: C, 51.54; H, 4.02; N, 17.17; Found: C, 51.30; H, 3.89; N, 17.19.
HRMS (EI$^+$): 326.0982(−0.8 mmu) [M$^+$]

Example 318

[α]$_D$−4100 (c=0.432, CHCl$_3$)
Elemental analysis (%): Calcd. for C14H13F3N4O2: C, 51.54; H, 4.02; N, 17.17; Found: C, 51.48; H, 3.97; N, 17.12.
HRMS (EI$^+$): 326.0982 (−0.8 mmu) [M$^+$]

Example 319

7-methoxy-4-propionyl-2-trifluoromethyl-pyrazolo[1,5-a]pyridine

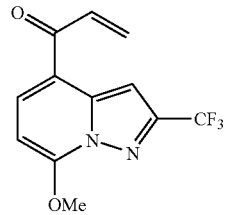

Vinyl magnesium chloride (1.32 mol/L tetrahydrofuran solution, 22.7 mL) was added dropwise to a solution of the compound of Example 115 (6.09 g) in tetrahydrofuran (250 mL) at −78° C. in a stream of argon gas. The mixture was allowed to gradually warm to room temperature. A saturated aqueous ammonium chloride solution was then added and the mixture was extracted with ethyl acetate. The organic layer was washed with saturated brine and dried over anhydrous sodium sulfate. The solvent was evaporated to give a pale yellow oil. This product was dissolved in chloroform (500 mL). To the solution, activated manganese dioxide (75%, 100 g) was added and the mixture was stirred at room temperature for 8 hours. Subsequently, additional activated manganese dioxide (75%, 50 g) was added and the mixture was stirred at room temperature overnight. Manganese dioxide was removed by filtration through Celite (thoroughly washed with ethyl acetate) and the solvent was evaporated to afford the title compound as a yellow powder (5.39 g).
$^1$H-NMR (400 MHz, CDCl$_3$) δ 4.29 (3H, s), 5.95 (1H, dd, J=1.5, 10.4 Hz), 6.34 (1H, d, J=8.0 Hz), 6.50 (1H, dd, J=1.5, 7.1 Hz), 7.21 (1H, dd, J=7.1, 10.4 Hz), 7.69 (1H, s), 8.02 (1H, d, J=8.0 Hz).

Example 320

3-benzyloxy-1-(7-methoxy-2-trifluoromethyl-pyrazolo[1,5-a]pyridine-4-yl)-propane-1-one

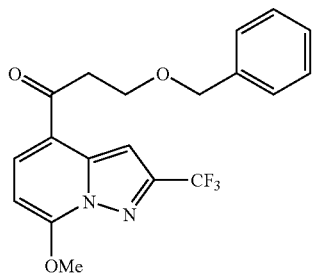

A solution of the compound of Example 319 (3.42 g) and benzyl alcohol (1.37 g) in dichloromethane (50 mL) was added to dichloro bis(acetonitrile) palladium (II) (329 mg) in a stream of argon gas. The mixture was stirred at room temperature overnight, followed by addition of benzyl alcohol (500 mL) and stirring overnight. The insoluble material was removed by filtration through Celite. The solvent was evaporated and the resulting residue was purified by silica gel column chromatography (hexane:ethyl acetate=3:2). The product was further purified by amino-silica gel column chromatography (hexane:ethyl acetate=3:2) to afford the title compound as a pale yellow powder (2.47 g).

$^1$H-NMR (400 MHz, CDCl$_3$) δ 3.28 (2H, t, J=6.4 Hz), 3.95 (2H, t, J=6.4 Hz), 4.27 (3H, s), 4.56 (2H, s), 6.30 (1H, d, J=8.0 Hz), 7.26-7.32 (5H, m), 7.69 (1H, s), 8.02 (1H, d, J=8.0 Hz).

Example 321

Dimethyl 2-[1-benzyloxymethyl-2-(7-methoxy-2-trifluoromethyl-pyrazolo[1,5-a]pyridine-4-yl)-2-oxo-ethyl]-malonate

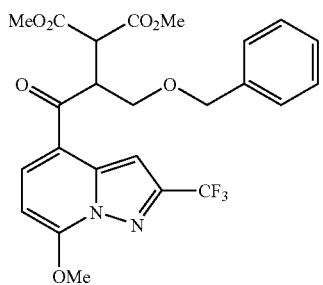

Copper (II) bromide (2.43 g) was added to a solution of the compound of Example 320 (1.88 g) in ethyl acetate (125 mL) in a stream of argon gas. The mixture was stirred at 70° C. for 2 hours. Subsequently, water was added and the insoluble material was removed by filtration through Celite. The organic layer was separated, sequentially washed with water and saturated brine and dried over anhydrous sodium sulfate. Evaporation of the solvent and subsequent purification by silica gel column chromatography (hexane:ethyl acetate=3:2) gave a green oil.

Meanwhile, 60% sodium hydride (298 mg) was added to a solution of dimethyl malonate (1.31 g) in N,N-dimethylformamide (30 mL) while the solution was stirred in an ice bath in a stream of argon gas. The mixture was stirred at room temperature for 15 min. While this mixture was stirred in an ice bath, the green oil product dissolved in N,N-dimethylformamide (20 mL) was added and the resulting mixture was stirred at room temperature overnight. Subsequently, a saturated aqueous ammonium chloride solution was added and the mixture was extracted with ethyl acetate. The organic layer was washed with water (×2) and saturated brine and dried over anhydrous sodium sulfate. Evaporation of the solvent and subsequent purification by silica gel column chromatography (hexane:ethyl acetate=1:1→2:3) afforded the title compound as a yellow amorphous material (1.03 g).

$^1$H-NMR (400 MHz, CDCl$_3$) δ 3.64-3.75 (8H, m), 4.17 (1H, d, J=10.7 Hz), 4.27 (3H, s), 4.38 (2H, d, J=2.4 Hz), 4.42-4.56 (1H, m), 6.30 (1H, d, J=8.3 Hz), 7.09-7.26 (5H, m), 7.62 (1H, s), 8.16 (1H, d, J=8.3 Hz).

Example 322

5-benzyloxymethyl-6-(7-methoxy-2-trifluoromethyl-pyrazolo[1,5-a]pyridine-4-yl)-4,5-dihydro-3-(2H)-pyridazinone

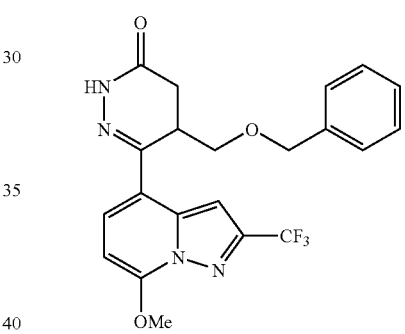

A 1 mol/L aqueous sodium hydroxide solution (4.47 mL) was added dropwise to a solution of Example 321 (1.03 g) in methanol (40 mL) under stirring in an ice bath. The mixture was stirred at room temperature for 3 hours. Subsequently, diluted hydrochloric acid was added to make the mixture acidic and the mixture was extracted with ethyl acetate. The organic layer was washed sequentially with water and saturated brine and dried over anhydrous sodium sulfate. Evaporation of the solvent gave a brown oil. This product was dissolved in ethanol (30 mL) and the solution was refluxed overnight. Subsequently, hydrazine monohydrate (0.295 mL) and acetic acid (0.797 mL) were added and the mixture was further stirred for 5 hours. Water was then added and the mixture was extracted with ethyl acetate. The organic layer was washed sequentially with water and saturated brine and dried over anhydrous sodium sulfate. Evaporation of the solvent and subsequent purification by silica gel column chromatography (ethyl acetate) afforded the title compound as a yellow powder (101 mg).

$^1$H-NMR (400 MHz, CDCl$_3$) δ 2.72 (1H, dd, J=5.5, 17.4 Hz), 2.91 (1H, d, J=17.4 Hz), 3.59-3.63 (3H, m), 4.22 (3H, s), 4.47 (1H, d, J=12.2 Hz), 4.51 (1H, d, J=12.2 Hz), 6.26 (1H, d, J=8.3 Hz), 7.18-7.33 (5H, m), 7.52 (1H, d, J=8.3 Hz), 7.57 (1H, s), 8.60 (1H, brs).

Example 323

5-hydroxymethyl-6-(7-methoxy-2-trifluoromethyl-pyrazolo[1,5-a]pyridine-4-yl)-4,5-dihydro-3-(2H)-pyridazinone

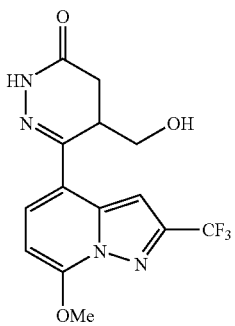

The compound of Example 322 (60 mg) was dissolved in ethanol (25 mL) and ethyl acetate (25 mL). To this solution, 10% palladium carbon (30 mg) was added and the mixture was stirred at room temperature for 8 hours in a stream of hydrogen gas (1 atm). The insoluble material was removed by filtration through Celite. Evaporation of the solvent and subsequent purification by thin-layer chromatography (silica gel, ethyl acetate:methanol=10:1) afforded the title compound as a pale yellow powder (12 mg).

HRMS (EI$^+$): 342.0949 (1.0 mmu) [M$^+$]

Example 324

4-t-butyldimethylsilyloxymethyl-7-hydroxymethyl-2-trifluoromethyl-pyrazolo[1,5-a]pyridine

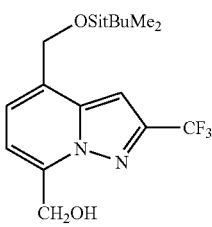

In an argon atmosphere, a 2.67 mol/L n-butyl lithium-hexane solution (14.0 mL) was added dropwise to a solution of the compound of Example 91 (12.4 g) in tetrahydrofuran (200 mL) at −78° C. The mixture was stirred at −78° C. for 30 min. Subsequently, the mixture was added dropwise to a solution of ethyl formate (9.06 mL) in tetrahydrofuran (100 mL) at −78° C. The mixture was then allowed to gradually warm to room temperature. A saturated aqueous ammonium chloride solution was added and the mixture was extracted with ethyl acetate (400 mL). The organic layer was washed sequentially with water and saturated brine and dried over anhydrous sodium sulfate. The extract was concentrated and the residue was purified by silica gel column chromatography (hexane:ethyl acetate=15:1) to give yellow crystals. This product was dissolved in methanol (200 mL). While the solution was kept at 0° C., sodium borohydride (1.56 g) was added and the mixture was stirred at 0° C. for 1 hour. Subsequently, a saturated aqueous ammonium chloride solution was added. The mixture was concentrated and extracted with ethyl acetate (700 mL).

The organic layer was washed sequentially with water and saturated brine and dried over anhydrous sodium sulfate. The extract was concentrated and purified by silica gel column chromatography (hexane:ethyl acetate=9:1) to afford the title compound as a colorless powder (9.86 g).

$^1$H-NMR (400 MHz, CDCl$_3$) δ 0.14 (6H, s), 0.96 (9H, s), 4.91 (2H, d, J=1.2 Hz), 5.06 (2H, s), 6.85 (1H, s), 6.94 (1H, d, J=7.3 Hz), 7.30 (1H, dt, J=7.3, 1.2 Hz).

Example 325

4-t-butyldimethylsilyloxymethyl-7-methoxymethyl-2-trifluoromethyl-pyrazolo[1,5-a]pyridine

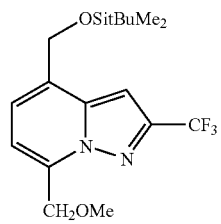

Silver oxide (30.0 g) and iodomethane (16.1 mL) were added to a solution of the compound of Example 324 (9.53 g) in acetonitrile (300 mL). The mixture was stirred at room temperature for 85 hours. Subsequently, the mixture was filtered through Celite. The filtrate was concentrated and purified by silica gel column chromatography (hexane:ethyl acetate=15:1) to afford the title compound as a pale yellow powder (8.76 g).

$^1$H-NMR (400 MHz, CDCl$_3$) δ 0.13 (6H, s), 0.95 (9H, s), 3.60 (3H, s), 4.91 (2H, s), 4.97 (2H, s), 6.83 (1H, s), 7.07 (1H, d, J=7.3 Hz), 7.32 (1H, d, J=7.3 Hz)

Example 326

4-hydroxymethyl-7-methoxymethyl-2-trifluoromethyl-pyrazolo[1,5-a]pyridine

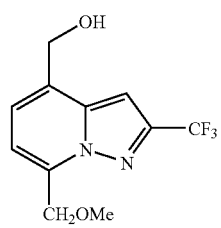

A 1 mol/L tetrabutylammonium fluoride-tetrahydrofuran solution (35.1 mL) was added dropwise to a solution of the compound of Example 325 (8.76 g) in tetrahydrofuran (120 mL) at 0° C. The mixture was stirred at 0° C. for 30 min. Subsequently, water was added and the mixture was extracted with ethyl acetate (300 mL). The organic layer was washed sequentially with water and saturated brine and dried over anhydrous sodium sulfate. The extract was concentrated and purified by silica gel column chromatography (hexane:ethyl acetate=3:1) to afford the title compound as a colorless powder (6.00 g).

$^1$H-NMR (400 MHz, CDCl$_3$) δ 1.79 (1H, br s), 3.61 (3H, s), 4.93 (2H, s), 4.98 (2H, s), 6.93 (1H, s), 7.07 (1H, d, J=7.3 Hz), 7.31 (1H, d, J=7.3 Hz).

Example 327

7-methoxymethyl-2-trifluoromethyl-pyrazolo[1,5-a]pyridine-4-carboaldehyde

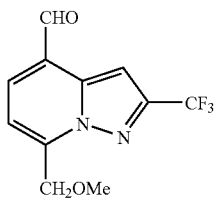

Activated manganese dioxide (20.0 g) was added to a solution of the compound of Example 326 (6.00 g) in chloroform (120 mL). The reaction mixture was stirred at 50° C. for 5 hours. Subsequently, the mixture was filtered through Celite. The filtrate was concentrated to afford the title compound as a pale yellow powder (5.74 g).

$^1$H-NMR (400 MHz, CDCl$_3$) δ 3.65 (3H, s), 5.06 (2H, s), 7.32 (1H, d, J=7.3 Hz), 7.65 (1H, s), 7.89 (1H, d, J=7.3 Hz), 10.10 (1H, s).

Example 328

4-(1-hydroxypropyl)-7-methoxymethyl-2-trifluoromethyl-pyrazolo[1,5-a]pyridine

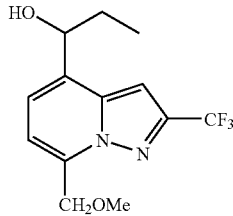

In an argon atmosphere, a 0.97 mol/L ethyl magnesium bromide-tetrahydrofuran solution (12.0 mL) was added dropwise to a solution of the compound of Example 327 (2.00 g) in tetrahydrofuran (50 mL) at −78° C. The mixture was allowed to gradually warm to room temperature. A saturated aqueous ammonium chloride solution was added and the mixture was extracted with ethyl acetate (200 mL). The organic layer was washed sequentially with water and saturated brine and dried over anhydrous sodium sulfate. The extract was concentrated and purified by silica gel column chromatography (hexane:ethyl acetate=7:1→2:1) to afford the title compound as a colorless powder (1.68 g).

$^1$H-NMR (400 MHz, CDCl$_3$) δ 0.98 (3H, t, J=7.3 Hz), 1.84-2.01 (2H, m), 3.61 (3H, s), 4.93 (1H, t, J=6.7 Hz), 4.97 (2H, s), 6.95 (1H, s), 7.06 (1H, d, J=7.3 Hz), 7.30 (1H, d, J=7.3 Hz).

Example 329

7-methoxymethyl-4-propionyl-2-trifluoromethyl-pyrazolo[1,5-a]pyridine

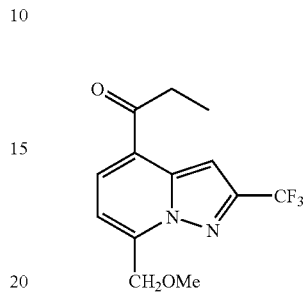

Triethylamine (7.56 mL) was added to a solution of the compound of Example 328 (1.55 g) in dimethylsulfoxide (60 mL). While the solution was stirred at room temperature, sulfur trioxide-pyridine complex (4.28 g) was added and the mixture was stirred at room temperature for 1 hour. Subsequently, water (300 mL) was added. The resulting crystals were collected by filtration and thoroughly dried to afford the title compound as a colorless powder (1.49 g).

$^1$H-NMR (400 MHz, CDCl$_3$) δ 1.29 (3H, t, J=7.3 Hz), 3.09 (2H, q, J=7.3 Hz), 3.64 (3H, s), 5.04 (2H, d, J=1.2 Hz), 7.20 (1H, dt, J=7.3, 1.2 Hz), 7.69 (1H, s), 7.99 (1H, d, J=7.3 Hz).

Example 330

6-(7-methoxymethyl-2-trifluoromethyl-pyrazolo[1,5-a]pyridine-4-yl)-5-methyl-4,5-dihydro-3-(2H)-pyridazinone

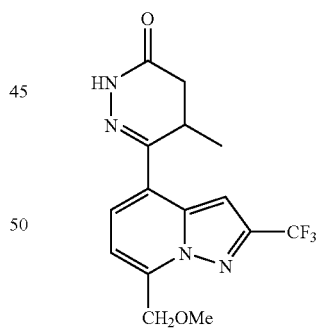

In an argon atmosphere, a 1 mol/L lithium bis(trimethylsilyl)amide/tetrahydrofuran solution (1.75 mL) was added to a solution of the compound of Example 329 (500 mg) in tetrahydrofuran (20 mL) at 0° C. The mixture was stirred at 0° C. for 30 min, followed by addition of t-butyl bromoacetate (321 µL) and stirring at room temperature for another 30 min. A saturated aqueous ammonium chloride solution was added and the mixture was extracted with ethyl acetate (100 mL). The organic layer was washed sequentially with water and saturated brine, dried over anhydrous sodium sulfate and concentrated. The product was dissolved in dichloromethane (20 mL). To this solution, trifluoro acetic acid (7 mL) was added and the mixture was left at room temperature overnight. Subsequently, the mixture was concentrated and a saturated aqueous sodium bicarbonate solution was added to make the mixture basic. The mixture was then extracted with ether (100 mL). A 1 mol/L aqueous hydrochloric acid was added to the aqueous layer to make it acidic and the mixture was extracted with ethyl acetate (200 mL). The organic layer was washed sequentially with water and saturated brine and dried over anhydrous sodium sulfate. The extract was concentrated and the residue was dissolved in ethanol (30 mL). Hydrazine monohydrate (255 μL) was added and the mixture was refluxed for 4 hours. Subsequently, the mixture was concentrated and purified by silica gel column chromatography (hexane:ethyl acetate=3:2) to afford the title compound as a pale yellow powder (215 mg).

$^1$H-NMR (400 MHz, CDCl$_3$) δ 1.31 (3H, d, J=7.3 Hz), 2.56 (1H, dd, J=17.1, 1.2 Hz), 2.79 (1H, dd, J=17.1, 6.7 Hz), 3.40-3.52 (1H, m), 3.63 (3H, s), 5.03 (2H, s), 7.16 (1H, d, J=7.3 Hz), 7.53 (1H, d, J=7.3 Hz), 7.60 (1H, s), 8.71 (1H, br s).

LRMS (EI$^+$): 340 [M$^+$]

Elemental analysis (%): Calcd. for C15H15F3N4O2,1/8H2O: C, 52.59; H, 4.49; N, 6.36; Found: C, 52.62; H, 4.44; N, 16.44.

Example 331

2-benzyl-6-(7-methoxy-2-trifluoromethyl-pyrazolo[1,5-a]pyridine-4-yl)-5-methyl-4,5-dihydro-3-(2H)-pyridazinone

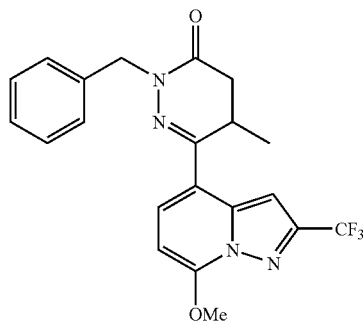

The compound of Example 211 (200 mg) was dissolved in N,N-dimethylformamide (6.1 mL) in an argon atmosphere. 60% sodium hydride (31.7 mg) was added at 0° C. and the mixture was stirred at room temperature for 30 min. Subsequently, benzyl bromide (94.1 mL) was added at 0° C. and the mixture was stirred at 60° C. for 3.5 hours. Water was then added and the mixture was extracted three times with ethyl acetate. The combined organic layer was washed with saturated brine, dried over sodium sulfate and filtered. The solvent of the filtrate was evaporated under reduced pressure and the resulting residue was purified by silica gel chromatography (hexane:ethyl acetate=1:4) to afford the title compound as a yellow powder (68.0 mg).

HRMS (EI$^+$): 416.1472 (+1.2 mmu).

$^1$H-NMR (CDCl$_3$, 400 MHz) δ 1.21 (3H, d, J=7.3 Hz), 2.59 (1H, dd, J=1.8, 16.5 Hz), 2.78 (1H, dd, J=6.1, 16.5 Hz), 3.33-3.36 (1H, m), 4.21 (3H, s), 5.10 (1H, d, J=14.7 Hz), 5.14 (1H, d, J=14.7 Hz), 6.25 (1H, d, J=7.9 Hz), 7.25-7.46 (7H, m).

Using different halogen derivatives and the compound of Example 211, the reactions were carried out as in Example 331 to obtain compounds shown in Table 19-2 below.

TABLE 19-2

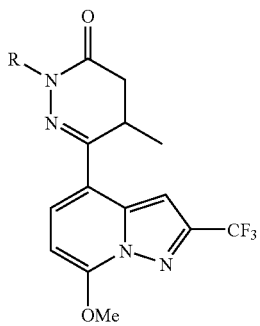

| Examples | R | Reaction temperature | Nature |
|---|---|---|---|
| 332 | CH$_2$CH$_2$—N(morpholine) | 60° C. | Yellow powder |
| 333 | CH$_2$CH$_2$Ph | Room temperature | Yellow powder |
| 334 | CH$_2$COOtBu | Room temperature | Colorless powder |
| 335 | COPh | Room temperature | Colorless powder |
| 336 | cycloheptyl | 60° C. | Colorless powder |
| 337 | 3-bromopropyl | Room temperature | Pale yellow powder |
| 338 | CHFCOOEt | Room temperature | Colorless powder |

Example 332

HRMS (EI$^+$): 439.1863 (+3.2 mmu).
$^1$H-NMR (CDCl$_3$, 400 MHz) δ 1.13 (3H, d, J=7.3 Hz), 2.32-2.79 (9H, m), 3.50-3.53 (4H, m), 3.80-3.82 (1H, m), 4.14-4.16 (1H, m), 4.20 (3H, s), 6.71 (1H, d, J=7.9 Hz), 7.59 (1H, s), 7.90 (1H, d, J=8.6 Hz).

Example 333

LRMS (EI$^+$): 430 (M)$^+$
Elemental analysis (%): Calcd. for C22H21F3N4O2.1/10H2O: C, 61.13; H, 4.94; N, 12.96; Found: C, 60.92; H, 4.98; N, 13.00.
$^1$H-NMR (CDCl$_3$, 400 MHz) δ 1.11 (3H, d, J=7.3 Hz), 2.49 (1H, dd, J=1.8, 16.5 Hz), 2.69 (1H, dd, J=6.7, 16.5 Hz), 3.06-3.13 (2H, m), 3.31-3.33 (1H, m), 4.12-4.16 (1H, m), 4.23 (3H, s), 4.30-4.34 (1H, m), 6.29 (1H, d, J=7.9 Hz), 7.15-7.19 (1H, m), 7.25-7.27 (4H, m), 7.47 (1H,d, J=7.9 Hz), 7.52 (1H, s)

Example 334

$^1$H-NMR (CDCl$_3$, 400 MHz) δ 1.36 (3H, d, J=7.3 Hz), 1.51 (9H, s), 2.59 (1H, dd, J=1.5, 16.8 Hz), 2.82 (1H, dd, J=6.4, 16.8 Hz), 3.36-3.43 (1H, m), 4.25 (3H, s), 4.56 (1H, d, J=17.1 Hz), 4.69 (1H, d, J=17.1 Hz), 6.31 (1H, d, J=7.9 Hz), 7.50 (1H, s), 7.52 (1H, d, J=7.9 Hz).

Example 335

HRMS (EI$^+$): 430.1234 (−1.9 mmu).
$^1$H-NMR (CDCl$_3$, 400 MHz) δ: 1.41 (3H, d, J=7.3 Hz), 2.74 (1H, dd, J=1.8, 16.5 Hz), 2.97 (1H, dd, J=6.7, 16.5 Hz), 3.55-3.57 (1H, m), 4.23 (3H, s), 6.29 (1H, d, J=7.9 Hz), 6.89 (1H, s), 7.58-7.61 (2H, m), 7.74-7.76 (2H, m).

Example 336

HRMS (EI⁺): 422.1949 (+1.9 mmu).

$^1$H-NMR (CDCl$_3$, 400 MHz) δ 1.22 (3H, d, J=7.3 Hz), 1.58-2.12 (12H, m), 2.52 (1H, dd, J=1.2, 16.5 Hz), 2.70 (1H, dd, J=6.7, 16.5 Hz), 3.31-3.33 (1H, m), 4.23 (3H, s), 4.89-4.94 (1H, m), 6.30 (1H, d, J=7.9 Hz), 7.49 (1H, d, J=7.9 Hz), 7.73 (1H, s).

Example 337

HRMS (EI⁺): 430.1286 (+2.2 mmu) [M⁺]

$^1$H-NMR (400 MHz, CDCl$_3$) δ 1.22 (3H, t, J=7.3 Hz), 1.29-1.33 (9H, m), 2.65 (1H, dd, J=1.8, 4.3 Hz), 2.69 (1H, dd, J=1.8, 4.9 Hz), 2.83-2.91 (2H, m), 3.46-3.51 (2H, m), 4.22-4.43 (4H, m), 4.24 (6H, s), 6.30 (2H, d, J=8.0 Hz), 6.86 (1H, d, J=12.2 Hz), 6.99 (1H, d, J=12.2 Hz), 7.39 (1H, s), 7.50 (1H, s), 7.55 (2H, d, J=8.0 Hz).

Example 338

LRMS (FAB⁺): 447 [M+H⁺]

$^1$H-NMR (400 MHz, CDCl$_3$): δ 1.25 (3H, d, J=7.3 Hz), 2.32-2.38 (2H, m), 2.55 (1H, dd, J=1.2, 16.5 Hz), 2.75 (1H, dd, J=6.7, 16.5 Hz), 3.36-3.51 (3H, m), 4.06-4.24 (2H, m), 4.24 (3H, s), 6.31 (1H, d, J=8.0 Hz), 7.52 (1H, d, J=8.0 Hz), 7.67 (1H, s).

Example 339

[6-(7-methoxy-2-trifluoromethyl-pyrazolo[1,5-a]pyridine-4-yl)-5-methyl-4,5-dihydro-3-(2H)-pyridazinone-2-yl]-acetic acid

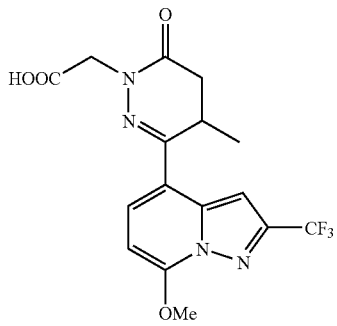

The compound of Example 334 (2.65 g) was dissolved in dichloromethane (30 mL). To this solution, trifluoroacetic acid (10 mL) was added and the mixture was left at room temperature overnight. Subsequently, the solvent and trifluoroacetic acid were evaporated under reduced pressure and the residue was triturated with diisopropyl ether to afford the title compound as a colorless powder (2.35 g).

Elemental analysis (%): Calcd. for C16H15F3N4O4: C, 50.00; H, 3.93; N, 14.58; Found: C, 49.70; H, 3.84; N, 4.40.

LRMS (EI)⁺: 384 (M)⁺

$^1$H-NMR (CDCl$_3$, 400 MHz) δ 1.17 (3H, d, J=7.3 Hz), 2.41 (1H, dd, J=1.2, 16.5 Hz), 2.82 (1H, dd, J=6.7, 16.5 Hz), 3.57-3.58 (1H, m), 4.20 (3H, s), 4.54 (1H, d, J=17.1 Hz), 4.63 (1H, d, J=17.1 Hz), 6.70 (1H, d, J=7.9 Hz), 7.56 (1H, s), 7.90 (1H, d, J=7.9 Hz), 12.87 (1H, s)

Example 340

2-(3-dimethylaminopropyl)-6-(7-methoxy-2-trifluoromethyl-pyrazolo[1,5-a]pyridine-4-yl)-5-methyl-4,5-dihydro-3-(2H)-pyridazin one

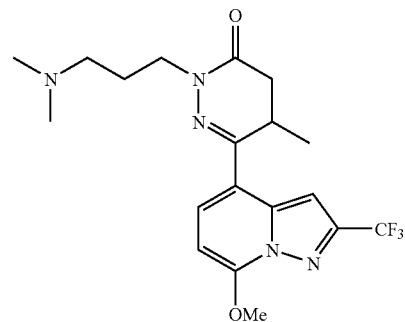

The compound of Example 337 (686 mg) was dissolved in tetrahydrofuran (5.00 mL). To this solution, a 2.00 mol/L dimethylamine/tetrahydrofuran solution (7.70 mL) was added and the mixture was stirred at 50° C. for 4 hours. Evaporation of the solvent and subsequent purification of the residue by silica gel column chromatography (hexane:ethyl acetate=1:4) afforded the title compound as a colorless powder (313 mg).

HRMS (EI⁺): 411.1889 (+0.7 mmu) [M⁺]

$^1$H-NMR (400 MHz, CDCl$_3$) δ 1.24 (3H, d, J=8.0 Hz), 1.91-1.98 (2H, m), 2.23 (6H, s), 2.38 (2H, t, J=7.3 Hz), 2.53 (1H, dd, J=1.2, 16.5 Hz), 2.74 (1H, dd, J=6.7, 16.5 Hz), 3.34-3.39 (1H, m), 3.94-4.10 (2H, m), 4.24 (3H, s), 6.30 (1H, d, J=8.0 Hz), 7.50 (1H, d, J=8.0 Hz), 7.66 (1H, s).

Example 341

6-[2-ethyl-7-(1-fluoroethyl)-pyrazolo[1,5-a]pyridine-4-yl]-5-methyl-4,5-dihydro-3-(2H)-pyridazinone

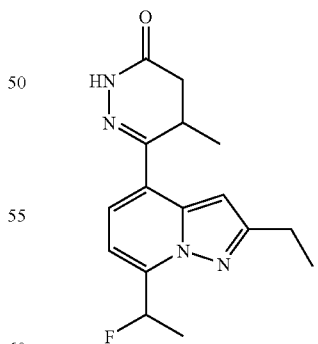

The compound of Example 232 (100 mg) was dissolved in dichloromethane (5.00 mL) in an argon atmosphere and diethylaminosulfur trifluoride (53.0 mL) was added at 0° C. The mixture was stirred at room temperature for 1 hour. Subsequently, the reaction mixture was poured into a saturated aqueous sodium bicarbonate solution and the mixture was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=1:1) afforded the title compound as a yellow powder (10.2 mg).

HRMS (EI$^+$): 302.1547 (+0.4 mmu) [M$^+$]

$^1$H-NMR (400 MHz, CDCl$_3$) δ 1.30 (3H, d, J=7.3 Hz), 1.37 (3H, t, J=7.3 Hz), 1.81 (1.5H, d, J=6.1 Hz), 1.87 (1.5H, d, J=6.1 Hz), 2.52-2.56 (1H, m), 2.75 (0.5H, t, J=6.7 Hz), 2.79 (0.5H, t, J=6.7 Hz), 2.88 (2H, q, J=7.3 Hz), 3.41-3.49 (1H, m), 6.31-6.35 (0.5H, m), 6.42-6.46 (0.5H, m), 6.91 (1H, d, J=7.3 Hz), 7.08 (1H, s), 7.40 (1H, d, J=7.3 Hz), 8.71 (1H, brs).

Example 342

6-[2-ethyl-7-(1-hydroxy-1-methyl-ethyl)-pyrazolo[1,5-a]pyridine-4-yl]-5-methyl-4,5-dihydro-3-(2H)-pyridazinone

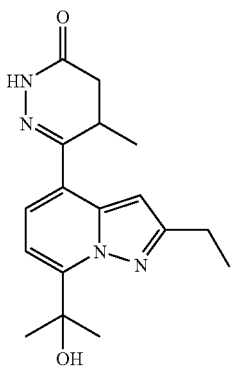

The compound of Example 235 (77.3 mg) was dissolved in tetrahydrofuran (5.00 mL) in an argon atmosphere and a 0.90 mol/L methylmagnesium bromide/tetrahydrofuran solution (720 mL) was added dropwise at −30° C. The reaction mixture was stirred for 3 hours as it was allowed to gradually warm to room temperature. Subsequently, a saturated aqueous solution of ammonium chloride was added and the mixture was extracted with ethyl acetate. The organic layer was washed sequentially with water and saturated brine and dried over anhydrous sodium sulfate. Evaporation of the solvent and subsequent purification of the residue by silica gel column chromatography (hexane:ethyl acetate=1:1) afforded the title compound as a yellow powder (33.2 mg).

Elemental analysis (%): Calcd. for C17H22N4O2: C, 64.95; H, 7.05; N, 17.82; Found: C, 64.71; H, 7.04; N, 17.62.

HRMS (EI$^+$): 314.1732 (−1.0 mmu) [M$^+$]

$^1$H-NMR (400 MHz, CDCl$_3$) δ 1.29 (3H, d, J=7.3 Hz), 1.38 (3H, t, J=7.3 Hz), 1.78 (6H, s), 2.51-2.55 (1H, m), 2.77 (1H, dd, J=6.7, 17.1 Hz), 2.90 (2H, q, J=7.3 Hz), 3.38-3.46 (1H, m), 6.72 (1H, d, J=7.3 Hz), 7.07 (1H, s), 7.14 (1H, brs), 7.35 (1H, d, J=7.3 Hz), 8.63 (1H, brs).

Example 343

6-[2-ethyl-7-(1-hydroxy-1-phenyl-ethyl)-pyrazolo[1,5-a]pyridine-4-yl]-5-methyl-4,5-dihydro-3-(2H)-pyridazinone

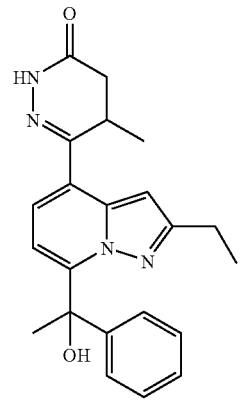

The compound of Example 235 (62.7 mg) was dissolved in tetrahydrofuran (5.00 mL) in an argon atmosphere and a 1.02 mol/L phenyl magnesium bromide/tetrahydrofuran solution (520 mL) was added dropwise at −30° C. The reaction mixture was stirred for 3 hours as it was allowed to gradually warm to room temperature. Subsequently, a saturated aqueous ammonium chloride folution was added and the mixture was extracted with ethyl acetate. The organic layer was washed sequentially with water and saturated brine and dried over an hydrous sodium sulfate. Evaporation of the solvent and subsequent purification of the residue by silica gel column chromatography (hexane:ethyl acetate=1:1) afforded the title compound as a yellow powder (34.3 mg).

Elemental analysis (%): Calcd. for C22H24N4O2: C, 70.19; H, 6.43; N, 14.88; Found: C, 69.95; H, 6.42; N, 14.76.

HRMS (EI$^+$): 376.1929 (+3.0 mmu) [M$^+$]

$^1$H-NMR (400 MHz, CDCl$_3$) δ 1.24 (3H, t, J=7.3 Hz), 1.31 (3H, d, J=7.3 Hz), 2.00 (3H, s), 2.73-2.79 (3H, m), 3.40-3.48 (1H, m), 6.83 (1H, d, J=7.3 Hz), 7.00 (1H, s), 7.21-7.29 (3H, m), 7.34-7.44 (3H, m), 7.64 (1H, brs), 8.61 (1H, brs).

Example 344

7-methoxy-4-(5-methyl-4,5-dihydro-3-(2H)-pyridazinone-6-yl)pyrazolo[1,5-a]pyridine-2-carboaldehyde oxime

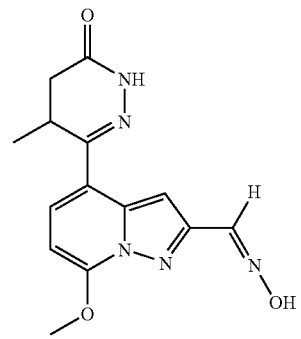

The compound of Example 237 (24.0 mg) was dissolved in methanol (3 mL). To this solution, sodium acetate (41.3 mg) and hydroxylamine hydrochloride (17.5 mg) were added at room temperature and the reaction mixture was stirred for 20 min. The solvent was evaporated under reduced pressure and water was added to the residue. The mixture was filtered to afford the title compound as a white powder (15.3 mg, a mixture of E-form and Z-form (E:Z=1:5)).

HRMS (EI+): 301.1223 (+4.8 mmu) [M+]

E-form $^1$H-NMR (400 MHz, DMSO-d$_6$) δ 1.09 (3H, d, J=7.3 Hz), 2.26 (1H, d, J=16.5 Hz), 2.73 (1H, dd, J=6.7, 16.5 Hz), 3.46-3.53 (1H, m), 4.15 (3H, s), 6.52 (1H, d, J=7.9 Hz), 7.69 (1H, s), 7.69 (1H, d, J=7.9 Hz), 7.91 (1H, s), 11.11 (1H, s), 11.83 (1H, s).

Z-form $^1$H-NMR (400 MHz, DMSO-d$_6$) δ 1.09 (3H, d, J=7.3 Hz), 2.26 (1H, d, J=16.5 Hz), 2.73 (1H, dd, J=6.7, 16.5 Hz), 3.46-3.53 (1H, m), 4.14 (3H, s), 6.45 (1H, d, J=7.9 Hz), 7.47 (1H, s), 7.69 (1H, d, J=7.9 Hz), 8.21 (1H, s), 11.06 (1H, s), 11.50 (1H, s).

Example 345

7-methoxy-4-(5-methyl-4,5-dihydro-3-(2H)-pyridazinone-6-yl)pyrazolo[1,5-a]pyridine-2-carbonitrile

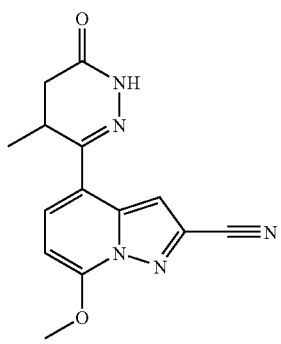

Triethylamine (0.291 mL) and trifluoroaceticanhydride (0.116 mL) were added to a suspension of the compound of Example 344 (63.0 mg) in methylene chloride (6 mL). The mixture was stirred at room temperature for 1 hour. Subsequently, a saturated aqueous sodium bicarbonate solution was added and the mixture was stirred for 30 min. The organic layer was separated and the aqueous layer was extracted with methylene chloride. The combined organic layer was dried over anhydrous magnesium sulfate. Evaporation of the solvent and subsequent purification of the residue by silica gel column chromatography (NH type, methylene chloride:methanol=9:1) afforded the title compound as a pale yellow powder (31.3 mg).

Elemental analysis (%): Calcd. for C14H13N5O2: C, 59.36; H, 4.62; N, 24.72; Found: C, 59.13; H, 4.63; N, 24.53.

HRMS (EI+): 283.1050 (−1.9 mmu) [M+]

$^1$H-NMR (400 MHz, DMSO-d$_6$) δ 1.08 (3H, d, J=7.3 Hz), 2.28 (1H, d, J=16.5 Hz), 2.75 (1H, dd, J=7.3, 16.5 Hz), 3.48-3.35 (1H, m), 4.19 (3H, s), 6.74 (1H, d, J=8.6 Hz), 7.70 (1H, s), 7.86 (1H, d, J=8.6 Hz), 11.90 (1H, s).

Example 346

7-methoxy-4-(5-methyl-4,5-dihydro-3-(2H)-pyridazinone-6-yl)pyrazolo[1,5-a]pyridine-2-carboxylic acid

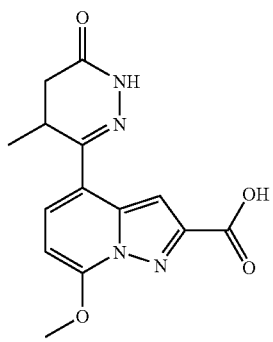

An aqueous solution (1 mL) of sodium hydroxide (41.9 mg) was added to an aqueous solution (3 mL) of silver nitrate (89.0 mg). To this mixture, the compound of Example 237 (60.0 mg) was added and the resulting mixture was stirred at room temperature for 1 hour. Subsequently, 5% hydrochloric acid was added to adjust the pH to 3. The insoluble material was separated by filtration and washed with a 7:1 mixture of chloroform and methanol. The filtrate and wash were combined. Sodium chloride was then added and the mixture was extracted with a 7:1 mixture of chloroform and methanol. The extract was dried over anhydrous magnesium sulfate and the solvent was evaporated. Methanol was added to the residue and the insoluble material was removed by filtration. The solvent of the filtrate was evaporated to afford the title compound as a pale yellow powder (46.3 mg).

HRMS (EI+): 302.1034 (+1.9 mmu) [M+]

$^1$H-NMR (400 MHz, DMSO-d$_6$) δ 1.09 (3H, d, J=7.3 Hz), 2.27 (1H, d, J=16.5 Hz), 2.74 (1H, dd, J=6.7, 16.5 Hz), 3.47-3.54 (1H, m), 4.16 (3H, s), 6.58 (1H, d, J=8.6 Hz), 7.64 (1H, s), 7.73 (1H, d, J=8.6 Hz), 11.08 (1H, s), 13.06 (1H, brs).

Example 347

2-ethyl-7-methoxy-pyrazolo[1,5-a]pyridine-4-carboaldehyde

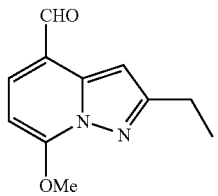

The compound of Example 58 (11.23 g) was dissolved in chloroform (540 mL). To this solution, manganese dioxide (15.7 g) was added at room temperature and the mixture was stirred at 50° C. for 2 hours. Subsequently, additional manganese dioxide (15.7 g) was added and the mixture was stirred at 50° C. for another 2 hours. The insoluble material in the mixture was removed by filtration through Celite. The solvent of the filtrate was evaporated to afford the title compound as a yellow powder (10.76 g).

$^1$H-NMR (400 MHz, CDCl$_3$) δ 1.38 (3H, t, J=8.0 Hz), 2.94 (2H, q, J=8.0 Hz), 4.25 (3H, s), 6.20 (1H, d, J=7.3 Hz), 7.17 (1H, s), 7.71 (1H, dd, J=1.2, 8.0 Hz), 9.92 (1H, d, J=1.2 Hz)

Example 348

2-ethyl-7-methoxy-pyrazolo[1,5-a]pyridine-4-carboxylic acid

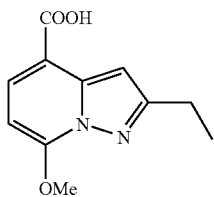

An aqueous suspension (526 mL) of silver nitrate (22.28 g) and sodium hydroxide (10.86 g, 15.1) was added to the compound of Example 347 (10.76 g). The mixture was stirred at room temperature for 1.5 hours. Subsequently, the insoluble material in the mixture was removed by filtration through Celite. The filtrate was washed with diethyl ether. Diluted hydrochloric acid was then added to the aqueous layer to make it acidic. The mixture was then extracted with ethyl acetate and the organic layer was dried over anhydrous sodium sulfate. Evaporation of the solvent afforded the title compound as a yellow powder (11.13 g).

$^1$H-NMR (400 MHz, CDCl$_3$) δ 1.40 (3H, t, J=8.0 Hz), 2.95 (2H, q, J=8.0 Hz), 4.24 (3H, s), 6.15 (1H, d, J=8.6 Hz), 7.02 (1H, s), 8.13 (1H, d, J=8.6 Hz).

Example 349

2-ethyl-7-methoxy-pyrazolo[1,5-a]pyridine-4-carboxylic acid methoxymethylamide

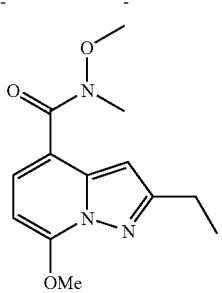

The compound of Example 348 (11.13 g) was dissolved in N,N-dimethylformamide (505 mL) in an argon atmosphere. While this solution was chilled in an ice bath, N,O-dimethylhydroxyamine hydrochloride (6.15 g) and diethyl cyanophosphonate were added, followed by dropwise addition of triethylamine (17.5 mL). The mixture was stirred first in an ice bath for 30 min and then at room temperature for 5 hours. Subsequently, water was added and the mixture was extracted with ethyl acetate. The organic layer was dried over anhydrous sodium sulfate. Evaporation of the solvent and subsequent purification of the residue by silica gel chromatography (ethyl acetate) afforded the title compound as a brown oil (12.12 g).

$^1$H-NMR (400 MHz, CDCl$_3$) δ 1.36 (3H, t, J=8.0 Hz), 2.91 (2H, q, J=8.0 Hz), 3.38 (3H, d, J=1.2 Hz), 3.59 (3H, d, J=1.2 Hz), 4.18 (3H, d, J=1.2 Hz), 6.05 (1H, d, J=8.0 Hz), 6.58 (1H, s), 7.53 (1H, dd, J=1.2, 8.0 Hz).

Example 350

2,7-diethyl-4-propionyl-pyrazolo[1,5-a]pyridine

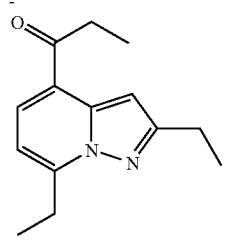

The compound of Example 349 (11.09 g) was dissolved in tetrahydrofuran (320 mL) in an argon atmosphere. While this solution was chilled in a ice salt water bath (−7° C.), ethyl magnesium bromide (100 mL, 0.91 mol/L tetrahydrofuran solution) was added dropwise and the mixture was stirred at room temperature for 1 hour. Subsequently, a saturated aqueous ammonium chloride solution was added while the mixture was chilled in an ice bath. The mixture was extracted with ethyl acetate and the extract was washed with saturated brine and dried over anhydrous sodium sulfate. Evaporation of the solvent and subsequent purification of the residue by silica gel chromatography (hexane:ethyl acetate=2:3→1:2→1:4→ethyl acetate) afforded the title compound as a yellow powder (4.21 g).

$^1$H-NMR (400 MHz, CDCl$_3$) δ 1.26 (3H, t, J=7.3 Hz), 1.38 (3H, t, J=7.3 Hz), 1.45 (3H, t, J=7.3 Hz), 2.92 (2H, q, J=7.3 Hz), 3.04 (2H, q, J=7.3 Hz), 3.24 (2H, q, J=7.3 Hz), 6.62 (1H, d, J=7.4 Hz), 7.20 (1H, s), 7.80 (1H, d, J=7.4 Hz).

Example 351

6-(2,7-diethyl-pyrazolo[1,5-a]pyridine-4-yl)-5-methyl-4,5-dihydro-3-(2H)-pyridazinone

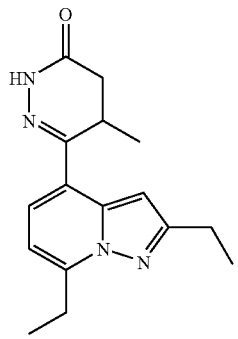

The compound of Example 350 (1.00 g) was dissolved in tetrahydrofuran (43 mL) in an argon atmosphere. While this solution was chilled in an ice bath, lithium bis(trimethylsilyl) amide (4.77 mL, 1.0 mol/L tetrahydrofuran solution) was added and the mixture was stirred for 15 min while ice-chilled. While the mixture was kept ice-chilled, t-butyl bromoacetate (0.954 mL) was added and the mixture was stirred at room temperature for 1 hour. With the mixture being ice-chilled, a saturated aqueous ammonium chloride solution was added and the mixture was extracted with ethyl acetate. The extract was washed with saturated brine and dried over anhydrous sodium sulfate. Evaporation of the solvent gave a yellow oil. This product was dissolved in dichloromethane (10 mL). While the solution was kept ice-chilled, trifluoroacetic acid (5 mL) was added and the mixture was stirred at room temperature for 19 hours. Subsequently, dichloromethane was evaporated and the residue was diluted with water, followed by addition of a 10% sodium hydroxide solution to make the mixture basic. The mixture was then washed with diethyl ether. Diluted hydrochloric acid was added to the aqueous layer to make it acidic and the mixture was extracted with ethyl acetate. The organic layer was dried over anhydrous sodium sulfate and the solvent was evaporated to give a yellow oil. This product was dissolved in ethanol (29 mL). To the solution, hydrazine monohydrate (0.40 mL) was added and the mixture was stirred for 4 hours under reflux. Evaporation of the solvent and subsequent purification of the residue by silica gel chromatography (hexane:ethyl acetate=2:3) afforded the title compound as a colorless amorphous material (1.00 g).

Elemental analysis (%): Calcd. for $C_{16}H_{20}N_4O$: C, 67.58; H, 7.09; N, 19.70; Found: C, 67.51; H, 7.15; N, 19.63.

LRMS (EI$^+$): 284 [M$^+$]

$^1$H-NMR (400 MHz, CDCl$_3$) δ 1.29 (3H, t, J=7.4 Hz), 1.38 (3H, t, J=7.4 Hz), 1.44 (3H, t, J=7.4 Hz), 2.52 (3H, d, J=17.1 Hz), 2.77 (3H, dd, J=6.7, 17.1 Hz), 2.91 (2H, q, J=7.4 Hz), 3.23 (2H, q, J=7.4 Hz), 3.44 (1H, m), 6.62 (1H, d, J=7.4 Hz), 7.08 (1H, s), 7.34 (1H, d, J=7.4 Hz), 8.73 (1H, brs).

Example 352

3-ethoxycarbonyl-4-hydroxymethyl-7-methoxy-2-pentafluoroethyl-pyrazolo[1,5-a]pyridine

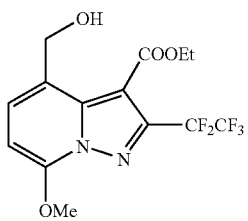

N,N-dimethylformamide (20 mL) and potassium carbonate (11.9 g) were added to a solution of ethyl 4,4,5,5,5-pentafluoro-pent-2-enoate* (6.17 g) and the compound of Example 10 (15.2 g) in tetrahydrofuran (200 mL). The mixture was stirred at room temperature overnight. Subsequently, the mixture was filtered through Celite. The filtrate was concentrated and extracted with ethyl acetate (1 L). The extract was washed sequentially with water and saturated brine and dried over anhydrous sodium sulfate. The extract was then concentrated and purified by silica gel column chromatography (hexane:ethyl acetate=4:1) to afford the title compound as a colorless powder (3.33 g).

*J. Org. Chem., 1992, 57, 5680-5686

$^1$H-NMR (400 MHz, CDCl$_3$) δ 1.41 (3H, t, J=7.3 Hz), 4.18 (3H, s), 4.28 (1H, t, J=7.3 Hz), 4.42 (2H, q, J=7.3 Hz), 4.79 (2H, d, J=7.3 Hz), 6.34 (1H, d, J=7.9 Hz), 7.41 (1H, d, J=7.9 Hz).

Example 353

4-hydroxymethyl-7-methoxy-2-pentafluoroethyl-pyrazolo[1,5-a]pyridine

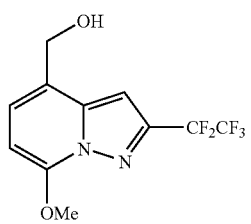

A 4 mol/L aqueous potassium hydroxide solution (7.0 mL) was added to a solution of the compound of Example 352 (3.33 g) in methanol (50 mL). The mixture was refluxed for 2 hours. Subsequently, the mixture was concentrated and made acidic. The resultant crystals were collected by filtration. To this product, 1,2-dichlorobenzene (50 mL) was added and the mixture was stirred at 150° C. overnight. Evaporation of the solvent and subsequent purification by silica gel column chromatography (hexane:ethylacetate=3:1→1:1) afforded the title compound as a colorless powder (1.28 g).

$^1$H-NMR (400 MHz, CDCl$_3$) δ 4.18 (3H, s), 4.88 (2H, s), 6.22 (1H, d, J=7.3 Hz), 6.93 (1H, s), 7.24-7.28 (1H, m).

Example 354

7-methoxy-2-pentafluoroethyl-pyrazolo[1,5-a]pyridine-4-carboaldehyde

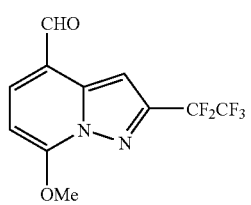

Activated manganese dioxide (3.75 g) was added to a solution of the compound of Example 353 (1.28 g) in chloroform (50 mL). The mixture was stirred at 50° C. for 4 hours. Subsequently, the mixture was filtered through Celite and the filtrate was concentrated to afford the title compound as a colorless powder (1.24 g).

$^1$H-NMR (400 MHz, CDCl$_3$) δ 4.31 (3H, s), 6.43 (1H, d, J=7.9 Hz), 7.67 (1H, s), 7.87 (1H, d, J=7.9 Hz), 9.98 (1H, s).

Example 355

4-(1-hydroxypropyl)-7-methoxy-2-pentafluoroethyl-pyrazolo[1,5-a]pyridine

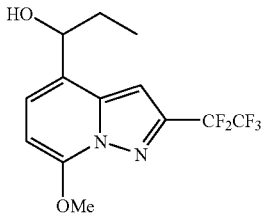

In an argon atmosphere, ethyl magnesium bromide (5.44 mL, 0.91 mol/L tetrahydrofuran solution) was added to a solution of the compound of Example 354 (1.24 g) in tetrahydrofuran (30 mL) at −78° C. The mixture was allowed to gradually warm to room temperature and was stirred at room temperature for 1 hour. Subsequently, a saturated aqueous ammonium chloride solution was added and the mixture was extracted with ethyl acetate (100 mL). The extract was washed sequentially with water and saturated brine and dried over anhydrous sodium sulfate. The extract was then concentrated and purified by amino-silica gel column chromatography (ethyl acetate) to afford the title compound as a pale yellow oil (1.41 g).

$^1$H-NMR (400 MHz, CDCl$_3$) δ 0.97 (3H, t, J=7.3 Hz), 1.88-1.96 (2H, m), 4.17 (3H, s), 4.88 (1H, t, J=6.7 Hz), 6.22 (1H, d, J=7.9 Hz), 6.94 (1H, s), 7.25 (1H, d, J=7.9 Hz).

Example 356

7-methoxy-2-pentafluoroethyl-4-propionyl-pyrazolo[1,5-a]pyridine

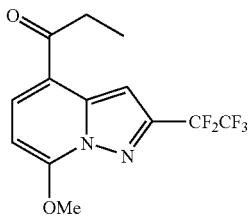

Triethylamine (6.08 mL) was added to a solution of the compound of Example 355 (1.41 g) in dimethylsulfoxide (30 mL). While the solution was stirred at room temperature, sulfur trioxide-pyridine complex (3.46 g) was added and the mixture was stirred at room temperature for 30 min. Water (150 mL) was then added and the resulting crystals were collected by filtration. The crystals were dissolved in ethyl acetate and the solution was dried over anhydrous sodium sulfate. Purification by amino-silica gel column chromatography (ethyl acetate) afforded the title compound as a colorless powder (1.16 g).

$^1$H-NMR (400 MHz, CDCl$_3$) δ 1.28 (3H, t, J=7.3 Hz), 3.03 (2H, q, J=7.3 Hz), 4.27 (3H, s), 6.31 (1H, d, J=7.9 Hz), 7.72 (1H, s), 8.01 (1H, d, J=7.9 Hz).

Example 357 t-butyl 4-(7-methoxy-2-pentafluoroethyl-pyrazolo[1,5-a]pyridine-4-yl)-3-methyl-4-oxobutyrate

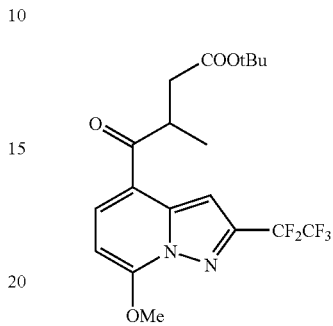

In an argon atmosphere, a 1 mol/L lithium bis(trimethylsilyl)amide/tetrahydrofuran solution (4.14 mL) was added dropwise to a solution of the compound of Example 356 (1.16 g) in tetrahydrofuran (30 mL) at 0° C. The mixture was stirred at 0° C. for 20 min. Subsequently, t-butyl bromoacetate (0.797 mL) was added at 0° C. and the mixture was stirred at room temperature for 1 hour. The reaction was quenched by adding a saturated aqueous ammonium chloride solution and the mixture was extracted with ethyl acetate (200 mL). The extract was washed sequentially with water and saturated brine and dried over anhydrous sodium sulfate. The extract was then concentrated and purified by silica gel column chromatography (hexane:ethyl acetate=2:1 v/v) to afford the title compound as a colorless powder (940 mg).

$^1$H-NMR (400 MHz, CDCl$_3$) δ 1.24 (3H, d, J=7.3 Hz), 1.38 (9H, s), 2.41 (1H, dd, J=17.1, 5.5 Hz), 2.93 (1H, dd, J=17.1, 9.2 Hz), 3.85-3.97 (1H, m), 4.28 (3H, s), 6.33 (1H, d, J=7.9 Hz), 7.70 (1H, s), 8.10 (1H, d, J=8.6 Hz).

Example 358

6-(7-methoxy-2-pentafluoro-pyrazolo[1,5-a]pyridine-4-yl)-5-methyl-4,5-dihydro-3-(2H)-pyridazinone

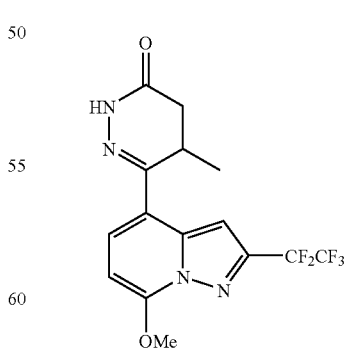

Trifluoroacetic acid (7.5 mL) was added to a solution of the compound of Example 359 (940 mg) in dichloromethane (15 mL). The mixture was left overnight. Subsequently, the mixture was concentrated and azeotropically distilled once with toluene. A saturated aqueous sodium bicarbonate solution was added to the residue. The aqueous phase was washed with ether and made acidic. The resulting crystals were collected by filtration. This product was dissolved in ethanol (15 mL), followed by addition of acetic acid (605 μL) and hydrazine monohydrate (233 μL) and refluxing for 3 hours. Subsequently, water (100 mL) was added and the resulting crystals were collected by filtration. The crystals were washed with diisopropyl ether and dissolved in acetone. The insoluble material was removed by filtration. The filtrate was concentrated and purified by recrystallization (ethanol-hexane) to afford the title compound as a colorless powder (229 mg).

$^1$H-NMR (400 MHz, CDCl$_3$) δ 1.31 (3H, d, J=7.3 Hz), 2.54 (1H, d, J=17.1 Hz), 2.77 (1H, dd, J=16.5, 6.7 Hz), 3.35-3.47 (1H, m), 4.23 (3H, s), 6.30 (1H, d, J=8.6 Hz), 7.51 (1H, d, J=7.9 Hz), 7.62 (1H, s), 8.63 (1H, s).

LRMS (EI$^+$): 376(M$^+$)

Elemental analysis (%): Calcd. for C15H13F5N4O2: C, 47.88; H, 3.48; N, 14.89; Found: C, 47.64; H, 3.29; N, 14.81.

The following experiments were conducted to demonstrate the effectiveness of the compounds of the present invention.

Experiment 1

Inhibition of Phosphodiesterase Activity

RT-PCR was performed to isolate cDNA fragments of PDE3A catalytic domain (indicated as "cat," hereinafter), PDE4Bcat, PDE5Acat and PDE10A1 from human RNA. Using Gateway system (Invitrogen) and Bac-to-Bac (registered trademark) Baculovirus Expression system (Invitrogen), the isolated cDNA fragments were transfected into Sf9 insect cells for expression of the PDE proteins. The recombinant PDE3Acat, PDE4Bcat, PDE5Acat and PDE10A1 proteins were isolated from culture supernatant or cell extracts of Sf9 cells expressed high levels of these proteins by ion-exchange chromatography and used for the following experiments.

4 mmol/L solution of each test compound was serially diluted 4-fold with 15% DMSO solution to prepare the solutions with concentrations of 15 nmol/L to 4 mmol/L (final concentrations=1.5 nmol/L-400 μmol/L). 10 μL of each test compound solution was added to each well of 96 plate with 10 μL of [$^3$H]-cAMP or [$^3$H]-cGMP solution, diluted with a buffer (40 mmol/L Tris-HCl (pH 7.4), 10 mmol/L MgCl$_2$) to the concentration shown in Table 20 and 40 μL of each of the human recombinant PDE proteins in units shown in Table 20. The plate was incubated at 30° C. for 20 min, and then at 65° C. for 2 min. Subsequently, 25 μL of 1 mg/mL 5'-nucleotidase (Crotalus atrox venom, Sigma) was added to each well and the plate was incubated at 30° C. for 10 min. 200 μL of Dowex solution (300 mg/mL Dowex 1×8-400 (Sigma Aldrich), 33% ethanol) was then added to each well and the plate was shaken at 4° C. for 20 min. Subsequently, 200 μL of MicroScint 20 (Packard) was added to each well and the radioactivity of each sample was measured by a scintillation counter (Topcount, Packard) IC$_{50}$ was calculated by GraphPad Prism v3.03 (GraphPad Software).

| Enzyme (amount) | Substrate | Substrate Conc. |
|---|---|---|
| PDE 3ACat (2 × 10$^{-6}$ units) | cAMP | 2 μmol/L |
| PDE 4BCat (2 × 10$^{-6}$ units) | cAMP | 2 μmol/L |
| PDE 5ACat (2 × 10$^{-6}$ units) | cGMP | 2 μmol/L |
| PDE 10Al (2 × 10$^{-7}$ units) | cAMP | 0.2 μmol/L |

*: 1 unit is defined as the amount of PDE required to hydrolyze 1 μmol/L cAMP or cGMP in 1 min at pH 7.5 at 30° C.

(−) indicates the IC$_{50}$ value is 10 μmol/L or more. (+) means the IC$_{50}$ value is 1 μmol/L or more and less than 10 μmol/L. (++) means the IC$_{50}$ value is 0.1 μmol/L or more and less than 1 μmol/L. (+++) indicates the IC$_{50}$ value is less than 1 μmol/L.

The results are shown in Table 21.

TABLE 21

| | IC$_{50}$(μmol/L) | | | |
|---|---|---|---|---|
| Ex. No. | PDE3 | PDE4 | PDE5 | PDE10 |
| 201 | + | − | − | + |
| 202 | − | − | − | + |
| 203 | − | ++ | NT | NT |
| 204 | + | + | NT | NT |
| 205(211) | + | +++ | − | + |
| 209 | − | ++ | NT | NT |
| 210 | − | + | − | − |
| 212 | − | +++ | NT | NT |
| 213 | − | ++ | NT | NT |
| 214 | +++ | + | NT | NT |
| 215 | + | ++ | NT | NT |
| 216 | − | ++ | − | + |
| 217 | + | ++ | NT | NT |
| 218 | + | ++ | NT | NT |
| 219 | NT | ++ | NT | NT |
| 220 | + | ++ | NT | NT |
| 221 | + | + | NT | NT |
| 222 | + | +++ | NT | NT |
| 223 | + | ++ | NT | NT |
| 224 | + | ++ | NT | NT |
| 225 | + | +++ | NT | NT |
| 226 | + | − | NT | NT |
| 228 | + | ++ | NT | NT |
| 229 | + | + | NT | NT |
| 236 | + | ++ | NT | NT |
| 238 | + | +++ | NT | NT |
| 240 | + | +++ | NT | NT |
| 241 | + | +++ | NT | NT |
| 244 | + | + | NT | NT |
| 245 | + | − | NT | NT |
| 247 | + | + | NT | NT |
| 249 | + | +++ | NT | NT |
| 250 | + | ++ | NT | NT |
| 251 | + | + | NT | NT |
| 252 | + | + | NT | NT |
| 266 | − | + | − | − |
| 267 | − | + | − | − |
| 272 | − | +++ | + | ++ |
| 273 | − | + | − | + |
| 274 | − | ++ | NT | NT |
| 275 | − | + | NT | NT |
| 276 | + | + | − | − |
| 278 | − | ++ | − | − |
| 279 | − | ++ | NT | NT |
| 281 | − | + | − | − |
| 282 | + | ++ | − | + |
| 283 | − | ++ | − | − |
| 284 | − | ++ | − | + |
| 285 | − | + | − | + |
| 287 | − | + | NT | NT |
| 289 | − | + | − | + |
| 290 | − | ++ | − | + |
| 291 | − | ++ | NT | NT |
| 292 | + | +++ | NT | NT |
| 293 | − | +++ | NT | NT |
| 294 | + | +++ | NT | NT |

TABLE 21-continued

| Ex. No. | IC$_{50}$(µmol/L) | | | |
|---|---|---|---|---|
| | PDE3 | PDE4 | PDE5 | PDE10 |
| 295 | + | +++ | NT | NT |
| 296 | − | +++ | NT | NT |
| 297 | − | +++ | NT | NT |
| 298 | − | ++ | NT | NT |
| 299 | − | +++ | NT | NT |
| 300 | − | − | − | + |
| 302 | + | ++ | NT | NT |
| 303 | − | + | NT | NT |
| 304 | + | − | − | − |
| 306 | + | + | − | − |
| 312 | − | + | − | − |
| 313 | + | + | − | ++ |
| 314 | − | ++ | − | − |
| 315 | + | + | − | + |
| 316 | − | +++ | − | − |
| 317 | ++ | +++ | − | + |

NT: Not Test

Experiment 2

Relaxant Effect on Histamine-Induced Contraction of Isolated Guinea Pig Tracheal Smooth Muscles Guinea pigs were exsanguinated and the trachea was immediately isolated and cut into 2 to 3 cartilage ring segments to prepare tracheal ring preparations. The tracheal rings were suspended in 10 mL of Tyrode's solution bubbled with a gaseous mixture of 95% $O_2$+5% $CO_2$ at 37° C. The composition of the Tyrode's solution (mM) was as follows: NaCl 136.9, KCl 2.7, $CaCl_2$ 1.8, $MgCl_2$ 1.0, $NaH_2PO_4$ 0.4, $NaHCO_3$ 11.9 and Gucose 5.6. The contractile response was measured by an isometric transducer (UM-203, KISHIMOTO) and recorded on a recorder (GRAPHTEC SERVO-CORDER SR6221). After about 1 hour incubation with 1.5 g of resting tention, histamine ($10^{-5}$ mol/L) was added to induce the contractile response. After confirming the response, the preparations were washed with Tyrode's solution (10 mL×3). Then indomethacin ($10^{-5}$ mol/L) was applied and the preparations were equilibrated for at least 30 min under 1.5 g tension. Subsequently, histamine ($10^{-5}$ mol/L) was applied. After the contraction reached a steady state, each compound was added in a cumulative manner ($10^{-8}$ mol/L-$3\times10^{-5}$ mol/L). Each compound was prepared as a $10^{-1}$ mol/L solution in DMSO, which was diluted with distilled water for use. After addition of test compounds, papaverine ($10^{-4}$ mol/L) was added to determine the maximum relaxation of the preparation. Relaxant response of test compounds were expressed as a percentage of the maximum response to papaverine. IC$_{50}$ was defined as a concentration of the compound required to 50% relaxation. DMSO was used as a control.

The results are shown in Table 22.

TABLE 22

| Ex. No. | IC$_{50}$(µmol/L) |
|---|---|
| 200 | 2.8 |
| 201 | 0.93 |
| 205(211) | 0.30 |
| 216 | 0.65 |
| 304 | 0.89 |
| 311 | 2 |

TABLE 22-continued

| Ex. No. | IC$_{50}$(µmol/L) |
|---|---|
| 313 | 0.50 |
| 316 | 0.676 |
| 317 | 0.127 |

Experiment 3

Histamine-Induced Bronchoconstriction in Guinea Pigs

Guinea pigs were anesthetized with pentobarbital (30 mg/kg, i.p.). A cannula for IV administeration, a cannula for collecting blood and measurement of blood pressure and a trachea cannula were inserted into the left exterior jugular vein, right interior carotid artery and trachea, respectively. The animals were placed under artificial respiration at 60 times/min and 10 mL/kg/stroke. The airflow through the branch of the tracheal cannula was measured by a bronchospasm transducer (Ugo-Basile) and recorded on a computer via Power Lab (ADInstruments Japan). The animals were immobilized with gallamine (10 mg/kg, i.v.), then administered histamine at 10-minute intervals (12.5 µg/kg, i.v.). After the histamine-induced bronchoconstriction had been constant, the test compounds (1 mg/kg, i.v.) were administered. To examine the inhibitory activity of test compound, the histamine-induced bronchoconstriction was measured after 30 seconds of drug administration. The bronchoconstriction was recorded as the change of the airflow: The results were shown by percentages of the maximum histamine-induced bronchoconstriction. Each test compound was prepared as a 10 mg/mL solution in DMSO. Gallamine was prepared as a 10 mg/mL solution in physiological saline. Histamine was prepared as a 1 mg/mL solution in physiological saline, which was diluted with physiological saline to 62.5 µg/mL for use.

(+++) indicates the inhibition is 90% or more. (++) means the inhibition is 80% or more and less than 90%. (+) means the inhibition is 70% or more and less than 80%.

The results are shown in Table 23.

TABLE 23

| Ex. No. | % inhibition |
|---|---|
| 201 | +++ |
| 202 | +++ |
| 203 | + |
| 205(211) | [+++] |
| 209 | [++] |
| 210 | +++ |
| 213 | + |
| 214 | [++] |
| 215 | [++] |
| 216 | +++ |
| 217 | [+++] |
| 218 | [+++] |
| 219 | [+++] |
| 220 | [+++] |
| 222 | [+] |
| 223 | [+++] |
| 225 | [++] |
| 232 | [+++] |
| 235 | [+++] |
| 239 | [+++] |
| 240 | [+++] |
| 241 | [+++] |
| 245 | [+++] |
| 247 | [+] |

TABLE 23-continued

| Ex. No. | % inhibition |
|---|---|
| 249 | [+++] |
| 250 | [+++] |
| 276 | +++ |
| 282 | +++ |
| 290 | + |
| 291 | [++] |
| 293 | [+] |
| 295 | [+] |
| 302 | [+++] |
| 304 | +++ |
| 306 | +++ |
| 313 | +++ |
| 314 | [++] |
| 315 | [+++] |
| 317 | [+++] |

[0.1 mg/kg]

The results of the experiments in animal models have demonstrated that the compounds of the present invention represented by the general formula (1) each serve as an effective PDE inhibitor.

INDUSTRIAL APPLICABILITY

As set forth, the present invention is based upon the finding that the novel pyrazolopyridine-4-yl pyridazinone derivatives and addition salts thereof are potent PDE inhibitors. Such PDE inhibitors are not only useful in the treatment of angina pectoris, heart failure and hypertension, but can also prevent platelet aggregation and are useful in the treatment and prevention of asthma, chronic obstructive pulmonary disease (COPD), interstitial pneumonia, allergic rhinitis, atopic dermatitis, rheumatoid arthritis, multiple sclerosis, Crohn's disease, inflammatory colitis, psychiatric disorders such as Huntington's disease, Alzheimer's disease, dementia, Parkinson's disease, depression and schizophrenia, and erectric dysfunction.

The invention claimed is:

1. A pyrazolopyridine-4-yl pyridazinone compound represented by the following formula (1):

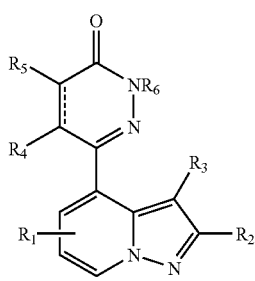

(1)

wherein:
$R_1$ is a hydrogen atom, a halogen atom, a lower alkyl group having 1 to 4 carbon atoms, a substituted or unsubstituted lower alkoxy group having 1 to 4 carbon atoms, a cyclopropylmethyloxy group, a lower alkylthio group having 1 to 4 carbon atoms, a lower alkylsulfinyl group having 1 to 4 carbon atoms, a lower alkylsulfonyl group having 1 to 4 carbon atoms, a substituted or unsubstituted lower alkylamino group having 1 to 4 carbon atoms, a phenylamino group, an aromatic or saturated heterocyclic ring that may contain 1 or 2 heteroatoms, a lower alkanoyl group having 1 to 4 carbon atoms, an alkanoylamino group having 1 to 4 carbon atoms, a substituted or unsubstituted phenyl group, a carbamoyl group, a cyano group, a lower alkoxycarbonyl group having 1 to 4 carbon atoms, or a carboxyl group;

$R_2$ is a hydrogen atom, a substituted or unsubstituted lower alkyl group having 1 to 4 carbon atoms, a cycloalkyl group having 3 to 8 carbon atoms, a lower alkenyl group having 2 to 4 carbon atoms, a lower alkanoyl group having 1 to 4 carbon atoms, or a lower alkylthio group having 1 to 4 carbon atoms;

$R_3$ is a hydrogen atom, a halogen atom, a carboxyl group, a lower alkoxycarbonyl group having 1 to 4 carbon atoms, or a hydroxyl group;

$R_4$ and $R_5$ are each independently a hydrogen atom or a lower alkyl group having 1 to 4 carbon atoms;

$R_6$ is a hydrogen atom, or $R_7$—$(CH_2)_m$— (wherein $R_7$ is a cycloalkyl group having 3 to 8 carbon atoms, a hydroxyl group, or an aromatic or saturated heterocyclic ring that may contain 1 or 2 heteroatoms, and m is an integer of 1 or 2); and -- is a single or double bond, an optical isomer thereof or a pharmaceutically acceptable salt thereof or a hydrate thereof.

2. The pyrazolopyridine-4-yl pyridazinone compound according to claim 1, an optical isomer thereof, or a pharmaceutically acceptable salt thereof or a hydrate thereof, wherein the compound represented by the formula (1) is represented by the following formula (1a):

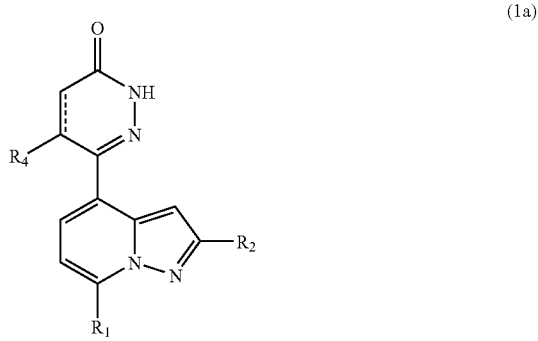

(1a)

wherein $R_1$, $R_2$, $R_4$ and -- are as defined above.

3. The pyrazolopyridine-4-yl pyridazinone compound according to claim 2, an optical isomer thereof, or a pharmaceutically acceptable salt thereof or a hydrate thereof, wherein in the formula (1a), $R_1$ is a methoxy group.

4. The pyrazolopyridine-4-yl pyridazinone compound according to claim 2, an optical isomer thereof, or a pharmaceutically acceptable salt thereof or a hydrate thereof, wherein in the formula (1a), $R_1$ is a methylthio group.

5. The pyrazolopyridine-4-yl pyridazinone compound according to claim 2, an optical isomer thereof, or a pharmaceutically acceptable salt thereof or a hydrate thereof, wherein in the formula (1a), $R_1$ is a methylamino group.

6. The pyrazolopyridine-4-yl pyridazinone compound according to claim 1, an optical isomer thereof, or a pharmaceutically acceptable salt thereof or a hydrate thereof, wherein the compound of the formula (1) is
6-(2-ethyl-7-methoxy-pyrazolo[1,5-a]pyridine-4-yl)-5-methyl-4,5-dihydro-3(2H)-pyridazinone,
(+)-6-(2-ethyl-7-methoxy-pyrazolo[1,5-a]pyridine-4-yl)-5-methyl-4,5-dihydro-3(2H)-pyridazinone, (−)-6-(2-ethyl-7-methoxy-pyrazolo[1,5-a]pyridine-4-yl)-5-methyl-4,5-dihydro-3(2H)-pyridazinone, 6-(2-ethyl-7-methylthio-pyrazolo[1,5-a]pyridine-4-yl)-5-methyl-4,5-dihydro-3(2H)-pyridazinone, 6-(2-ethyl-7-methylamino-pyrazolo[1,5-a]pyridine-4-yl)-5-methyl-4,5-dihydro-3(2H)-pyridazinone, 6-(7-methoxy-2-trifluoromethyl-pyrazolo[1,5-a]pyridine-4-yl)-5-methyl-4,5-dihydro-3(2H)-pyridazinone, (+)-6-(7-methoxy-2-trifluoromethyl-pyrazolo[1,5-a]pyridine-4-yl)-5-methyl-4,5-dihydro-3(2H)-pyridazinone, (−)6-(7-methoxy-2-trifluoromethyl-pyrazolo[1,5-a]pyridine-4-yl)-5-methyl-4,5-dihydro-3(2H)-pyridazinone, 6-(7-methoxy-2-trifluoromethyl-pyrazolo[1,5-a]pyridine-4-yl)-4,5-dihydro-3(2H)-pyridazinone, 6-(7-methoxy-2-trifluoromethyl-pyrazolo[1,5-a]pyridine-4-yl)-5-methyl-3(2H)-pyridazinone, or 6-(7-methoxy-2-trifluoromethyl-pyrazolo[1,5-a]pyridine-4-yl)-3(2H)-pyridazinone.

7. A pharmaceutical composition comprising as an active ingredient the pyrazolopyridine-4-yl pyridazinone compound according to claim 1, an optical isomer thereof or a pharmaceutically acceptable salt thereof or a hydrate thereof, and a pharmaceutically acceptable carrier.

8. A pharmaceutical composition comprising as an active ingredient the pyrazolopyridine-4-yl pyridazinone compound according to claim 2, an optical isomer thereof or a pharmaceutically acceptable salt thereof or a hydrate thereof, and a pharmaceutically acceptable carrier.

9. A pharmaceutical composition comprising as an active ingredient the pyrazolopyridine-4-yl pyridazinone compound according to claim 3, an optical isomer thereof or a pharmaceutically acceptable salt thereof or a hydrate thereof, and a pharmaceutically acceptable carrier.

10. A pharmaceutical composition comprising as an active ingredient the pyrazolopyridine-4-yl pyridazinone compound according to claim 4, an optical isomer thereof or a pharmaceutically acceptable salt thereof or hydrate thereof, and a pharmaceutically acceptable carrier.

11. A pharmaceutical composition comprising as an active ingredient the pyrazolopyridine-4-yl pyridazinone compound according to claim 5, an optical isomer thereof or a pharmaceutically acceptable salt thereof or a hydrate thereof, and a pharmaceutically acceptable carrier.

12. A pharmaceutical composition comprising as an active ingredient the pyrazolopyridine-4-yl pyridazinone compound according to claim 6, an optical isomer thereof or a pharmaceutically acceptable salt thereof or a hydrate thereof, and a pharmaceutically acceptable carrier.

\* \* \* \* \*